US005155118A

United States Patent [19]

Carini et al.

[11] Patent Number: 5,155,118

[45] Date of Patent: Oct. 13, 1992

[54] METHOD AND COMPOSITION FOR PREVENTING NSAID-INDUCED RENAL FAILURE

[75] Inventors: David J. Carini, Wilmington; John J. V. Duncia, Newark; Pancras C. B. Wong, Wilmington, all of Del.

[73] Assignee: E. I. Du Pont de Nemours and Company, Wilmington, Del.

[21] Appl. No.: 436,281

[22] Filed: Nov. 13, 1989

Related U.S. Application Data

[60] Division of Ser. No. 279,194, Dec. 6, 1988, abandoned, which is a continuation-in-part of Ser. No. 142,580, Jan. 7, 1988, abandoned, which is a continuation-in-part of Ser. No. 50,341, May 22, 1987, abandoned, which is a continuation-in-part of Ser. No. 884,920, Jul. 11, 1986, abandoned.

[51] Int. Cl.[5] .................... A01N 43/64; A01N 43/50; A01N 57/00; A01N 43/58

[52] U.S. Cl. .................................... 514/381; 514/94; 514/235.8; 514/252; 514/326; 514/359; 514/374; 514/383; 514/397; 514/398; 514/399; 514/400

[58] Field of Search ............... 514/258, 267, 381, 256, 514/400, 94, 235.8, 252, 326, 359, 374, 383, 397, 398, 399

[56] References Cited

U.S. PATENT DOCUMENTS

| | | | |
|---|---|---|---|
| 3,772,315 | 11/1973 | Regel et al. | 260/296 R |
| 4,207,324 | 6/1980 | Matsumura et al. | 424/273 |
| 4,226,878 | 10/1980 | Iizuka et al. | 424/273 R |
| 4,228,167 | 10/1980 | Yamamoto et al. | 514/267 |
| 4,301,169 | 11/1981 | Yamanaka et al. | 424/273 R |
| 4,328,349 | 5/1982 | Grayboyes et al. | 548/343 |
| 4,340,598 | 7/1982 | Furukawa et al. | 424/273 |
| 4,347,364 | 8/1982 | Walser et al. | 546/256 |
| 4,347,365 | 8/1982 | Walser et al. | 546/256 |
| 4,355,040 | 10/1982 | Furukawa et al. | 424/273 |
| 4,379,927 | 4/1983 | Vorbrüggen et al. | 548/343 |
| 4,402,966 | 9/1983 | Yamanaka et al. | 424/273 R |
| 4,435,395 | 3/1984 | Loev et al. | 424/248.5 |
| 4,448,781 | 5/1984 | Cross et al. | 424/273 |
| 4,463,011 | 7/1984 | Ogata | 424/273 |
| 4,532,331 | 7/1985 | Frazee et al. | 548/342 |
| 4,533,669 | 8/1985 | Yamanaka et al. | 514/307 |
| 4,539,322 | 9/1985 | Campbell et al. | 514/253 |
| 4,602,031 | 7/1986 | Yamanaka et al. | 514/300 |
| 4,689,182 | 8/1987 | Rafferty | 260/404 |
| 4,755,518 | 7/1988 | Rafferty | 514/269 |
| 4,772,602 | 9/1988 | Cho et al. | 514/235.8 |
| 4,883,798 | 11/1989 | Petöcz et al. | 514/256 |
| 4,927,826 | 5/1990 | Guthrie et al. | 514/256 |

FOREIGN PATENT DOCUMENTS

| | | |
|---|---|---|
| 028834 | 5/1981 | European Pat. Off. . |
| 90978 | 10/1983 | European Pat. Off. . |
| 103647 | 3/1984 | European Pat. Off. . |
| 125033 | 11/1984 | European Pat. Off. . |
| 125783 | 11/1984 | European Pat. Off. . |
| 142754 | 5/1985 | European Pat. Off. . |
| 146228 | 6/1985 | European Pat. Off. . |
| 0253310 | 1/1988 | European Pat. Off. . |
| 3426081 | 1/1986 | Fed. Rep. of Germany . |
| 3426195 | 1/1986 | Fed. Rep. of Germany . |
| 8298270 | 6/1982 | Japan . |

OTHER PUBLICATIONS

Wong et al., Abstract No. 30, *Hypertension*, p. 340, vol. 12, No. 3, Sep. 1988, High Blood Pressure Council Mtg., San Francisco, CA, Sep. 18-Oct. 1, 1988, "X-6803 Methyl-2-N-Butyl-1-(4-(2-Carboxybenzamido)Benzyl-4-Chloroimidazole-5-Acetate, Sodium Salt): A Novel Nonpeptide Angiotension II Receptor Antagonist".

(List continued on next page.)

*Primary Examiner*—Frederick E. Waddell
*Assistant Examiner*—T. J. Criares

[57] ABSTRACT

Substituted imidazoles such as

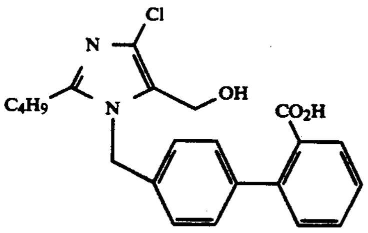

are useful as angiotensin II blockers. These compounds have activity in treating hypertension and congestive heart failure.

54 Claims, 2 Drawing Sheets

OTHER PUBLICATIONS

Chiu et al., "Abstract No. 118.11, *The Pharmacologist,* vol. 30, p. A165, 1988, for ASPET Mtg., Montreal, Canada, Oct. 9-12, 1988:" Nonpeptide Angiotensin II (AII) Receptor Antagonists: Structure Function Studies.

Wong et al., Nonpeptide Angiotensin II Receptor Antagonists. I Pharmacological Characterization of 2-n-Butyl-Chloro-1(2-chlorobenzyl)imidazole-5-acetic Acid, Sodium Salt (S-8307), "J. Pharmacology and Experimental Therapeutics," vol. 147, No. 1, pp. 1-7 (Jun. 10, 1988).

Chiu et al., "Non-peptide Angiotensin II Receptor Antagonists, II, Pharmacology of S-8308," European Journal of Pharmacology, vol. 157, pp. 13-21 (Aug. 23, 1988).

Lindgren et al., "Potentiation of inflammatory reactions in guinea-pig skin by an angiotensin converting enzyme inhibitor (MK 422)", *European Journal Pharmacolgy* vol. 135, pp. 383-387, Jan. 1987.

Schmidt et al., *J. Cardiovascular Pharmacology,* vol. 8, pp. S100-105, Jun. 1986.

H. Torii, *Takeda Kenkyuissholo,* 40, No. 3/4, 180-191 (Aug. 2, 1982).

Pals et al., *Circulation Research,* 29, 673 (Dec. 1971).

Streeten and Anderson, *Handbook of Hypertension, vol. 5, Clinical Pharmogy of Antihypertensive Drugs, A. E. Doyle (Editor), Elsevier Science Publishers B. V., p. 246 (1984).*

Satoh et al., *Cir. Res.,* 36/37 & Suppl. I: I-89, Jun. 1975.

METHOD AND COMPOSITION FOR PREVENTING NSAID-INDUCED RENAL FAILURE

RELATED APPLICATION

This application is a division of U.S. application Ser. No. 07/279,194, filed Dec. 6, 1988, now abandoned, which is a continuation-in-part of U.S. application Ser. No. 07/142,580, filed Jan. 7, 1988, now abandoned, which is a continuation-in-part of U.S. application Ser. No. 050,341, filed May 22, 1987, now abandoned, which is a continuation-in-part of U.S. application Ser. No. 884,920, filed Jul. 11, 1986, now abandoned.

BACKGROUND OF THE INVENTION

1. Field of the Invention

This invention relates to novel substituted imidazoles, and processes for their preparation. The invention also relates to pharmaceutical compositions containing the novel imidazoles and pharmaceutical methods using them, alone and in conjunction with other drugs, especially diuretics and non-steroidal anti-inflammatory drugs (NSAID's).

The compounds of this invention inhibit the action of the hormone angiotensin II (AII) and are useful therefore in alleviating angiotensin induced hypertension. The enzyme renin acts on a blood plasma $\alpha_2$-globulin, angiotensinogen, to produce angiotensin I, which is then converted by angiotensin converting-enzyme to AII. The latter substance is a powerful vasopressor agent which has been implicated as a causitive agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. The compounds of this invention are also useful for the treatment of congestive heart failure. Administration of a compound of this invention with a diuretic such as furosemide or hydrochlorothiazide, either as a stepwise combined therapy (diuretic first) or as a physical mixture, enhances the antihypertensive effect of the compound. Administration of a compound of this invention with a non-steroidal anti-inflammatory drug (NSAID) can prevent renal failure which sometimes results from administration of a NSAID.

K. Matsumura, et al., in U.S. Pat. No. 4,207,324 issued Jun. 10, 1980 discloses 1,2-disubstituted-4-haloimidazole-5-acetic acid derivatives of the formula:

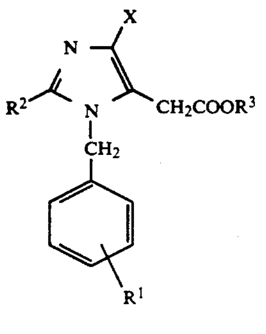

wherein $R^1$ is hydrogen, nitro or amino; $R^2$ is phenyl, furyl or thienyl optionally substituted by halogen, lower alkyl, lower alkoxy or di-lower alkylamino; $R^3$ is hydrogen or lower alkyl and X is halogen; and their physiologically acceptable salts. These compounds have diuretic and hypotensive actions.

Furukawa, et al., in U.S. Pat. No. 4,355,040 issued Oct. 19, 1982 discloses hypotensive imidazole-5-acetic acid derivatives having the formula:

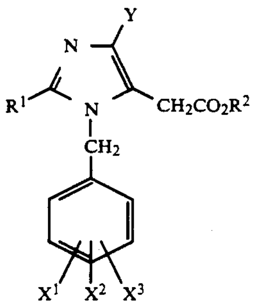

wherein $R^1$ is lower alkyl, cycloalkyl, or phenyl optionally substituted; $X^1$, $X^2$, and $X^3$ are each hydrogen, halogen, nitro, amino, lower alkyl, lower alkoxy, benzyloxy, or hydroxy; Y is halogen and $R^2$ is hydrogen or lower alkyl; and salts thereof.

Furukawa, et al., in U.S. Pat. No. 4,340,598, issued Jul. 20, 1982, discloses hypotensive imidazole derivatives of the formula:

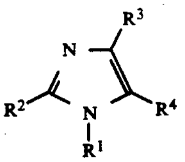

wherein $R^1$ is lower alkyl or, phenyl $C_{1-2}$ alkyl optionally substituted with halogen or nitro; $R^2$ is lower alkyl, cycloalkyl or phenyl optionally substituted; one of $R^3$ and $R^4$ is $-(CH_2)_nCOR^5$ where $R^5$ is amino, lower alkoxyl or hydroxyl and n is 0, 1, 2 and the other of $R^3$ and $R^4$ is hydrogen or halogen; provided that $R^1$ is lower alkyl or phenethyl when $R^3$ is hydrogen, $n=1$ and $R^5$ is lower alkoxyl or hydroxyl; and salts thereof.

Furukawa et al., in European Patent Application 103,647 discloses 4-chloro-2-phenylimidazole-5-acetic acid derivatives useful for treating edema and hypertension of the formula:

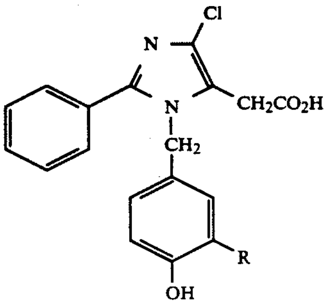

where R represents lower alkyl and salts thereof.

The metabolism and disposition of hypotensive agent 4-chloro-1-(4-methoxy-3-methylbenzyl)-2-phenyl-imidazole-5-acetic acid is disclosed by H. Torii in *Takeda Kenkyushoho,* 41, No 3/4, 180–191 (1982).

Frazee et al., in European Patent Application 125,033-A discloses 1-phenyl(alkyl)-2-(alkyl)-thioimidazole derivatives which are inhibitors of dopamine-$\beta$-hydroxylase and are useful as antihypertensives, diuretics and cardiotonics.

European Patent Application 146,228 filed Oct. 16, 1984 by S. S. L. Parhi discloses a process for the preparation of 1-substituted-5-hydroxymethyl-2-mercaptoimidazoles.

A number of references disclose 1-benzyl-imidazoles such as U.S. Pat. No. 4,448,781 to Cross and Dickinson (issued May 15, 1984); U.S. Pat. No. 4,226,878 to Ilzuka et al. (issued Oct. 7, 1980); U.S. Pat. No. 3,772,315 to Regel et al. (issued Nov. 13, 1973); U.S. Pat. No. 4,379,927 to Vorbruggen et al. (issued Apr. 12, 1983); amongst others.

Pals et al., *Circulation Research,* 29, 673 (1971) describe the introduction of a sarcosine residue in position 1 and alanine in position 8 of the endogenous vasoconstrictor hormone AII to yield an (octa)peptide that blocks the effects of AII on the blood pressure of pithed rats. This analog, [$Sar^1$, $Ala^8$] AII, initially called "P113" and subsequently "Saralasin", was found to be one of the most potent competitive antagonists of the actions of AII, although, like most of the so-called peptide-AII-antagonists, it also possesses agonistic actions of its own. Saralasin has been demonstrated to lower arterial pressure in mammals and man when the (elevated) pressure is dependent on circulating AII (Pals et al., *Circulation Research,* 29, 673 (1971); Streeten and Anderson, Handbook of Hypertension, Vol. 5, Clinical Pharmacology of Antihypertensive Drugs, A. E. Doyle (Editor), Elsevier Science Publishers B.V., p. 246 (1984)). However, due to its agonistic character, saralasin generally elicits pressor effects when the pressure is not sustained by AII. Being a peptide, the pharmacological effects to saralasin are relatively shortlasting and are only manifest after parenteral administration, oral doses being ineffective. Although the therapeutic uses of peptide AII-blockers, like saralasin, are severely limited due to their oral ineffectiveness and short duration of action, their major utility is as a pharmaceutical standard.

To date there are no known non-peptide antagonists of AII which are useful orally or which bind in vitro in the $IC_{50}$ ranges we observe.

Some known non-peptide antihypertensive agents act by inhibiting an enzyme, called angiotensin converting enzyme (ACE), which is responsible for conversion of angiotensin I to AII. Such agents are thus referred to as ACE inhibitors, or converting enzyme inhibitors (CEI's). Captopril and enalapril are commercially available CEI's. Based on experimental and clinical evidence, about 40% of hypertensive patients are non-responsive to treatment with CEI's. But when a diuretic such as furosemide or hydrochlorothiazide is given together with a CEI, the blood pressure of the majority of hypertensive patients is effectively normalized. Diuretic treatment converts the non-renin dependent state in regulating blood pressure to a renin-dependent state. Although the imidazoles of this invention act by a different mechanism, i.e., by blocking the AII receptor rather than by inhibiting the angiotensin converting enzyme, both mechanisms involve interference with the renin-angiotensin cascade. A combination of the CEI enalapril maleate and the diuretic hydrochlorothiazide is commercially available under the trademark Vaseretic® from Merck & Co. Publications which relate to the use of diuretics with CEI's to treat hypertension, in either a diuretic-first, stepwise approach or in physical combination, include Keeton, T. K. and Campbell, W. B., Pharmacol. Rev., 31:81 (1981) and Weinberger, M. H., Medical Clinics N. America, 71:979 (1987). Diuretics have also been administered in combination with saralasin to enhance the antihypertensive effect.

Non-steroidal anti-inflammatory drugs (NSAID's) have been reported to induce renal failure in patients with renal underperfusion and high plasma level of AII. (Dunn, M. J., Hospital Practice, 19:99, 1984). Administration of an AII blocking compound of this invention in combination with an NSAID (either stepwise or in physical combination) can prevent such renal failure. Saralasin has been shown to inhibit the renal vasoconstrictor effect of indomethacin and meclofenamate in dogs (Satoh et al., *Circ. Res.* 36/37 (Suppl. I):I-89, 1975; Blasingham et al., *Am. J. Physiol.* 239:F360, 1980). The CEI captopril has been demonstrated to reverse the renal vasoconstrictor effect of indomethacin in dogs with non-hypotensive hemorrhage. (Wong et al., *J. Pharmacol. Exp. Ther.* 219:104, 1980).

SUMMARY OF THE INVENTION

According to the present invention there are provided novel compounds of formula (I) which have angiotensin II-antagonizing properties and are useful as antihypertensives.

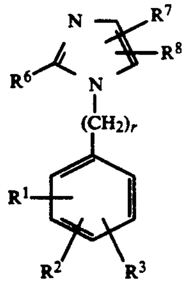

(I)

wherein $R^1$ is

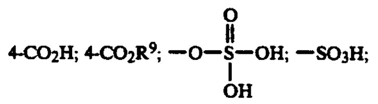

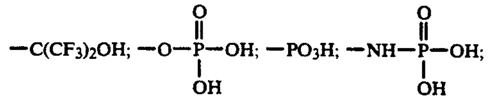

4-$NHSO_2CH_3$; 4-$NHSO_2CF_3$; $-CONHOR^{12}$;

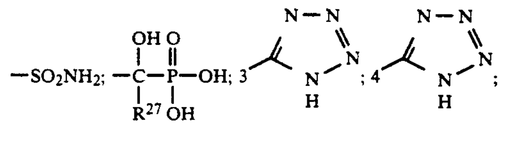

-continued

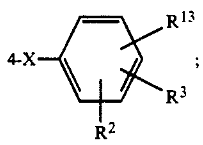
;
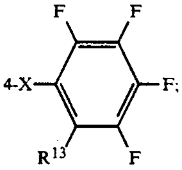
;

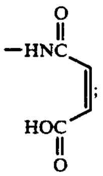
;
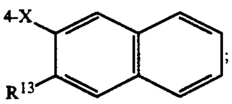
;

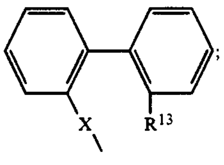
;
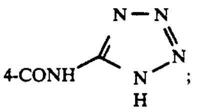
;

4-CONHNHSO2CF3;
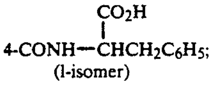
;
(l-isomer)

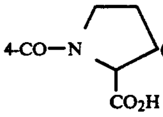
(l-isomer);
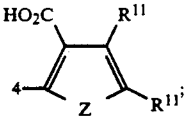

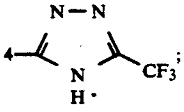
;
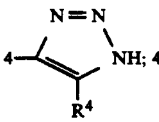
;
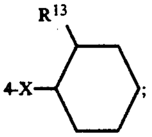
;

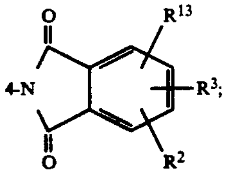
;

or

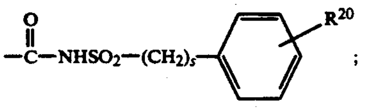
;

$R^2$ is H; Cl; Br; I; F; $NO_2$; CN; alkyl of 1 to 4 carbon atoms; acyloxy of 1 to 4 carbon atoms; alkoxy of 1 to 4 carbon atoms; $CO_2H$; $CO_2R^9$; $NHSO_2CH_3$; $NHSO_2CF_3$; $CONHOR^{12}$; $SO_2NH_2$;

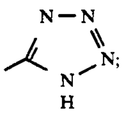
;

aryl; or furyl;

$R^3$ is H; Cl, Br, I or F; alkyl of 1 to 4 carbon atoms or alkoxy of 1 to 4 carbon atoms;

$R^4$ is CN, $NO_2$ or $CO_2R^{11}$;

$R^5$ is H, alkyl of 1 to 6 carbon atoms, cycloalkyl of 3 to 6 carbon atoms alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms, cycloalkylalkyl, of 4 to 10 carbon atoms; cycloalkylalkenyl or cycloalkylalkynyl of 5 to 10 carbon atoms; $(CH_2)_sZ(CH_2)_mR^5$ optionally substituted with F or $CO_2R^{14}$; benzyl or benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1-6, $C_6F_5$; CN;

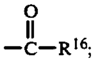
;

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the aliphatic portion is 2 to 6 carbon atoms; $-(CH_2)_m$-imidazol-1-yl; $-(CH_2)_m$-1,2,3-triazolyl optionally substituted with one or two groups selected from $CO_2CH_3$ or alkyl of 1 to 4 carbon atoms; $-(CH_2)_s$-tetrazolyl;

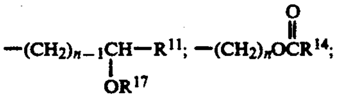

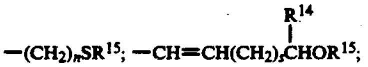

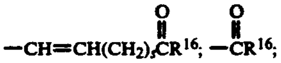

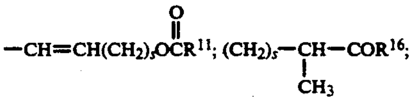

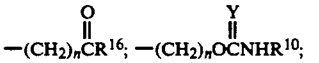

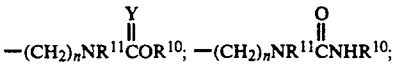

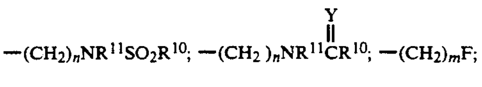

$-(CH_2)_mONO_2$; $-CH_2N_3$; $-(CH_2)_mNO_2$;

-continued $-CH=N-NR^{11}R^{17}$; 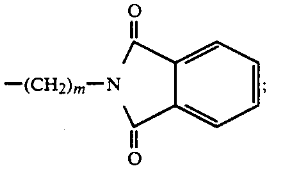

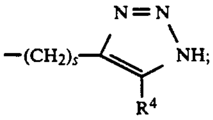 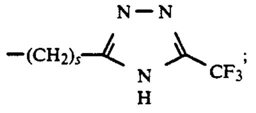

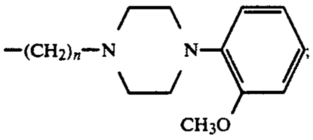

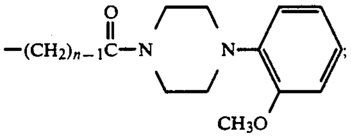

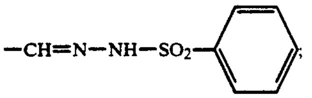

or 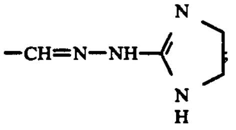

$R^9$ is

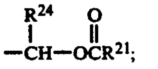

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl or benzyl;

$R^{13}$ is $-CO_2H$; $-CO_2R^9$; $-CH_2CO_2H$, $-CH_2CO_2R^9$;

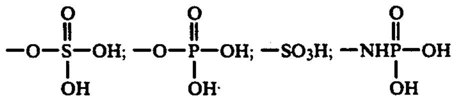

$-PO_3H$; $-C(CF_3)_2OH$; $-NHSO_2CH_3$; $-NHSO_2CF_3$;

$-NHCOCF_3$; $-CONHOR^{12}$; $-SO_2NH_2$;

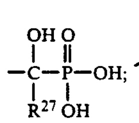 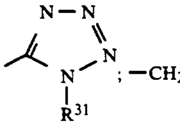 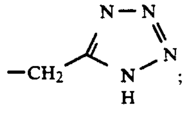

-continued

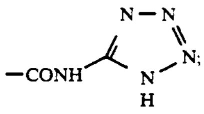 $-CONHNHSO_2CF_3$;

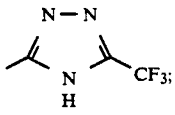 or 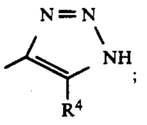

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently are H, alkyl of 1 to 4 carbon atoms, phenyl, benzyl, α-methylbenzyl, or taken together with the nitrogen form a ring of the formula

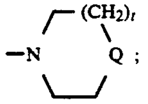

Q is $NR^{20}$, O or $CH_2$;

$R^{20}$ is H, alkyl of 1–4 carbon atoms, or phenyl;

$R^{21}$ is alkyl of 1 to 6 carbon atoms, $-NR^{22}R^{23}$, or

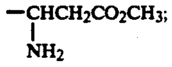

$R^{22}$ and $R^{23}$ independently are H, alkyl of 1 to 6 carbon atoms, benzyl, or are taken together as $(CH_2)_u$ where u is 3–6;

$R^{24}$ is H, $CH_3$ or $-C_6H_5$;

$R^{25}$ is $NR^{27}R^{28}$, $OR^{28}$, $NHCONH_2$, $NHCSNH_2$,

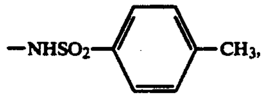 or 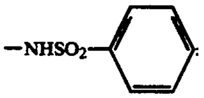

$R^{26}$ is hydrogen, alkyl with from 1 to 6 carbon atoms, benzyl, or allyl;

$R^{27}$ and $R^{28}$ are independently hydrogen, alkyl with from 1 to 5 carbon atoms, or phenyl;

$R^{29}$ and $R^{30}$ are independently alkyl of 1–4 carbon atoms or taken together are $-(CH_2)_q-$;

$R^{31}$ is H, alkyl of 1 to 4 carbon atoms, $-CH_2CH=CH_2$ or $-CH_2C_6H_4R^{32}$;

$R^{32}$ is H, $NO_2$, $NH_2$, OH or $OCH_3$;

X is a carbon-carbon single bond, $-CO-$, $-CH_2-$, $-O-$, $-S-$, $-NH-$,

-continued

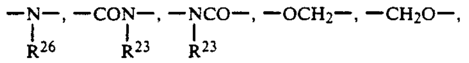

$-SCH_2-$, $-CH_2S-$, $-NHC(R^{27})(R^{28})$, $-NR^{23}SO_2-$, $-SO_2NR^{23}-$, $-C(R^{27})(R^{28})NH-$, $-CH=CH-$, $-CF=CF-$, $-CH=CF-$, $-CF=CH-$, $-CH_2CH_2-$, $-CF_2CF_2-$, 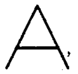,

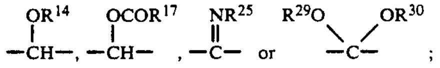

Y is O or S;
Z is O, $NR^{11}$, or S;
m is 1 to 5;
n is 1 to 10;
p is 0 to 3;
q is 2 to 3;
r is 0 to 2;
s is 0 to 5;
t is 0 or 1;

and pharmaceutically acceptable salts of these compounds; provided that:

(1) the $R^1$ group is not in the ortho position;

(2) when $R^1$ is

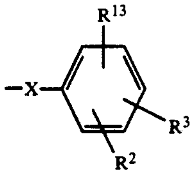

X is a single bond, and $R^{13}$ is $CO_2H$, or

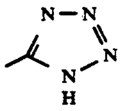

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

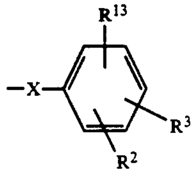

and X is other than a single bond, then $R^{13}$ must be ortho except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$, or $CH_2CO_2H$;

(6) when $R^1$ is

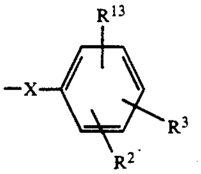

X is $-OCH_2-$, and $R^{13}$ is 2-$CO_2H$, and $R^7$ is H then $R^6$ is not $C_2H_5S$;

(7) when $R^1$ is

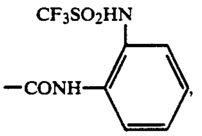

and $R^6$ is n-hexyl then $R^7$ and $R^8$ are not both hydrogen;

(8) when $R^1$ is

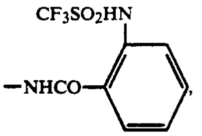

$R^6$ is not methoxybenzyl;

(9) the $R^6$ group is not

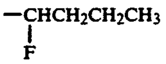

or $CH_2OH$;

(10) when r=0, $R^1$ is

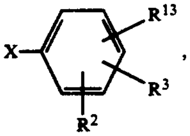

X is

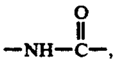

$R^{13}$ is 2-$NHSO_2CF_3$, and $R^6$ is n-propyl, then $R^7$ and $R^8$ are not $-CO_2CH_3$;

(11) when r=0, $R^1$ is

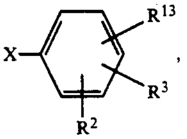

X is

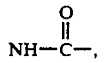

$R^{13}$ is 2-COOH, and $R^6$ is n-propyl, then $R^7$ and $R^8$ are not $-CO_2CH_3$;

(12) when r=1,

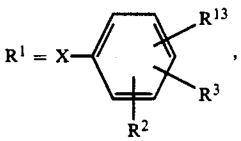

X is a single bond, $R^7$ is Cl, and $R^8$ is —CHO, then $R^{13}$ is not 3-(tetrazol-5-yl);

(13) when r=1,

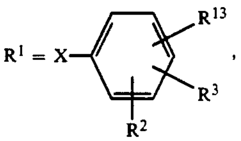

X is a single bond, $R^7$ is Cl, and $R^8$ is —CHO, then $R^{13}$ is not 4-(tetrazol-5-yl).

Preferred for their antihypertensive activity are novel compounds having the formula:

(II)

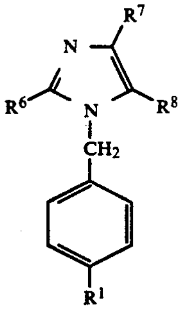

wherein $R^1$ is $-CO_2H$; $-NHSO_2CF_3$;

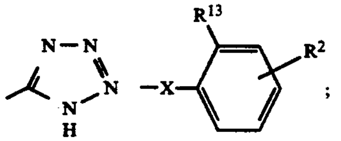

or

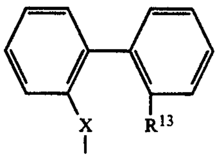

$R^6$ is alkyl of 3 to 10 carbon atoms, alkenyl of 3 to 10 carbon atoms, alkynyl of 3 to 10 carbon atoms, cycloalkyl of 3 to 8 carbon atoms, benzyl substituted on the phenyl ring with up to two groups selected from alkoxy of 1 to 4 carbon atoms, halogen, alkyl of 1 to 4 carbon atoms, and nitro;

$R^8$ is phenylalkenyl wherein the aliphatic portion is 2 to 4 carbon atoms, $-(CH_2)_m$-imidazol-1-yl, $-(CH_2)_m$—1,2,3-triazolyl optionally substituted with one or two groups selected from $CO_2CH_3$ or alkyl of 1 to 4 carbon atoms,

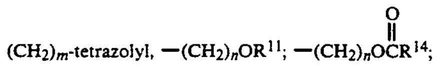

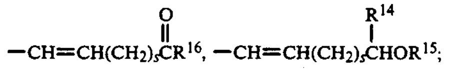

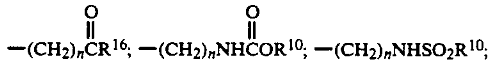

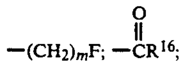

$R^{13}$ is $-CO_2H$, $-CO_2R^9$, $NHSO_2CF_3$; $SO_3H$; or 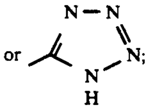

$R^{16}$ is H, alkyl of 1 to 5 carbon atoms, $OR^{17}$, or $NR^{18}R^{19}$;

X is carbon-carbon single bond,

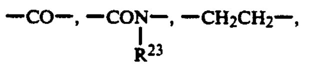

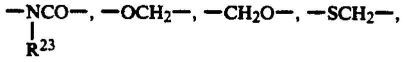

$-CH_2S-$, $-NHCH_2-$, $-CH_2NH-$ or $-CH=CH-$;

and pharmaceutically acceptable salts of these compounds.

More preferred are compounds of the preferred scope where:

$R^2$ is H, alkyl of 1 to 4 carbon atoms, halogen, or alkoxy of 1 to 4 carbon atoms;

$R^6$ is alkyl, alkenyl or alkynyl of 3 to 7 carbon atoms;

$R^7$ is H, Cl, Br, $C_vF_{2v+1}$, where v=1-3, or

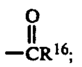

$R^8$ is

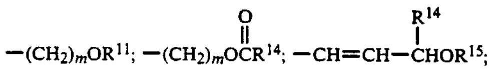

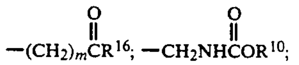

-continued $-(CH_2)_mNHSO_2R^{10}$; 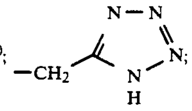; or $-COR^{16}$;

$R^{10}$ is $CF_3$, alkyl of 1 to 6 carbon atoms or phenyl;

$R^{11}$ is H, or alkyl of 1 to 4 carbon atoms;

$R^{13}$ is $CO_2H$; $CO_2CH_2OCOO(CH_3)_3$; $NHSO_2CF_3$ and

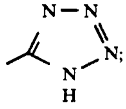;

$R^{14}$ is H, or alkyl of 1 to 4 carbon atoms;

$R^{15}$ is H, alkyl of 1 to 4 carbon atoms, or acyl of 1 to 4 carbon atoms;

$R^{16}$ is H, alkyl of 1 to 5 carbon atoms; $OR^{17}$; or

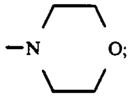;

m is 1 to 5;

X=single bond, —O—; —CO—; —NHCO—; or —$OCH_2$—;

and pharmaceutically acceptable salts.

Specifically preferred for their antihypertensive activity are:

2-Butyl-4-chloro-1-[(2'-(1H-tetrazol-5-yl)biphenyl-4-yl)methyl]-5-(hydroxymethyl)imidazole.

2-Butyl-4-chloro-1-[(2'-carboxybiphenyl-4-yl)methyl]-5-(hydroxymethyl)imidazole.

2-Butyl-4-chloro-1-[(2'-carboxybiphenyl-4-yl)methyl]-5-[(methoxycarbonyl)aminomethyl]imidazole.

2-Butyl-4-chloro-1-[(2'-carboxybiphenyl-4-yl)methyl]-5-[(propoxycarbonyl)aminomethyl]imidazole.

2-Butyl-4-chloro-1-[(2'-carboxybiphenyl-4-yl)methyl-]imidazole-5-carboxaldehyde.

2-Butyl-1-[(2'-carboxybiphenyl-4-yl)methyl]imidazole-5-carboxaldehyde.

2-(1E-Butenyl)-4-chloro-1-[(2'-carboxybiphenyl-4-yl)methyl]-5-(hydroxymethyl)imidazole.

2-(1E-Butenyl)-4-chloro-1-[(2'-carboxybiphenyl-4-yl)methyl]imidazole-5-carboxaldehyde.

2-Propyl-4-chloro-1-[(2'-(1H-tetrazol-5-yl)biphenyl-4-yl)methyl]-5-(hydroxymethyl)imidazole.

2-Propyl-4-chloro-1-[(2'-(1H-tetrazol-5-yl)biphenyl-4-yl)methyl]imidazole-5-carboxaldehyde.

2-Butyl-4-chloro-1-[2'-(1H-tetrazol-5-yl)biphenyl-4-yl)methyl]imidazole-5-carboxaldehyde.

2-(1E-Butenyl)-4-chloro-1-[(2'-(1H-tetrazol-5-yl)biphenyl-4-yl)methyl]-5-hydroxymethyl)imidazole.

2-(1E-Butenyl)-4-chloro-1-[(2'-(1H-tetrazol-5-yl)biphenyl-4-yl)methyl]imidazole-5-carboxaldehyde.

2-Butyl-4-chloro-1-[(2'-(1H-tetrazol-5-yl)biphenyl-4-yl)methyl]imidazole-5-carboxylic acid.

2-Propyl-4-chloro-1-[(2'-(1H-tetrazol-5-yl)biphenyl-4-yl)methyl]imidazole-5-carboxylic acid.

2-Propyl-4-trifluoromethyl-1-[(2'-(1H-tetrazol-5-yl)biphenyl-4-yl)methyl]imidazole-5-carboxylic acid.

2-Propyl-4-trifluoromethyl-1-[(2'-(1H-tetrazol-5-yl)biphenyl-4-yl)methyl]-5-(hydroxylmethyl-)imidazole.

2-Butyl-4-trifluoromethyl-1-[(2'-(1H-tetrazol-5-yl)biphenyl-4-yl)methyl]imidazole-5-carboyxlic acid.

2-Propyl-4-trifluoromethyl-1-[(2'-(carboxybiphenyl-4-yl)methyl]imidazole-5-carboxaldehyde.

2-Propyl-4-pentafluoroethyl-1-[(2'-(1H-tetrazol-5-yl)biphenyl-4-yl)methyl]-5-(hydroxymethyl-)imidazole.

2-Propyl-1-[(2'-(1H-tetrazol-5-yl)biphenyl-4-yl)methyl-]imidazole-4,5-dicarboxylic acid.

2-Propyl-4-pentafluoroethyl-1-[(2'-(1H-tetrazol-5-yl)biphenyl-4-yl)methyl]imidazole-5-carboxylic acid.

2-Propyl-4-pentafluoroethyl-[(2'-(1H-tetrazol-5-yl)biphenyl-4-yl)methyl]imidazole-5-carboxaldehyde, and pharmaceutically acceptable salts thereof.

Note that throughout the text when an alkyl substituent is mentioned, the normal alkyl structure is meant (i.e., butyl is n-butyl) unless otherwise specified.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydroscopicity and solubility. Preferred salts of this invention for the reasons cited above include potassium, sodium, calcium and ammonium salts.

Also within the scope of this invention are pharmaceutical compositions comprising a suitable pharmaceutical carrier and a compound of Formula (I), and methods of using the compounds of Formula (I) to treat hypertension and congestive heart failure. The pharmaceutical compositions can optionally contain one or more other therapeutic agents, such as a diuretic or a non-steroidal antiinflammatory drug. Also within the scope of this invention is a method of preventing renal failure resulting from administration of a non-steroidal antiinflammatory drug (NSAID) which comprises administering a compound of Formula (I) in stepwise or physical combination with the NSAID. The compounds of this invention can also be used as diagnostic agents to test the renin angiotensin system.

It should be noted in the foregoing structural formula, when a radical can be a substituent in more than one previously defined radical, that first radical can be selected independently in each previously defined radical. For example, $R^1$, $R^2$ and $R^3$ can each be $CONHOR^{12}$. $R^{12}$ need not be the same substituent in each of $R^1$, $R^2$ and $R^3$ but can be selected independently for each of them.

SYNTHESIS

Figure 1:
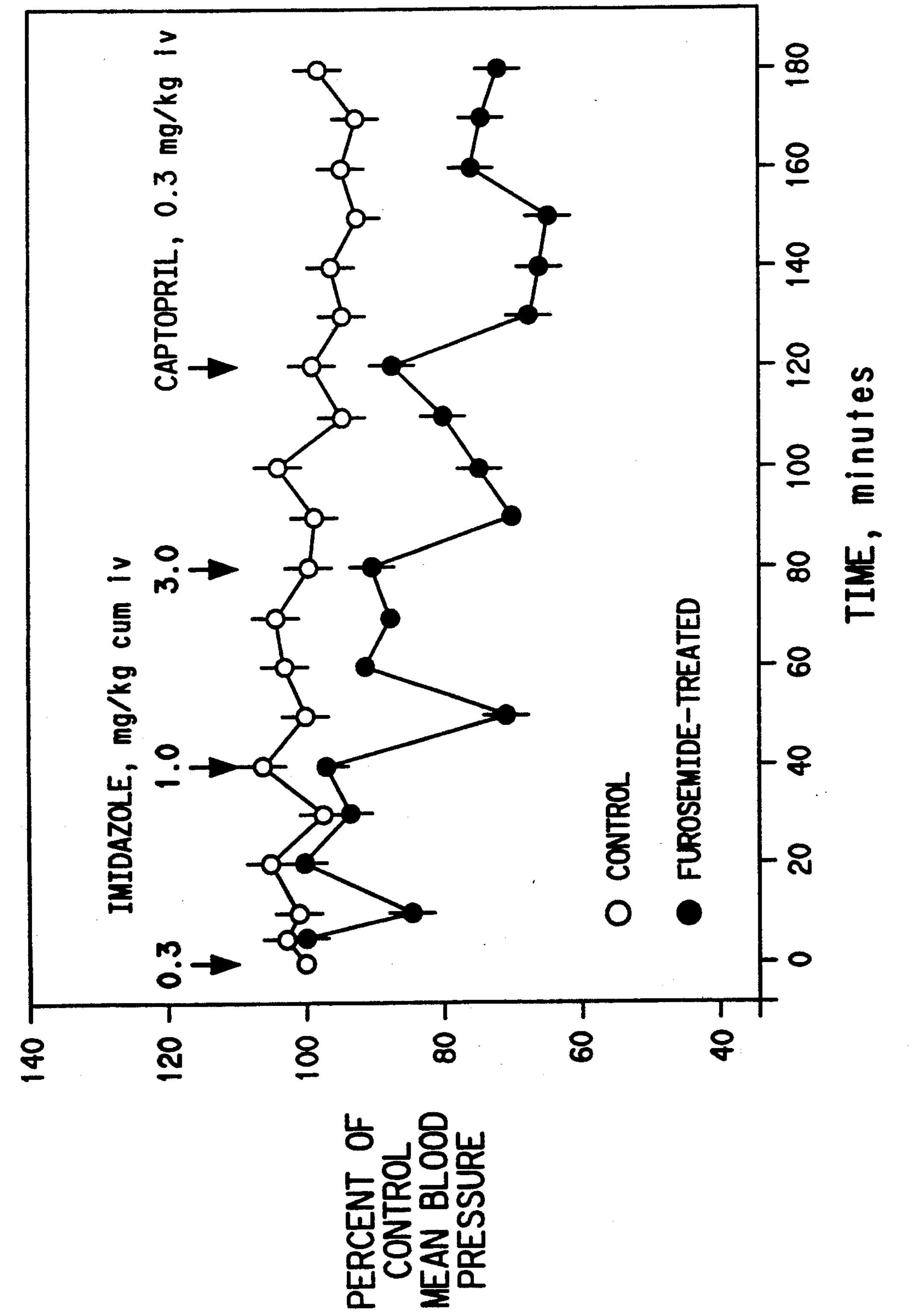
FIG. 1 shows furosemide enhancement of imidazole hypertensive effect.

The novel compounds of Formula (I) may be prepared using the reactions and techniques described in this section. The reactions are performed in a solvent appropriate to the reagents and materials employed and suitable for the transformation being effected. It is understood by those skilled in the art of organic synthesis that the functionality present on the imidazole and other portions of the molecule must be consistent with the chemical transformations proposed. This will frequently necessitate judgment as to the order of synthetic steps, protecting groups required, deprotection conditions, and activation of a benzylic position to enable attachment to nitrogen on the imidazole nucleus. Throughout the following section, not all compounds of Formula (I) falling into a given class may necessarily be prepared by all methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used.

Scheme 1

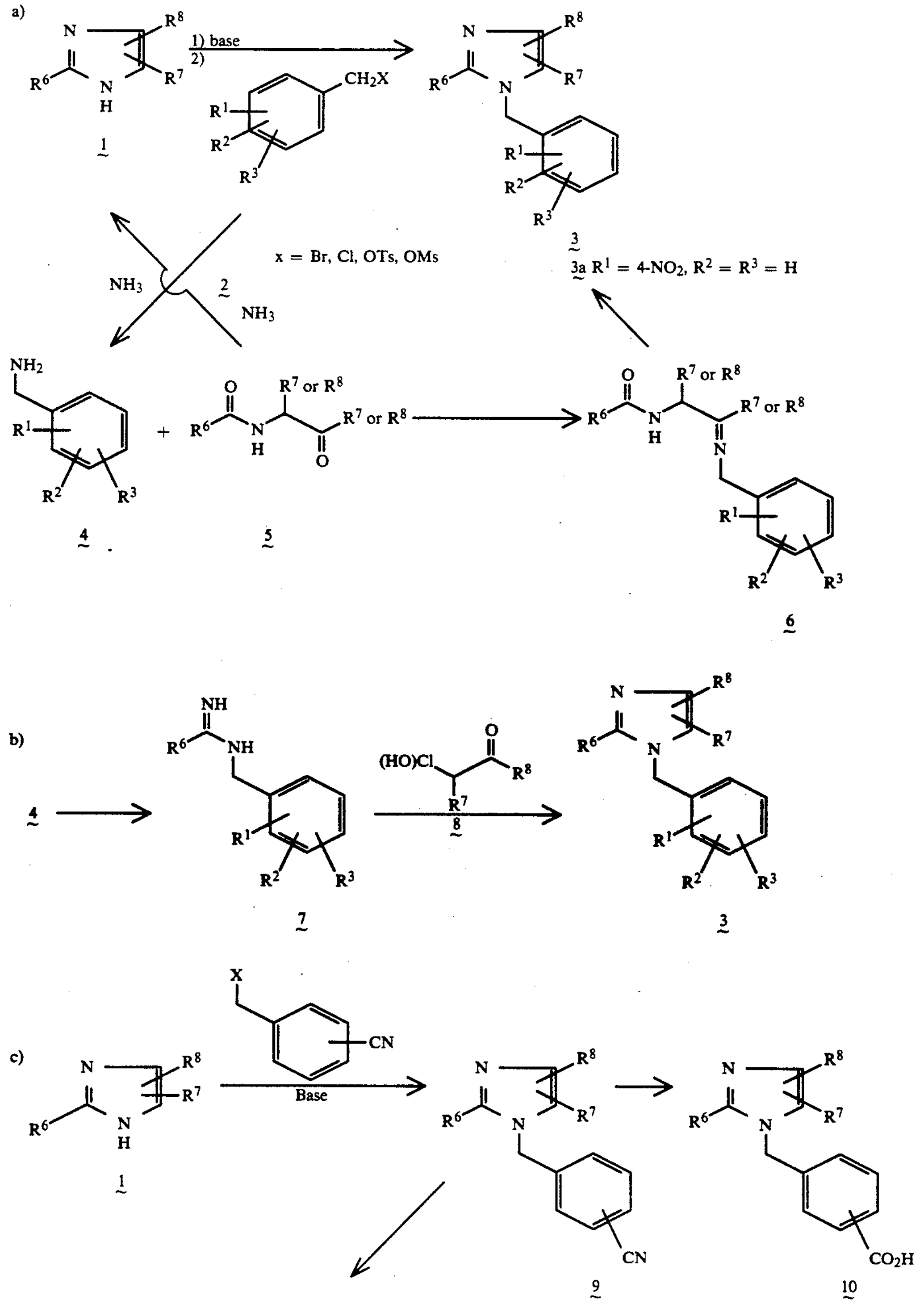

-continued

Scheme 1

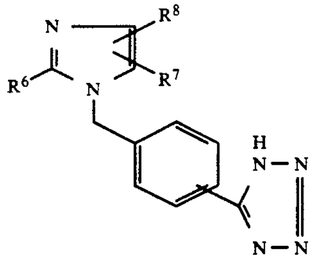

11

Generally, compounds of Formula (3) can be prepared by direct alkylation onto imidazole (1) prepared as described in U.S. Pat. No. 4,355,040 and references cited therein, with an appropriately protected benzyl halide, tosylate or mesylate (2) in the presence of base, as shown in path a). Preferably, the metallic imidazolide salt is prepared by reacting imidazole (1) with a proton acceptor such as MH where M is lithium, sodium or potassium in a solvent such as dimethylformamide (DMF) or by reacting it with a metal alkoxide of formula MOR where R is methyl, ethyl, t-butyl or the like in an alcohol solvent such as ethanol or t-butanol, or a dipolar aprotic solvent such as dimethylformamide. The imidazole salt is dissolved in an inert aprotic solvent such as DMF, and treated with an appropriate alkylating agent (2). Alternatively, imidazole (1) can be alkylated with a benzyl halide (2, where X=Br, Cl) in the presence of a base such as sodium carbonate, potassium carbonate, triethylamine or pyridine. The reaction is run in an inert solvent such as DMF or DMSO at 20° C. to the reflux temperature of the solvent for 1-10 hours.

For example, the 4-nitrobenzyl intermediate (3a, wherein $R^1$=4-$NO_2$, $R^2$=$R^3$=H) may be obtained by direct alkylation onto imidazole (1) with a 4-nitrobenzyl halide, tosylate or mesylate in the presence of base.

If $R^7$ and $R^8$ are different, mixtures of two regioisomer alkylation products (3b, and 3c) are obtained in which $R^7$ and $R^8$ are interchanged. When $R^8$ is CHO the alkylation is such that the benzyl group becomes attached to the adjacent nitrogen preferentially. These isomers posses distinct physical and biological properties and can usually be separated and isolated by conventional separation techniques such as chromatography and/or crystallization.

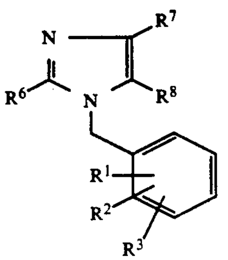

3b

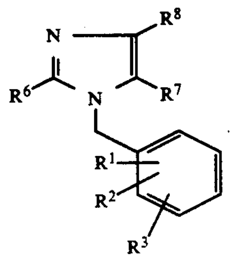

3c

-continued

3d; $R^6$ = n-Bu, $R^7$ = Cl
$R^8$ = $CH_2CO_2Me$,

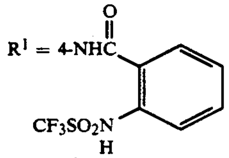

$R^2$ = $R^3$ =H

3e; $R^6$ = n-Bu,
$R^7$ = Cl
$R^8$ = $CH_2OH$

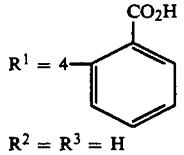

$R^2$ = $R^3$ = H

In all series examined, the more rapidly eluted isomer of a given pair has greater biological potency than the less rapidly eluted isomer. The absolute structure of the compounds 3d and 3e has been confirmed by X-ray crystallographic analysis to establish the relationship between structure, physical properties and biological activity. Sulfonamide 3d is the more rapidly eluted isomer in its series, acid 3e is the less rapidly eluted isomer in its series.

Alternatively, any properly functionalized benzylamine derivative (4) may be converted to imine (6) by treatment with an acylamino ketone (5) in the presence of an inert solvent such as benzene, toluene, or the like, and a catalytic amount of p-toluenesulfonic acid or molecular sieves, N. Engel, and W. Steglich, *Liebigs Ann. Chem.*, 1916, (1978), or in the presence of alumina, F. Texier-Boulet, *Synthesis*, 679 (1985). The resulting imine (6) can be cyclized to the N-benzyl imidazole (3) with phosphorus pentachloride ($PCl_5$), phosphorus oxychloride ($POCl_3$) or triphenylphosphine ($PPh_3$) in dichloroethane in the presence of a base such as triethylamine, N. Engel and W. Steglich, *Liebigs Ann. Chem.*, 1916, (1978).

Acylamino ketone (5) is readily obtainable from amino acids via the Dakin-West reaction, H. D. Dakin, R. West, *J. Biol. Chem.*, 78, 95 and 745 (1928), and various modifications thereof, W. Steglich, G. Höfle, *Angew. Chem. Int. Ed. Engl.*, 8, 981 (1969); G. Höfle, W. Steglich, H. Vorbrüggen, *Angew. Chem. Int. Ed. Engl.*, 17, 569 (1978); W. Steglich, G. Höfle, *Ber.*, 102, 883 (1969), or by selective reduction of acyl cyanides, A. Pfaltz, S. Anwar, *Tet. Lett.* 2977 (1984), or from α-halo, α-tosyl or α-mesyl ketones via the appropriate substitution reactions that one skilled in the art will readily recognize.

The functionalized benzylamines (4) may be made from the corresponding benzyl halide, tosylate or mesylate (2) via displacement with a nitrogen nucleophile, a procedure familiar to one skilled in the art. This displacement may be achieved using azide ion, ammonia, or phthalimide anion, etc., in a neutral solvent such as dimethylformamide, dimethylsulfoxide etc., or under phase transfer conditions. The benzyl halide (2) may be made by a variety of benzylic halogenation methods familiar to one skilled in the art, for example benzylic bromination of toluene derivatives with N-bromosuccinimide in an inert solvent such as carbon tetrachloride in the presence of a radical initiator such as benzoyl peroxide at temperatures up to reflux conditions.

A wide variety of toluene derivatives may be made from simple electrophilic substitution reactions on an aromatic ring. This includes nitration, sulfonation, phosphorylation, Friedel-Crafts alkylation, Friedel-Crafts acylation, halogenation, and other similar reactions known to one skilled in the art, G. A. Olah, "Friedel-Crafts and Related Reactions," Vol. 1-5, Interscience, New York, (1965).

Another way to synthesize functionalized benzyl halides is via chloromethylation of the corresponding aromatic precursor. Thus, the appropriately substituted benzene ring may be chloromethylated with formaldehyde and hydrochloric acid (HCl) for example with or without an inert solvent such as chloroform, carbon tetrachloride, light petroleum ether or acetic acid. A Lewis acid such as zinc chloride ($ZnCl_2$) or a mineral acid such as phosphoric acid may also be added as a catalyst or condensing agent, R. C. Fuson, C. H. McKeever, *Org. Reactions,* 1, 63 (1942).

Alternatively, N-benzylimidazoles (3) can also be prepared as shown in path b) by forming an $R^6$ substituted amidine (7) from an appropriately substituted benzylamine (4) which is in turn reacted with an α-haloketone, α-hydroxyketone (8), α-haloaldehyde, or α-hydroxyaldehyde, F. Kunckell, *Ber.,* 34, 637 (1901).

As shown in path a), imidazole (1) may be alkylated by a variety of benzyl derivatives. These include compounds with latent acid functionalities such as o, m, and p-cyanobenzylhalides, mesylates or tosylates as shown in path c). Nitriles of formula (9) may be hydrolyzed to carboxylic acids of formula (10) by treatment with strong acid or alkali. Preferably, treatment with a 1:1 (v/v) mixture of concentrated aqueous hydrochloric acid/glacial acetic acid at reflux temperatures for 2–96 hours or by treatment with 1N sodium hydroxide in an alcohol solvent such as ethanol or ethylene glycol for 2–96 hours at temperatures from 20° C. to reflux can be used. If another nitrile group is present it will also be hydrolyzed. The nitrile functionality can also be hydrolyzed in two steps by first stirring in sulfuric acid to form the amide followed by hydrolysis with sodium hydroxide or a mineral acid to give the carboxylic acid (10).

The nitriles (9) can be converted into the corresponding tetrazole derivative (11) by a variety of methods using hydrazoic acid. For example, the nitrile can be heated with sodium azide and ammonium chloride in DMF at temperatures between 30° C. and reflux for 1–10 days, J. P. Hurwitz and A. J. Tomson, *J. Org. Chem.*, 26, 3392 (1961). Preferably, the tetrazole is prepared by the 1,3-dipolar cycloaddition of trialkyltin or triaryltin azides to the appropriately substituted nitrile as described in detail by Scheme 15.

The starting imidazole compounds (1) are readily available by any of a number of standard methods. For example, acylaminoketone (5) can be cyclized with ammonia or equivalents thereof, D. Davidson, et al., *J. Org. Chem.*, 2, 319 (1937) to the corresponding imidazole as shown in Scheme 1. The corresponding oxazole can also be converted to imidazole (1) by action of ammonia or amines in general, H. Bredereck, et al., *Ber.*, 88, 1351 (1955); J. W. Cornforth and R. H. Cornforth, *J. Chem. Soc.*, 96, (1947).

Several alternative routes to imidazoles (1) are illustrated in Scheme 2. As shown in Scheme 2 equation a), reaction of the appropriate $R^6$ substituted imidate esters (12) with an appropriately substituted α-hydroxy- or α-haloketone or aldehyde (8) in ammonia leads to imidazoles of formula (1), P. Dziuron, and W. Schunack, *Archiv. Pharmaz.*, 307 and 470 (1974).

The starting imidazole compounds (1) wherein $R^7$ and $R^8$ are both hydrogen can be prepared as shown in equation b) by reaction of the appropriate $R^6$-substituted imidate ester (12) with α-aminoacetaldehyde dimethyl acetal (13), M. R. Grimmett, *Adv. Heterocyclic Chem.*, 12, 103 (1970).

As shown in equation c), imidazole (15; wherein $R^7$=hydrogen and $R^8$=$CH_2OH$) can be prepared by treatment of the imidate ester (12) with 1,3-dihydroxyacetone (14) in ammonia by the procedure described in *Archive der Pharmazie*, 307, 470 (1974). Halogenation of imidazole (15) or any imidazole wherein $R^7$ or $R^8$ is hydrogen is preferably accomplished by reaction with one to two equivalents of N-halosuccinimide in a polar solvent such as dioxane or 2-methoxyethanol at a temperature of 40°–100° C. for 1–10 hours. Reaction of the halogenated imidazole (16) with a benzylhalide (2) in the manner described in Scheme 1 affords the corresponding N-benzylimidazole (17); wherein $R^7$ is halogen and $R^8$ is $CH_2OH$). This procedure is described in U.S. Pat. No. 4,355,040. Alternatively, imidazole (17) can be prepared by the procedure described in U.S. Pat. No. 4,207,324.

Compounds of formula (17) can also be prepared by treatment of the starting imidazole compound (1) wherein $R^7$ and $R^8$ are both hydrogen, with the appropriate benzyl halide followed by functionalization of $R^7$ and $R^8$ by treatment with formaldehyde as described in E. F. Godefroi, et al., *Recueil*, 91, 1383 (1972) followed by halogenation as was described above.

As shown in equation d) the imidazoles (1) can also be prepared by reaction of $R^6$ substituted amidines (18) with an α-hydroxy- or α-haloketone or aldehyde (8) as described by F. Kunckel, *Ber.*, 34, 637, (1901).

As shown in equation e), preparation of the nitroimidazoles (1, $R^7$ or $R^8$=$NO_2$) is preferably accomplished by heating the appropriate starting imidazole in a 3:1 mixture of conc. sulfuric acid/conc. nitric acid at 60°–100° C. for 1–6 hours. Nitration of the imidazole (15) can be achieved by first converting the hydroxymethylimidazole to the corresponding chloromethylimidazole (22) employing thionyl chloride or oxalyl chloride. Nitration, as described above, followed by hydrolysis provides the nitroimidazoles (24).

Imidazoles (21) where $R^7$ and $R^8$=CN can be prepared as shown in equation f) by reaction of $R^6$ substituted ortho esters, ortho acids or aldehydes (followed by oxidation of the aldehyde) with diaminomaleonitrile (20) by the procedure described by R. W. Begland et al., *J. Org. Chem.*, 39, 2341 (1974). Likewise, $R^6$ substituted imidate esters (12) also react with diaminomaleonitrile to give 4,5 dicyanoimidazoles (21). The nitrile groups can be further elaborated into other functional groups by methods familiar to one skilled in the art.

Compounds of Formula (1) wherein $R^7$=alkyl of 1-6 (straight or branched), phenyl, phenalkyl where alkyl is 1-3 carbon atoms, etc. and $R^8$=$CH_2OH$ can be prepared as shown in equation g). The imidazoles (1) were prepared as described in L. A. Reiter, *J. Org. Chem.*, 52, 2714 (1987). Hydroxymethylation of (1) as described by U. Kempe, et al. in U.S. Pat. No. 4,278,801 provides the hydroxymethylimidazoles (1a).
Scheme 2
a)
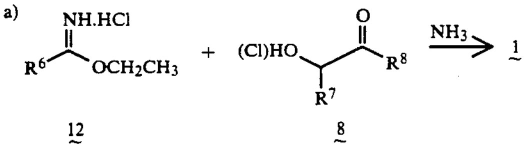
12 8 1
b)
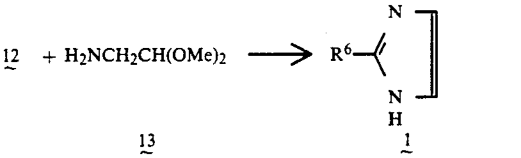
13 1
(wherein $R^7 = R^8 = H$)
c)
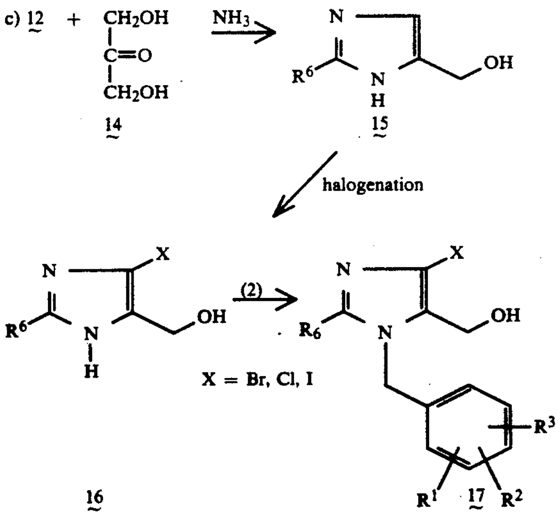
14 15 16 17
d)
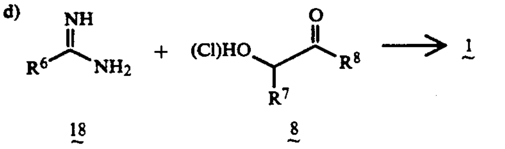
18 8 1
e)
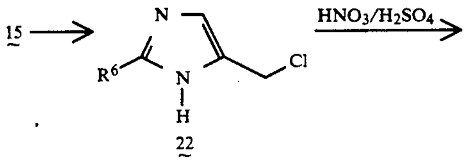
15 22
-continued
Scheme 2
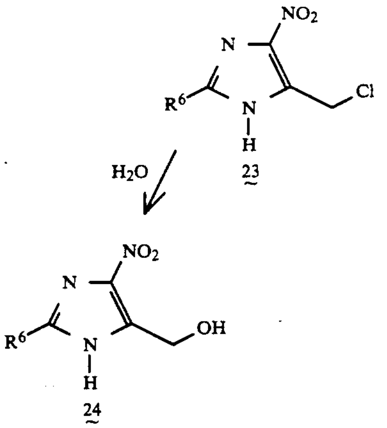
23 24
f)
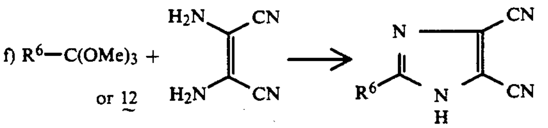
or 12
19 20 21
$R^7, R^8 = CN$
g)
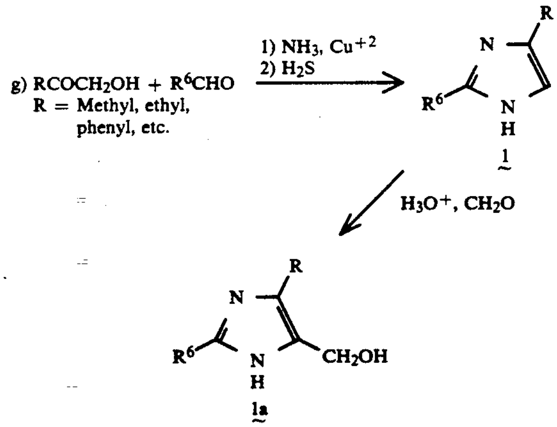
R = Methyl, ethyl, phenyl, etc.
1 1a
Scheme 3
a)
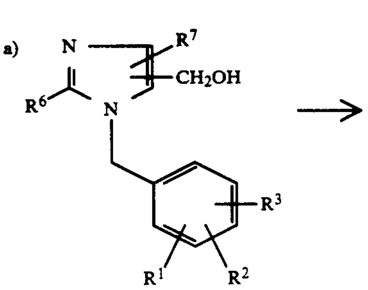
(where $R^7 = Cl$)
17

-continued

Scheme 3

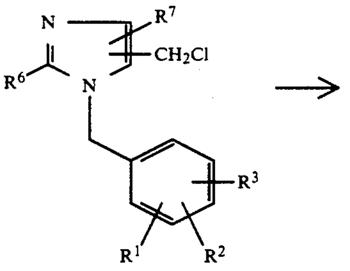

25

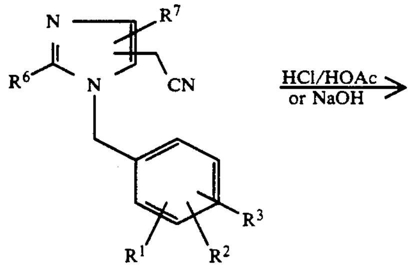

26

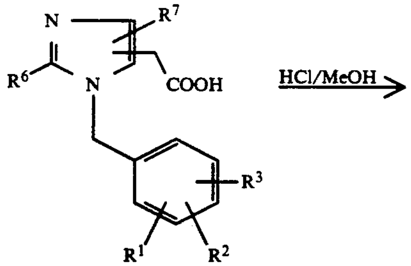

27

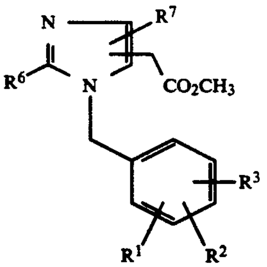

28 b) 17

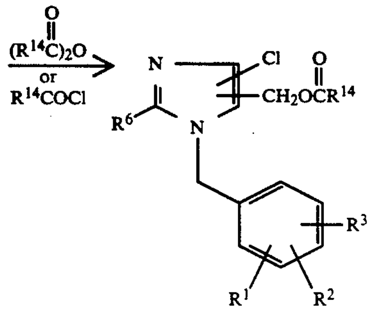

29

-continued

Scheme 3 c)

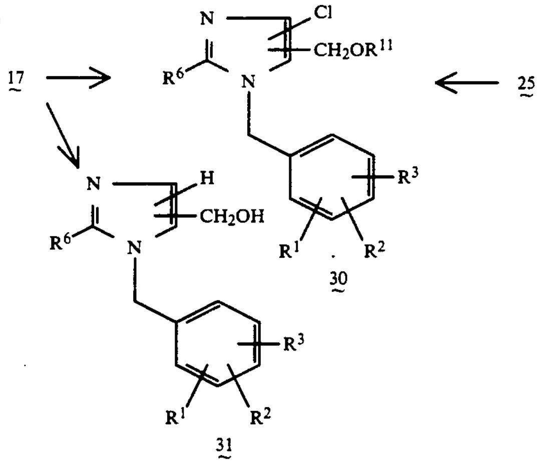

30

31 d)

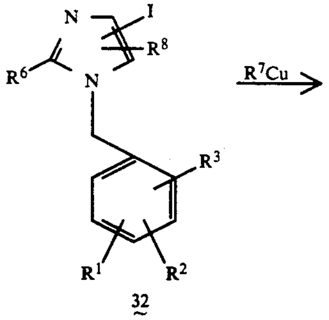

32

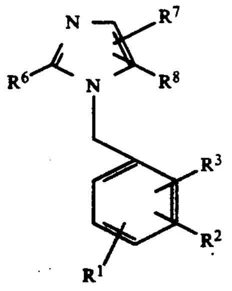

(wherein $R^7 = C_vF_{2v+1}$ or $C_6F_5$ and v = 1-6)

33

As shown in Scheme 3, path a) for benzylimidazoles (17) where $R^7$=Cl and $R^8$=$CH_2OH$, the hydroxymethyl groups may be easily converted to the corresponding halide, mesylate or tosylate by a variety of methods familiar to one skilled in the art. Preferably, the alcohol (17) is converted to the chloride (25) with thionyl chloride in an inert solvent at temperatures of 20° C. to the reflux temperature of the solvent.

Chloride (25) may be displaced by a variety of nucleophiles by nucleophilic displacement reaction procedures familiar to one skilled in the art. For example, excess sodium cyanide in DMSO may be used to form cyanomethyl derivatives (26) at temperatures of 20° C. to 100° C.

Nitrile (26) may be hydrolyzed to an acetic acid derivative (27), by a variety of methods. These methods include methods described previously for the hydrolysis of nitriles of formula (9). Examples of desired acids and bases for this hydroylsis include mineral acids such as sulfuric acid, hydrochloric acid, and mixtures of either of the above with 30–50% acetic acid (when solubility is a problem), and alkali metal hydroxides such as sodium hydroxide or potassium hydroxide. The hydrolysis reaction proceeds under heating at temperatures ranging from 50°-160° C. for 2–48 hours. Carboxylic acid (27) may be esterified by a variety of methods without affecting other parts of the molecule. Preferably, (27) is refluxed in a hydrochloric acid/methanol solution for 2–48 hours to give ester (28).

Ester (28) may be hydrolyzed to carboxylic acid (27), for instance, after $R^1$, $R^2$ and $R^3$ have been elaborated. Various methods, acidic or basic, may be used. For example, compound (28) is stirred with 0.5N potassium hydroxide in methanol, or if base soluble, it is stirred in 1.0N sodium hydroxide for 1–48 h at 20° C. to reflux temperatures.

Hydroxymethyl derivative (17) may be acylated to give (29) by a variety of procedures. As shown in path b) acylation can be achieved with 1-3 equivalents of an acyl halide or an anhydride in a solvent such as diethyl ether, tetrahydrofuran, methylene chloride or the like in the presence of a base such as pyridine or triethylamine. Alternatively (17) may be acylated by reaction with a carboxylic acid and dicyclohexylcarbodiimide (DCC) in the presence of a catalytic amount of 4-(N,N-dimethylamino)pyridine (DMAP) via the procedure described by A. Hassner, *Tet. Lett.*, 46, 4475 (1978). Treatment of (17) with a solution of carboxylic acid anhydride in pyridine optionally with a catalytic amount of DMAP at temperatures of 20°-100° C. for 2–48 hours is the preferred method.

The ether (30) can be prepared from the alcohol (17) as shown in path c) by methods such as treatment of (17) in a solvent such as dimethylformamide or dimethylsulfoxide with potassium t-butoxide, sodium hydride, or the like followed by treatment with $R^{11}L$ at 25° C. for 1–20 hours, where L is a halogen, tosylate or mesylate.

Alternatively, treatment of (17) with 1–5 equivalents of thionyl chloride in chloroform for 2–6 hours at 25° C. followed by treatment of the intermediate (25) with 1–3 equivalents of $MOR^{11}$, where M is sodium or potassium, for 2–10 hours at 25° C. either in $R^{11}OH$ as solvent or in a polar solvent such as dimethylformamide or the like will also yield ether (30).

The ether (30) can also be prepared for example by heating (17) for 3–15 hours at 60°-160° C. in $R^{11}OH$ containing an inorganic acid such as a hydrochloric acid or sulfuric acid.

Compound (17) can be dehalogenated to compound (31) preferably by catalytic hydrogenolysis (over an appropriate catalyst such as 10% palladium on carbon) in methanol at 25° C. for 1–6 hours or by treatment with zinc metal in acetic acid.

As shown in Scheme 3, the perfluoroalkylimidazoles (33, $R^7=C_vF_{2v+1}$) can be prepared from the corresponding iodoimidazoles (32) by treatment with the appropriate perfluoroalkyl copper reagents [*J. Am. Chem. Soc.*, 108, 832 (1986); *J. Fluorine Chem.*, 27, 291 (1985); *J. Fluorine Chem.*, 22, 541 (1983); *Tetrahedron*, 25, 5921; (1969); and references cited therein.] Analogously, the pentafluorophenylimidazoles (33; $R^7=C_6F_5$) can be produced by the treatment of 32 with pentafluorophenyl copper [*Org. Syn.*, 59, 122 (1980) and references cited therein.]

N-arylimidazoles of formula I (compounds wherein r=o) can be prepared by the following methods, it being understood by one skilled in the art that certain manipulations, protecting and deprotecting steps, and other synthetic procedures disclosed above may be necessary to produce compounds with the desired combinations of $R^6$, $R^7$, $R^8$ and $R^{13}$.

As shown in Scheme 4, equation a) the reaction of aniline derivative (34) with imidate ester (12) to form the substituted amidine (35) provides material which can be cyclized with dihydroxyacetone to form structure (36). Subsequent elaboration into (I) provides the N-arylimidazole compounds of the invention.

Alternatively as shown by equation b) the Marckwald procedure, described by Marckwald et. al., *Ber.*, 22, 568, 1353 (1889); *Ber.*, 25, 2354 (1892) can form a 2-mercaptoimidazole (38) from aniline derivative (34) via isothiocyanate (37). Desulfurization of (38) with dilute nitric acid followed by anion formation at the 2-position of the imidazole (39) and reaction with $R^6X$ where X is Cl, Br, I, allows the formation of (40) which can be subsequently elaborated to I.

A variation of Marckwald's process as shown in equation c) using an α-aminoketone (41) and isothiocyanate (37) can also be employed, see Norris and McKee, *J. Amer. Chem. Soc.*, 77, 1056 (1955) can also be employed. Intermediate (42) can be converted to (I) by known sequences. The general procedure of Carboni et al., *J. Amer. Chem. Soc.*, 89, 2626 (1967) (illustrated by equation d)) can also be used to prepare N-aryl substituted imidazoles from appropriate haloaromatic compounds (43; X=F, Cl, Br) and imidazoles (1):

Scheme 4 a)

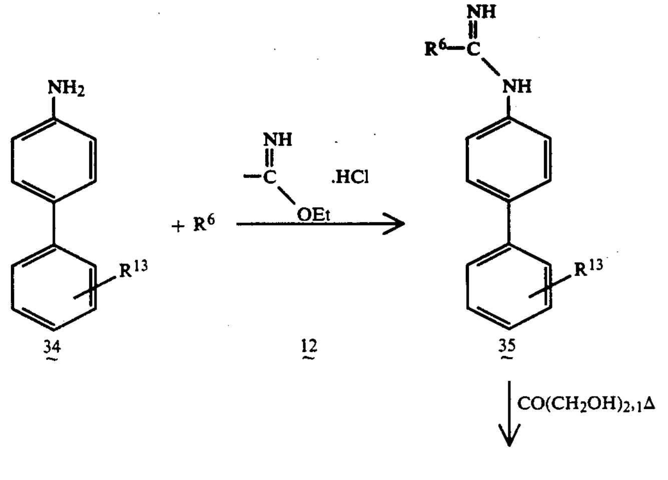

34 12 35

-continued
Scheme 4
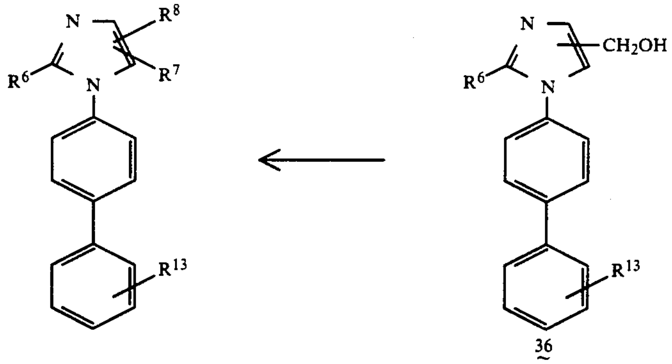
36
I; (wherein $R^1$ = R 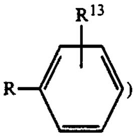 )
$R^2$, $R^3$ = H
b)
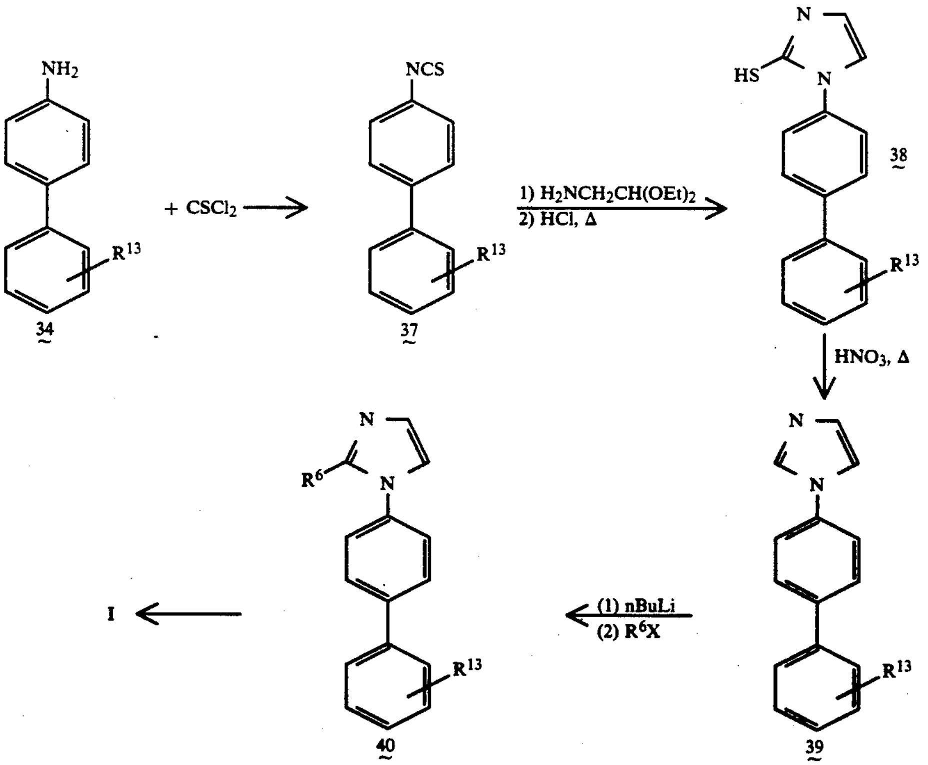
34 37 38 39 40
c) $R^8COCH_2NH_2$ + 37
41
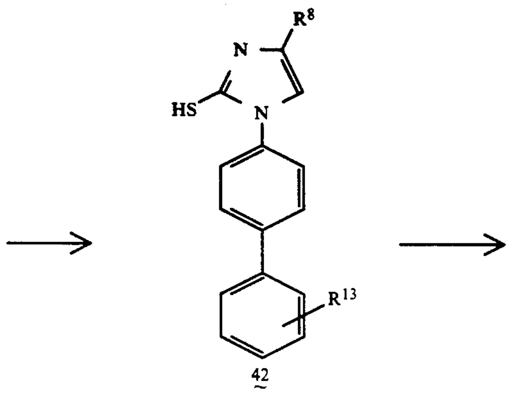
42

-continued

Scheme 4 d)

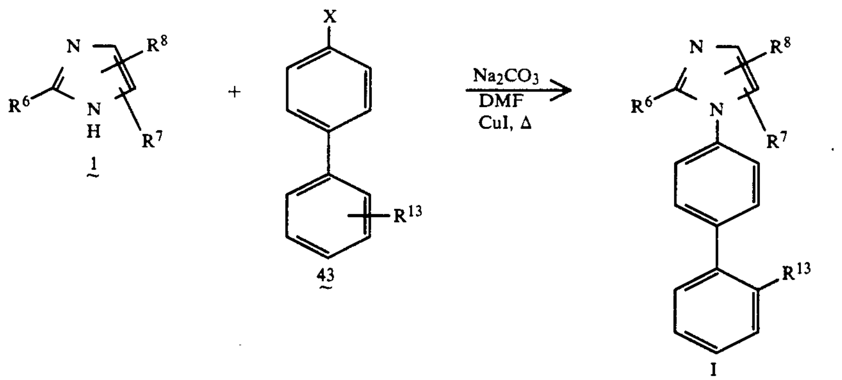

1 43 I

In various synthetic routes $R^1$, $R^2$ and $R^3$ do not necessarily remain the same from the starting compound to the final products, but are often manipulated through known reactions in the intermediate steps as shown in Schemes 5-22. All of the transformations shown in Schemes 5-10 and 12 and also be carried out on the terminal aromatic ring (i.e., biphenyl ring).

Scheme 5

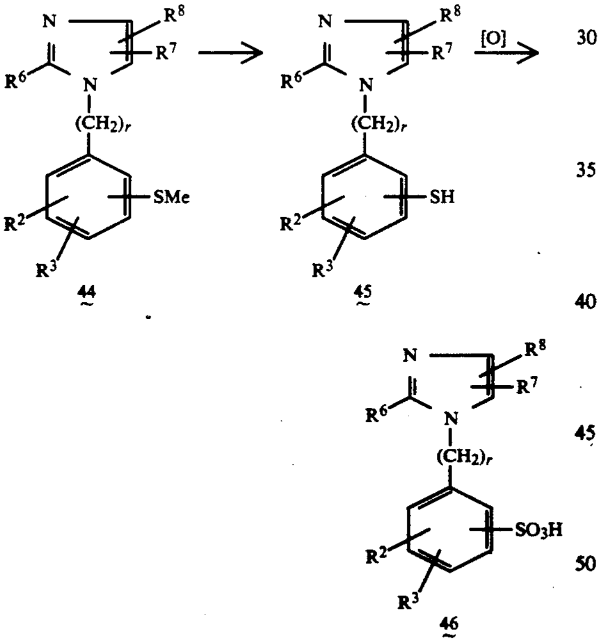

44 45 46

As shown in Scheme 5, compounds where $R^1$ is a sulfonic acid group may be prepared by oxidation of the corresponding thiol (45). Thus, an N-benzylimidazole derivative bearing a thiol group may be converted into a sulfonic acid (46) by the action of hydrogen peroxide, peroxyacids such as metachloroperoxybenzoic acid, potassium permanganate or by a variety of other oxidizing agents, E. E. Reid, *Organic Chemistry of Bivalent Sulfur*, 1, Chemical Publishing Co., New York, 120-121 (1958).

Aromatic hydroxy or thiol groups are obtained from deprotection of the corresponding alkyl ether or thioethers. Thus, for example, a methyl ether or a methyl thioether derivative (44) of an N-benzylimidazole containing one or more aromatic rings may be converted into the free phenol or thiophenol (45) by the action of boron tribromide methyl sulfide, P. G. Willard and C. F. Fryhle, *Tet. Lett.*, 21, 3731 (1980); trimethylsilyl iodide, M. E. Jung and M. A. Lyster, *J. Org. Chem.*, 42, 3761 (1977); KSEt and derivatives thereof, G. I. Feutrill, R. N. Mirrington, *Tet. Lett.*, 1327, (1970), and a variety of other reagents.

Alternatively, N-benzylimidazoles may be sulfonated by stirring with $H_2SO_4$ at a variety of different concentrations or with other sulfonating agents such as chlorosulfonic acid or sulfur trioxide with or without complexing agents such as dioxane or pyridine at temperatures from 0° to 200° C. with or without solvent, K. LeRoi Nelson in *Friedel-Crafts and Related Reactions*, III part 2, G. A. Olah, ed., Interscience Publ., 1355 (1964).

The synthesis of compounds where $R^1$ is a sulfate, phosphate or phosphonic acid are depicted in Scheme 6:

Scheme 6 a)

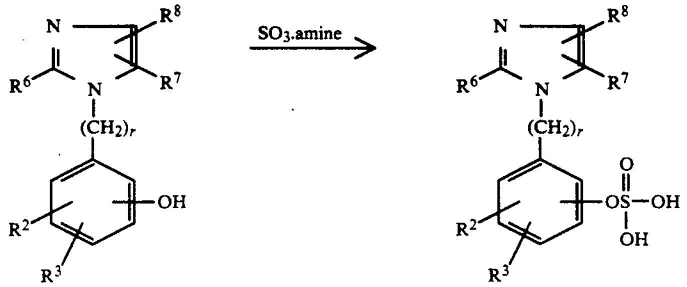

47 48

-continued
Scheme 6
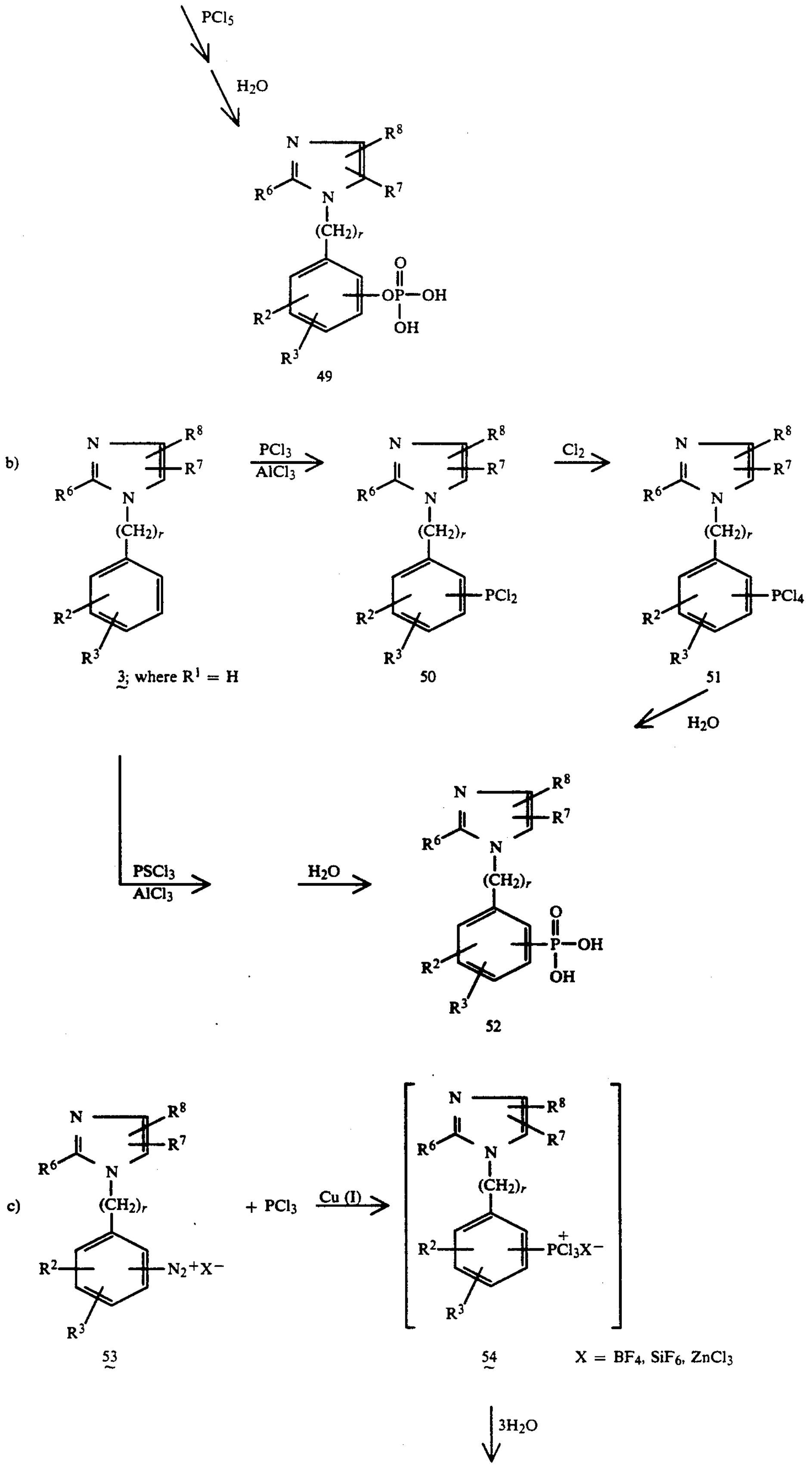
49
3; where $R^1$ = H
50
51
52
53
54
X = $BF_4$, $SiF_6$, $ZnCl_3$ -continued Scheme 6

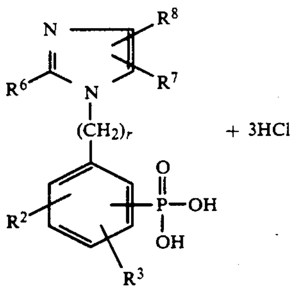

52

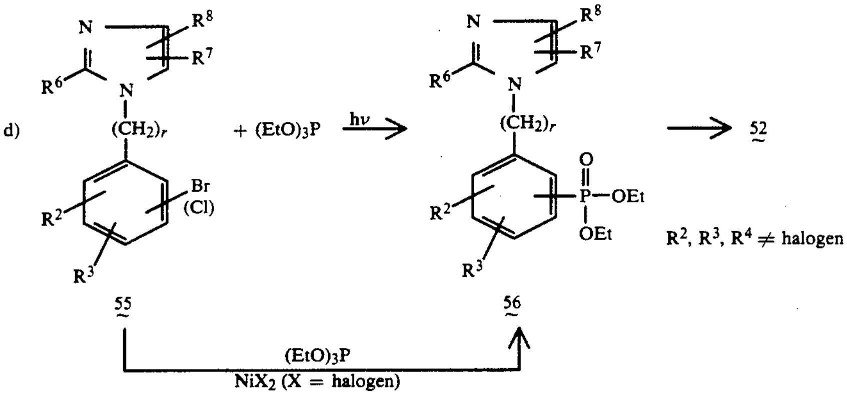

55 56 52

N-Benzylimidazoles containing a phenolic hydroxyl group (47) may be readily converted into the corresponding sulfate (48) or phosphate (49). As shown in equation a), reaction of the phenol with a sulfur trioxide-amine complex will give the corresponding sulfate (48), E. E. Gilbert, *Sulfonation and Related Reactions*, Interscience, New York, chapter 6 (1965). Reaction of the phenol (47) with phosphorus pentachloride followed by hydrolysis will give the corresponding phosphate (49), G. M. Kosolapoff, *Organophosphorus Compounds*, John Wiley, New York, 235 (1950).

As shown in equation b) N-benzylimidazoles may be converted into the corresponding phosphonic acids by reaction with phosphorus trichloride ($PCl_3$) and aluminum chloride ($AlCl_3$) in an inert solvent for 0.5-96 hours from temperatures of 25° C. to the reflux temperatures of the solvent. Appropriate workup followed by reaction with chlorine ($Cl_2$) and subsequent hydrolysis of the tetrachloride (51) gives the phosphonic acid derivative (52), G. M. Kosolapoff in *Org. Reactions*, 6, R. Adams, editor, John Wiley and Sons, New York, 297 (1951). Another more direct route involves reaction of the N-benzylimidazole with $PSCl_3$ and $AlCl_3$ followed by hydrolysis, R. S. Edmunson in *Comprehensive Organic Chemistry*, Vol. 2, D. Barton and W. D. Ollis editors, Pergamon Press, New York, 1285 (1979).

Alternatively, equation c) illustrates that aryl phosphonic acids (52) may be formed from reaction of the corresponding diazonium salt (53) with $PCl_3$ in the presence of Cu(I) followed by hydrolysis with water (ibid, p. 1286).

As shown in equation d), the aryl halides (55) may be photolyzed in the presence of phosphite esters to give phosphonate esters (56), R. Kluger, J. L. W. Chan, *J. Am. Chem. Soc.*, 95, 2362, (1973). These same aryl halides also react with phosphite esters in the presence of nickel or palladium salts to give phosphonate esters, P. Tavs, *Chem. Ber.*, 103, 2428 (1970), which can be subsequently converted to phosphonic acids (52) by procedures known to one skilled in the art.

N-Benzylimidazoles containing an aldehyde or ketone (57) may be reacted with a phosphorus trihalide followed by water hydrolysis to give α-hydroxyphosphonic acid derivatives, G. M. Kosolapoff, op. cit., 304, as shown in Scheme 7.

Scheme 7

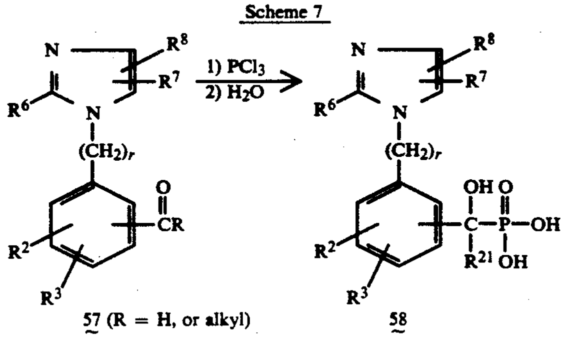

57 (R = H, or alkyl) 58

Compounds where $R^1$ is —CONHOR$^{12}$ may be prepared as shown in Scheme 8, by the treatment of a carboxylic acid (10) with 1-4 equivalents of thionyl chloride for 1-10 hours. This reaction can be run without solvent or in a nonreactive solvent such as benzene or chloroform at temperatures of 25°-65° C. The intermediate acid chloride is then treated with 2-10 equivalents of the appropriate amine derivative, $H_2N—OR^{12}$, for 2-18 hours at temperatures of 25°-80° C. in a polar aprotic solvent such as tetrahydrofuran or dimethylsulfoxide to give the hydroxamic acid (59).

Scheme 8

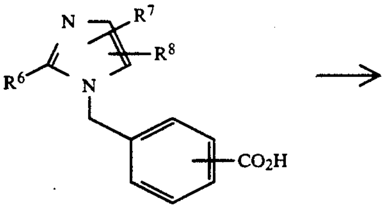

10

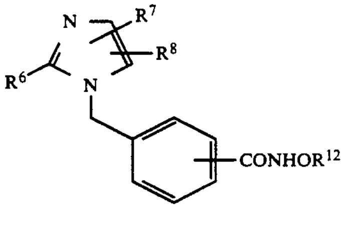

59

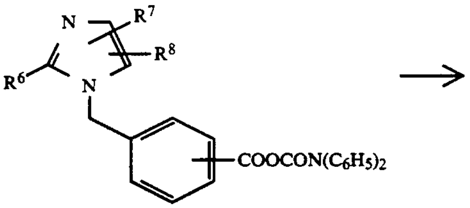

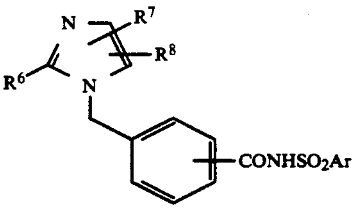

59a

Alternatively, the carboxylic acid (10) can be converted to the hydroxamic acid (59) according to the procedure in *J. Med. Chem.*, 28, 1158 (1985) by employing dicyclohexylcarbodiimide, 1-hydroxybenzotriazole, and $H_2NOR^{12}$ or according to the procedure described in *Synthesis*, 929 (1985) employing the Vilsmeier reagent and $H_2NOR^{12}$.

Compounds where $R^1$ is $-CONHSO_2Ar$ (59a, Ar= phenyl, o-tolyl, etc.) may be produced by treatment of the intermediate acid chlorides from the preparation of the hydroxamic acids (59), with $ArSO_2NHNa$. Alternatively, these acylsulfonamides (59a) can be prepared from the carboxylic acids (10) through the corresponding N,N-diphenylcarbamoyl anhydrides (10a) as described by F. J. Brown, et al. in Eur. Pat. Appl. EP 199543 (see Scheme 8).

Scheme 9

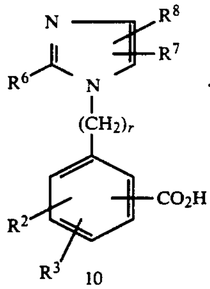

10

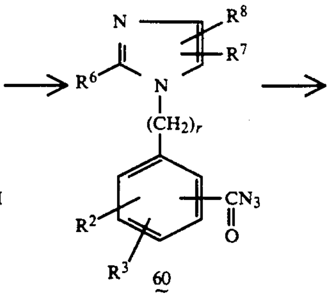

60

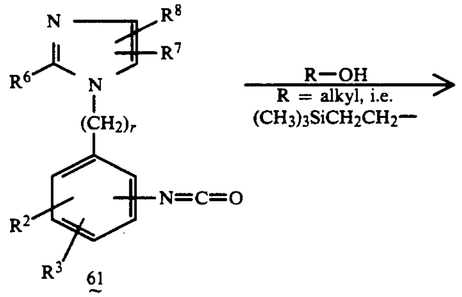

61

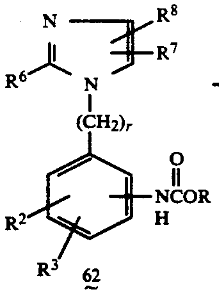

62

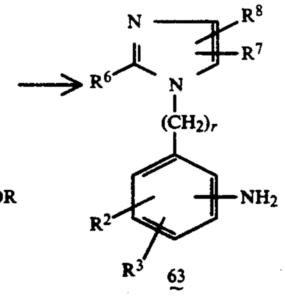

63

Aniline intermediates (63) are disclosed in U.S. Pat. No. 4,355,040 and may be obtained from the corresponding nitro compound precursor by reduction. A variety of reduction procedures may be used such as iron/acetic acid, D. C. Owsley, J. J. Bloomfield, *Synthesis*, 118, (1977), stannous chloride, F. D. Bellamy, *Tet. Lett.*, 839, (1984) or careful hydrogenation over a metal catalyst such as palladium.

As shown in Scheme 9, aniline intermediates of N-benzylimidazoles may also be prepared from the corresponding carboxylic acid (10) or acid chloride via a Curtius rearrangement of an intermediate acyl azide (60). More modern methods include using diphenylphosphoryl azide as a source of azide, T. Shioiri, K. Ninomiya, S. Yamada, *J. Am. Chem. Soc.*, 94, 6203 (1972), and trapping the intermediate isocyanate (61) produced by the Curtius rearrangement with 2-trimethylsilylethanol and cleaving the resultant carbamate (62) with fluoride to liberate the amine (63), T. L. Capson and C. D. Poulter, *Tet. Lett.*, 25, 3515 (1984). Classical procedures familiar to one skilled in the art may also be employed.

Compounds where $R^1$ is $-SO_2NH_2$ may be made as shown in Scheme 10:

Scheme 10

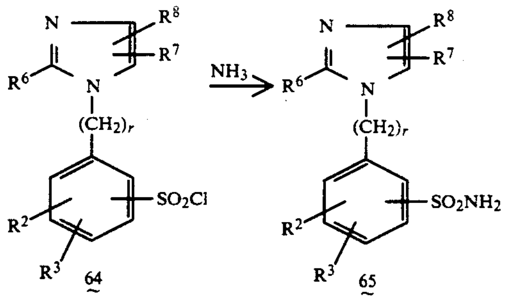

64 65

Sulfonamide compounds (65) may be made by reacting an arylsulfonyl chloride (64) with ammonia, or its equivalent. Unsubstituted arylsulfonamides are made by reaction with ammonia in aqueous solution or in an inert organic solvent, F. H. Bergheim and W. Braker, *J. Am. Chem. Soc.*, 66, 1459 (1944), or with dry powdered ammonium carbonate, E. H. Huntress and J. S. Autenrieth, *J. Am. Chem. Soc.*, 63, 3446 (1941); E. H. Huntress and F. H. Carten, *J. Am. Chem. Soc.*, 62, 511 (1940).

The sulfonyl chloride precursor may be prepared by chlorosulfonation with chlorosulfonic acid on the aromatic ring directly, E. H. Huntress and F. H. Carten, ibid.; E. E. Gilbert, op. cit., 84, or by reacting the corresponding aromatic diazonium chloride salt (53) with sulfur dioxide in the presence of a copper catalyst, H. Meerwein, et al., *J. Prakt. Chem.*, [ii], 152, 251 (1939), or by reacting the aromatic sulfonic acid (46) with $PCl_5$ or $POCl_3$, C. M. Suter, *The Organic Chemistry of Sulfur*, John Wiley, 459 (1948).

Linked ester compounds of formula (I) where $R^1$ is $$-CO_2CH(R^{24})O\overset{O}{\overset{\|}{C}}R^{21}$$

can be made by procedures well known in penicillin and cephalosporin chemistry. The purpose is to provide materials which are more lipophilic and which will be useful orally by rapid transit from the gut into the bloodstream, and which will then cleave at a sufficiently rapid rate to provide therapeutically useful concentrations of the active carboxylic acid form. The following review articles and references cited therein discuss this concept and the chemistry involved in preparing such compounds V. J. Stella, et al., *Drugs*, 29, 455–473 (1985); H. Ferres, *Drugs of Today*, 19 (9), 499–538 (1983); A. A. Sirkula, *Ann. Repts. Med. Chem.*, 10, 306–315 (1975).

Experimental procedures which are applicable to the preparation of chemically stable linked esters are illustrated by equations a-e of Scheme 11.

Scheme 11

$$\underset{10}{RCO_2Na} + (CH_3)_3CCO_2CH_2Br \longrightarrow \underset{66}{RCO_2CH_2OCOC(CH_3)_3} \quad (a)$$

G. Francheschi et al., J. Antibiotics, 36, (7), 938–941 (1983).

-continued

Scheme 11

(b)

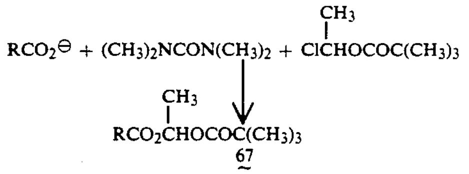

67

J. Budavin, U.S. Pat. No. 4,440,942

(c)

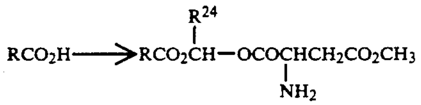

68

B. Daehne et al., G.B. Patent 1,290,787

(d)

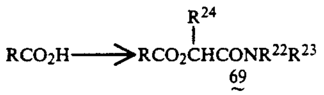

69

Ferres, Chem. Ind., 435–440 (1980)

(e)

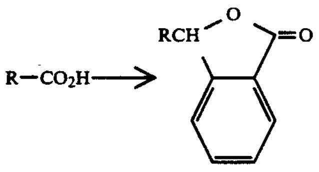

70

Clayton et al., Antimicrob. Agents Chemotherapy, 5, (6), 670–671 (1974)

In equations a-e: R =

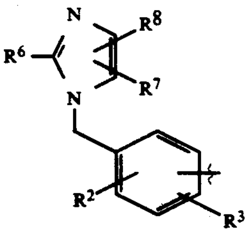

Compounds of Formula I where $R^1$ is $-C(CF_3)_2OH$ may be prepared as shown in Scheme 12.

Scheme 12

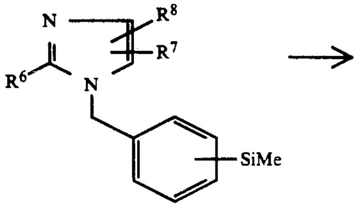

71

-continued

Scheme 12

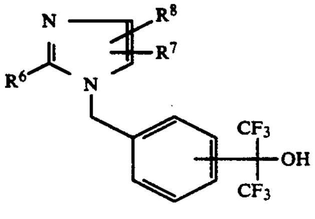

72

Hexafluoroisopropanol compounds (72) may be prepared by treatment of arylsilane (71) with 1-5 equivalents of hexafluoroacetone in a solvent such as methylene chloride at temperatures ranging from about −50° to 25° C. for a period of 2-10 hours. The requisite arylsilane (71) can be prepared using methods known to one skilled in the art such as the procedures described in Chapter 10 of Butterworth's "Silicon in Organic Chemistry".

Scheme 13

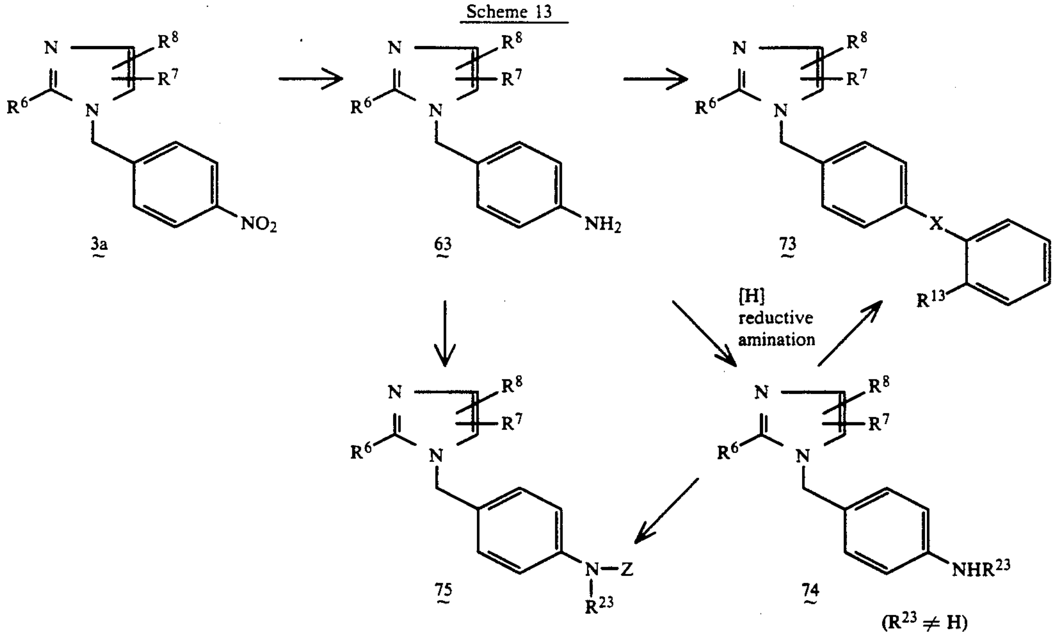

3a 63 73 75 74

($R^{23} \neq H$)

76 Z = 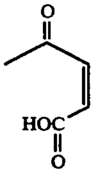

77 Z = 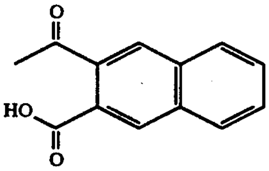

78 Z = 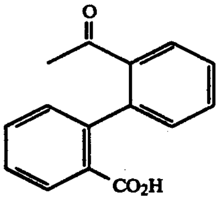

As shown in Scheme 13, compound (73) in which X=—NHCO and $R^{13}$=—COOH may be easily prepared, for example, by reacting aniline precursor (63) with a phthalic anhydride derivative in an appropriate solvent such as benzene, chloroform, ethyl acetate, etc. Often the carboxylic acid product will precipitate from solution with the reactants remaining behind, M. L. Sherrill, F. L. Schaeffer, E. P. Shoyer, *J. Am. Chem. Soc.*, 50, 474 (1928).

When $R^{13}$=$NHSO_2CH_3$, $NHSO_2CF_3$ or tetrazolyl (or a variety of other carboxylic acid equivalents), compound (73) may be obtained by reacting aniline (63) with the requisite acid chloride by either a Schotten-Baumann procedure, or simply stirring in a solvent such as methylene chloride in the presence of a base such as sodium bicarbonate, pyridine, or triethylamine.

Likewise, aniline (63) may be coupled with an appropriate carboxylic acid via a variety of amide or peptide bond forming reactions such as DCC coupling, azide coupling, mixed anhydride synthesis, or any other coupling procedure familiar to one skilled in the art.

Aniline derivatives (63) will undergo reductive amination with aldehydes and ketones to form secondary amines (74). Thus the aniline is first stirred with the carbonyl compound in the presence of a dehydration catalyst such as molecular sieves or p-toluenesulfonic acid. Afterwards the resultant imine is reduced to the amine with a borohydride reducing agent such as sodium cyanoborohydride or sodium borohydride. Standard catalytic hydrogenation reagents such as hydrogen and palladium/carbon can also be employed.

Alternatively, aniline (63) may be monoalkylated by reaction with ethyl formate followed by reduction with, for example, lithium aluminum hydride to produce the N-methyl derivative (74). Anilines (74) may in turn be reacted with carboxylic acid anhydrides and acid chlorides or carboxylic acids by any of the coupling procedures described previously to yield (73) where $X = —N(CH_3)CD—$.

Aniline (63) or (74) or other intermediate anilines where the amino group may be located on another aromatic ring for example, also react with other anhydrides to make amide-carboxylic acid derivatives of formula (75). Thus, for example, maleic anhydride, 2,3-naphthalenedicarboxylic acid anhydride, and diphenic anhydride are reacted in a similar fashion to phthalic anhydride with aniline (63) or (74) to yield carboxylic acids (76), (77), and (78), respectively.

Phthalimide derivatives of aniline (63) may be made by a variety of methods, preferably by stirring aniline (63) with phthalic anhydride in acetic acid at a temperature between 20° C. and reflux, G. Wanag, A. Veinbergs, *Ber.*, 75, 1558 (1942), or by stirring (63) with phthaloyl chloride, a base such as triethylamine, and an inert solvent.

Aniline (63) may be converted into its trifluoromethanesulfonamide derivative or its trifluoroacetamido derivative preferably by reacting it with triflic anhydride or trifluoroacetic anhydride and a base such as triethylamine in an inert solvent such as methylene chloride at −78° C. followed by warming to room temperature.

Compounds of structure (I) where X is a carbon-carbon linkage which are depicted as (80) can be made as shown in Scheme 14.

Scheme 14

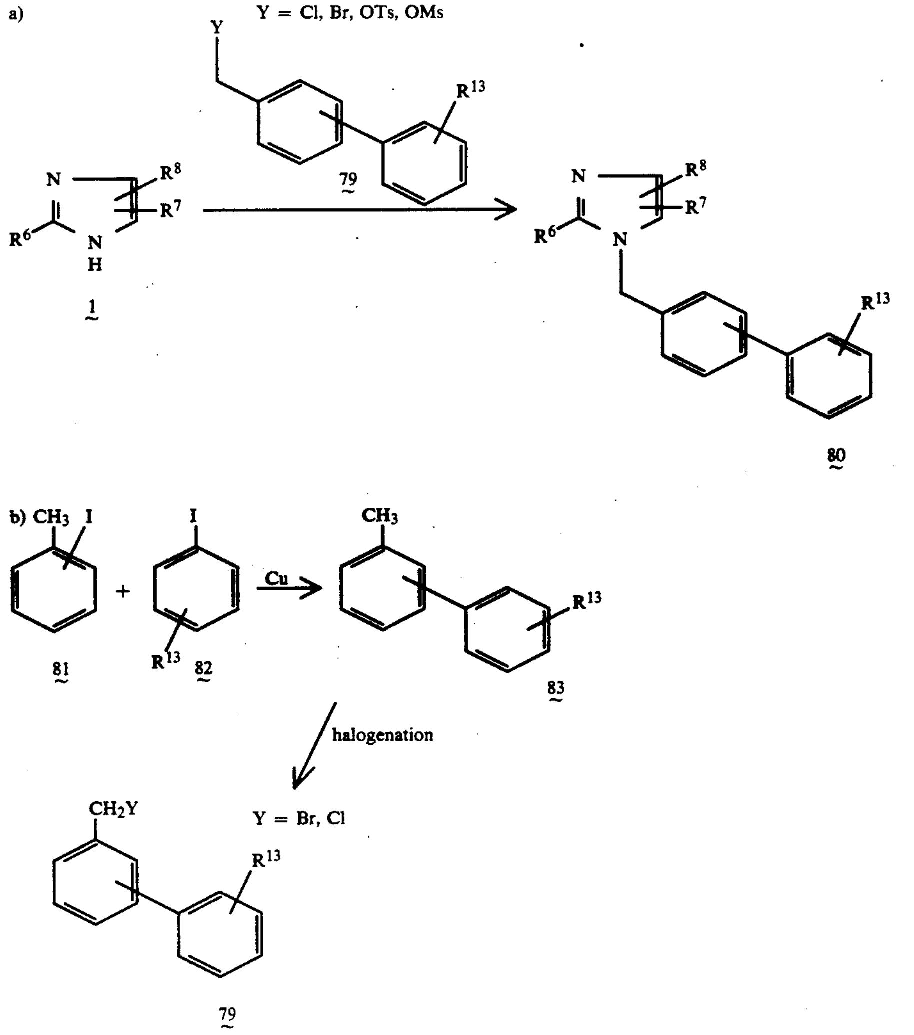

1
79
80
81
82
83
79

-continued
Scheme 14
c)
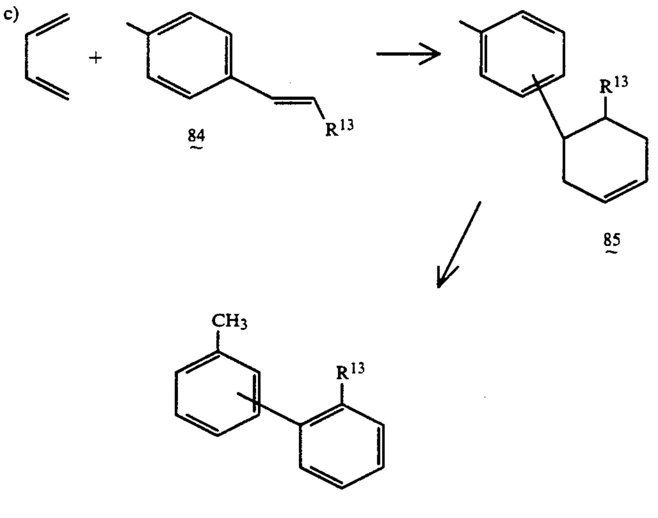
84 85 83a
d)
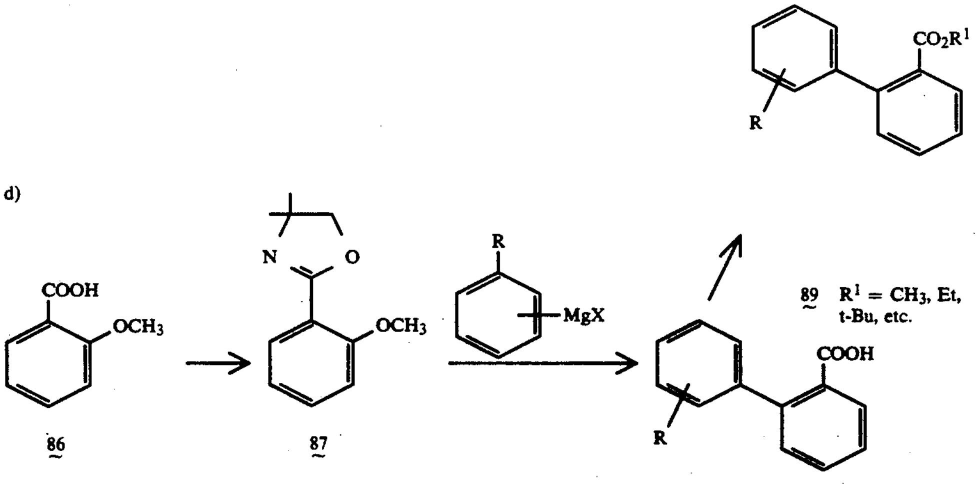
86 87 88
e)
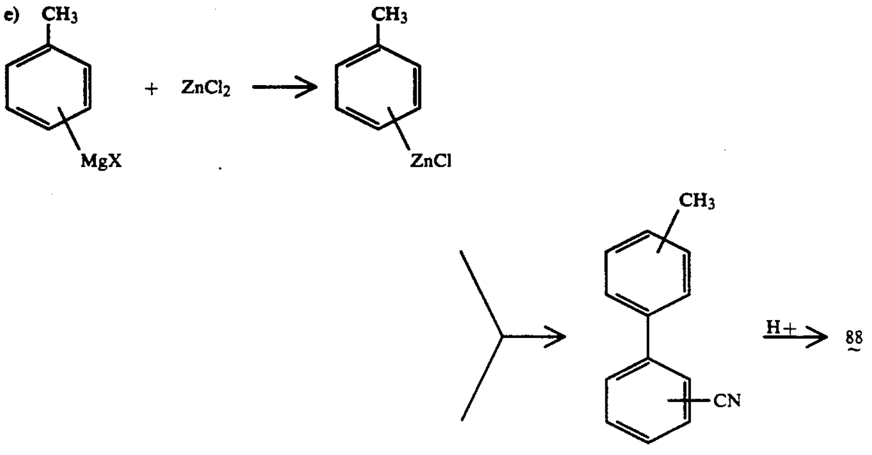

-continued

Scheme 14

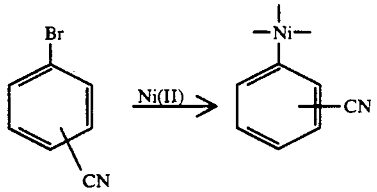

Equation a) illustrates that the biphenyl compounds (80) can be prepared by alkylation of imidazole (1) with the appropriate halomethylbiphenyl compound (79) by the general procedure described in Scheme 1.

The requisite halomethylbiphenyl intermediates (79) are prepared by Ullman Coupling of (81) and (82) as described in "Organic Reactions", 2, 6 (1944) to provide intermediates (83), which are in turn halogenated. Halogenation can be accomplished by refluxing (83) in an inert solvent such as carbon tetrachloride for 1-6 hours in the presence of a N-halosuccinimide and an initiator such as azobisisobutyronitrile (equation b).

As shown in equation c), derivatives of intermediate (83) in which $R^{13}$ is at the 2' position (83a) can also be prepared by the method described in *J. Org. Chem.*, 41, 1320 (1976), that is Diels-Alder addition of a 1,3-butadiene to a styrene (84) followed by aromatization of intermediate (85).

Alternatively, the substituted biphenyl precursors (83; where $R^{13}$=COOH) and their esters (89) can be prepared as illustrated in equation d), which involves oxazoline compounds as key intermediates, A. I. Meyers and E. D. Mihelich, *J. Am. Chem. Soc.*, 97, 7383 (1975).

Further, as shown in Equation e), nickel-catalyzed cross-coupling of an arylzinc halide with a halobenzonitrile yields a biphenylnitrile which can in turn be hydrolyzed by standard methods to afford acid 88.

The substituted biphenyl tetrazoles (83; where

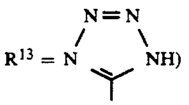

can be prepared from the nitrile precursors ($R^{13}$=CN) by the methods described in Scheme 1, equation c) and Scheme 15, equation c).

However, a preferred method for preparing tetrazoles is described in Scheme 15, equations a) and b). Compounds (90) may be prepared by the 1,3-dipolar cycloaddition of trialkyltin or triphenyltin azides to the appropriately substituted nitrile (83) as in equation a). Alkyl is defined as normal alkyl of 1-6 carbon atoms and cyclohexyl. An example of this technique is described by S. Kozima, et al., *J. Organometallic Chemistry*, 337 (1971). The required trialkyl or triaryltin azides are made from the requisite commercial trialkyl or triaryl tin chloride and sodium azide. The trialkyl or triaryltin group is removed via acidic or basic hydrolysis and the tetrazole can be protected with the trityl group by reaction with trityl chloride and triethylamine to give (91). Bromination as previously described herein with N-bromosuccinimide and dibenzoylperoxide affords compound (92). Alkylation of (1) with the appropriately substituted benzyl halide using conditions previously described followed by deprotection of the trityl group via hydrolysis affords (80; $R^{13}$=tetrazole). Other protecting groups such as p-nitrobenzyl and 1-ethoxyethyl can be used instead of the trityl group to protect the tetrazole moiety. These groups as well as the trityl group can be introduced and removed by procedures described in Greene, *Protective Groups in Organic Synthesis*, Wiley-Interscience, (1980).

Scheme 15

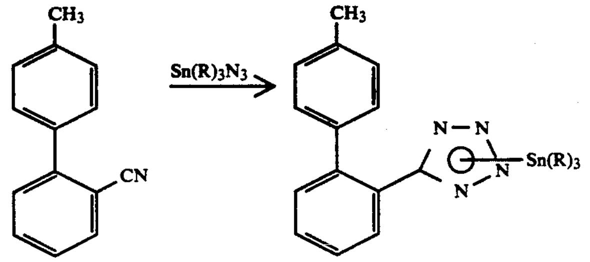

83 ($R^{13}$ = CN)

90 R = alkyl of 1 to 6 carbon atoms, phenyl

1) H+

2) (PH)3CCl, TEA

-continued
Scheme 15
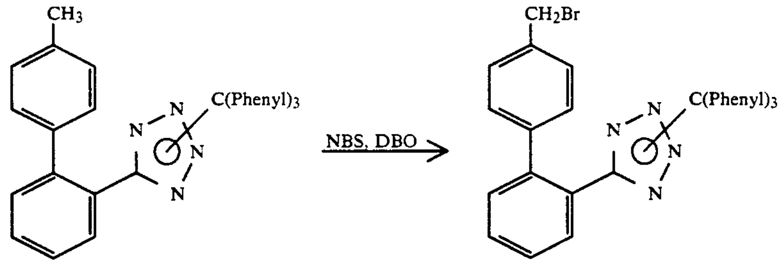
91 92
b)
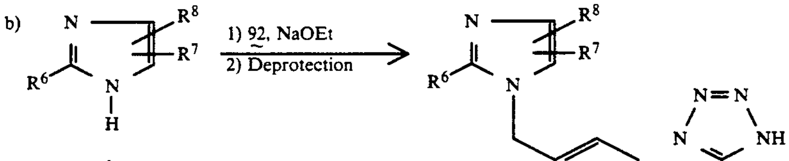
1
80 ($R^{13}$ = tetrazole)
c)
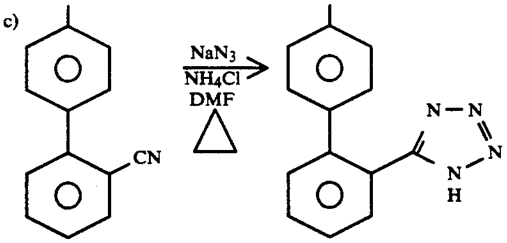
83 83a
Compounds of structure 93-95 where X is an —O—, —S—, or
 linkage
can be prepared as shown in Scheme 16 by alkylation of imidazole (1) with the appropriate benzyl halide (96).
Scheme 16
a)
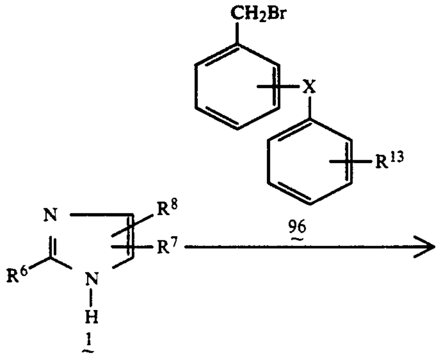
96
1
-continued
Scheme 16
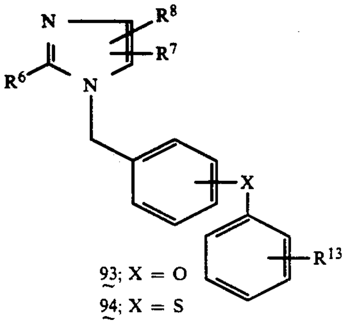
93; X = O
94; X = S
95; X = $NR^{26}$ -continued Scheme 16

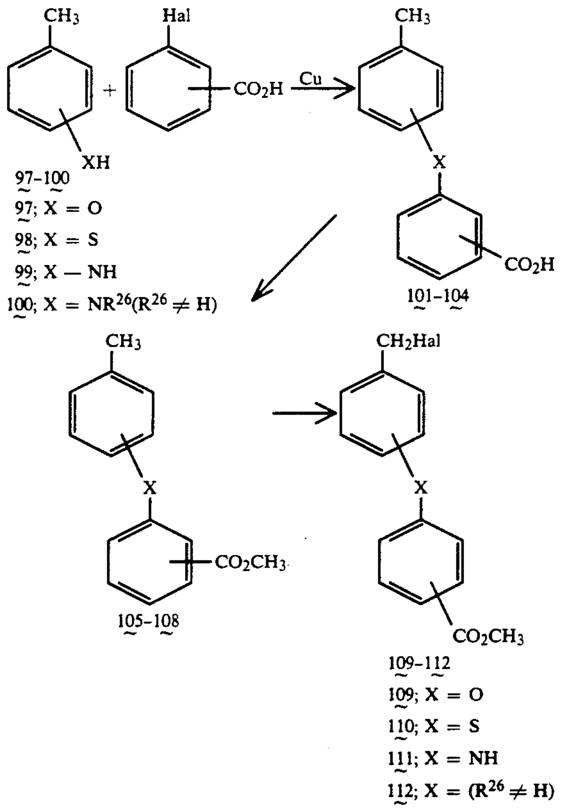

97-100
97; X = O
98; X = S
99; X — NH
100; X = $NR^{26}(R^{26} \neq H)$
101-104
105-108
109-112
109; X = O
110; X = S
111; X = NH
112; X = $(R^{26} \neq H)$ The halomethyldiphenyl ether (109) employed as an alkylating agent in the present invention is prepared as shown in equation b). An Ullman ether condensation of the phenol (97) and a halobenzoic acid as described in *Russian Chemical Reviews*, 43, 679 (1974) provides the intermediate acid (101). The conversion of (101) into (109) is accomplished by esterification with diazomethane to afford (105) followed by halogenation employing the procedure used in the preparation of (79). The diphenylsulfide (110) and the diphenylamine (111) can be prepared from the appropriate thiophenol (98) or aniline (99) by this procedure.

The tertiary diphenylamine (112) can be prepared from the secondary aniline (100) by the above procedure. Alternatively (107) can be alkylated by one of the following procedures: 1) direct alkylation of (107) with $R^{26}L$ where L is a leaving group such as a halogen or tosylate employing phase-transfer conditions and ultrasound as described in *Tetrahedron Letters*, 24, 5907 (1983), 2) treatment of (107) with 1-1.5 equivalents of an appropriate aldehyde and 0.5-5.0 equivalents of sodium cyanoborohydride in a solvent such as methanol at 25° C. at a pH of 3-6 for 1-24 hours, or 3) reductive amination of (107) employing an appropriate carboxylic acid and sodium borohydride as described in *J. Am. Chem. Soc.*, 96, 7812 (1974). The tertiary amine (108) is then halogenated by the procedure previously described to give (112).

Scheme 17

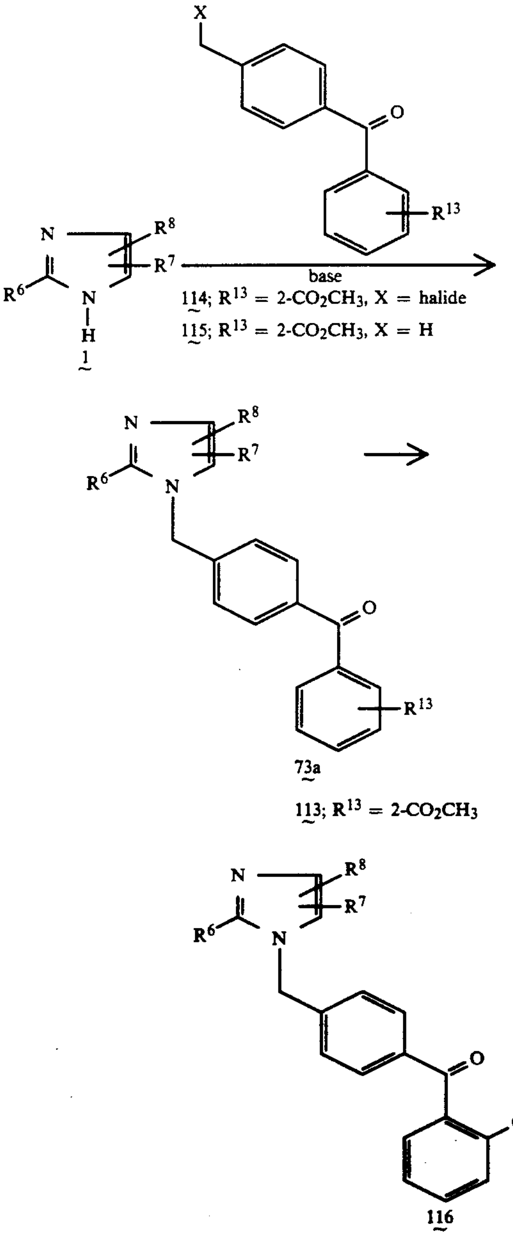

1
114; $R^{13}$ = 2-$CO_2CH_3$, X = halide
115; $R^{13}$ = 2-$CO_2CH_3$, X = H
73a
113; $R^{13}$ = 2-$CO_2CH_3$
116

Compounds of structure (73) where X is —CO— are prepared as shown in Scheme 17 by alkylation of imidazole (1) with the requisite benzoylbenzyl halides. For example, esters (113) where $R^{13}$ is 2—$CO_2CH_3$ are prepared by alkylation of imidazole (1) with carbomethoxybenzoyl benzyl halide (114). Ester (113) may be hydrolyzed to the corresponding carboxylic acid (116) by a variety of methods including hydrolysis with a base such as sodium hydroxide or potassium hydroxide in an alcoholic aqueous solvent such as methanol/$H_2O$ at a temperature from 20° C. to the reflux temperature of the solvent.

Carboalkoxybenzoylbenzyl halides (114) are prepared by benzylic halogenation of the corresponding toluoylbenzene precursor by a variety of methods previously described herein. For example, methyl 2-(4-methylbenzoyl)benzoate (115) can be refluxed for 2-48 hours with N-bromosuccinimide, benzoyl peroxide and carbon tetrachloride to effect benzylic bromination.
As shown in Scheme 18 the toluoyl ketones (73; where X=CO) may be further transformed into a vari-
Scheme 18
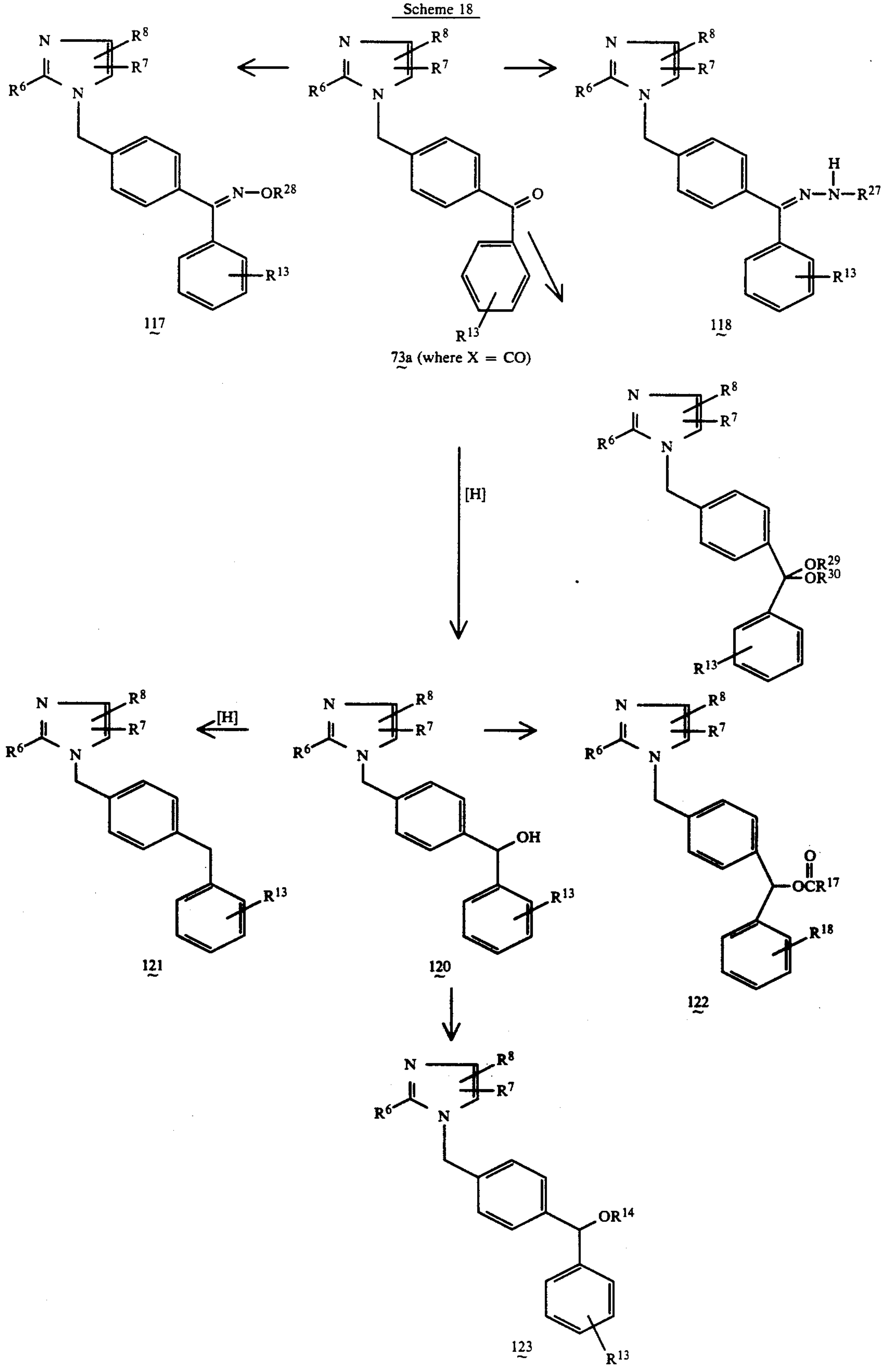
117
73a (where X = CO)
118
121
120
122
123 ety of ketone derivatives including compounds where X is

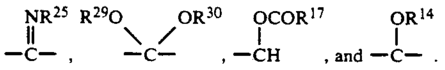

Reaction of ketone (73a) with a hydroxylamine or an appropriately substituted hydrazine will give the requisite oximes (117) and hydrazones (118). Reaction with alcohols in the presence of an acidic catalyst with removal of water will give ketals (119). Reduction, with lithium aluminum hydride, a metal borohydride, zinc/acetic acid or catalytic hydrogenation will give the corresponding alcohol (120) or fully reduced methylene compound (121). These alcohols may be acylated by a variety of anhydrides or acid halides in the presence of a base with or without solvent to give the corresponding esters (122). The alcohols (120) may be converted into their corresponding ethers (123) by reaction of the metal alkoxide with an alkyl halide, mesylate or tosylate in the appropriate solvent or by treatment with a mineral acid in an alcoholic solvent, or by reaction of the alcohol with diazomethane as described in G. Hilgetag and A. Martini, "Preparative Organic Chemistry", John Wiley, New York, 355-368 (1972).

Compounds of formula (I) where X is $-OCH_2-$, $-SCH_2-$, and $-NHCH_2-$ are prepared as shown in Scheme 19.

Scheme 19 a)

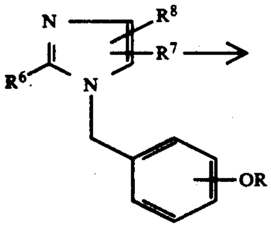

124; R = $CH_2Ph$
125; R = $CH_3$

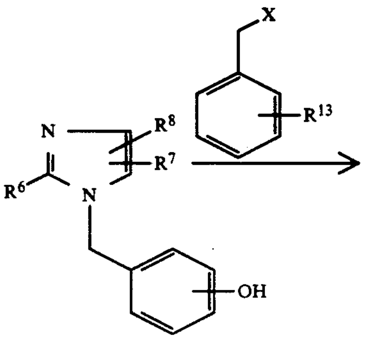

126

-continued

Scheme 19

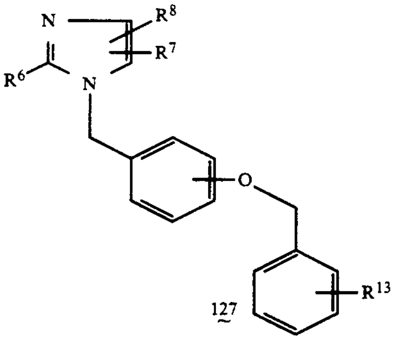

127 b)

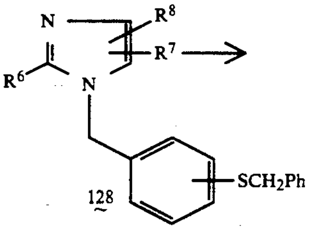

128

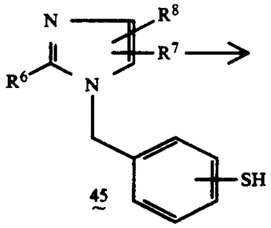

45

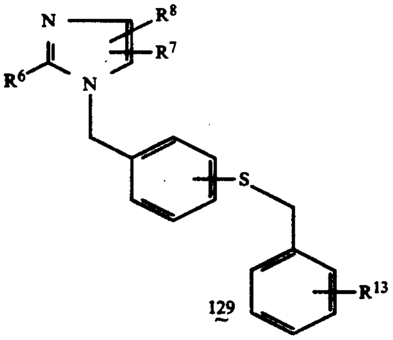

129 c)

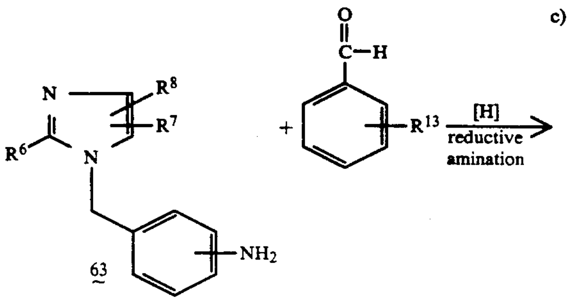

63

-continued

Scheme 19

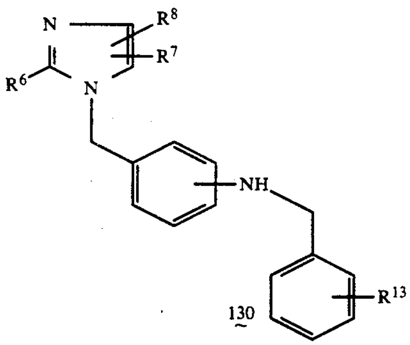

130

As illustrated in Scheme 19, equation a, hydrolysis of benzyl ether (124) or methyl ether (125) affords hydroxy compound (126) which can be alkylated with the appropriate benzyl halide to give (127). In the case of the methyl ethers (125), the hydrolysis step can be effected by heating the ether at temperatures of 50°-150° C. for 1-10 hours in 20-60% hydrobromic acid, or heating at 50°-90° C. in acetonitrile with 1-5 equivalents of trimethylsilyl iodide for 10-50 hours followed by treatment with water. Hydrolysis can also be carried out by treatment with 1-2 equivalents of boron tribromide in methylene chloride at 10°-30° C. for 1-10 hours followed by treatment with water, or by treatment with an acid such as aluminum chloride and 3-30 equivalents of a sulfur-containing compound such as thiophenol, ethanedithiol, or dimethyl disulfide in methylene chloride at 0°-30° C. for 1-20 hours followed by treatment with water. For compound (124), hydrolysis can be accomplished by refluxing in trifluoroacetic acid for 0.2-1 hours or by catalytic hydrogenolysis in the presence of a suitable catalyst such as 10% palladium on carbon. Deprotonation of (126) with a base, such as sodium methoxide, sodium hydride or the like in a solvent such as dimethylformamide or dimethylsulfoxide at room temperature followed by alkylation with an appropriate benzyl halide at 25° C. for 2-20 hours affords ethers of formula (127), as shown in equation a.

The sulfide (129) can be prepared from the thiophenol (45) by the procedure described above to prepare the ether (127) from the phenol (126). The thiophenol (45) can be prepared for example by treatment of the benzylsulfide (128) with sodium in liquid ammonia.

The amine (130) can be prepared as shown in equation c, from the aniline (63), itself available from reduction of the corresponding p-nitro compound (3a) which has previously been described. The reductive amination can be carried out by the same procedure as described in Scheme 13 for the preparation of compound (74).

Compounds of Formula (I) where the X linkage is —CH=CH—, —$CH_2CH_2$—, and

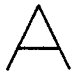

are prepared as shown in Scheme 20.

Scheme 20

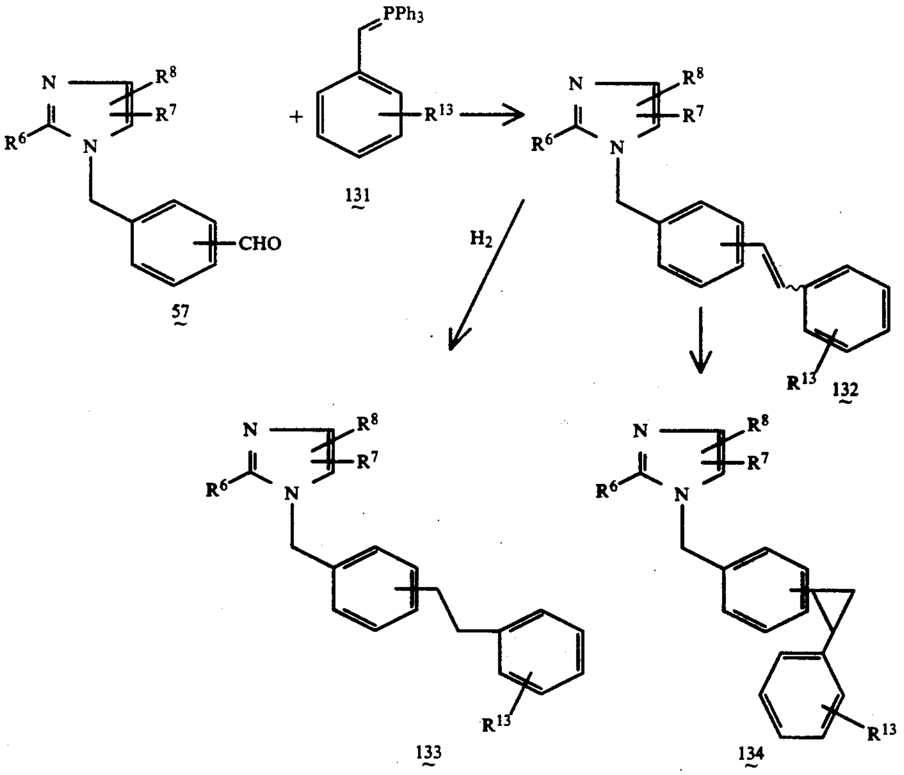

131 57 132 133 134

The cis or trans stilbene (132) can be obtained by employing a Wittig reaction between the aldehyde (57) and the phosphorane (131).

The stilbene (132) can readily be converted to the saturated derivative (133) for example by catalytic hydrogenation employing a heterogeneous catalyst such as palladium/carbon or platinum/carbon or alternatively with a homogeneous catalyst such as tristriphenylphosphine rhodium chloride. The reduction is performed in a solvent such as benzene, tetrahydrofuran or ethanol at 25° C. under 1-3 atmospheres of hydrogen for 1-24 hours.

The cyclopropane (134) can be prepared by treating the stilbene (132) with the Simmons-Smith reagent as described in *J. Am. Chem. Soc.*, 81, 4256 (1959), or by treating (132) with methylene diiodide and copper powder as described in *J. Am. Chem. Soc.*, 101, 2139 (1979), or by treatment with the iron-containing methylene-transfer reagent described in *J. Am. Chem. Soc.*, 101, 6473 (1979).

The preparation of compounds of formula (I) where X is $-CF_2CH_2-$, $-CF{=}CH-$, $-CH{=}CF-$, $-CF{=}CF-$ and $-CF_2CF_2-$ are depicted in Scheme 21.

Scheme 21

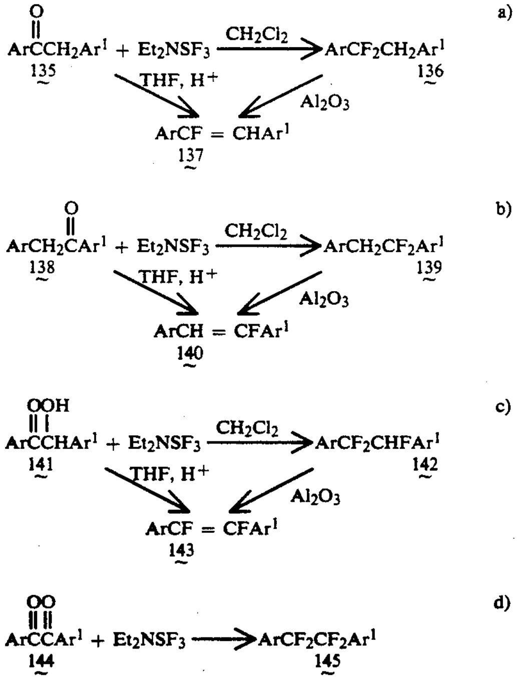

Vinylene fluorides (137) and (140) can be prepared by reaction of $SF_4$ or $Et_2NSF_3$ (DAST) with the appropriate ketone (135) or (138) in which Ar bears a methyl group convertible to a benzylic halide suitable for attachment to an imidazole nitrogen, and Ar' bears a cyano, nitro, ester, or other suitable group which can be subsequently converted to $CO_2H$, $NHSO_2CF_3$, etc. The initially formed difluoroethylene (136) and (139) can be formed in a non-polar solvent such as methylene chloride and subsequently converted to the vinylene fluoride by means of alumina, or converted directly into the unsaturated fluoride by running the reaction in a polar solvent such as tetrahydrofuran, diglyme or N-methylpyrrolidone in the presence of mineral acid. [Equations a and b]. Experimental details of such procedures are found in D. R. Strobach and G. A. Boswell, *J. Org. Chem.*, 36, 818 (1971); G. A. Boswell, U.S. Pat. Nos. 3,413,321 (1968) and 4,212,515 (1980).

As shown in equation c) an appropriate benzoin (141) may be similarly converted to the corresponding 1,2-difluorostilbene (143). Likewise as shown in equation d) an appropriate benzil (144) can be converted to a tetrafluorodiarylethylene (145) using DAST or $SF_4$. Experimental details are described in M. E. Christy, et al., *J. Med. Chem.*, 20, (3), 421-430, (1977).

Compounds of formula 1 where X=

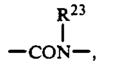

$-CH_2O-$, $-CH_2S-$, $-CH_2NH-$, can be made as shown in Scheme 22.

Scheme 22

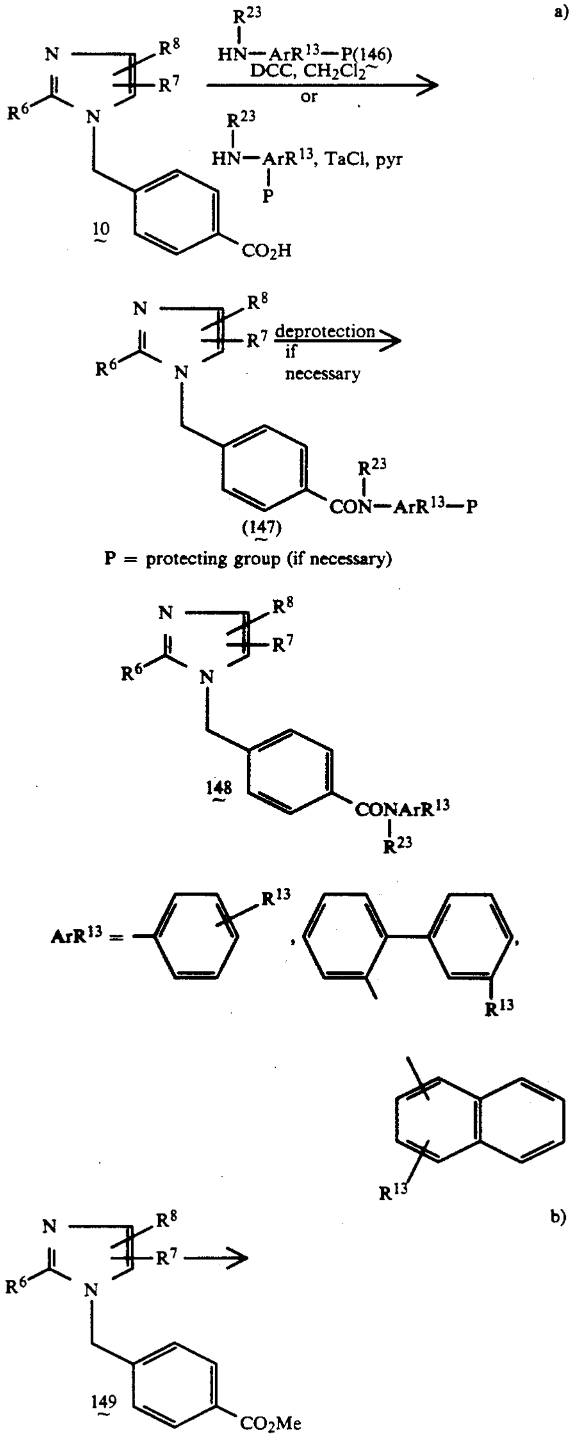

-continued

Scheme 22

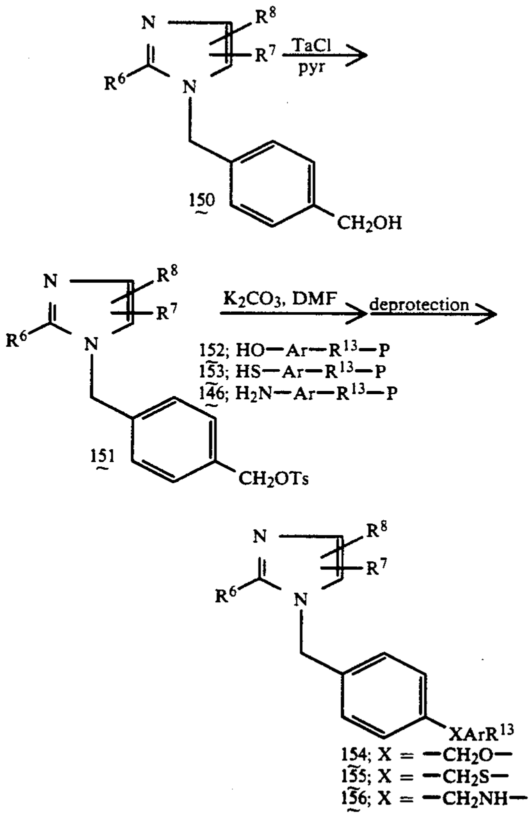

As previously described, acid (10) can be made by alkylating the appropriate imidazole with methyl 4-chloromethylbenzoate in the presence of a base such as potassium carbonate in a polar solvent such as dimethylformamide followed by hydrolysis of the resulting ester. Compound (10) can be converted to (148) by reaction with the requisite amine (146) ($R^{13}$ may need to be protected and subsequently deprotected) and dicyclohexyl carbodiimide (DCC) in methylene chloride [J. R. Beek, et al., *J. Am. Chem. Soc*, 90, 4706 (1968)] or by reaction with tosyl chloride in pyridine [J. H. Brewster and C. J. Ciotti, Jr., J. Am. Chem. Soc., 77, 6214 (1955)]. Yet another process involves conversion of carboxylic acid (10) to its acid chloride with, for example, thionyl chloride followed by reaction with the amine in aqueous base (Schotten-Baumann conditions) or in an organic solvent in the presence of an acid scavenger such as $NaHCO_3$, pyridine or triethylamine, or by other procedures known to form an amide bond between an aromatic acid and an amine.

The compounds where X=—$CH_2O$—, —$CH_2S$—, and —$CH_2NH_2$— can be made as shown in pathway b. The ester (149) is reduced with a reducing agent such as lithium aluminum hydride in an inert solvent to form the alcohol (150) which can then be reacted with tosyl chloride in pyridine to form tosylate (151), which is in turn reacted in the presence of base with a corresponding phenol (152) thiophenol (153), or aniline (146; where $R^{23}$=H) to form compounds (154), (155) or (156). Again this may require that $R^{13}$ be protected with a suitable protecting group, however modifications necessary because of specific functional groups are understood to be incorporated by one skilled in the art of organic: synthesis.

Alternatively, the alcohol (150) can be converted to the corresponding halide with $SOCl_2$, $(COCl)_2$, etc, and the resulting halide can then be reacted with a phenol, thiophenol or aniline in the presence of base to form the desired compound, where X is —$CH_2O$—, —$CH_2S$—, —$CH_2NH$— respectively.

Scheme 23

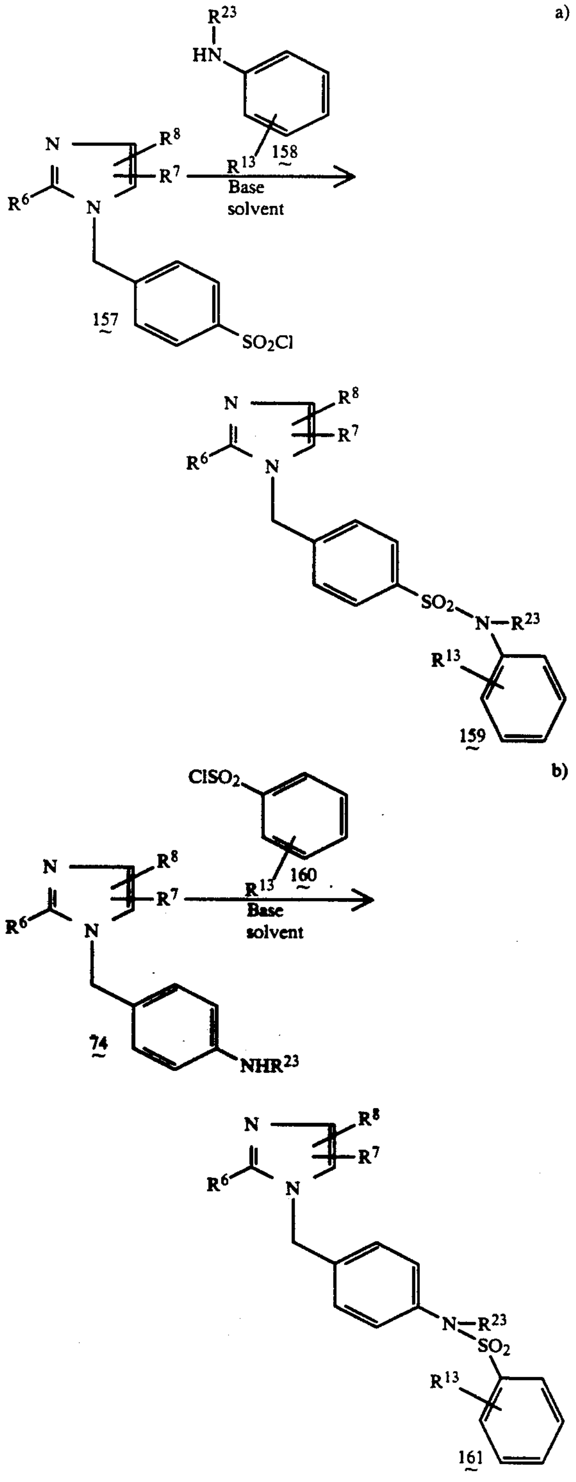

Compounds of Formula (I) where $X = -SO_2NR^{23}-$ and $-NR^{23}SO_2-$ may be prepared as shown in Scheme 23. As shown in equation a, sulfonylchloride derivative (157) can be reacted with aniline derivative (158) in a solvent in the presence of an acid scavenger such as sodium bicarbonate, triethylamine or pyridine or under Schotten-Baumann like conditions to give (159). Sulfonychloride derivative (157) can be obtained by sulfonation of the corresponding benzyl derivative as described earlier, followed by reaction with $PCl_5$ or $POCl_3$. Likewise, aniline (74) may be reacted in the same manner as described above with sulfonylchloride derivative (160) to give (161).

Scheme 24 shows the preparation of furan analogs of the biphenyl compounds (80). Thus, α-ketoester (162), W. Wierenga and H. I. Skulnick, *J. Org. Chem.*, 44, 310 (1979), or the corresponding nitrile (E=CN) can be easily alkylated via standard procedures already mentioned by an alkyl bromide derivative to give (163). The alkene moiety of (163) can be subsequently cleaved by oxidation, for example, with osmium tetroxide, Fieser and Fieser, V.1, p. 812 (Lemieux-Johnson oxidation) to yield dicarbonyl-containing compound (164). Cyclization in mineral acids, acidic ion-exchange resin, $POCl_3$/pyridine, or trifluoroacetic anhydride with a catalytic amount of trifluoroacetic acid yields furan (165; Z=O). Reaction of (164) with $P_4S_{10}$, for example, will yield the corresponding thiophene (165; Z=S). Reaction of (164) with an amine in refluxing benzene, with azeotropic removal of water or by using molecular sieves to absorb the water will yield the corresponding pyrrole (165; $Z=NR^{11}$). Compounds (166) may be prepared from (165) by standard procedures already described.

Scheme 24

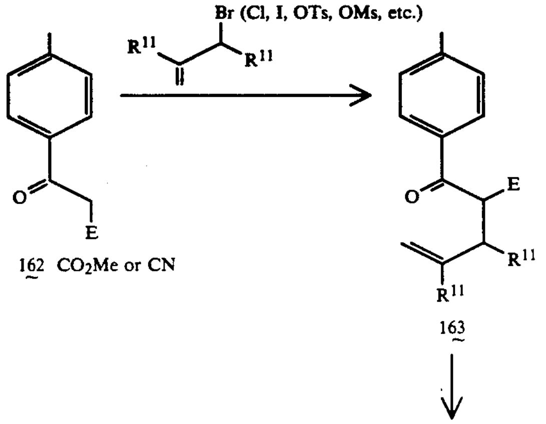

162 $CO_2Me$ or CN

163

-continued

Scheme 24

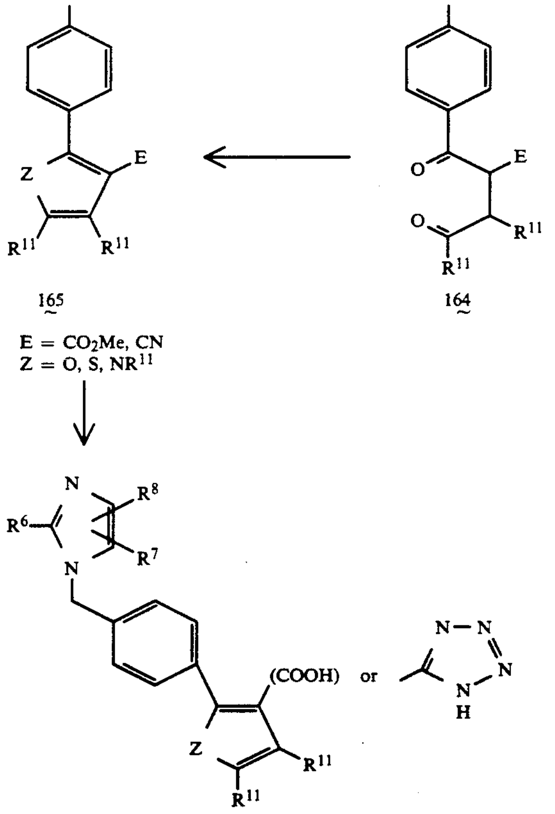

165

164

E = $CO_2Me$, CN
Z = O, S, $NR^{11}$

166 Z = O, S, $NR^{11}$

Compounds wherein a methylene group is inserted between the terminal aromatic ring and the acidic functionality may be prepared as shown in Scheme 25, equation a). Thus reduction of ester (167) with, for example, lithium aluminum hydride, gives alcohol (168). Conversion of (168) to the chloride (169) via thionyl chloride followed by reaction with cyanide anion as previously described yields nitrile (170). Compound (170) may be hydrolyzed to carboxylic acid (171) by methods already described or reacted with a hydrazoic acid equivalent to produce tetrazole (172).

Compounds wherein $R^{13}$ is a trifluoromethylsulfonyl hydrazide acidic functional group were prepared by the procedure described in equation b). That is, conversion of ester (167) to the hydrazide (173) by standard hydrazinolysis followed by reaction with triflic anhydride affords hydrazides (174).

Scheme 25

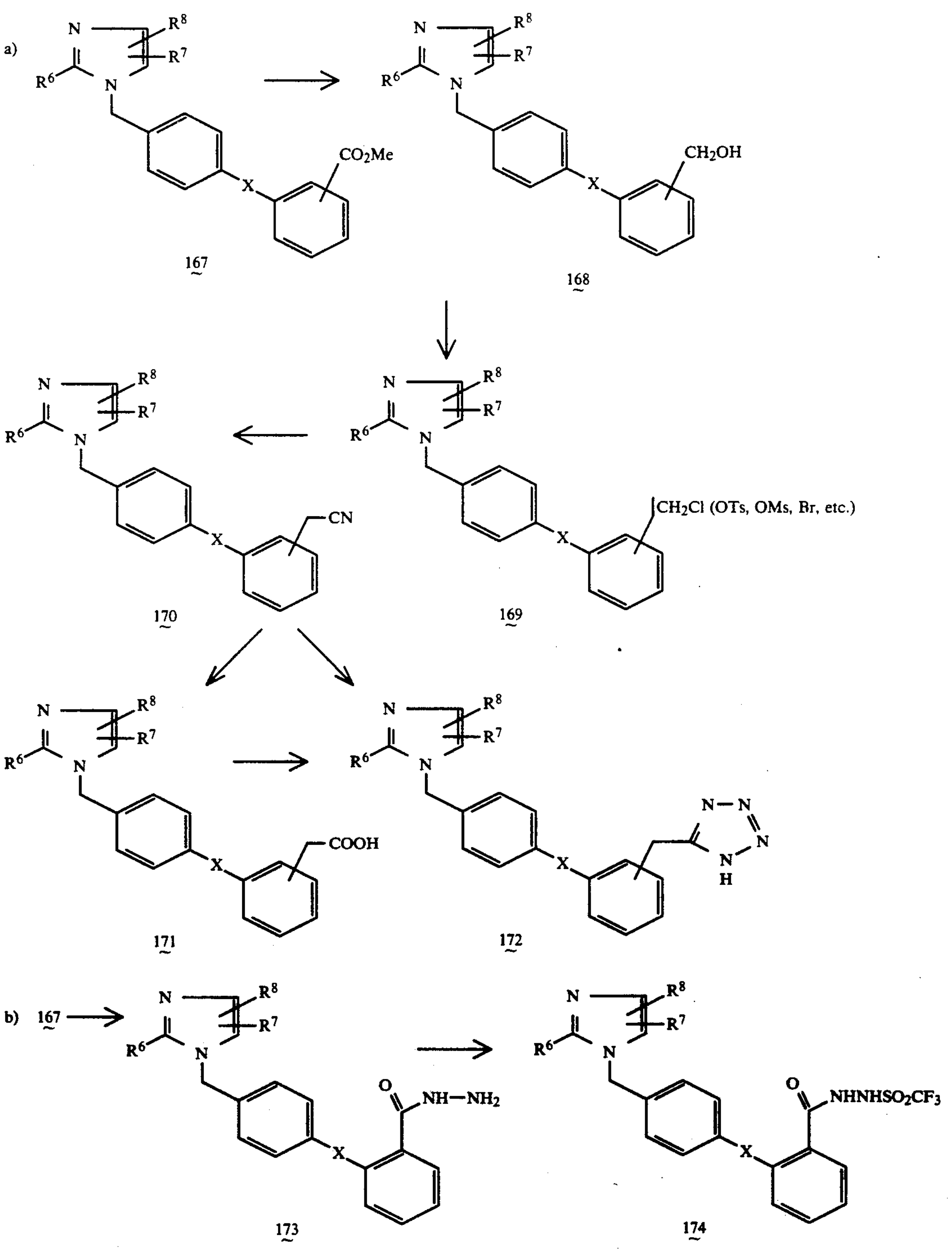

a) 167 168 169 170 171 172 b) 167 173 174

The syntheses of compounds wherein $R^{13}$ is substituted and unsubstituted 1,2,3-triazoles are described in Scheme 26. Thus reduction of ester (175) with a reducing agent such as lithium aluminum hydride or diisobutylaluminum hydride gives alcohol (176). Oxidation with $MnO_2$ or pyridinium chlorochromate converts (176) into aldehyde (177). Nitroethylene derivative (178) is prepared by condensation of aldehyde (177) with nitromethane in the presence of a catalyst, R. M. Letcher and M. P. Sammes, *J. Chem. Ed.*, 62, 262 (1985). Reaction of (178) with sodium azide produces the 1,2,3-triazole (179), (N. S. Zefirov, et al., *J. Chem. Soc. Chem. Comm.*, 1001 (1971)) which may be transformed via procedures already described into product (180).

Aldehyde (177) can also be converted into substituted 1,2,3-triazoles (183) via the sulfone (181), G. Beck, D. Güunther *Chem. Ber.*, 106, 2758 (1973), followed by reaction with sodium azide to give the 1,2,3-triazole (182). Subsequent standard manipulations lead to 1,2,3- triazoles (183) where E=CN and $CO_2R^{11}$. The nitrotriazole (183; $E=NO_2$) may be synthesized from the unprotected triazole (179; P=H) via nitration, R. Hüttel, et al., *Chem. Ber.*, 88, 1586 (1955), C. L. Habraken and P. Cohen-Fernandes *J. Chem. Soc.*, 37 (1972), or from bromonitroethylene derivative (184), G. Kh. Khisamutdinov, et al., *Zh. Org. Khim.*, 11, 2445 (1975), by reaction with sodium azide.

A variety of protecting groups may be used in the manipulation of the above triazoles, amongst which is the trityl group. This group may be easily attached by reaction of the triazole with triphenylmethyl bromide or chloride in an inert solvent such as methylene chloride in the presence of an acid scavenger such as triethyl amine. The trityl group may be later removed by stirring or refluxing in an acidic medium such as trifluoroacetic acid/water, HCl in methylene chloride, or acetic acid/water. The trityl group may also be hydrogenolyzed using a noble metal catalyst such as palladium and hydrogen.

Scheme 26

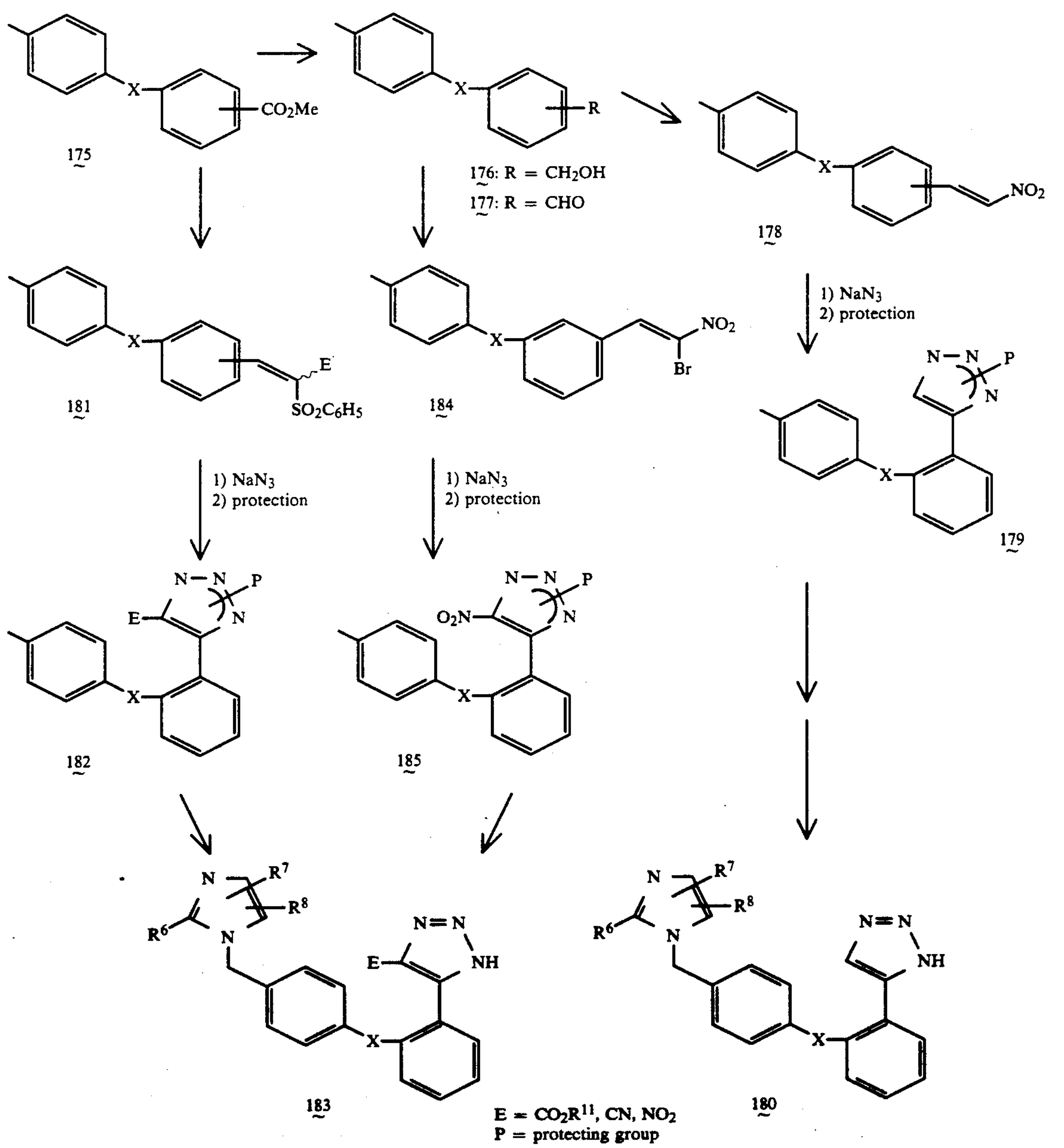

The synthesis of trifluoromethyl-1,2,4-triazoles (190) is depicted in Scheme 27. Acid chloride (186) is converted to amide (187) using standard procedures familiar to one skilled in the art. A preferred protecting group is the 2-propionitrile group ($P=CH_2CH_2CN$). Thus (187; $P=CH_2CH_2CN$) can be synthesized from (186) and $\beta$-aminopropionitrile under Schotten-Baumann like conditions, using aqueous base in an organic solvent to help solubilize (186) and (187). Amide (187) is converted to amidrazone (188) by reaction with $PCl_5$ or phosgene to make an iminoyl chloride which then in turn is reacted with excess hydrazine. Amidrazone (188) is cyclized to the trifluoromethyl-1,2,4-triazole (189) with trifluoroacetic anhydride and then converted to 190 via bromination, alkylation and deprotection as previously described.

Scheme 27

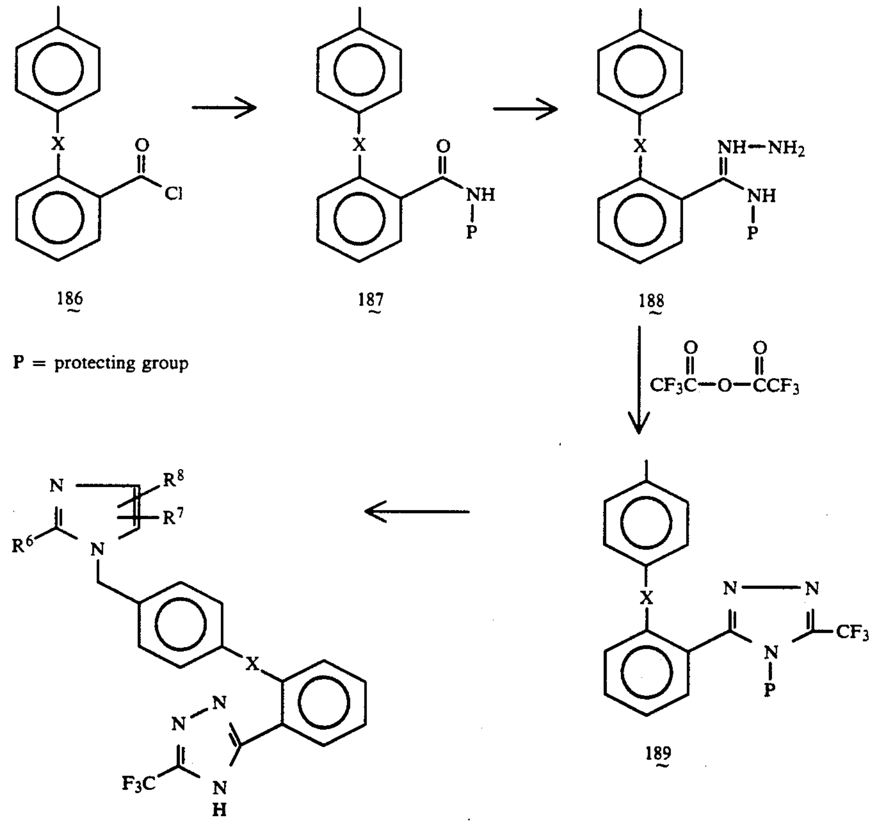

186 187 188 189 190

P = protecting group

Pertinent $R^6$ groups may be variously introduced by many procedures including those described in Scheme 28 which describes imidazole construction.

The $R^6$ groups so introduced may stand unchanged or may be further elaborated if appropriately functionalized, according to methods familiar to those skilled in the art such as are illustrated in Scheme 28.

Scheme 28

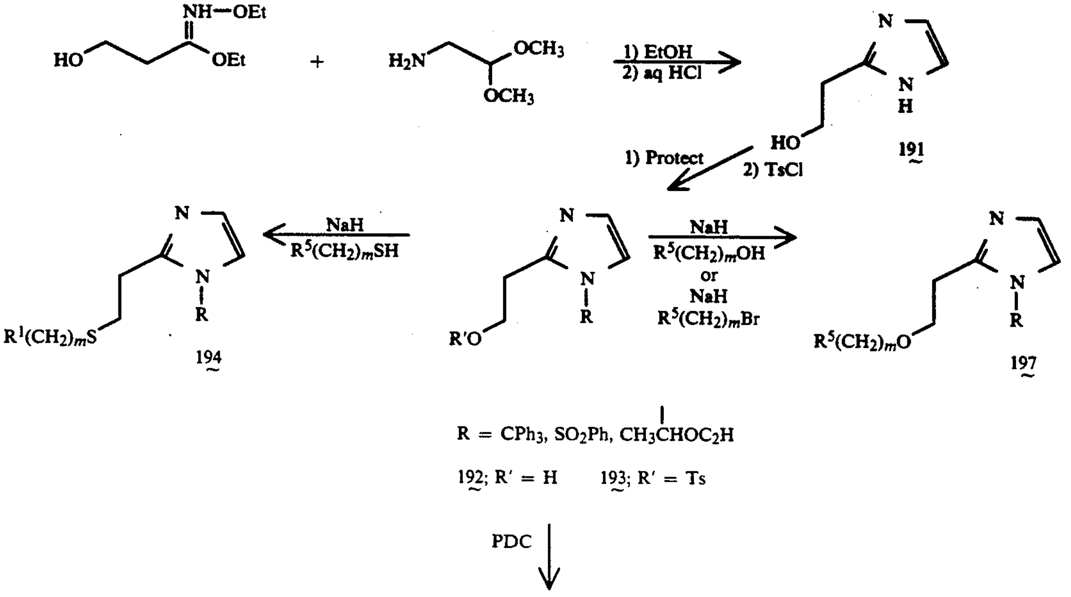

191 194 197

R = $CPh_3$, $SO_2Ph$, $CH_3CHOC_2H$

192; R' = H 193; R' = Ts

-continued

Scheme 28

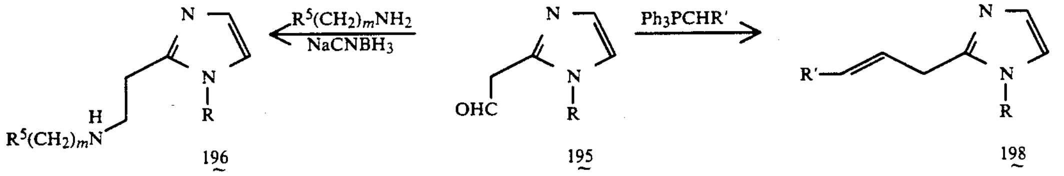

196 195 198

The 2-alkenylimidazoles (201) can be prepared by bromination of the 2-alkylimidazoles (199) followed by elimination of hydrogen bromide. The bromination is preferably accomplished by UV-irradiation for 1–4 hours of imadazole (199) and N-bromosuccinimide, in an inert solvent, such as carbon tetrachloride at 25° C. Treatment of the intermediate bromide (200) with a base, such as DBU, triethylamine, or potassium t-butoxide, affords the trans 2-alkenylimidazoles (201). Cis alkenyl derivatives (203) are prepared from the trans alkenyl compounds by treatment with osmium tetroxide and sodium periodate to afford aldehydes (202) followed by Wittig reaction.

Alternatively, $R^6$ groups may be introduced by metallation of a protected imidazole or protected 2-methylimidazole followed by addition of an appropriate electrophile as illustrated in Scheme 30, equations a) and b). The products (alcohols, esters, halides, aldehydes, alkyls) are suitable for further elaboration by methods familiar to those skilled in the art. Metallation of imidazoles is described in K. L. Kirk, *J. Org. Chem.*, 43, 4381 (1978); R. J. Sundberg, *J. Het. Chem.*, 14, 517 (1977); J. V. Hay et al., *J. Org. Chem.*, 38, 4379 (1973); B. Iddon, *Heterocycles*, 23, 417 (1985).

Condensation of 2-methylimidazole and appropriate electrophiles (equation b) with catalytic acid or base as Scheme 29

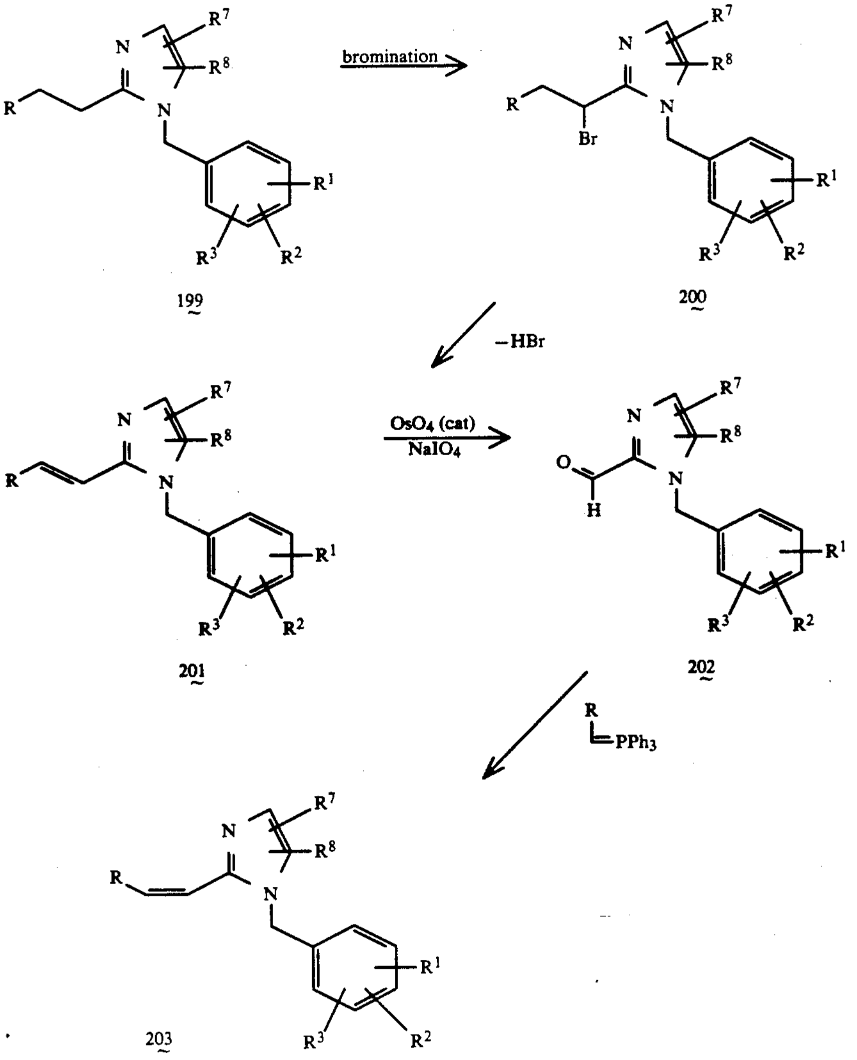

199 200 201 202 203

R = alkyl, cycloakyl described in A. R. Katritzky (Ed.), "Comprehensive Heterocyclic Chemistry", Vol. 5, p. 431, *Pergamon Press*, N.Y., 1984 affords products wherein $R_6$ is alkenyl which are suitable for further elaboration.

Scheme 30

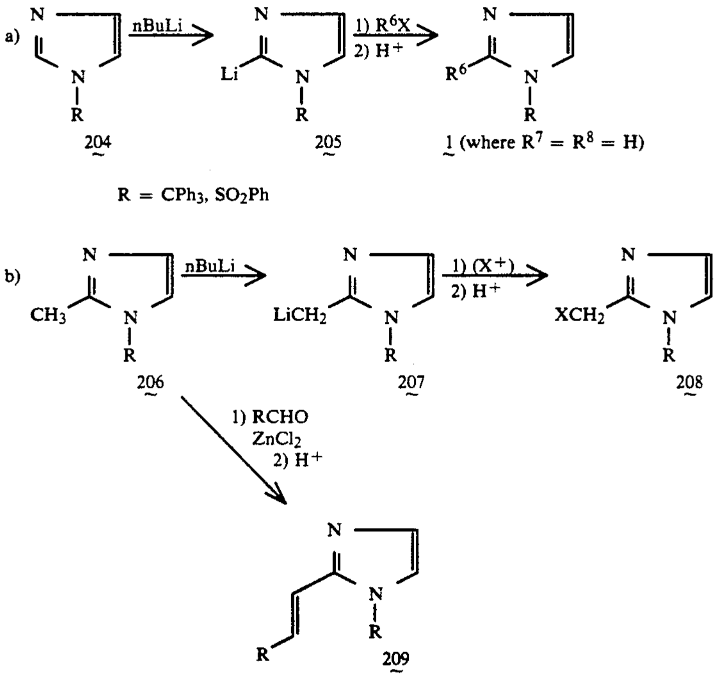

204 205 1 (where $R^7 = R^8 = H$)

R = $CPh_3$, $SO_2Ph$ 206 207 208

209

Various 2-substituted imidazoles can be prepared by reaction of a protected 2-trimethylsilylimidazole with a suitable electrophile by the method described by F. H. Pinkerton and S. F. Thames, *J. Het. Chem.*, 9, 67 (1972), which can be further elaborated as desired. Alternatively, $R^6$ may also be introduced by nickel catalyzed cross-coupling of Grignard reagents with 2-(methylthio)imidazoles (Scheme 31) as described by E. Wenkert and T. W. Ferreira, *J. Chem. Soc., Chem. Commun.*, 840, (1982); E. Wenkert et al., *J. Chem. Soc., Chem. Commun.*, 637, (1979); and H. Sugimura and H. Takei, *Bull. Chem. Soc. Japan*, 58, 664 (1985). The 2-(methylthio)imidazoles can be produced by the procedure described in German Patent No. 2,618,370 and the references cited therein.

Scheme 31

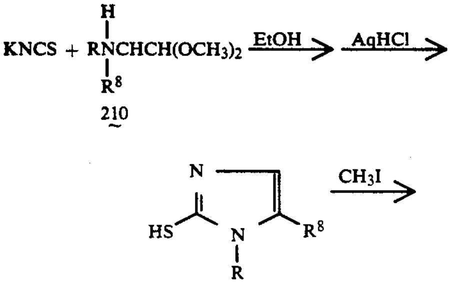

210

211

-continued

Scheme 31

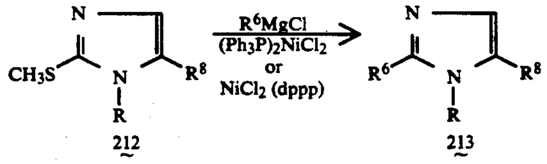

212 213

As shown in Schemes 32-35, elaboration of $R^8$ can be accomplished by procedures described in Schemes 3, 28 and 30b and by chain extension reactions familiar to those skilled in the art in which $R^8$ bears a reactive terminal functional group, e.g. —OH, halogen, —CHO, $—CO_2R$, $—CO_2H$, $—CH=CH_2$, $—NH_2$, $—NO_2$, —CN,

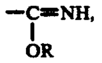

etc., or by degradation reactions such as conversion of an ester to an acid or an alkene to an aldehyde.

Specifically, the hydroxymethyl group can be activated for the displacement reaction by reacting with thionyl chloride, $PCl_5$ or with carbon tetrachloride/triphenylphosphine to form a corresponding chloro derivative. By a similar reaction bromo and iodo derivatives can be obtained. The hydroxymethyl group can also be activated by forming the corresponding p-toluenesulfonate, methanesulfonate and trifluoromethane sulfonate derivatives. The hydroxyl group can be converted to its corresponding fluoro compound by various fluorinating agents such as DAST as shown in Scheme 32.

Scheme 32

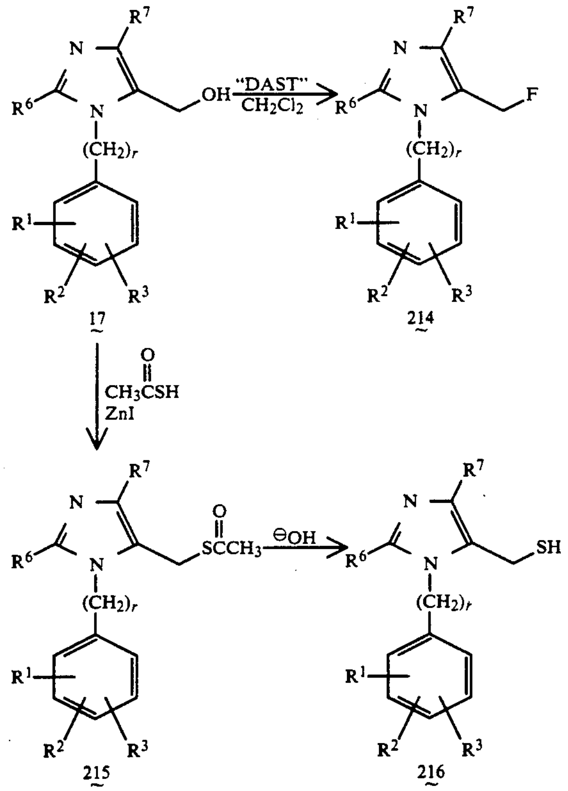

17 214 215 216

Also as shown in Scheme 32, the hydroxyl group can be converted to thiolacetic acid derivative (215), J. Y. Gauthier, *Tet. Lett.*, 15 (1986), and to thiol derivative (216) by subsequent hydrolysis.

The hydroxymethyl group on compound (17) can be readily oxidized to an aldehyde group by means of manganese dioxide or ceric ammonium nitrate. The aldehyde group will undergo chain extension reactions such as the Wittig and Wittig-Horner reactions and enter into typical carbon-carbon bond forming reactions with Grignard and lithium reagents as well as with compounds bearing activated methylene groups. Alternatively, the hydroxymethyl group can be oxidized directly to an acid functionality which can in turn be converted to ester and amide derivatives. The esters and amides can be prepared directly from the aldehydes by manganese dioxide oxidation in the presence of sodium cyanide and an alcohol or amine, *J. Am. Chem. Sec.*, 90, 5616 (1968) and *J. Chem. Soc.* (C), 2355 (1971).

As shown in Scheme 33, the chlorine on compound (25) can be displaced by the anion of dialkyl malonate to give the corresponding malonate derivative (217). The saponification of (217) with NaOH (or KOH) gives the corresponding diacid which can be decarboxylated to give the corresponding propionic acid derivative (218) by heating to 120° C. Alternatively, (218) can be directly obtained by refluxing (217) with a mineral acid such as HCl or sulfuric acid. The free acid (218) can be esterified by heating in a medium of the various alcohols and a catalytic amount of mineral acids such as HCl or sulfuric acid to give the corresponding esters (219). Alternatively the esters can be obtained by reacting the free acid (218) and the corresponding alcohols in the presence of coupling reagents such as DDQ or EEDQ. A similar reaction with various mono-substituted and disubstituted amines produces the corresponding amides (220). A similar reaction with various mercaptans produces the corresponding thioesters.

Scheme 33

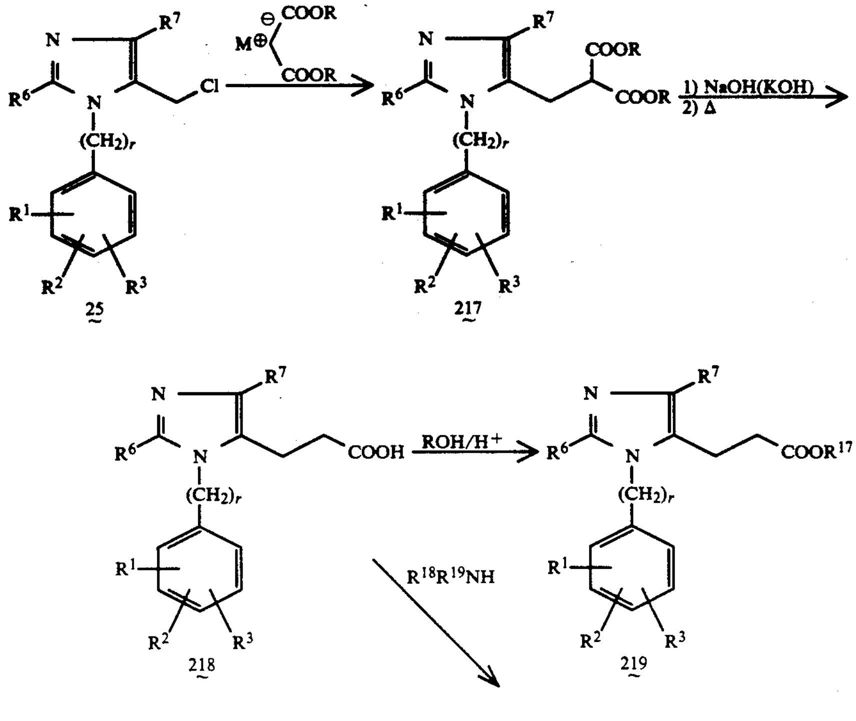

25 217 218 219

-continued

Scheme 33

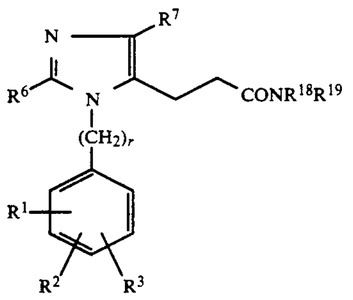

220

As shown in Scheme 34, the chloro group on (25) can be displaced by the sodium salt or potassium salt of the alkyl, aryl or arylalkyl mercaptans to give the corresponding sulfide derivatives (221). The amine derivative (222) can be obtained by treating (25) with ammonia or with the corresponding mono-substituted amines. Alternatively, the chloro group may be displaced by sodium azide to give an azide intermediate which upon reduction with $H_2$ over a noble metal catalyst or with a reducing agent such as chromous chloride (W. K. Warburton, *J. Chem. Soc.,* 2651 (1961)) yields (222) where $R^{10}$ and $R^{11}$ are hydrogen. This amine c be subsequently alkylated with alkyl halides, or reductively alkylated with aldehydes and ketones to give alkyl derivatives of (222). The amines (222) are converted to the corresponding carbamates (224), sulfonamides (225), amides (226) or ureas (227) by standard procedures illustrated in Scheme 34 and familiar to one skilled in the art. The nitro compound (223) can be obtained by the treatment of (25) with sodium nitrite or potassium nitrite. The nitrate (228) may be synthesized by treatment of (25) with $AgNO_3$, A. F. Ferris, et al., *J. Am. Chem. Soc.,* 75, 4078 (1953).

Scheme 34

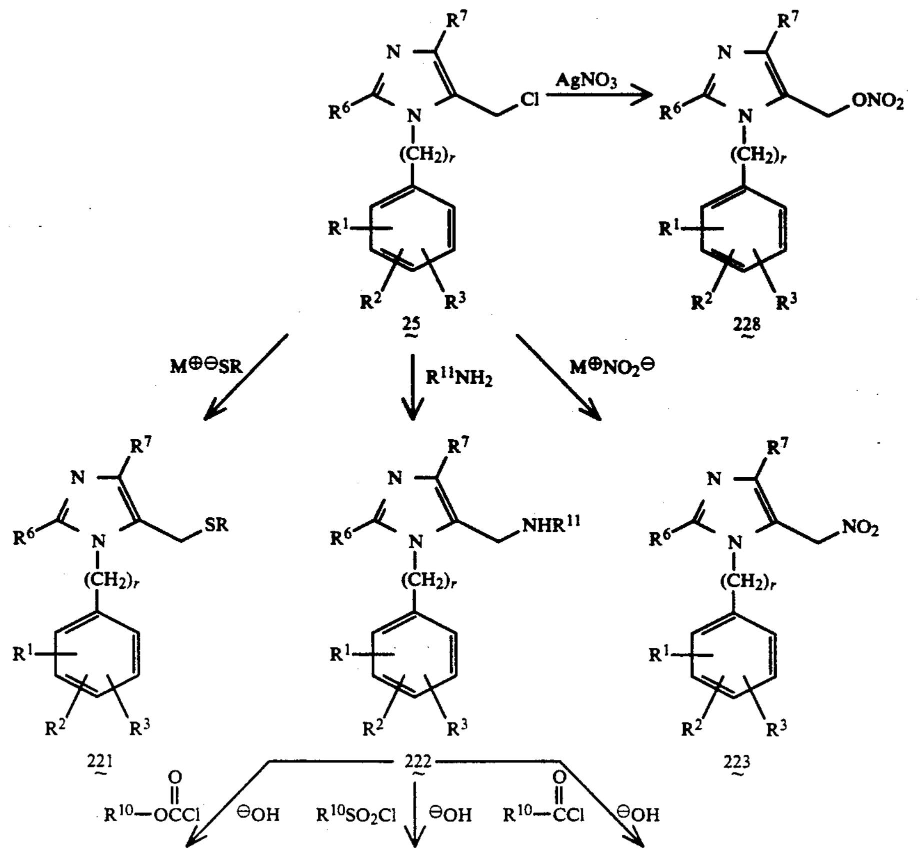

-continued

Scheme 34

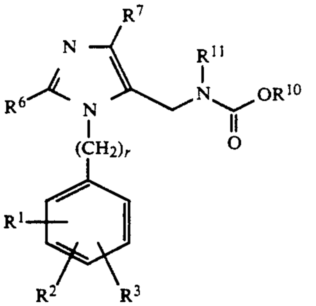

224

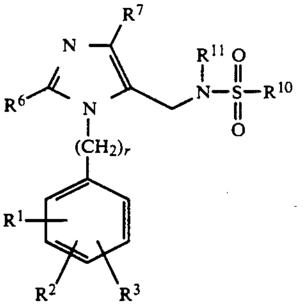

225

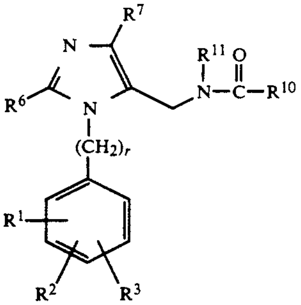

226

222

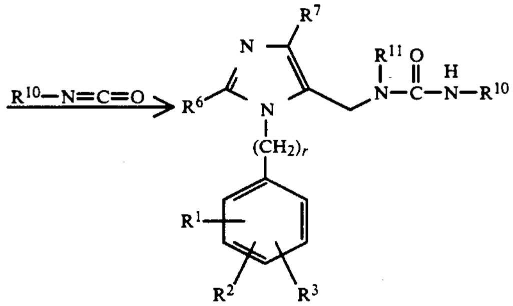

227

The reaction between the thiopyridyl ester (229) and a suitable Grignard reagent produces the ketones (230).

Scheme 35

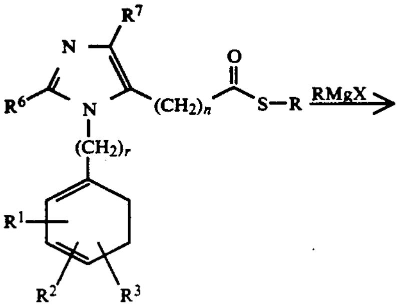

R⁻ R 229 (R = pyridyl)

-continued

Scheme 35

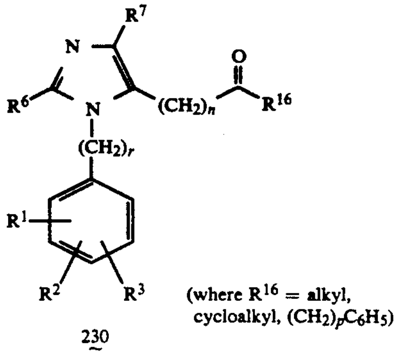

(where $R^{16}$ = alkyl, cycloalkyl, $(CH_2)_pC_6H_5$)

230

As shown in Scheme 36 when the imidazole 4 and/or 5-position contains an aldehyde (231) then derivatives can be formed such as hydrazones (232). Reaction with organometallic reagents such as Grignard or alkyl/aryl-lithium reagents will yield alcohols (233) which in turn may be transformed into a variety of other functionality familiar to one skilled in the art.

Scheme 36

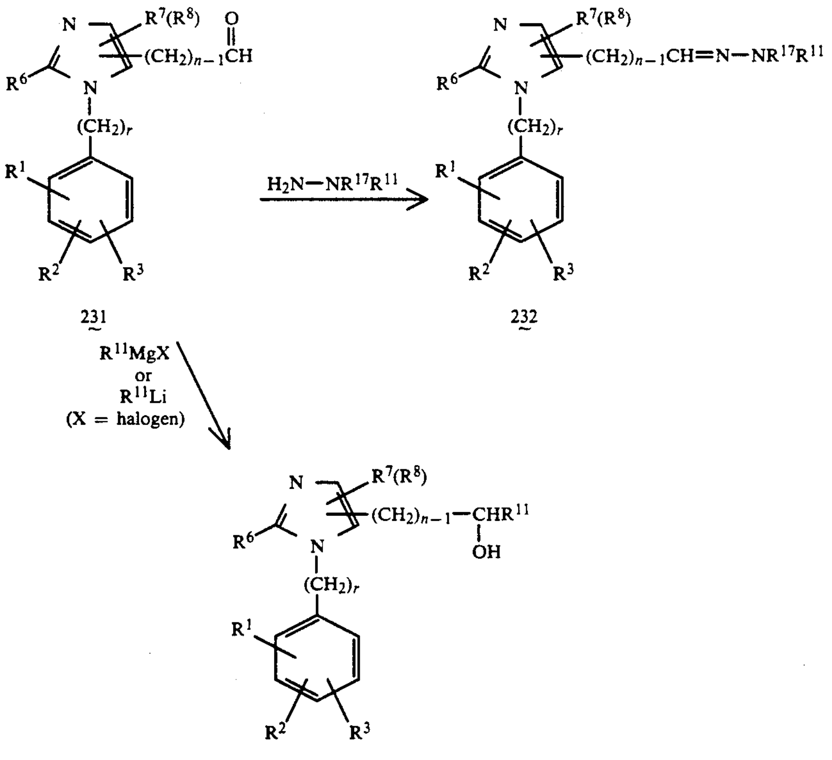

231 232 233

Compounds (234) containing an alkyl chain substituted with 4-((2-methoxy)phenyl)piperazine (236) may be prepared by alkylating alkylhalides such as 237 with the piperazine derivative 236 in a solvent such as DMF, ethanol, DMSO, THF, etc., with or without an added acid scavenger such as potassium or sodium carbonate, DBU, etc. as is shown in Scheme 37. An alternative method involves coupling carboxylic acid 238 with piperazine 236 with DCC or any other amide-bond forming reaction familiar to one skilled in the art to yield 239. The amide can then be reduced with lithium aluminum hydride, Red-Al (Lithium tris(trimethoxyethoxy)aluminum hydride), diborane, etc. to yield 234.

Scheme 37

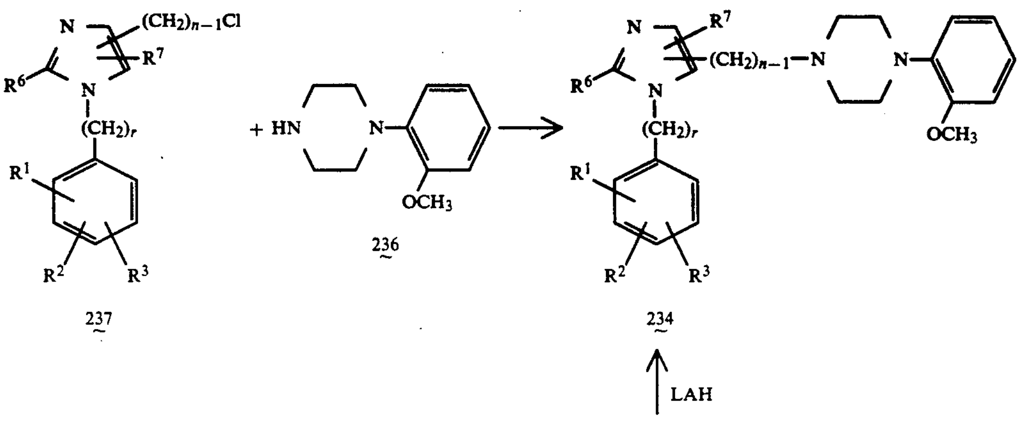

237 236 234

-continued

Scheme 37

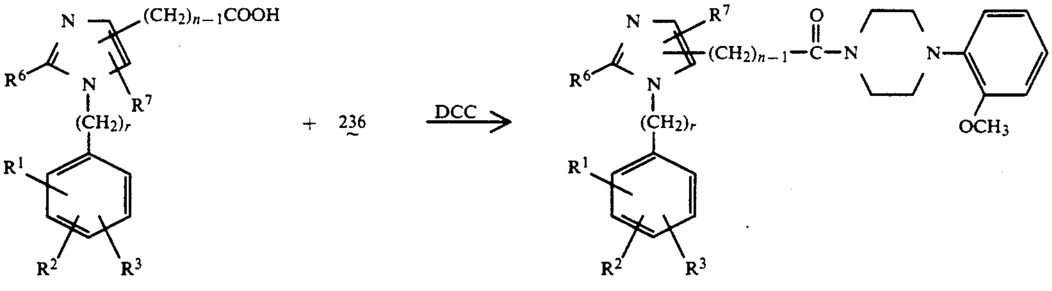

238 + 236 → 239

Alternatively 239 can be prepared via the formation of a nitrogen anion of 236 with a strong base such as n-BuLi, t-BuLi, etc., followed by reaction with ester 240.

Scheme 38

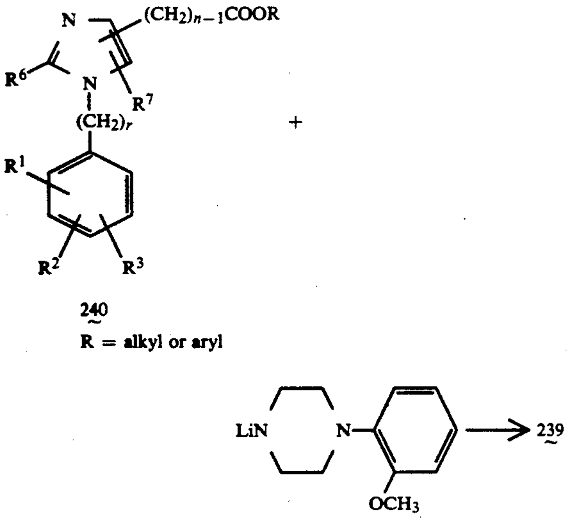

240 R = alkyl or aryl

+

236 Li salt → 239

As shown in Scheme 39, ester 240 may be obtained by esterification of acid 238 (familiar to one skilled in the art) or by direct oxidation of aldehyde 231 with NaCN, $MnO_2$ in methanol (Corey, E. J., et al. *J. Am. Chem. Soc.* (1968) 90, 5616). Oxidation of 231 with NaCN, $MnO_2$, $NH_3$ in methanol leads to the corresponding amide 241 (Gilman, N. W. *Chem. Comm.* (1971) 733).

Scheme 39

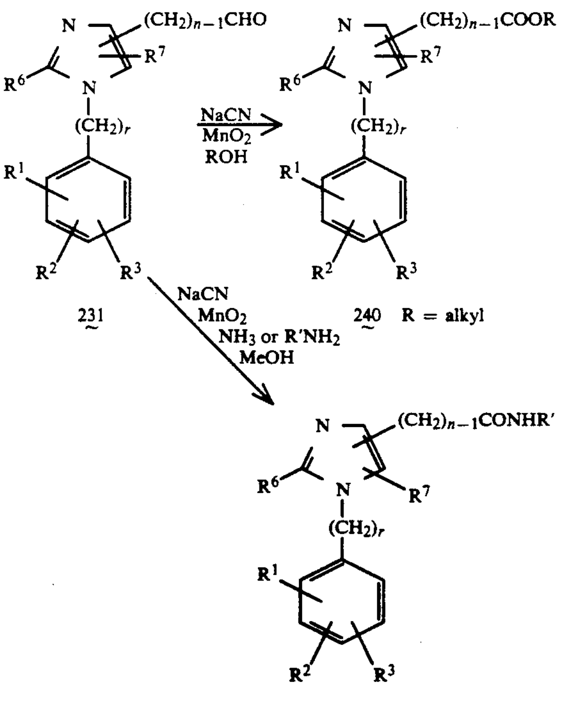

231

240 R = alkyl

241 R' = H or alkyl

Saponification of ester 240 will lead to carboxylic acid 238.

Aldehyde 231, in turn, may be made from the corresponding alcohol 17 by a variety of methods familiar to one skilled in the art, including pyridium chlorochromate (PCC), Swern and ceric ammonium nitrate (CAN) oxidations.

Likewise, the unalkylated hydroxymethylimidazole derivative 16 may undergo the transformations to the aldehyde, ester, carboxylic acid and carboxamide by the reactions mentioned above for the alkylated case.

The aldehyde functionality on compound 231 may be converted to an acidic heterocycle by the reactions described in Scheme 26.

Scheme 41 illustrates that imidazoles, especially those substituted with electron-withdrawing groups react as their anions with 4-nitrofluorobenzene in DMF or DMSO to yield the N-phenylimidazole 245. Compounds such as aldehyde 242, ester 243, and diester 244 work especially well. The nitro group can be further elaborated as in Scheme 13.

Scheme 40

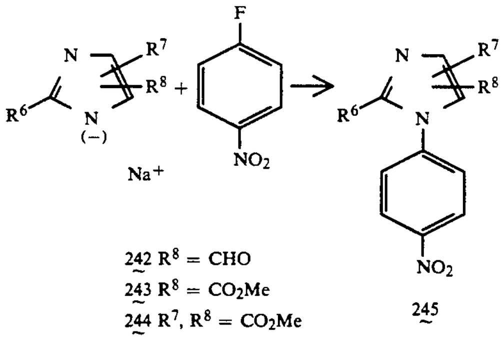

242 $R^8$ = CHO
243 $R^8$ = $CO_2Me$
244 $R^7$, $R^8$ = $CO_2Me$

245

Scheme 41 illustrates that imidazole 4,5-dicarboxylic acid 246 (prepared by the method of R. G. Fargher and F. L. Pyman (*J. Chem. Soc.* (1919) 115, 217) can easily be esterified to the diester 247 and then alkylated by the procedures mentioned previously to yield 248. Selective reduction of the diester to the 4-carboalkoxy-5-hydroxymethylimidazole 249 is accomplished with sterically bulky reducing agents such as lithium tri-t-butoxyaluminum hydride. Esters 248 and 249 may be saponified by the usual methods familiar to one skilled in the art.

Scheme 41

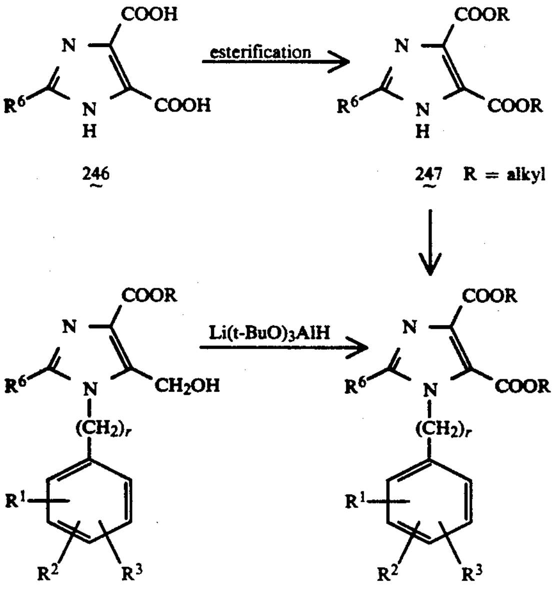

246; 247 R = alkyl; 249; 248

The compounds of this invention and their preparation can be understood further by the following examples, which do not constitute a limitation of the invention. In these examples, unless otherwise indicated, all temperatures are in degrees centigrade and parts and percentages are by weight.

EXAMPLE 1

Part A: Preparation of 2-Butyl-4-chloro-1-(4-cyanobenzyl)-5-hydroxymethylimidazole To a solution of 2-butyl-4-chloro-5-hydroxymethylimidazole (prepared as described in U.S. Pat. No. 4,355,040; 3.56 g, 40 mmol, 1 eq) in 300 mL methanol was added dropwise a freshly prepared sodium methoxide solution (0.92 g Na, 40 mmol, 1 eq, in 30 mL MeOH). After stirring for 0.5 hours, the methanol was removed in vacuo and the resultant glass was dissolved in 100 mL DMF. To this mixture was added a solution of α-bromo-p-tolunitrile (8.60 g, 44 mmol, 1.1 eq) in DMF and the entire contents stirred overnight under $N_2$ at room temperature. The solvent was then removed in vacuo and the residue dissolved in 300 mL ethyl acetate and 300 mL $H_2O$. The layers were separated and the aqueous layer was extracted twice with 300 mL portions of ethyl acetate. The organic layers were dried and evaporated and the crude product flash chromatographed over silica gel in 1:1 hexane/ethyl acetate to give 6.83 g of one regioisomer as a white solid; m.p. 92.5°-98.0°. NMR (200 MHz, $CDCl_3$) δ 7.65 (d, 2H, J=8 Hz); 7.13 (d, 2H, J=8 Hz); 5.30 (s, 2H); 4.46 (s, 2H); 2.49 (t, 2H, J=7 Hz); 1.59 (m, 2H); 1.28 (m, 2H); 0.84 (t, 3H, J=7 Hz). Mass Calcd. for $C_{16}H_{18}N_3OCl$: 303.1138. Found: 303.1124.

Continued elution gave 3.56 g of the second regioisomer as a white solid, listed below as the first entry in Table 1.

The intermediates shown below were prepared or could be prepared in accordance with the procedure described in Example 1, Part A using the appropriately substituted imidazole and benzyl halide as starting material.

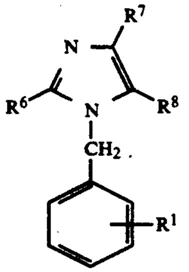

| $R^1$ | $R^6$ | $R^7$ | $R^8$ | MP(°C.) |
|---|---|---|---|---|
| 4-CN | n-butyl | $CH_2OH$ | Cl | 98.0-100.0 |
| 4-$NO_2$ | n-butyl | Cl | $CH_2OH$ | 56.8-59.5 |
| 4-$NO_2$ | n-butyl | $CH_2OH$ | Cl | 114.5-116.5 |
| 2-CN | n-butyl | Cl | $CH_2OH$ | 93.0-95.5 |

Part B: Preparation of 2-Butyl-4-chloro-1-(4-cyanobenzyl)-5-cyanomethylimidazole Thionyl chloride (3.60 mL, 49 mmol, 5 eq) was slowly dripped into a solution of 2-butyl-4-chloro-1-(4-cyanobenzyl)-5-hydroxymethylimidazole (3.0 g, 9.9 mmol, 1 eq) in a minimum of $CHCl_3$. The mixture was stirred for 2 hours at room temperature after which the solvent was removed in vacuo and the residue suspended in toluene (200 mL). The toluene was removed on the rotary evaporator and this procedure was repeated again to remove all traces of thionyl chloride. The chloride was then dissolved in DMSO (minimum to dissolve) and added to a solution of sodium cyanide (2.90 g, 59 mmol, 6 eq) in DMSO (200 mL). The solution was stirred overnight under $N_2$ at room temperature after which 500 mL $H_2O$ was added and the aqueous layer was extracted three times with 300 mL of ethyl acetate. The organic layers were dried and concentrated and the residue flash chromatographed in 4:1 hexane/ethyl acetate over silica gel to give 1.62 g of a light yellow solid; m.p. 109.5°-113.0° NMR (200 MHz, $CDCl_3$) δ 7.70 (d, 2H, J= 10 Hz); 7.12 (d, 2H, J=10 Hz); 3.51 (s, 2H); 2.60 (t, 2H, J=7 Hz); 1.70 (m, 2H); 1.40 (m, 2H); 0.90 (t, 3H, J=7 Hz). Mass spectrum shows M+=312/314. Mass Calcd. for $C_{17}H_{17}ClN_4$: 312.1139, Found 312.1126.

The intermediates shown below were prepared, or could be prepared, in accordance with the procedure described in Example 1, Part B using the appropriately substituted imidazole and benzyl halide as starting material.

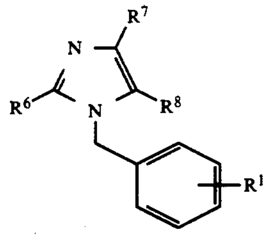

| R[1] | R[6] | R[7] | R[8] | MP(°C.) |
|---|---|---|---|---|
| 4-CN | n-butyl | $CH_2CN$ | Cl | (oil)[a] |
| 4-$NO_2$ | n-butyl | Cl | $CH_2CN$ | 117.0–119 |
| 4-$NO_2$ | n-butyl | $CH_2CN$ | Cl | (oil)[b] |
| 2-CN | n-butyl | Cl | $CH_2CN$ | (oil)[c] |
| 3-CN | n-butyl | Cl | $CH_2CN$ | (oil)[d] |

[a]NMR(200MHz, $CDCl_3$)δ7.66(d, 2H, J=7Hz); 7.12(d, 2H, 2, J=7Hz); 5.15(s, 2H); 3.69(s, 2H), 2, 56(t, 2H, J=7Hz); 1.62(t of t, 2H, J=7, 7Hz); 1.33(t of q, 2H, J=7, 7Hz); 0.87(t, 3H, J 32 7Hz).

[b]NMR(200MHz, $CDCl_3$)δ8.24(d, 2H, J=10Hz); 7.18(d, 2H, J=10Hz); 5.20(s, 2H); 3.67(s, 2H); 2.55(t, 2H, j=7Hz); 1.64(m, 2H); 1.34(m, 2H); 0.85(t, 3H, J=7Hz).

[c]NMR(200MHz, $CDCl_3$)δ7.80(d, 1H, J=10Hz); 7.64(d of d, 1H, J=10Hz); 7.53(d of d, 1H, J=10Hz); 6.74(d, 1H, J=10Hz); 5.37(s, 2H); 3.64(s, 2H); 2.55(t, 2H, J=7Hz); 1.67(m, 2H); 1.34(m, 2H); 0.85(t, 3H, J=7Hz).

[d]NMR(200MHz, $CDCl_3$)δ7.66(d, 1H, J=7Hz); 7.54(d of d, 1H, J=7, 7Hz); 7.33(s, 1H); 7.25(d, 1H, J=7Hz); 5.25(s, 2H); 3.56(s, 2H); 2.61(t, 2H, J=7Hz); 1.69(m, 2H); 1.35(m, 2H); 0.91(t, 3H, J=7Hz).

Part C: Preparation of 2-Butyl-1-(4-carboxybenzyl)-4-chloroimidazole-5-acetic acid 2-Butyl-4-chloro-1-(4-cyanobenzyl)-5-(cyanomethyl-)imidazole (0.5 g) and a solution of 1:1 12N HCl/glacial acetic acid (10 mL) were mixed and refluxed for 6 hours. The solvents were removed by rotary evaporation and the resultant solids were washed with isopropanol, and filtered. The mother liquor was flash chromatographed on silica gel in 1:1 hexane-ethyl acetate to give 60 mg of product. Further flushing of the column with isopropanol followed by preparatory TLC of the evaporated residue gave an additional 100 mg of product. NMR (200 MHz, DMSO-$d_6$) δ 7.90 (d, 2H, J=8 Hz); 7.12 (d, 2H, J=8 Hz); 5.30 (s, 2H); 3.08 (s, 2H); 2.50 (t, 2H, J=7 Hz); 1.49 (m, 2H); 1.24 (m, 2H); 0.79 (t, 3H, J=7 Hz). Mass. Calcd. for $C_{13}H_{19}ClN_2O_4$: 350.1033. Found 350.1066.

EXAMPLE 2

Part A: Preparation of 2-Butyl-4-chloro-1-(4-nitrobenzyl)imidazole-5-acetic acid 2-Butyl-4-chloro-5-(cyanomethyl)-1-(4-nitrobenzyl-)imidazole (7.08 g) and a 1:1 mixture of 12N HCl and glacial acetic acid (175 mL) were mixed and refluxed for 6 hours. The solvents were removed by rotary evaporation and water (300 mL) was then added to the residue. After a few minutes, the product precipitated and was collected and dried to give 7.35 g of a solid; m.p. 207.0°-210.0°. NMR (200 MHz, DMSO-$d_6$/$CDCl_3$) δ 8.20 (d, 2H, J=10 Hz); 7.22 (d, 2H, J=10 Hz); 5.28 (s, 2H); 3.42 (s, 2H); 2.52 (t, 2H, J=7 Hz); 1.64 (m, 2H); 1.34 (m, 2H); 0.86 (t, 3H, J=7 Hz). Anal. Calcd. for $C_{16}H_{18}ClN_3O_4$; C, 54.63; H, 5.16; N, 11.94. Found: C, 54.52; H, 5.05; N, 12.21.

Part B: Preparation of Methyl 2-butyl-4-chloro-1-(4-nitrobenzyl)imidazole-5-acetate 2-Butyl-4-chloro-1-(4-nitrobenzyl)imidazole-5-acetic acid (7.35 g, 20.9 mmol, leq); 3.1M HCl in dioxane (34.0 mL, 105.4 mmol, 5 eq) and 100 mL methanol were mixed and refluxed for 7.5 hours. The solvents were removed by rotary evaporation and the residue taken up in methylene chloride and 1N NaOH (300 mL each). The layers were separated and the organic layer washed two more times with 1N NaOH (300 mL each), dried and concentrated to give 5.43 g of a light pink solid; m.p. 97.5°-100.0°. NMR (200 MHz, DMSO-$d_6$) δ 8.23 (d, 2H, J=9 Hz); 7.33 (d, 2H, J=9 Hz); 5.50 (s, 2H); 3.73 (s, 2H); 3.40 (s, 3H); 2.66 (t, 2H, J=7 Hz); 1.53 (m, 2H); 1.22 (m, 2H); 0.76 (t, 3H, J=7 Hz). Mass Calcd. for $C_{17}H_{20}N_3O_4Cl$: 365.1140. Found: 365.1158.

Methyl 2-butyl-5-chloro-1-(4-nitrobenzyl)-imidazole-5-acetate was also prepared by the procedure described in Example 2 Part B from 2-butyl-5-chloro-1-(4-nitrobenzyl)imidazole-5-acetic acid. NMR (200 MHz, $CDCl_3$) δ8.23 (d, 2H, J=10 Hz); 7.20 (d, 2H, J=10 Hz); 5.21 (s, 2H); 3.75 (s, 3H); 3.67 (s, 2H); 2.58 (t of t, 2H, J=7 Hz); 1.32 (q of t, 2H, J=7 Hz); 0.86 (t, 3H, J=7 Hz). Mass Calcd. for $C_{17}H_{20}ClN_3O_4$; 365.1142. Found 365.1132.

Part C: Methyl 2-butyl-4-chloro-1-(4-aminobenzyl)-imidazole-5-acetate

A mixture of methyl 2-butyl-4-chloro-1-(4-nitrobenzyl)imidazole-5-acetate (5.00 g, 13.7 mmol, 1 eq), iron (2.67 g, 47.8 mmol, 3.5 eq), glacial acetic acid (5.47 mL, 95.3 mmol, 7 eq), and methanol (250 mL) was refluxed for 5.5 hours. The solvent was removed by rotary evaporation. The residue was diluted with water (300 mL) and extracted five times with 300 mL portions of ethyl acetate. The organic layers were dried and concentrated. The residue was flash chromatographed in 75:25 hexane/ethyl acetate over silica gel to give 4.53 g of a golden yellow oil which crystallized after standing for several days. NMR (200 MHz, $CDCl_3$) δ 6.72 (d, 2H, J=7 Hz); 6.60 (d, 2H, J=7 Hz); 4.99 (s, 2H); 3.61 (s, 3H); 3.47 (s, 2H); 2.60 (t, 2H, J=7 Hz); 1.68 (m, 2H); 1.35 (m, 2H); 0.86 (t, 3H, J=7 Hz). Mass spectrum shows M+=335/337. Mass Calcd. for $C_{17}H_{22}N_3O_2Cl$: 335.1400. Found: 335.1407.

The following intermediates were prepared by the procedure described in Example 2, Part C from the corresponding nitro intermediates:

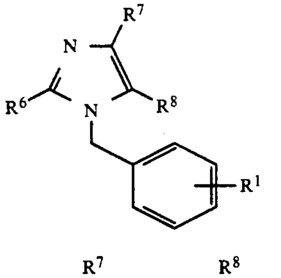

| $R^1$ | $R^6$ | $R^7$ | $R^8$ | MP(°C.) |
|---|---|---|---|---|
| 4-$NH_2$ | n-butyl | $CH_2CO_2CH_3$ | Cl | (oil)[a] |
| 4-$NH_2$ | n-butyl | Cl | $OCOCH_3$ | (oil)[b] |
| 4-$NH_2$ | n-butyl | Cl | $CH_2OH$ | (oil)[c] |

[a]NMR(200MHz, $CDCl_3$)δ6.85(d, 2H, J=7Hz); 6.63(d, 2H, J=7Hz); 4.95(s, 2H); 3.69(s, 3H); 2.57(t, 2H, J=7Hz); 1.59(t of t, 2H, J=7, 7Hz); 1.30(t of q, 2H, J=7, 7Hz); 0.86(t, 3H, J=7Hz).
[b]NMR(200MHz, $CDCl_3$)δ6.74(d, 2H, J=10Hz); 6.60(d, 2H, J=10Hz); 4.97(s, 2H); 4.95(s, 2H); 3.56(t, 2H, J=7Hz); 1.86(s, 3H); 1.64(t of t, 2H, J=7, 7Hz); 1.33(t of q, 2H, J=7, 7Hz); 0.85(t, 3H, J=7Hz).
[c]NMR(200MHz, $CDCl_3$)δ6.80(d, 2H, J=10Hz); 6.69(d, 2H, J=10Hz); 5.05(s, 2H); 4.43(s, 2H); 2.56(t, 2H, J=7Hz); 1.56(t of t, 2H, J=7, 7Hz); 1.26(t of q, 2H, J=7, 7Hz); 0.83(t, 3H, J=7Hz).

Part D: Preparation of Methyl 2-butyl-1-[4-(2-carboxybenzamido)benzyl]-4-chloroimidazole-5-acetate A chloroform solution (10 mL) of methyl 2-butyl-4-chloro-1-(4-aminobenzyl)imidazole-5-acetate (500 mg, 1.5 mmol, 1 eq) was mixed with a chloroform solution (10 mL) of phthalic anhydride (221 mg, 1.5 mmol, 1 eq). After five minutes of stirring at room temperature, product began to precipitate. After 24 hours, the product was filtered, washed with a minimum amount of $CHCl_3$ and dried to give 400 mg of a white solid. After some evaporation, the mother liquor yielded an additional 220 mg of product, both of which had identical melting points; m.p. 109.5°-112.5°. NMR (200 MHz, DMSO-$d_6$) δ 10.37 (S, 1H); 7.85 (d, 2H, J=8 Hz); 7.71-7.50 (m, 5H); 6.96 (d, 2H, J=10 Hz); 5.12 (s, 2H); 3.60 (s, 2H); 3.49 (s, 3H); 2.55 t, 2, J=7 Hz); 1.52 (m, 2H); 1.27 (m, 2H); 0.83 (t, 3H, J=7 Hz). The carboxylic acid could be titrated with 1.000N NaOH to form the sodium salt. High resolution mass spectrum shows M-18 (loss of $H_2O$). Calcd. Mass for $C_{25}H_{26}ClN_3O_5$: 465.1455. Found: 465.1440.

EXAMPLE 3

Part A: Preparation of 2-Butyl-5-chloro-1-(4-nitrobenzyl)imidazole-4-acetic acid 2-Butyl-5-chloro-4-cyanomethyl-1-(4-nitrobenzyl)-imidazole (4.48 g) was converted to the corresponding carboxylic acid by the procedure described in Example 2, Part A. No product precipitated upon the addition of water (300 mL) until the pH was raised to about 3 with conc. ammonium hydroxide to liberate the imidazole from its HCl salt. The precipitated solids were amorphous and ethyl acetate (5×300 mL) was used to extract the product. The organic layers were dried and concentrated to give 3.93 g of a yellow solid. Recrystallization from hexane/ethyl acetate gave 3.06 g of a white solid; m.p.=138.0°-139.5°. NMR (200 MHz, $CDCl_3$) δ 8.25 (d, 2H, J=10 Hz); 7.21 (d, 2H, J=10 Hz); 5.23 (s, 2H); 3.30 (s, 2H); 2.63 (t, 2H, J=7 Hz); 1.63 (t of t, 2H, J=7,7 Hz); 1.32 (t of q, 2H, J=7,7 Hz); 0.87 (t, 3H, J=7 Hz). Anal. Calcd. for $C_{16}H_{18}ClN_3O_4$; C, 54.63; H, 5.16; N, 11.94. Found: C, 54.75; H, 5.29; N, 12.14.

Part B: Preparation of Methyl 2-butyl-1-[4-(2-carboxybenzamido)benzyl]-5-chloroimidazole-4-acetate 2-Butyl-5-chloro-1-(4-nitrobenzyl)imidazole-4-acetic acid (Part A) was carried on to methyl 2-butyl-1-[4-(2-carboxybenzamido)benzyl]-5-chloroimidazole-4-acetate; m.p. 150.5°-152.5° by the procedure described in Example 2. NMR (200 MHz, DMSO-$d_6$) δ 13.00 (bs, 1H); 10.40 (s, 1H), 7.87 (d, 1H, J=8 Hz); 7.67 (d, 2H, J=8 Hz); 7.71-7.52 (m, 3H); 7.02 (d, 2H, J=8 Hz); 5.13 (s, 2H); 3.61 (s, 3H); 3.52 (s, 2H); 2.59 (t, 2H, J=7 Hz); 2.53 (t of t, 2H, J=7,7 Hz); 1.28 (t of q, 2H, J=7,7 Hz); 0.82 (t, 3H, J=7 Hz). Mass Calcd. for $C_{25}H_{26}ClN_3O_5$.-$H_2O$: 465.1455. Found, 465.1460.

EXAMPLE 4

Part A: Preparation of 2-n-Butyl-4-chloro-5-methoxymethyl-1-(4-nitrobenzyl-)imidazole 2-n-butyl-4-chloro-5-hydroxymethyl-1-(4-nitrobenzyl)imidazole (10.5 g, 32.4 mmol, 1 eq), conc. sulfuric acid (26 mL) and methanol (300 mL) were mixed and refluxed overnight. The solvent was removed in vacuo and the residue taken up in water (about 300 mL). The pH was adjusted to 5 with 1N NaOH and then this aqueous portion extracted with ethyl acetate (3× 250 mL). The organic layers were collected, dried ($MgSO_4$) and the solvent removed in vacuo to yield 11.57 g of an amber oil. NMR (200 MHz, $CDCl_3$) δ 8.22 (d, 2H, J=8 Hz); 7.15 (d, 2H, J=8 Hz); 5.26 (s, 2H); 4.25 (s, 2H); 3.23 (s, 3H); 2.52 (t, 2H, J=7 Hz); 1.64 (t of t, 2H, J=7,7 Hz); 1.28 (t of q, 2H, J=7,7 Hz); 0.81 (t, 3H, J=7 Hz). Anal. Calcd. for $C_{16}H_{20}ClN_3O_3.(H_2O)_{0.5}$: C, 55.41; H, 6.10; Cl, 10.22. Found: C, 55.21; H, 6.22; Cl, 9.92.

Part B: Preparation of 1-(4-Aminobenzyl)-2-n-butyl-4-chloro-5-(methoxymethyl)imidazole To a solution of 2-n-butyl-4-chloro-5-methoxymethyl-1-(4-nitrobenzyl)imidazole (11.22 g) in methanol (100 mL) under $N_2$ was carefully added 1.0 g of 10% palladium on charcoal. Hydrogen gas was then bubbled through the solution for 4 hours. The solution was filtered through Celite® and the solvent removed in vacuo to yield 9.23 g of an amber oil. NMR (200 MHz, $CDCl_3$) δ 7.99 (s, 1H); 6.78 (d of d, 4H, J=5,5 Hz); 5.05 (s, 2H); 4.24 (s, 2H); 3.27 (s, 3H); 2.59 (t, 2H, J=7 Hz); 1.62 (t of t, 2H, J=7,7 Hz); 1.32 (t of q, 2H, J=7,7 Hz); 0.84 (t, 3H,J=7 Hz). Mass Calcd. for $C_{16}H_{23}ClN_3O$; 307.1451. Found: 307.1460.

Part C: Preparation of 2-Butyl-1-[4-(2-carboxybenzamido)benzyl]-4-chloro-5-(methoxymethyl)-imidazole The above compound was prepared from 1-(4-aminobenzyl)-2-n-butyl-4-chloro-5-(methoxymethyl) imidazole (3.00 g, 9.7 mmol, 1 eq) and phthalic anhydride (1.44 g, 9.7 mmol, 1 eq) using the procedure of Example 2, Part D. Work-up yielded 1.71 g of an off-white powder, which was washed with acetonitrile. The insoluble material was filtered and dried to yield 1.17 g of a white powder; m.p. 165.5°-166.5° C. NMR (200 MHz, DMSO-$d_6$) δ 13.01 (m, 1H); 10.39 (s, 1H); 7.87 (d, 1H, J=7 Hz); 7.75-7.46 (m, 5H); 7.03 (d, 2H, J=8 Hz); 5.16 (s, 2H); 4.30 (s, 2H); 3.20 (s, 3H); 2.54 (t, 2H, J=7 Hz); 1.54 (t of t, 2H, J=7,7 Hz); 1.30 (t of q, 2H, J=7,7 Hz); 0.83 (t, 3H, J=7 Hz). Anal. Calcd. for $C_{24}H_{26}ClN_3O_4$: C, 63.22; H, 5.75; Cl, 7.78. Found: C, 63.54; H, 5.76; Cl, 7.58.

Examples 5-18 shown in Table 1 were prepared or could be prepared by the procedures described in Examples 2-4 from the appropriately substituted aniline derivative and a suitable anhydride or acid chloride. Other solvents, such as benzene or ethyl acetate may be substituted for chloroform.

TABLE 1

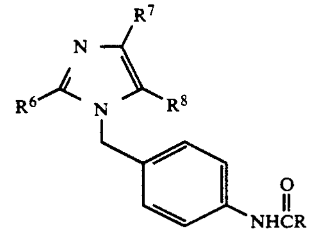

| Ex. No. | R | $R^6$ | $R^7$ | $R^8$ | MP(°C.) |
|---|---|---|---|---|---|
| 5 | 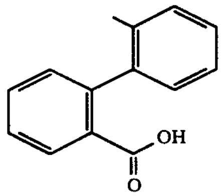 | n-butyl | Cl | $CH_2CO_2CH_3$ | (oil)[a] |
| 6 | 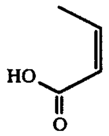 | n-butyl | Cl | $CH_2CO_2CH_3$ | 138.0-141.0 |
| 7 | 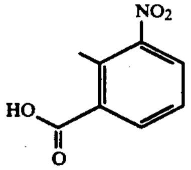 | n-butyl | Cl | $CH_2CO_2CH_3$ | 184.0-186.0 |
| 8 | 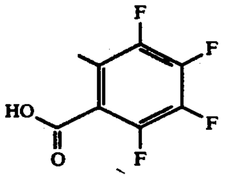 | n-butyl | Cl | $CH_2CO_2CH_3$ | 169.0-170.5 |
| 9 | 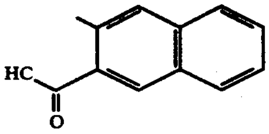 | n-butyl | Cl | $CH_2CO_2CH_3$ | 172.0-173.5 |
| 10 | 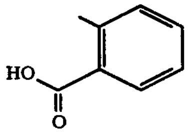 | n-butyl | Cl | $CH_2O\overset{O}{\overset{\|}{C}}CH_3$ | 140.0-144.5 |
| 11 | 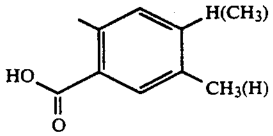 | n-butyl | Cl | $CH_2CO_2CH_3$ | 129-131 |

TABLE 1-continued
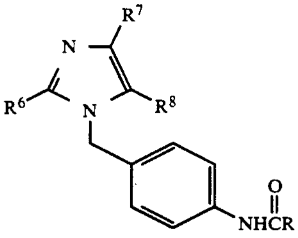
| Ex. No. | R | $R^6$ | $R^7$ | $R^8$ | MP(°C.) |
|---|---|---|---|---|---|
| 12 | 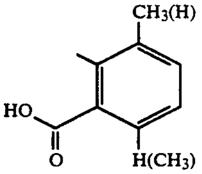 | n-butyl | Cl | $CH_2CO_2CH_3$ | 119-121 |
| 13 | 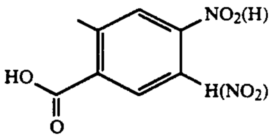 | n-butyl | Cl | $CH_2CO_2CH_3$ | 148-151 |
| 14 | 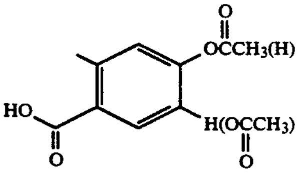 | n-butyl | Cl | $CH_2CO_2CH_3$ | 159-160 |
| 15 | 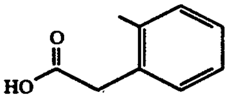<br>or<br>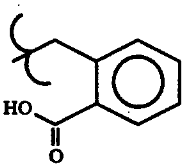 | n-butyl | Cl | $CH_2CO_2CH_3$ | 175-176 |
| 16 | 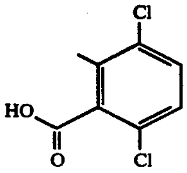<br>(DCHA salt) | n-butyl | Cl | $CH_2CO_2CH_3$ | 199.0-200.0 |
| 17 | 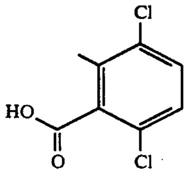 | n-butyl | Cl | $CH_2OCH_3$ | 173.5-177.0 |

TABLE 1-continued

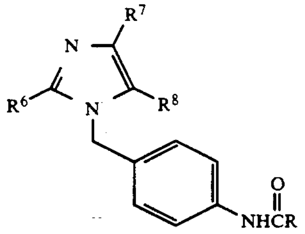

| Ex. No. | R | $R^6$ | $R^7$ | $R^8$ | MP(°C.) |
|---|---|---|---|---|---|
| 18 | 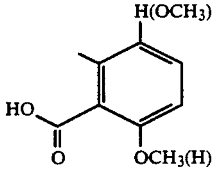 | n-butyl | Cl | $CH_2CO_2CH_3$ | 151-153 |
| 18a | 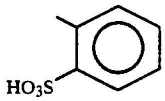 | n-butyl | Cl | $CH_2OCH_3$ | glass[b] |

[a]NMR(200MHz, $CDCl_3$)δ9.48(bs, 1H); 7.87-7.61(m, 2H); 7.5-7.04(m, 8H); 6.69(d, 2H, J=9Hz); 4.98(s, 2H); 3.45(s, 3H); 3.40(s, 2H); 2.56(m, 2H); 1.48(m, 2H); 1.26(m, 2H); 0.72(t, 3H, J=7Hz).
[b]NMR(200MHz, DMSO-$D_6$)δ11.40(s, 1H); 7.93(m, 1H); 7.75(m, 1H); 7.65(d, 2H, J=9Hz); 7.52(m, 2H); 7.07(d, 2H, J=9Hz); 5.18(s, 2H); 4.30(s, 2H); 3.22(s, 3H); 2.54(t, 2H, J=7Hz); 1.53(t of t, 2H, J=7, 7Hz); 1.31(t of q, 2H, J=7, 7Hz); 0.84(t, 3H, J=7Hz).

EXAMPLE 19

Preparation of 2-Butyl-4-chloro-5-hydroxymethyl-1-(4-carboxybenzyl)imidazole The title compound was prepared from 2-butyl-4-chloro-5-hydroxymethyl-1-(4-cyanobenzyl)imidazole by the method described in Example 2, Part A. NMR (200 MHz, $CDCl_3$+DMSO-$d_6$) δ 7.96 (d, 2H, J=8 Hz); 7.13 (d, 2H, J=8 Hz); 5.33 (s, 2H); 4.40 (s, 2H); 2.50 (t, 2H, J=7 Hz); 1.57 (t of t, 2H, J=7,7 Hz); 1.27 (t of q, 2H, J=7,7 Hz); 0.85 (t, 3H, J=7 Hz).

EXAMPLE 20

Preparation of 5-Acetoxymethyl-2-butyl-1-(4-carboxybenzyl)-4-chloroimidazole 2-Butyl-1-(4-carboxybenzyl)-4-chloro-5-(hydroxymethyl)imidazole (2.00 g, 6.2 mmol, 1 eq), acetic anhydride (1.46 mL, 15.5 mmol, 2.5 eq), triethylamine (2.59 mL, 18.6 mmol, 3 eq) and THF (50 mL) were mixed and stirred for 3 days. Water (200 mL) was added to the solution and the mixture was stirred for 0.5 hours. The pH was lowered to 5 with conc. HCl and the mixture extracted with ethyl acetate (3×100 mL). The organic layers were dried ($MgSO_4$) and concentrated to give 2.47 g of a brown oil. This product (2.16 g) was dissolved in a minimum of ethyl acetate and dicyclohexylamine (DCHA) (1.18 mL, 1 eq) was added and mixed. The solution was allowed to slowly evaporate overnight. The DCHA salt so obtained (1.43 g) was subsequently taken up in ethyl acetate (100 mL) and washed with 1N HCl (3×100 mL), followed by brine. The organic layer was dried ($MgSO_4$) and concentrated to give a yellow oil (670 mg). NMR (200 MHz, $CDCl_3$) δ 8.09 (d, 2H, J=10 Hz); 7.05 (d, 2H, J=10 Hz); 5.20 (s, 2H); 4.98 (s, 2H); 2.58 (t, 2H, J=7 Hz); 1.82 (t of t, 2H, J=7,7 Hz); 1.33 (t of q, 2H, J=7,7 Hz); 0.86 (t, 3, J=7 Hz). Anal. Calcd. for $C_{18}H_{21}ClN_2O_4$; C, 59.26; H, 5.80, N, 7.68. Found: C, 58.89; H, 6.17; N, 7.39. Mass Calcd. for $C_{18}H_{21}ClN_2O_4$: 364.1200. Found: 364.1167.

EXAMPLE 21

Preparation of Methyl 2-butyl-4-chloro-1-[4-(trifluoromethylsulfonamido)benzyl]imidazole-5-acetate A solution of triflic anhydride (0.88 mL, 5.2 mmol, 1 eq) in methylene chloride (5 mL) was dripped into a solution of methyl 2-butyl-1-(4-aminobenzyl)-4-chloroimidazole-5-acetate (1,74 g, 5.2 mmol, 1 eq) and triethylamine (1.44 mL, 10.4 mmol, 2 eq) in 20 mL of methylene chloride at −78° C. The solution was kept at −78° C. for 1 hour after which it was allowed to warm to room temperature. After 24 hours, the reaction was quenched with water (100 mL) and the pH adjusted to 5 with conc. HCl and the aqueous extracted with methylene chloride (5×100 mL). The organic layers were dried ($MgSO_4$), concentrated, and the residue flash chromatographed in 1:1 hexane/ethyl acetate on silica gel. The crystalline product which formed in the 1:1 hexane/ethyl acetate solution while the crude product was being applied to the column was isolated (1.03 g). Chromatography of the mother liquor yielded an additional 1.03 g of the title compound as a white solid; m.p. 154.0°-157.0°. The product could be titrated with 1 equivalent of 1.000N NaOH. NMR (200 MHz, $CDCl_3$) δ 7.32 (d, 2H, J=10 Hz; 6.91 (d, 2H, J=10 Hz); 5.15 (s, 2H); 3.62 (s, 3H); 3.46 (s, 2H); 2.55 (t, 2H, J=7 Hz); 1.56 (m, 2H); 1.26 (m, 2H); 0.72 (t, 3H, J=7 Hz). Mass Calcd. for $C_{18}H_{21}N_3O_4SF_3Cl$: 467.0890. Found: 467.0872.

Examples 22-25 in Table 2 were prepared or could be prepared by the procedure described in the above example employing the appropriately substituted 1-(aminobenzyl)-imidazole, which in some instances is followed by ester hydrolysis familiar to one skilled in the art.

TABLE 2

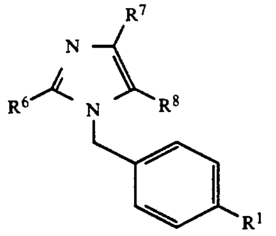

| Ex. No. | $R^1$ | $R^6$ | $R^7$ | $R^8$ | MP(°C.) |
|---|---|---|---|---|---|
| 22 | $NHSO_2CF_3$ | n-butyl | Cl | $CH_2OH$ | |
| 23 | $NHSO_2CF_3$ | n-butyl | Cl | $CH_2OCH_3$ | |
| 24 | $NHSO_2CF_3$ | n-butyl | Cl | 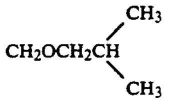 | |
| 25 | $NHSO_2CF_3$ | n-butyl | Cl | $CH_2CO_2H$ | (oil)[a] |

[a]NMR(200MHz, $CDCl_3$)δ7.29(d, 2H, J=10Hz); 6.64(d, 2H, J=10Hz); 5.11(s, 2H); 3.45(s, 2H); 2.56(t, 2H, J=7Hz); 1.60(m, 2H); 1.30(m, 2H); 0.85(t, 3H, J=7Hz)

EXAMPLE 26

Preparation of 2-Butyl-4-chloro-5-[(1H-tetrazol-5-yl)methyl]-1-[3-(1H-tetrazol-5-yl)benzyl]imidazole 2-Butyl-4-chloro-1-(3-cyanobenzyl)-5-(cyanomethyl-)imidazole (2.00 g, 6.4 mmol, 1 eq); ammonium chloride (0.91 g, 17 mmol, 2.7 eq); sodium azide (1.11 g, 17 mmol, 2.7 eq) and DMF (25 mL) were mixed and stirred at 80° C. for 24 hours. The mixture was filtered and the solvent removed by rotary evaporation. The residue was dissolved in water (100 mL) and methylene chloride (100 mL). The layers were separated and the aqueous layer extracted again with methylene chloride (2×100 mL). The aqueous was then acidified with conc. HCl to pH of 3. The solid which precipitated was collected and dried to give 560 mg of the title compound as a tan solid; m.p. 254° (darken), 258° (dec.). The product when titrated with 1.000N NaOH showed the presence of exactly two acidic functionalities. NMR (200 MHz, DMSO-$d_6$) δ 8.79 (d, 1H, J=7 Hz); 7.69 (s, 1H); 7.53 (t, 1H, J=7 Hz); 7.10 (d, 1H, J=7 Hz); 5.37 (s, 2H); 4.23 (s, 2H); 2.57 (t, 2H, J=7 Hz); 1.53 (t of t, 2H, J=7 Hz); 1.27 (t of q, 2H, J=7 Hz); 0.80 (t, 3H, J=7 Hz); Anal. Calcd. for $C_{17}H_{19}ClN_{10}$: C, 51.19; H, 4.80. Found: C, 51.04; H, 4.69.

EXAMPLE 27

Preparation of 2-Butyl-4-chloro-5-[(1H-tetrazol-5-yl)methyl]-1-[4-(1H-tetrazol-5-yl)benzyl]imidazole The title compound was prepared from 2-butyl-4-chloro-1-(4-cyanobenzyl)-5-(cyanomethyl)imidazole by the procedure described in Example 26; m.p. 228 (dark), 229.0°-230° (dec). Titration with 1.000N NaOH showed the presence of exactly two acid functionalities. NMR (200 MHz, DMSO-$d_6$) δ 7.95 (d, 2, J=7 Hz); 7.13 (d, 2, J=7 Hz); 5.34 (s, 2); 4.23 (s, 2); 2.53 (t, 2, J=7 Hz); 1.50 (t of t, 2, J=7,7 Hz); 1.26 (t of q, 2, J=7 Hz); 0.79 (t, 3, J=7 Hz); IR 3420 br, 1930 br, 740 $cm^{-1}$. Mass Calcd. for $C_{13}H_{19}ClN_{10}$: 398.1482. Found: 398.1509.

EXAMPLE 28

Preparation of 2-Butyl-4-chloro-5-hydroxymethyl-1-(4-N-phthalimidobenzyl)imidazole 1-(4-Aminobenzyl)-2-butyl-4-chloro-5-(hydroxymethyl)imidazole (1.00 g, 3.4 mmol, 1 eq) in 20 mL of methylene chloride was dripped into a stirred solution of phthaloyl chloride (0.49 mL, 3.4 mmol, 1 eq), triethylamine (0.95 mL, 6.82 mmol, 2 eq) and methylene chloride (500 mL). After 11 days, the solvent was removed by rotary evaporation and the residue flash chromatographed in 1:1 hexane/ethyl acetate over silica gel to give 240 mg of the title compound as a light yellow glassy solid; m.p. 65.0°-73.5°, NMR (200 MHz, $CDCl_3$) δ (key peaks only) 7.97 (m, 2H); 7.79 (m, 2H); 7.43 (d, 2, J=10 Hz); 7.11 (d, 2H, J=10 Hz); 4.50 (s, 2H); 2.57 (t, 2H, J=7 Hz); 1.67 (m, 2H); 1.34 (m, 2H); 0.87 (t, 3H, J=7 Hz). Mass Calcd. for $C_{23}H_{22}ClN_3O_3$: 423.1349. Found: 423.1324.

EXAMPLE 29

Preparation of Methyl 2-butyl-4-chloro-1-(4-N-phthalimidobenzyl)imidazole-5-acetate Methyl 2-butyl-1-[4-(2-carboxybenzamido)benzyl]-4-chloroimidazole-5-acetate (1.00 g), methanol (50 mL) and 3.6 mL of 3.1N HCl in dioxane were refluxed for 6 days. The solvent was removed in vacuo and the residue taken up in ethyl acetate (100 mL). The organic phase was washed with 1N NaOH (2×100 mL) and brine (1×100 mL), dried ($MgSO_4$) and concentrated. The residue was flash chromatographed over silica gel in 75:25 hexane/ethyl acetate to give 400 mg of an oil which eventually crystallized; m.p. 141.5°-143.0°. NMR (200 MHz, $CDCl_3$) δ 7.92 (m, 2H); 7.80 (m, 2H); 7.43 (d, 2H, J=10 Hz); 7.08 (d, 2H, J=10 Hz); 5.17 (s, 2H); 3.62 (s, 3H); 3.50 (s, 2H); 2.62 (t, 2H, J=7 Hz); 1.71 (t of t, 2H, J=7,7 Hz); 1.36 (t of q, 2H, J=7,7 Hz); 0.89 (t, 3H, J=7 Hz). Mass Calcd. for $C_{25}H_{24}ClN_3O_4$: 465.1455. Found: 465.1440.

EXAMPLE 30

Preparation of Methyl 2-butyl-4-chloro-1-[4-((N-trifluoromethanesulfonyl)anthranilamido)benzyl]imidazole-5-acetate Methyl-1-(4-aminobenzyl)-2-butyl-4-chloro-5-imidazoleacetate (1.00 g, 2.98 mmol, 1 eq), N-(trifluoromethanesulfonyl)anthranoyl chloride which is described in EP 003836, (0.86 g, 2.99 mmol, 1 eq), and sodium bicarbonate (1.25 g, 14.9 mmol, 5 eq) were mixed and stirred in 50 mL methylene chloride (acid chloride was added last). The reaction was worked up after 2.5 hours by filtering, removing the solvent from the filtrate in vacuo and recrystallizing the residue from ethyl acetate/hexane to give 1.07 g of light yellow crystals; m.p. 151.0°-152.0°. NMR (200 MHz, $CDCl_3$) δ 9.32 (s, 1H); 8.02 (d, 1H, J=10 Hz); 7.79 (d, 1H, J=10 Hz); 7.56 (d of d, 2H, J=10, 10 Hz); 7.50 (d, 2H, J=10 Hz); 7.78 (d of d, 1H, J=10, 10 Hz); 6.86 (d, 2H, J=10 Hz); 5.10 (s, 2H); 3.58 (s, 3H); 3.45 (s, 2H); 2.45 (t, 2H, J=7 Hz); 1.52 (t of t, 2H, J=7,7 Hz); 1.22 (t of q, 2H, J=7,7 Hz); 0.75 (t, 3H, J=7 Hz). Titration of the product with 1.000N NaOH shows the presence of exactly one acidic functionality. Anal. Calcd. for $C_{25}H_{26}ClF_3N_4O_5S$: C, 51.15; H, 4.46; N, 9.54. Found: C, 50.95; H, 4.26; N, 9.67.

Mass Calcd. for $C_{25}H_{26}ClF_3N_4O_5S$: 586.1264. Found: 586.1222.

EXAMPLE 31

Preparation of 2-Butyl-4-chloro-1-[4-((N-trifluoro methanesulfonyl)anthranilamido)benzyl]imidazole-5-acetic acid Methyl 2-butyl-4-chloro-1-[4-((N-trifluoromethanesulfonyl)anthranilamido)benzyl]imidazole-5-acetate (400 mg, 0.66 mmol, 1 eq) was stirred in 1.0N NaOH (0.66 mL, 0.66 mmol, 1 eq) for 3 hours under $N_2$. The pH was adjusted to 5 with 1.0N HCl and the product precipitate was collected and dried affording 120 mg of the title compound as a white solid. The NMR spectrum shows the methyl ester to be missing. Mass spectrum shows M-$CO_2$ peak. Mass Calcd. for $C_{23}H_{24}ClF_3N_4O_3S$: 528.1209. Found: 528.1236.

EXAMPLE 32

Preparation of 2-Butyl-1-[4-(2-carboxybenzamido)benzyl]-4-chloroimidazole-5-acetic acid The title compound was prepared from methyl 2-butyl-1-[4-(2-carboxybenzamido)benzyl]-4-chloroimidazole-5-acetate by the procedure described in Example 31; m.p. 170.5°-175.0°.

Examples 33-53 in Table 3 were prepared or could be prepared by the procedures described in Examples 30 and 31 using the appropriate aniline and acid chloride starting materials.

TABLE 3

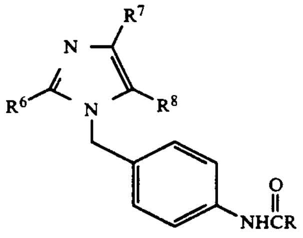

| Ex. No. | R | $R^6$ | $R^7$ | $R^8$ | MP(°C.) |
|---|---|---|---|---|---|
| 33 | 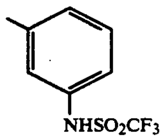 | n-butyl | Cl | $CH_2CO_2CH_3$ | (oil)[a] |
| 34 | 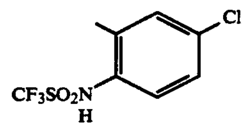 | n-butyl | Cl | $CH_2CO_2CH_3$ | |
| 35 | 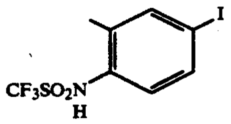 | n-butyl | Cl | $CH_2CO_2CH_3$ | 226-228 |
| 36 | 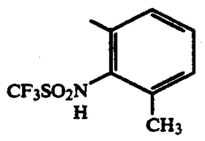 | n-butyl | Cl | $CH_2CO_2CH_3$ | 153-156 (dec.) |
| 37 | 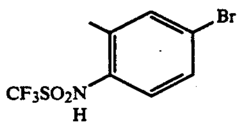 | n-propyl | Cl | $CH_2OH$ | |
| 38 | 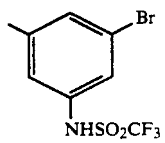 | n-hexyl | H | $CH_2CO_2CH_3$ | |

TABLE 3-continued
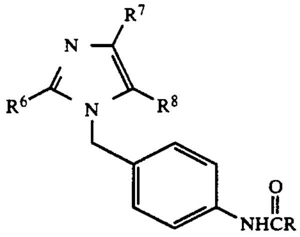
| Ex. No. | R | $R^6$ | $R^7$ | $R^8$ | MP(°C.) |
|---|---|---|---|---|---|
| 39 | 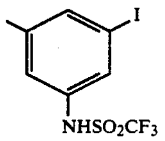 | n-propyl | Cl | $CH_2OH$ | |
| 40 | 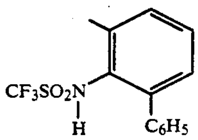 | n-butyl | Cl | $CH_2CO_2CH_3$ | |
| 41 | 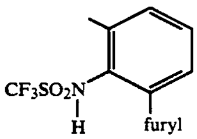 | n-propyl | Cl | $CH_2CO_2CH_3$ | |
| 42 | 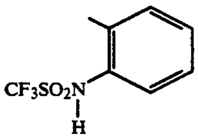 | n-butyl | Cl | $CH_2OH$ | |
| 43 | 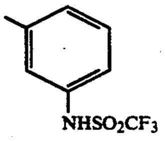 | $CH_3CH_2CH{=}CH-$ | Cl | $CH_2OH$ | |
| 44 | 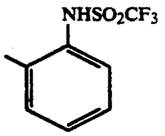 | n-butyl | Cl | $CH_2OCOCH_3$ | |
| 45 | 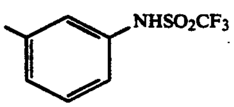 | n-butyl | Cl | $CH_2OCOCH_3$ | |
| 46 | 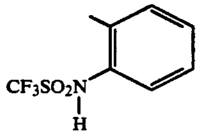 | n-butyl | $CH_2CO_2H$ | Cl | |
| 47 | 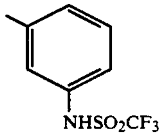 | n-butyl | Cl | $CH_2CO_2H$ | |

TABLE 3-continued
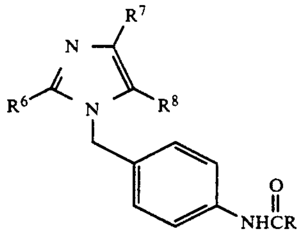
| Ex. No. | R | $R^6$ | $R^7$ | $R^8$ | MP(°C.) |
|---|---|---|---|---|---|
| 48 | 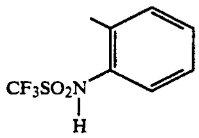 | n-butyl | Cl | n-butyl | |
| 49 | 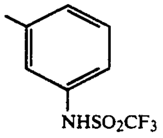 | n-butyl | $CH_2CO_2H$ | Cl | |
| 50 | 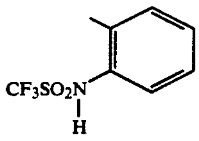 | n-hexyl | Cl | $CH_2CO_2H$ | |
| 51 | 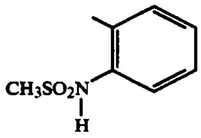 | n-butyl | Cl | $CH_2CO_2CH_3$ | 74.0–79.5 |
| 52 | 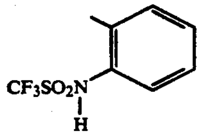 | n-butyl | Cl | 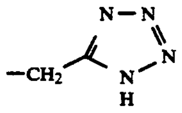 | 200.5–205.0 |
| 53 | 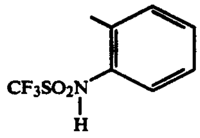 | n-propyl | Cl | 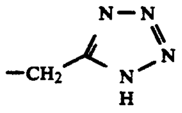 | |
| 53A | 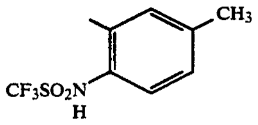 | n-butyl | Cl | $CH_2CO_2CH_3$ | 188.5–189.5 |
| 53B | 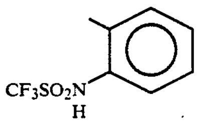 | n-butyl | Cl | $CH_2OH$ | 99.0–102.5 |

TABLE 3-continued

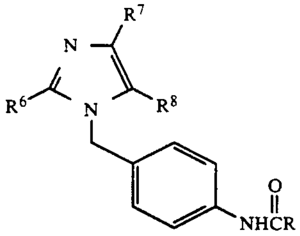

| Ex. No. | R | $R^6$ | $R^7$ | $R^8$ | MP(°C.) |
|---|---|---|---|---|---|
| 53C | 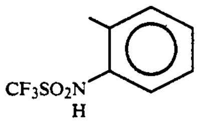 | n-butyl | H | $CH_2OH$ | (glass)[b] |

[a]NMR(200MHz, $CDCl_3$)δ8.69(s, 1H); 7.82(s, 1H); 7.75(d, 1H, J=7Hz); 7.59(d, 2H, J=10Hz); 7.55(d, 1H, J=7Hz); 7.45(t, 1H, J=7Hz); 6.87(d, 2H, J=10Hz); 5.06(s, 2H); 3.60(s, 3H); 3.46(s, 2H); 2.54(t, 2H, J=7Hz); 1.55(t of t, 2H, J=7, 7Hz); 1.24(t of q, 2H, J=7, 7Hz); 0.78(t, 3H, J=7Hz).
[b]NMR(DMSO-$d_6$)δ14.14(bs, 1H); 13.12(bs, 1H), 7.98(d, 1H, J=9Hz); 7.65(d, 2H, J=9Hz); 7.62(s, 1H); 7.48(d, 1H, J=9Hz); 7.31(t, 1H, J=9Hz); 7.17(d, 2H, J=9Hz); 6.98(t, 1H, J=9Hz); 5.43(s, 2H); 4.43(s, 2H); 2.88(t, 2H, J=7Hz); 1.46(t of t, 2H, J=7, 7Hz); 1.23(t of q, 2H, J=7, 7Hz), 0.77(t, 3H, J=7Hz).

EXAMPLE 54

Part A: Preparation of Ethyl n-heptylimidate hydrochloride

To a solution of caprylonitrile (30 g, 0.24 mol) in 25 mL of absolute ethanol cooled to 0° was bubbled HCl gas (9.6 g, 0.26 mol). After 7 days at 0° the viscous solution was diluted with 250 mL of anhydrous ether and the precipitated product was filtered with suction onto a coarse frit and washed liberally with ether before placing under a vacuum to remove residual solvent. The product was stored under nitrogen at 0° to yield 22 g (44%) of a white solid. NMR (200 MHz, DMSO-$d_6$) δ 4.40 (q, 2H, J=7 Hz); 3.30 (m, 4H); 2.45 (m, 4H); 1.40–0.75 (m, 12H). Mass. Spec. 172 (M-Cl).

Part B: Preparation of 2-Heptyl-5-(hydroxymethyl)imidazole

In a high-pressure (bomb) reactor was placed ethyl n-heptylimidate hydrochloride (22 g, 0.11 mol), 1,3-dihydroxyacetone dimer (9.5 g, 0.053 mol) and liquid ammonia (60 g, 3.5 mol). The reactor was sealed and heated to 70° for 12 hours. The crude product (24.7 g) was purified by flash chromatography (silica gel, 300 g; 10:1 EtOAc/EtOH) to give 12.7 g (61%) of a light yellow solid; m.p. 82°–84°. NMR (200 MHz, $CDCl_3$/Acetone-$d_6$) δ 6.75 (s, 1H); 4.50 (s, 2H); 4.50–4.25 (br s, 2H); 2.60 (t, 2H, 8 Hz); 1.75–1.60 (m, 2H); 1.40–1.15 (m, 8H); 0.95–0.75 (m, 3H). Mass Spec. 196, 167 (M-Et), 149 (M-Et-$H_2O$).

Part C: Preparation of 4-Chloro-2-heptyl-5-hydroxymethylimidazole

To a solution of 2-heptyl-5-(hydroxymethyl)imidazole (10.0 g, 51 mmol) in EtOH/1,4-dioxane (1:1; 600 mL) was added N-chlorosuccinimide (7.9 g, 59 mmol). After being stirred for 1 hour at room temperature the solvents were removed on a rotary evaporator and the solid residue was partitioned between ethyl acetate and water (300 mL each). The organic phase was washed with water (150 mL), dried ($MgSO_4$), filtered and concentrated to afford 12.4 g crude product. Recrystallization (1:1 EtOAc/hexane, 60 mL) gave 5.7 g (45%) of white crystals; m.p. 134°–140°. NMR (200 MHz, $CDCl_3$/$CD_3OD$) δ 4.50 (s, 2H); 4.00–3.80 (br s, 2H); 2.65 (t, 2H, 5 Hz); 1.80–1.60 (m, 2H); 1.40–1.20 (m, 8H); 0.90–0.80 (m, 3H). Mass Spec. 230.

Part D: Preparation of 4-Chloro-2-heptyl-5-(hydroxymethyl)-1-(4-nitrobenzyl)imidazole To a solution of 4-chloro-2-heptyl-5-(hydroxymethyl)imidazole (5.2 g, 20.7 mmol) in dry DMF (100 mL) was added anhydrous $K_2CO_3$ (4.3 g, 31.1 mmol) followed by 4-nitrobenzylbromide (5.4 g, 24.9 mmol). The solution was stirred 3–5 hours at 65°–70°. The reaction mixture was poured into a separatory funnel containing EtOAc and $H_2O$ (300 mL each). The aqueous phase was extracted with EtOAc (150 mL) and the combined organic phases were washed three times with $H_2O$ (150 mL) before being dried ($MgSO_4$), filtered and concentrated to give 9.0 g brown crude oil. Chromatography (silica gel, 450 g; 1:1 EtOAc/hexanes) gave 1.3 g (17% overall, 35% of theoretical); m.p. 110°–115°. NMR (200 MHz, $CDCl_3$) δ 8.20 (d, 2H, 5 Hz); 7.20 (d, 2H, 5 Hz); 5.35 (s, 2H); 4.45 (s, 2H); 3.10–3.00 (m, 1H); 2.50 (t, 2H, 5 Hz); 1.75–1.50 (m, 2H); 1.40–1.10 (m, 8H); 0.90–0.75 (m, 3H). Mass Spec. 365.

Part E: Preparation of 1-(4-Aminobenzyl)-4-chloro-2-heptyl-5-hydroxymethylimidazole To a solution of 4-chloro-2-heptyl-5-hydroxymethyl-1-(4-nitrobenzyl)imidazole (1.00 g, 2.7 mmol) in EtOH (30 mL) and glacial acetic acid (5 mL) was added iron powder (2.5 g, 44.8 mmol). The mixture was stirred while being refluxed for 20 minutes. The solution was cooled, the iron was removed by filtration, and the solution was partitioned between EtOAc and 20% aq. $K_2CO_3$ (150 mL each). The organic phase was washed with saturated aqueous NaCl, dried ($MgSO_4$), filtered and concentrated to afford 0.8 g yellow-orange oil. Flash chromatography (silica gel, 25 g; EtOAc/hexanes, 1:1) gave 0.74 g (80%) of yellow-orange oil. NMR (200 MHz, $CDCl_3$) δ 6.80–6.60 (ABq, 4H, 7 Hz,32 Hz); 5.10 (s, 2H); 4.45 (s, 2H); 3.75–3.60 (m, 2H); 2.55 (t, 2H, 5 Hz); 1.75–1.65 (m, 2H); 1.30–1.15 (m, 8H); 0.90–0.80 (m, 3H). Mass Spec. 335.

Part F: Preparation of 4-Chloro-2-heptyl-5-hydroxymethyl-1-[4-((N-trifluoromethanesulfonyl)anthranilamido)benzyl-]imidazole To a solution of 1-(4-aminobenzyl)-4-chloro-2-heptyl-5-(hydroxymethyl)imidazole (211 mg, 0.63 mmol) in dry methylene chloride (10 mL) was added anhydrous sodium bicarbonate (263 mg, 3.1 mmol) followed by N-(trifluoromethanesulfonyl)anthranoyl chloride (180 mg, 0.63 mmol). After 2 hours the mixture was filtered, the filtrate was concentrated and the residue was purified by flash chromatography (silica gel, 10 g; EtOAc) to provide 298 mg (81%) of pale yellow solid; m.p. 90°-95° (dec.). NMR (200 MHz, $CDCl_3/CD_3OD$) δ 7.75-6.80 (m, 8H); 5.10 (s, 2H); 4.40 (s, 2H); 2.50 (t, 2H, 7 Hz); 1.75-1.50 (m, 2H); 1.35-1.15 (m, 8H); 0.95-0.80 (m, 3H). Mass Spec-no mass ion observed due to apparent decomposition; 424 ($M—NHSO_2CF_3—CH_3$).

EXAMPLE 55

Part A: Preparation of Ethyl 3-methoxypropylimidate hydrochloride

This compound was prepared according to the procedure described in Example 54, Part A. From 3-methoxypropionitrile (30 g, 0.35 mol) and hydrogen chloride (14.1 g, 0.39 mol) in ethanol (25 mL) there was obtained 37.7 g (64%) white solid. Mass Spec. 132 (M-Cl).

Part B: Preparation of 5-Hydroxymethyl-2-(2-methoxyethyl)imidazole

This compound was prepared according to the procedure described in Example 54, Part B. From ethyl 3-methoxypropylimidate (36.7 g, 0.22 mol), 1,3-dihydroxyacetone dimer (19.7 g, 0.11 mol) and liquid ammonia (90 g, 5.3 mol) there was obtained 14.0 g (41%) of an off-white solid following chromatography, m.p. 100°-107°. NMR (200 MHz, DMSO-$d_6$) δ 6.70 (s, 1H); 4.30 (s, 2H); 3.6 (t, 2H, 5 Hz); 3.20 (s, 3H); 2.80 (t, 2H, 5 Hz). Mass Spec. 156.

Part C: Preparation of 4-Chloro-5-hydroxymethyl-2-(2-methoxyethyl-)imidazole

This compound was prepared according to the procedure described in Example 54, Part C. From 4-hydroxymethyl-2-(2-methoxyethyl)imidazole (13.5 g, 81.7 mmol) and N-chlorosuccinimide (13.8 g, 103 mmol) was obtained 4.8 g (29%) of light yellow solid following chromatography (silica gel, 500 g; EtOAc); m.p. 102°-108°. NMR (200 MHz, $CDCl_3/CD_3OD$) δ 4.50 (s, 2H); 3.65 (m, 4H); 3.40 (s, 3H); 2.90 (t, 2H, 5 Hz). Mass Part D: Preparation of 4-Chloro-5-hydroxymethyl-2-(2-methoxyethyl)-1-(4-nitrobenzyl)imidazole This compound was prepared according to the procedure described in Example 54, Part D. From 4-chloro-5-hydroxymethyl-2-(2-methoxyethyl)imidazole (4.3 g, 22.6 g) was obtained 2.2 g (30% overall, 60% of theoretical) of light yellow solid; m.p. 91°-95°. NMR (200 MHz, $CDCl_3$) δ 8.15 (d, 2H, 8 Hz); 7.20 (d, 2H, 8 Hz); 5.45 (s, 2H); 4.45 (s, 2H); 3.60 (t, 2H, 5 Hz); 3.20 (s, 3H); 3.15 (s, 1H); 2.80 (t, 2H, 5 Hz). Mass Spec. 325.

Part E: Preparation of 1-(4-Aminobenzyl)-4-chloro-5-hydroxymethyl-2-(2-methoxyethyl)imidazole This compound was prepared according to the procedure described in Example 54, Part E. From 4-chloro-5-hydroxymethyl-2-(2-methoxyethyl)-1-(4-nitrobenzyl-)imidazole (2.2 g, 6.75 mmol) and iron powder (6.7 g, 120 mmol) there was obtained 1.6 g (80%) of light yellow solid; m.p. 164°-167°. NMR (200 MHz, $CDCl_3/CD_3OD$) δ 6.80 (d, 2H, 7 Hz); 6.65 (d, 2H, 7 Hz); 5.15 (s, 2H); 4.45 (s, 2H); 4.30 (s, 3H); 3.60 (t, 2H, 5 Hz); 3.25 (s, 3H); 2.8 (t, 2H, 5 Hz). Mass Spec. 295.

Part F: Preparation of 1-[4-(2-Carboxybenzamido)benzyl]-4-chloro-5-hydroxymethyl-2-(2-methoxyethyl)imidazole To an acetonitrile solution (12 mL) of 1-(4-aminobenzyl)-4-chloro-5-hydroxymethyl-2-(2-methoxyethyl-)imidazole (150 mg, 0.51 mmol) was added an acetonitrile solution (2 mL) of phthalic anhydride (75 mg, 0.51 mmol). After stirring overnight at room temperature a light yellow precipitate was produced. The mixture was cooled to 0°, filtered with suction onto a fine fritted funnel and the solid was washed with cold acetonitrile, chloroform and finally ether (2 mL each) to afford 180 mg (80%) of light tan solid, m.p. 185°-186° (dec.). NMR (200 MHz, $CDCl_3/CD_3OD$) δ 8.05-6.95 (m, 8H); 5.30 (s, 2H); 4.50 (s, 2H); 3.60 (t, 2H, 5 Hz); 3.25 (s, 3H); 2.8 (t, 2H, 5 Hz). Mass Spec. Calcd. for $C_{22}H_{18}ClN_3O_3$ ($M-2H_2O$): 407.1037. Found: 407.1031.

EXAMPLE 56

Preparation of 4-Chloro-5-hydroxymethyl-2-(2-methoxyethyl)-1-[4-((N-trifluoromethanesulfonyl)anthranilamido)benzyl-]imidazole This compound was prepared according to the procedure described in Example 54, Part F. From 1-(4-aminobenzyl)-4-chloro-5-hydroxymethyl-2-(2-methoxyethyl)imidazole (200 mg, 0.68 mmol), N-(trifluoromethanesulfonyl)anthranoyl chloride (190 mg, 0.68 mmol) and sodium bicarbonate (280 mg, 3.3 mmol) in acetonitrile (5 mL) was obtained 300 mg (81%) of tan solid after chromatography (silica gel, 20 g; EtOAc/EtOH, 20:1); m.p. 75°-95° (slow dec.); one spot by TLC. NMR (200 MHz, $CDCl_3/CD_3OD$) δ 8.00-6.80 (m, 8H); 5.15 (s, 2H); 4.45 (s, 2H); 3.60 (t, 2H, 5 Hz); 3.15 (s, 3H); 2.75 (t, 2H, 5 Hz).

The following compounds listed in Table 4 were prepared by the procedures described in Examples 54, Parts D, E and 54, Part F or 55, Part F.

TABLE 4
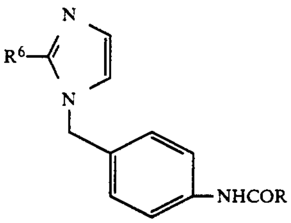
| Ex. No. | R | $R^6$ | MP (°C.) |
|---|---|---|---|
| 57 | 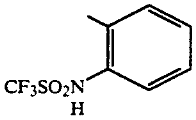 | ethyl | (amorphous solid)[a] |
| 58 | 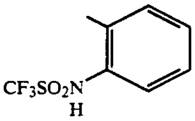 | i-propyl | (amorphous solid)[b] |
| 59 | 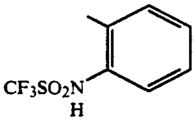 | n-butyl | (amorphous solid)[c] |
| 60 | 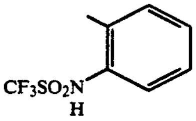 | n-pentyl | (amorphous solid)[d] |
| 61 | 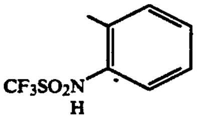 | 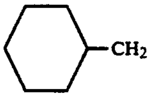 | (amorphous solid)[e] |
| 62 | 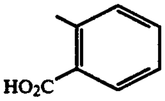 | ethyl | 188-189.5 (free acid) |
| 63 | 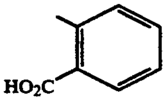 | n-propyl | 181.5-183 (free acid) |
| 64 | 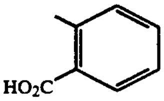 | n-butyl | 188.5-189.5 (Ma+ salt) |
| 65 | 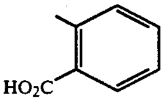 | n-pentyl | 170.5-171.5 |
| 66 | 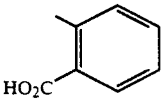 | n-hexyl | 171-171.5 |

TABLE 4-continued

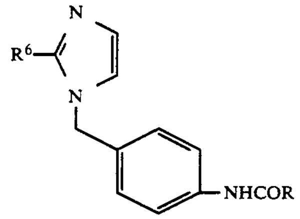

| Ex. No. | R | $R^6$ | MP (°C.) |
|---|---|---|---|
| 67 | 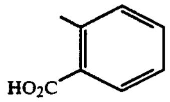 | n-heptyl | 181-182 |
| 68 | 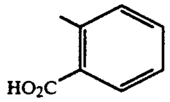 | 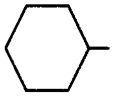 | |
| 69 | 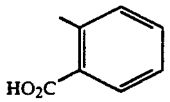 | 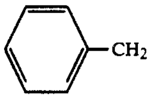 | |
| 70 | 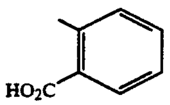 | 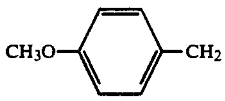 | 150-152 |
| 71 | 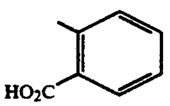 | 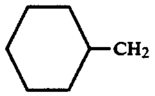 | 175-177 |

[a]NMR δ 8.05(d, 1H); 7.62(d, 2H); 7.52(d, 1H); 7.30(t, 1H); 7.17(m, 3H); 6.93(m, 2H); 5.13(s, 2H); 2.61(quart., 2H); 1.15(t, 3H).
[b]NMR δ 8.04(d, 1H); 7.63(d, 2H); 7.51(d, 1H); 7.28(t, 1H); 7.13(m, 3H); 6.89(m, 2H); 5.14(s, 2H); 3.11(sept., 1H); 1.11(d, 6H).
[c]NMR δ 8.05(d, 1H); 7.64(d, 2H); 7.52(d, 1H); 7.30(t, 1H); 7.17(m, 3H); 6.92(m, 2H); 5.15(s, 2H); 2.66(t, 2H); 1.53(quint., 2H); 1.28(sext., 2H); 0.83(t, 3H).
[d]NMR δ 8.07(d, 1H); 7.68(d, 2H); 7.52(m, 2H); 7.30(m, 4H); 6.93(t, 1H); 5.29(s, 2H); 2.83(t, 2H); 1.56(m, 2H); 1.24(m, 4H); 0.82(t, 3H).
[e]NMR δ 8.03(d, 1H); 7.61(d, 2H); 7.51(d, 1H); 7.28(t, 1H); 7.10(m, 3H); 6.91(t, 1H); 6.78(s, 1H); 5.09(s, 2H); 2.46(d, 2H); 1.62(m, 6H); 0.99(m, 5H).

EXAMPLE 72

Part A: Preparation of 5-Hydroxymethyl-2-mercapto-1-(4-nitrobenzyl-)imidazole A mixture of 4-nitrobenzylamine hydrochloride (75 g, 0.40 mol), 1,3-dihydroxyacetone dimer (32.1, 0.17 mol) and potassium thiocyanate (51.9 g, 0.53 mol) in n-butanol (250 mL) and glacial acetic acid (40 mL) was stirred vigorously at room temperature for 48 hours. The mixture was suction filtered and the solid was washed thrice with water (300 mL) and thrice with ether (300 mL) before being dried overnight under vacuum to give 70.9 g (75%) of a yellow tan powder; m.p. 214°-215° (dec.). NMR (200 MHz, DMSO-$d_6$) δ 12.25 (s, 1H; absent in $D_2O$ shake); 8.20 (d, 2H, 8 Hz); 7.40 (d, 2H, 8 Hz); 6.90 (s, 1H); 5.40 (s, 2H); 5.25 (t, 1H, 5 Hz; absent in $D_2O$ shake); 4.15 (d, 2H, 5 Hz; s in $D_2O$ shake). Mass Spec. 265.

Part B: Preparation of 5-Hydroxymethyl-2-methylthio-1-(4-nitrobenzyl-)imidazole An ethanolic solution of sodium ethoxide was prepared by the gradual addition of sodium hydride (0.70 g of 60% NaH in mineral oil, 17.6 mmol) to absolute ethanol (150 mL). To this 5-hydroxymethyl-2-mercapto-1-(4-nitrobenzyl)imidazole (3.9 g, 14.7 mmol) was added and after being stirred 5-10 minutes, iodomethane (2.5 g, 1.1 mL, 17.6 mmol) was added. After being stirred 3 hours at room temperature, the mixture was concentrated on a rotary evaporator and the residue was partitioned between ethyl acetate (500 mL) and water (250 mL). The aqueous phase was further extracted with ethyl acetate (250 mL) and the combined organic phases were washed with water (150 mL), saturated aqueous sodium chloride (150 mL), dried ($MgSO_4$), filtered and concentrated to leave 4.1 g of yellow-brown solid. Recrystallization from ethyl acetate gave 2.6 g (64%) of light yellow-brown powder; m.p. 160°-162°. NMR (200 MHz, DMSO-$d_6$) δ 8.20 (d, 2H, 7 Hz); 7.30 (d, 2H, 7 Hz); 6.95 (s, 1H); 5.40 (s, 2H);

5.20 (t, 1H, 5 Hz; absent in $D_2O$ shake); 4.40 (d, 3H, 5 Hz; s in $D_2O$ shake); 3.40 (s, 2H; monohydrate; δ 3.5 in $D_2O$); 2.45 (s, 3H). Mass Spec. 279.

Part C: Preparation of 1-(4-Aminobenzyl)-5-hydroxymethyl-2-(methylthio)imidazole This compound was prepared according to the procedure described in Example 54, Part E, from 5-hydroxymethyl-2-methylthio-1-(4-nitrobenzyl)imidazole (21 g, 75.2 mmol) and iron powder (75 g, 1.3 mol) there was obtained 13.5 g (72%) of a yellow hygroscopic solid. NMR (200 MHz, $CDCl_3$) δ 6.90 (s, 1H); 6.85–6.45 (q, 4H, 5 Hz, 51 Hz); 5.10 (s, 2H); 4.40 (s, 2H); 2.40 (s, 3H). Mass Spec. 249.

Part D: Preparation of 1-[4-(2-Carboxybenzamido)benzyl]-5-hydroxymethyl-2-(methylthio)imidazole This compound was prepared according to the procedure described in Example 55, Part F, though in this case the reaction was run in chloroform and the filtered product was washed with chloroform and ether. From 1-(4-aminobenzyl)-5-hydroxymethyl-2-(methylthio)imidazole (323 mg, 1.3 mmol) and phthalic anhydride (192 mg, 1.3 mmol) there was obtained 488 mg (95%) of the title compound as a yellow powder; m.p. 115°–118° (dec.). NMR (200 MHz, $CDCl_3$/DMSO-$d_6$) δ 9.80 (s, 1H); 8.00–6.85 (m, 9H); 5.20 (s, 2H); 4.40 (s, 2H); 2.50 (s, 3H). Mass Spec. 379 (M-$H_2O$).

EXAMPLE 73

Preparation of 1-[4-(2-Carboxybenzamido)benzyl-5-hydroxymethyl-2-methoxyimidazole By repeating Example 72, Parts C and D, but substituting 5-hydroxymethyl-2-methoxy-1-(4-nitrobenzyl)imidazole as starting material in Part C, the compound 1-[4-(2-carboxybenzamido)benzyl]-5-hydroxymethyl-2-methoxyimidazole can be prepared.

EXAMPLE 74

Part A: Preparation of trans-2-(Trifluoromethanesulfonamido)cyclohexanecarboxylic acid Ethyl trans-2-(trifluoromethanesulfonamido)cyclohexanecarboxylate was synthesized from ethyl trans-2-aminocyclohexanecarboxylate [E. J. Moriconi and P. H. Mazzocchi, *J. Org. Chem.*, 31, 1372 (1966)] by the procedure described in Example 21. The crude product (2.59 g, 8.55 mmol, 1 eq) was then hydrolyzed by refluxing in 1.00N NaOH (26.5 mL, 26.5 mmol, 3.1 eq) overnight under $N_2$. Water (100 mL) was then added and the pH adjusted to 3 using 1N HCl. The aqueous was extracted with ethyl acetate (3×100 mL), the organic layers dried ($MgSO_4$) and concentrated to yield a crystalline white solid which was recrystallized from n-butyl chloride. Obtained 1.71 g of product; m.p. 114.5°–118.5°. NMR (200 MHz, DMSO-$d_6$) δ 12.47 (bs, 1H); 9.52 (bs, 1H); 2.35 (d of d of d, 1H, J=10,10,4 Hz); 2.10–1.13 (m, 9H). Anal. Calcd. for $C_8H_{12}F_3NO_4S$: C, 34.91; H, 4.39; N, 5.09. Found, C, 34.73; H, 4.22; N, 5.04.

Part B: Preparation of Methyl 2-butyl-4-chloro-1-[4-(trans-2-(trifluoromethanesulfonamido)cyclohexanecarboxamido)benzyl]imidazole-5-acetate and methyl 2-butyl-4-chloro-1-[4-(cis-2-(trifluoromethanesulfonamido)cyclohexanecarboxamido)benzyl]imidazole-5-acetate trans-2-(Trifluoromethanesulfonamido)cyclohexanecarboxylic acid (500 mg, 1.82 mmol, 1 eq) and thionyl chloride (2.30 mL, 31.5 mmol, 17.3 eq) were mixed and refluxed for 2 hours. The excess thionyl chloride was removed in vacuo and the residue suspended in toluene. The toluene was removed by rotary evaporation and the procedure repeated to remove traces of thionyl chloride. Final rotary evaporation yielded 460 mg of white crystalline acid chloride product which was used without further purification (IR 1789 $cm^{-1}$).

Methyl 2-butyl-4-chloro-1-(4-aminobenzyl)imidazole-5-acetate (530 mg, 1.57 mmol, 1 eq), trans-2-(trifluoromethanesulfonamido)cyclohexanoyl chloride (460 mg, 1.57 mmol, 1 eq) and sodium bicarbonate (400 mg, 4.70 mmol, 3 eq) were mixed and stirred in chloroform (20 mL) overnight. Water (100 mL) was then added, and the pH adjusted to 4 with 1N HCl. The aqueous was extracted with methylene chloride (3×100 mL) and the organic layers dried and concentrated. Gradient flash chromatography of the residue in 60:40 hexane/ethyl acetate to 100% ethyl acetate over silica gel yielded two isomers; both of which were isolated as glasses. The faster eluting product being the minor cis isomer (170 mg) while the slower being the major trans isomer (520 mg).

trans-Isomer; NMR (200 MHz, $CDCl_3$) δ 8.18 (s, 1H); 7.42 (d, 2H, J=10 Hz); 6.84 (d, 2H, J=10 Hz); 6.47 (bd, 1H, J=8 Hz); 5.07 (s, 2H); 3.72 (m, 1H); 3.57 (s, 3H); 3.47 (s, 2H); 2.53 (t, 2H, 7 Hz); 2.24–1.12 (m, 13 Hz); 0.82 (t, 3H, J=7 Hz). Anal. Calcd. for $C_{25}H_{32}ClF_3N_4O_5S$: C, 50.63; H, 5.44; N, 9.45. Found: C, 50.64; H, 5.44; N, 9.16. Mass Calcd. for $C_{25}H_{32}ClF_3N_4O_5S$: 592.1734. Found: 592.1731.

cis-Isomer; NMR (200 MHz, $CDCl_3$) δ 7.94 (s, 1H); 7.42 (d, 2H, J=10 Hz); 6.88 (d, 2H, J=10 Hz); 6.52 (bd, 2H, J=8 Hz); 5.11 (s, 2H); 3.75 (m, 1H); 3.63 (s, 3H); 3.48 (s, 2H); 2.56 (t, 2H, 7 Hz); 2.29–1.25 (m, 13H); 0.86 (t, 3H, J=7 Hz). Anal. Calcd. for $C_{25}H_{32}ClF_3N_4O_5S$: C, 50.63; H, 5.44. Found: C, 49.87; H, 5.65. Mass Calcd. for $C_{25}H_{32}ClF_3N_4O_5S$: 592.1734. Found: 592.1689.

EXAMPLE 75

Part A: Preparation of 2-Butyl-4,5-dicyanoimidazole

Ethyl pentanimidate hydrochloride (42.66 g, 257.8 mmol, 1 eq), diaminomaleonitrile (27.90 g, 258.1 mmol, 1 eq) and pyridine (400 mL) were mixed and refluxed for 48 hours under $N_2$. The solvent was removed by rotary evaporation.

The residue was taken up in ethyl acetate and filtered through a pad (3″×4″) of florisil. The solvent was removed in vacuo and the residue flash chromatographed in 60:40 hexane/ethyl acetate over silica gel to give 16.59 g of a yellow solid which was used in the following step without further purification. An analytical sample was prepared by recrystallizing the crude product (3.03 g) from ether/hexane to give 1.55 g of yellow crystals; m.p. 108.0°–109.0°. NMR (200 MHz, $CDCl_3$) δ 2.86 (t, 2H, J=7 Hz); 1.77 (t of t, 2H, J=7,7 Hz); 1.41 (t of q, 2H, J=7,7 Hz); 0.98 (t, 3H, J=7 Hz). Anal. Calcd.

for $C_9H_{10}N_4$; C, 62.05; H, 5.79; N, 32.16. Found: c, 62.28; H, 5.81; N, 32.22. Mass spectrum shows M-H peak. Mass Calcd. for $C_9H_{10}N_4$-H: 173.0827. Found: 173.0785.

Part B: Preparation of 2-Butyl-4,5-dicyano-1-(4-nitrobenzyl)imidazole 2-n-Butyl-4,5-dicyano-1-(4-nitrobenzyl)imidazole was prepared from 2-n-butyl-4,5-dicyanoimidazole by the procedure in Example 1, Part A using 4-nitrobenzyl bromide as the alkylating agent. The product was obtained as an oil. NMR (200 MHz, $CDCl_3$) δ 8.29 (d, 2H, J=10 Hz); 7.29 (d, 2H, J=10 Hz); 5.36 (s, 2H); 2.67 (t, 2H, J=7 Hz); 1.70 (t of t, 2H, J=7,7 Hz); 1.36 (t of q, 2H, J=7,7 Hz); 0.86 (t, 3H, J=7 Hz); Mass Calcd. for $C_{16}H_{15}N_5O_2$: 309.1225. Found: 309.1211.

Part C: Preparation of 1-(4-Aminobenzyl)-2-butyl-4,5-dicyanoimidazole

A mixture of 2-butyl-4,5-dicyano-1-(4-nitrobenzyl-)imidazole (2.00 g, 6.5 mmol, 1 eq), tin dichloride dihydrate (7.30 g, 32.3 mmol, 5 eq) and ethanol (13 mL) was stirred and heated at 70° for 50 minutes. The reaction was terminated by pouring the mixture onto ice and adjusting the pH to 8 with saturated aqueous $NaHCO_3$. The aqueous mixture was extracted with ethyl acetate (3×100 mL) and the organic layers were dried ($MgSO_4$) and concentrated to give a thick amber oil. This oil was flash chromatographed over silica gel in 75:25 to 70:30 hexane/ethyl acetate yielding 330 mg of yellow crystals; m.p. 99.0°-103.5°. NMR (200 MHz, $CDCl_3$) δ 6.97 (d, 2H, J=10 Hz); 6.68 (d, 2H, J=10 Hz); 5.10 (s, 2H); 2.69 (t, 2H, J=7 Hz); 1.72 (t of t, 2H, J=7,7 Hz); 1.38 (t of q, 2H, J=7,7 Hz); 0.91 (t, 3H, J=7 Hz). Mass Calcd. for $C_{16}H_{17}N_5$: 279.1483. Found: 279.1489.

Part D: Preparation of 2-Butyl-4,5-dicyano-1-[4-(N-trifluoromethanesulfonyl-)anthranilamido)benzyl]imidazole The title compound was prepared by the procedure described in Example 30 starting with 1-(4-aminobenzyl)-2-butyl-4,5-dicyanoimidazole and N-(trifluoromethanesulfonyl)anthranilic acid chloride. NMR (200 MHz, $CDCl_3$+DMSO-$d_6$) δ 7.98 (d, 1H, J=7 Hz); 7.32 (d, 2H, J=7 Hz); 7.62 (d, 1H, J=7 Hz); 7.47 (d of d, 1H, J=7,7 Hz); 7.24 (d of d, 1H, J=7,7 Hz); 7.15 (d, 2, J=7,7 Hz); 5.32 (s, 2H); 2.75 (t, 2H, J=7 Hz); 1.70 (t of t, 2H, J=7,7 Hz); 1.37 (t of q, 2H, J=7,7 Hz); 0.92 (t, 3H, J=7 Hz). Mass Calcd. for $C_{24}H_{21}F_3N_6O_3S$: 503.1348. Found: 530.1343.

EXAMPLE 76

Part A: Preparation of Methyl 1-[4-(N-benzylamino)benzyl]-2-butyl-4-chloroimidazole-5-acetate A mixture of methyl 1-(4-aminobenzyl)-2-butyl-4-chloroimidazole-5-acetate (1.00 g, 3.0 mmol, 1 eq), benzaldehyde (0.30 mL, 3.0 mmol, 1 eq), 4A° powdered molecular sieves (enough to make a slurry) and 40 mL THF was stirred overnight. The next day, more benzaldehyde (0.2 mL) and acidic $Al_2O_3$ (activity 1, 1 g) were added and the slurry stirred another 24 hours. The solids were filtered and the solvent from the filtrate removed in vacuo. The residue was dissolved in methanol (10 mL) and sodium cyanoborohydride was added (0.19 g, 3.0 mmol, 1 eq). The mixture was stirred for 24 hours, after which the solvent was removed in vacuo to yield a green oil which was flash chromatographed over silica gel in 70:30 hexane/ethyl acetate to give 740 mg of product as an oil. NMR (200 MHz, $CDCl_3$) δ 7.42-7.24 (m, 5H); 6.74 (d, 2H, J=7 Hz); 6.56 (d, 2H, J=7 Hz); 4.98 (s, 2H); 4.31 (s, 2H); 3.61 (s, 3H); 3.48 (s, 2H); 2.60 (t, 2H, J=7 Hz); 1.67 (t of t, 2H, J=7,7 Hz); 1.35 (t of q, 2H, J=7,7 Hz); 0.89 (t, 3H, J=7 Hz). Mass Calcd. for $C_{24}H_{28}ClN_3O_2$: 425.1868. Found: 425.1853.

Part B: Preparation of Methyl 2-butyl-1-[4-(N-benzyl-N-(2-(trifluoromethanesulfonamido)benzoyl)amino)benzyl]-4-chloroimidazole-5-acetate The title compound was prepared from the compound of Part A by the procedure described in Example 30. NMR (200 MHz, $CDCl_3$) δ 7.59 (d, 1H, J=10 Hz); 7.33-7.16 (m, 6H); 6.89 (d, 2H, J=10 Hz); 6.76 (d, 2H, J=10 Hz); 6.93-6.70 (m, 2H); 5.12 (s, 2H); 5.02 (s, 2H); 3.55 (s, 3H); 3.39 (s, 2H); 2.47 (t, 2H, J=7 Hz); 1.64 (t of t, 2H, J=7,7 Hz); 1.30 (t of q, 2H, J=7,7 Hz); 0.88 (t, 3H, J=7 Hz). Anal. Calcd. for $C_{32}H_{32}ClF_3N_4O_5S$: C, 56.76; H, 4.76; N, 8.27. Found: C, 56.64; H, 4.90; N, 7.98.

EXAMPLE 77

Part A: Preparation of 2-n-Butyl-4-chloro-5-methoxymethyl-1-[N-methyl-4-aminobenzyl]imidazole 1-(4-Aminobenzyl)-2-n-butyl-4-chloro-5-(methoxymethyl)imidazole (10.94 g) and ethyl formate (150 mL) were mixed and refluxed overnight. The excess ethyl formate was removed in vacuo and another 150 mL added and the mixture was refluxed overnight again. The excess ethyl formate was removed in vacuo and the residue flash chromatographed over silica gel in 1:1 hexane/ethyl acetate to yield 9.52 g of a golden oil which slowly crystallized after several days. This oil (9.40 g, 28 mmol, 1 eq) was dissolved in THF and to it LAH (1M in THF, 84.0 mmol, 84mmol, 3 eq) was slowly added via syringe under $N_2$. After stirring for 1 h, the mixture was worked up as described in Fieser and Fieser, V.1 pg. 584 (Steinhardt procedure) to yield 8.47 g of an orange oil. NMR (200 MHz, $CDCl_3$) δ 6.84 (d, 2H, J=10 Hz); 6.55 (d, 2H, J=10 Hz); 5.02 (s, 2H); 4.26 (s, 2H); 3.27 (s, 3H); 2.81 (s, 3H); 2.58 (t, 2H, J=7 Hz); 1.67 (t of t, 2H, J=7,7 Hz); 1.35 (t of q, 2H, J=7,7 Hz); 0.87 (t, 3H, J=7 Hz). Anal. Calcd. for $C_{17}H_{24}ClN_3O$: C, 63.44; H, 7.52; N, 13.06. Found: C, 63.60; H, 7.61; N, 12.86.

Part B: Preparation of 2-n-Butyl-4-chloro-5-methoxymethyl-1-[4-(N-methyl-2-carboxy-3,6-dichlorobenzamid)benzyl]imidazole 2-n-Butyl-4-chloro-5-methoxymethyl-1-[N-methyl-4-aminobenzyl]imidazole (2.00 g, 6.2 mmol, 1 eq) and 3,6-dichlorophthalic anhydride (1.35 g, 6.2 mmol, 1 eq) were reacted by the procedure described in Example 2, Part D to give 2.37 g of a white powder; m.p. 120.0°-123.5°. The NMR shows a 7:2 mixture of conformers in DMSO-$d_6$. NMR (200 MHz, DMSO-$d_6$) δ (major conformer only) 14.25 (m, 1H); 7.76-6.85 (m, 6H); 5.09 (s, 2H); 4.18 (s, 2H); 3.06 (s, 3H); 2.37 (t, 2H, J=7 Hz); 1.38 (t of t, 2H, J=7,7 Hz); 1.21 (t of q, 2H, J=7,7 Hz); 0.77 (t, 3H, J=7 Hz). Anal. Calcd. for $C_{25}H_{26}Cl_3N_3O_4$: C, 55.72; H, 4.86; Cl, 19.74. Found: C, 55.48; H, 4.88; Cl, 19.77.

EXAMPLE 78

Part A: Preparation of
2-n-Butyl-1-(4-carbomethoxybenzyl)-4-chloro-5-(methoxymethyl)imidazole)

2-Butyl-4-chloro-5-hydroxymethyl-1-(4-carboxybenzyl)imidazole (17.6 g), methanol (500 mL) and conc. sulfuric acid (50 mL) were mixed and refluxed overnight. Potassium carbonate (100 g) was then carefully added to the solution which was cooled over ice. The reaction mixture was then stirred for 2.5 hours. The solvent was removed in vacuo and the residue dissolved in water (1 L). This aqueous mixture was extracted with ethyl acetate (3×400 mL). The organic layers were combined, dried ($MgSO_4$) and the solvent removed in vacuo to yield 15.2 g of an oil. NMR (200 MHz, DMSO-$d_6$) δ 8.46 (d, 2H, J=9 Hz); 7.68 (d, 2H, J=9 Hz); 5.82 (s, 2H); 4.80 (s, 2H); 4.37 (s, 3H); 3.66 (s, 3H); 3.02 (t, 2H, J=7 Hz); 2.01 (t of t, 2H, J=7,7 Hz); 1.77 (t of q, 2H, J=7,7 Hz); 1.33 (t, 3H, J=7 Hz). Anal. Calcd. for $C_{18}H_{23}ClN_2O_3$: C, 61.62; H, 6.61; N, 7.99. Found: C, 61.79; H, 6.78; N, 7.82.

Part B: Preparation of
2-n-Butyl-1-(4-carboxybenzyl)-4-chloro-5-(methoxymethyl)imidazole 2-n-Butyl-1-(4-carbomethoxybenzyl)-4-chloro-5-(methoxymethyl)imidazole (15.2 g, 43.3 mmol, 1 eq), 0.5 N KOH in methanol (130 mL, 65.0 mmol, 1.5 eq), water (10 mL) and methanol (50 mL) were mixed and refluxed for 4 hours. The solvent was removed in vacuo and the residue dissolved in water (300 mL). The pH was adjusted to 4 with conc. HCl and this aqueous mixture extracted with ethyl acetate (3×300 mL). The organic layers were combined, dried ($MgSO_4$), the solved removed in vacuo and the crude residue recrystallized from hexane/butyl chloride to yield 9.6 g of white solid; m.p. 126.5°-127.5°. NMR (200 MHz, DMSO-$d_6$) δ 12.95 (bs, 1H); 7.93 (d, 2H, J=9 Hz); 7.16 (d, 2H, J=9 Hz); 5.30 (s, 2H); 4.31 (s, 2H); 3.19 (s, 3H); 2.50 (t, 2H, J=7 Hz); 1.49 (t of t, 2H, J=7,7 Hz); 1.24 (t of q, 2H, J=7,7 Hz); 0.80 (t, 3H, J=7 Hz). Anal. Calcd. for $C_{17}H_{21}ClN_2O_3$: C, 60.62; H, 6.29; N, 8.32. Found: C, 60.89; H, 6.10; N, 8.03.

Part C: Preparation of
2-n-Butyl-1-[4-(N-(2-carboxyphenyl)carboxamido)benzyl]-4-chloro-5-methoxymethyl)imidazole 2-n-Butyl-1-(4-carboxybenzyl)-4-chloro-5-(methoxymethyl)imidazole (6.00 g, 17.8 mmol, 1 eq), thionyl chloride (13.0 mL, 178 mmol, 10 eq) and chloroform (100 mL) were mixed and refluxed for 6 h. The solvent was removed in vacuo, and the residue dissolved in toluene. The solvent was removed on the rotary evaporator and the evaporation from toluene repeated to remove all of the thionyl chloride. This yielded 6.0 g of acid chloride as an amber gum. IR 1776, 1745 $cm^{-1}$. Anthranilic acid (0.737 g, 5.36 mmol, 1 eq) was dissolved in 1.000N NaOH (10.75 mL, 10.7 mmol, 2 eq) and water (100 mL) and cooled over ice. The aforementioned acid chloride (1.91 g, 5.36 mmol, 1 eq) dissolved in THF (50 mL) was slowly added via a dropping funnel to the stirred and cooled anthranilic acid solution. The following day, more anthranilic acid (74 mg, 0.536 mmol, 0.1 eq) was added to bring the reaction to completion. After 1.5 h, the solution was acidified to pH=5 with 1N HCl and extracted with ethyl acetate (1×100 mL). The ethyl acetate layer was then washed with water (3×50 mL), and brine (1×50 mL), dried ($MgSO_4$) and the solvent removed in vacuo to yield 2.28 g of a brown glass. This glass was dissolved in a minimum amount of ethyl acetate and dicyclohexylamine ("DCHA", 1 eq) was added thereto. The salt did not crystallize and therefore was flash chromatographed over silica gel starting in 100% ethyl acetate and finishing in 1:1 ethyl acetate/isopropanol to yield 1.44 g of an oil. This oil was dissolved in ethyl acetate (100 mL) and a minimum of methanol, and washed with 1N HCl (2×50 mL). The ethyl acetate layer was dried ($MgSO_4$) and the solvent removed in vacuo to yield 0.52 g of an amber oil. NMR (200 MHz, $CDCl_3$) δ 12.53 (s, 1H); 8.91 (d, 1H, J=8 Hz); 8.23 (d, 1H, J=7 Hz); 8.08 (d, 3H, J=7 Hz); 7.62 (t, 1H, J=6 Hz); 7.11 (t, 2H, J=7 Hz); 5.30 (s, 2H); 4.30 (s, 2H); 3.30 (s, 3H); 2.72 (t, 2H, J=7 Hz); 1.72 (t of t, 2H, J=7,7 Hz); 1.31 (t of q, 2H, J=7,7 Hz); 0.83 (t, 3H, J=7 Hz). Anal. Calcd. for $C_{25}H_{25}ClN_3O_4.(H_2O)_{1.5}$: C, 59.81: H, 5.85; Cl, 7.36. Found: C, 59.78; H, 6.38; Cl, 7.51.

Examples 79-84 in Table 5 were made or could be made by procedures described in Example 78 and by methods familiar to one skilled in the art.

TABLE 5

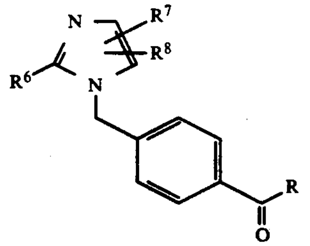

| Ex. No. | $R^6$ | $R^7$ | $R^8$ | R | MP(°C.) |
|---|---|---|---|---|---|
| 79 | n-butyl | Cl | $CH_2OCH_3$ | 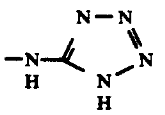 | (>300)[a] |
| 80 | n-butyl | Cl | $CH_2OCH_3$ | 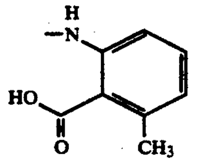 | (glass)[b] |
| 81 | n-butyl | Cl | $CH_2OCH_3$ | 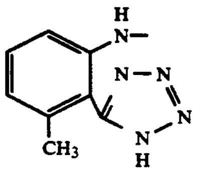 | (white solid)[c] |
| 82 | n-butyl | Cl | $CH_2OCH_3$ | 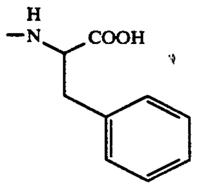 l-isomer | 149-152 |

TABLE 5-continued

| | | | | | |
|---|---|---|---|---|---|
| 83 | n-butyl | Cl | $CH_2OCH_3$ | 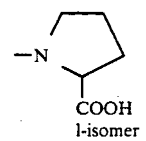 l-isomer | 134.5-136.0 |
| 84 | n-butyl | Cl | $CH_2OCH_3$ | 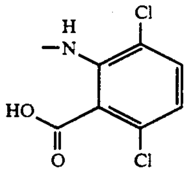 | |

[a]NMR(200MHz, DMSO-$d_6$)δ8.01(d, 2H, J=7Hz); 7.17(d, 2H, J=7Hz); 5.31(s, 2H); 4.27(s, 2H); 3.18(s, 3H); 2.50(t, 2H, J=7Hz); 1.50(t of t, 2H, J=7, 7Hz); 1.21(t of q, 2H, J=7, 7Hz); 0.80(t, 3H, J=7Hz).
[b]NMR(200MHz, $CDCl_3$)δ11.52(s, 1H)8.55(d, 1H, J=7Hz); 8.0(d, 2H, J=7Hz)7.41(t, 1H, J=7Hz); 7.14(d, 2H, J=7Hz); 7.04(d, 1H, J=7Hz); 5.30(s, 2H); 4.25(s, 2H); 3.30(s, 3H); 2.73(t, 2H, J=7Hz); 2.60(s, 3H); 1.68(t of t(br), 2H); 1.29(t of q, 2H, J=7, 7Hz); 0.81(t, 3H, J=7Hz).
[c]NMR(200MHz, $CDCl_3$)δ12.05(s, 1H); 8.88(d, 1H, J=7Hz); 8.23(d, 2H, J=8Hz); 8.11(d, 1H, J=7Hz); 7.51(t, 1H, J=7Hz); 7.25-7.11(m, 3H); 5.29(s, 2H); 4.31(s, 2H); 3.29(s, 3H); 2.62(t, 2H, J=7Hz); 1.63(t of t, 2H, J=7, 7Hz); 1.26(t of q, 2H J=7, 7Hz); 0.75(t, 3H, J=7Hz)IR: 1621, 753 $cm^{-1}$.

EXAMPLE 85

Part A: Preparation of Methyl 4'-methylbiphenyl-3-carboxylate

To a stirred solution of 25.2 g of methyl 3-iodobenzoate and 21.0 g of 4-iodotoluene at 180°-190° under nitrogen was added 30.3 g of copper powder portionwise over 1 hour. When approximately one-third of the copper had been added, the reaction initiated and the temperature increased spontaneously to 240°. The mixture was allowed to cool to 210°, then was held at 210° during the addition of the remaining copper and for an additional hour. The mixture was allowed to cool to room temperature and was filtered employing benzene as solvent; the resulting filtrate was concentrated in vacuum to provide the crude product. Column chromatography on silica gel (elution=50-100% benzene/hexane) followed by distillation furnished 7.60 g of methyl 4'-methylbiphenyl-3-carboxylate [bp: 114°-115° C. (0.025 torr)] as a colorless oil; NMR (200 MHz, $CDCl_3$): δ 8.27 (br S, 1H); 7.99 (d, 1H); 7.77 (d, 1H); 7.50 (t, 1H); 7.39 ($A_2B_2$, 4H); 3.94 (s, 3H); 2.41 (s, 3H).

The following methylbiphenyl starting materials were prepared employing the above procedure.

| | | NMR(200MHz, $CDCl_3$) |
|---|---|---|
| a) | 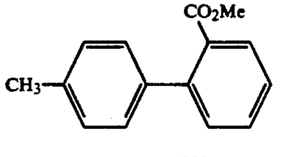 | δ7.78(d, 1H); 7.46(d, 1H); 7.35(t, 2H); 7.19 (s, 4H); 3.64(s, 3H); 2.37(s, 3H) |
| b) | 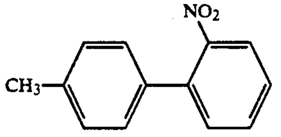 | δ7.80(d of d, 1H); 7.57 (t of d, 1H); 7.41(m, 2H); 7.19(s, 4H); 2.37 (s, 3H) |

Alternatively methyl 4'-methylbiphenyl-2-carboxylate (compound a) and tert-butyl 4'-methylbiphenyl-2-carboxylate can be prepared by chemistry described by A. Meyers via the following five-step procedure.

Step 1: Preparation of 2-Methoxybenzoyl chloride

To 30 g of 2-anisic acid in 500 mL of round-bottom flask was added dropwise 50 mL of thionyl chloride. After all of the thionyl chloride was added the reaction mixture was stirred at room temperature for 18 hours. Excess thionyl chloride was then distilled off by water aspirator and the remaining liquid was vacuum distilled (82°/0.7 mm Hg). Desired 2-methoxybenzoyl chloride was obtained as a colorless liquid, 32 g.

Step 2: Preparation of 4,4-Dimethyl-2-(2-methoxyphenyl)oxazoline 20 g of 2-Amino-2-methyl-1-propanol was dissolved in 100 mL of methylene chloride and the mixture was cooled with ice. Meanwhile, 17 g of 2-methoxybenzoyl chloride prepared from Step 1 was placed in a dropping funnel, diluted with 50 mL of methylene chloride and added dropwise. After the addition of the acid chloride, the cooling ice bath was removed and the reaction mixture was stirred at room temperature for 2 hours.

The reaction mixture was concentrated to remove the solvent and the solids obtained were triturated with water, collected by filtration and washed with water. Thus obtained solids were dried in vacuo to give a colorless light solid, 20.5 g.

The solid was placed in 200 mL of round-bottom flask and 22 mL of thionyl chloride was added slowly to the solid without any solvent. At the beginning of the addition the reaction was vigorous but was controllable. After the addition of thionyl chloride was complete, the yellow reaction mixture was stirred at room temperature for 1 hour. The reaction mixture was poured into 200 mL of ether and the resulting solids were collected and washed with ether. The solids were dissolved in 100 mL of water and the pH of the solution was adjusted to 10 by adding 1N NaOH. The aqueous solution was extracted into ether 3 times. The combined ether extracts were dried ($Na_2SO_4$) and concentrated to give the desired product as a white solid, 18 g, m.p. 70°-72°.

Step 3: Preparation of 2-(4'-Methylbiphenyl-2-yl)-4,4-dimethyloxazoline

4-Methylphenyl Grignard reagent was prepared from 2.5 g of magnesium and 13 mL of 4-bromotoluene in 200 mL of anhydrous THF. The Grignard reagent was added to 10 g of the product from Step 2 in 100 mL of anhydrous THF and the reaction mixture was stirred at room temperature for 2 hours. The reaction mixture was concentrated and the residue was treated with 200 mL of saturated $NH_4Cl$ solution and the mixture was stirred at room temperature for 30 minutes. The aqueous solution was then extracted with ethyl acetate. The crude product obtained upon concentration of the ethyl acetate extracts were purified by flash column chromatography (silica gel, hexane:ethyl acetate=2:1) to give the desired compound as a colorless liquid, 11.8 g.

Step 4: Preparation of 4'-Methylbiphenyl-2-carboxylic acid

A mixture of 10 g of the product from Step 3 and 200 mL of 4.5N HCl was refluxed for 12 hours. During this period of time the desired compound was isolated as a brownish oil floating on the surface of the reaction medium. The reaction mixture was cooled to room temperature. The product which was oily initially began to solidify upon cooling. The product was extracted with ethyl ether. Upon concentration of the ether extract the desired product was obtained as a colorless solid, 7 g, m.p. 140°-142°.

Step 5. Esterification of 4'-methylbiphenyl-2-carboxylic acid

Preparation of methyl 4'-methylbiphenyl-2-carboxylate

To 100 mL of methanol was added dropwise 5 mL of acetyl chloride with ice cooling. After stirring the mixture for 15 minutes, 5 g of the acid from Step 4 was added at once and the mixture was refluxed for 4 hours. The reaction mixture was concentrated to remove the solvent and the desired methyl ester was obtained as a thick liquid, 5 g.

Preparation of tert-butyl 4'-methylbiphenyl-2-carboxylate

To a solution of 42.4 g of 4'-methylbiphenyl-2-carboxylic acid in 200 mL of methylene chloride at 0° was added dropwise 20 mL of oxalyl chloride. The reaction was allowed to warm to 25° and then was stirred at 25° for 3 hours. The solvent was removed in vacuo. The residue was dissolved in benzene, and the benzene then removed in vacuo to provide 46.1 g of crude acid chloride.

The acid chloride prepared above was dissolved in 600 mL of tetrahydrofuran. To this solution at 0° was added 26.0 g of potassium t-butoxide portionwise such that the reaction temperature did not exceed 15°-20° C. The resulting mixture was then allowed to stir at 25° C. for 1 hour. The reaction mixture was poured into water, and the resulting emulsion was extracted with diethyl ether. The combined organic phases were washed with brine, dried over anhydrous sodium sulfate, filtered, and concentrated. Distillation provided 49.5 g of tertbutyl 4'-methyl-biphenyl-2-carboxylate (bp 115°-120°/0.05 torr). NMR (200 MHz, $CDCl_3$): δ 7.73 (d of d, 1H), 7.46-7.27 (m, 3H); 7.18 (s, 4H); 2.40 (s, 3H); 1.30 (s, 9H).

Part B: Preparation of Methyl 4'-bromomethylbiphenyl-3-carboxylate

A solution of 7.31 g of Methyl 4'-methylbiphenyl-3-carboxylate, 5.75 g of N-bromosuccinimide, 0.125 g of azo(bisisobutyronitrile), and 500 mL of carbon tetrachloride was refluxed for 3 hours. After cooling to room temperature the resulting suspension was filtered and then concentrated in vacuo to provide 9.90 g of crude methyl 4'-bromomethylbiphenyl-3-carboxylate which was used in a subsequent reaction without further purification; NMR (200 MHz, $CDCl_3$): δ 8.28 (s, 1H); 8.05 (d, 1H); 7.79 (d, 1H); 7.67-7.48 (m, 5H); 4.55 (s, 2H); 3.98 (s, 3H).

The following bromomethylbiphenyl intermediates were prepared employing the above procedure.

| | | NMR(200MHz, $CDCl_3$) |
|---|---|---|
| a) | 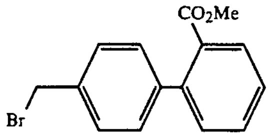 | δ7.82(d, 1H); 7.59-7.23 (m, 7H); 4.52(s, 2H); 3.62(s, 3H) |

-continued

| | | NMR(200MHz, $CDCl_3$) |
|---|---|---|
| b) | 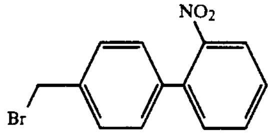 | δ7.86(d of d, 1H); 7.62 (t of d, 1H); 7.53-7.21 (m, 6H); 4.52(s, 2H) |
| c) | 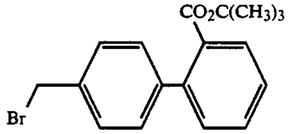 | δ7.79(d, 1H); 7.56-7.24 (m, 7H); 4.51(s, 2H); 1.25(s, 9H). |

Part C: Preparation of 1-[(3'-Carbomethoxybiphenyl-4-yl)methyl]-2-butyl-4-chloro-5-hydroxymethylimidazole To a suspension of 1.43 g of sodium methoxide in 20 mL of dimethylformamide at 25° was added a solution of 5.00 g of 2-butyl-4(5)-chloro-5(4)-hydroxymethyl imidazole in 15 mL of DMF. The resulting mixture was stirred at 25° for 0.25 hours, and then to this mixture was added dropwise a solution of 9.90 g of methyl 4'-bromomethylbiphenyl-3-carboxylate in 15 mL of DMF. Finally, the reaction mixture was stirred at 40° for 4 hours. After cooling to 25°, the solvent was removed in vacuo. The residue was dissolved in ethyl acetate, and this solution was washed with water and brine, dried over anhydrous sodium sulfate, filtered, and concentrated. The crude product contains two regioisomers, the faster moving one by TLC being the more potent isomer. Column chromatography on silica gel (elution: 10-25% ethyl acetate/benzene) afforded 3.85 g of 1-[(3'-carbomethoxybiphenyl-4-yl)methyl]-2-butyl-4-chloro-5-hydroxymethylimidazole (m.p. 162°-163°), the regioisomer of higher $R_f$. NMR (200 MHz, $CDCl_3$) 8.24 (s, 1H); 8.03 (d, 1H); 7.76 (d, 1H); 7.52 (t, 1H); 7.33 ($A_2B_2$, 4H); 5.27 (s, 2H); 4.52 (d, 2H); 3.93 (S, 3H); 2.60 (t, 2H); 1.89 (t, 1H); 1.67 (quint., 2H); 1.35 (sext., 2H); 0.88 (t, 3H).

Part D: Preparation of 1-[(3'-Carbomethoxybiphenyl-4-yl)methyl]-2-butyl-5-hydroxymethylimidazole A mixture of 1.00 g of 10% palladium/carbon and 1.00 g of 1-[(3'-carbomethoxybiphenyl-4-yl)methyl]-2-butyl-4-chloro-5-hydroxymethyl imidazole in 20 mL of methanol was stirred at 25° for five minutes. Hydrogen gas was bubbled into the solution, and the mixture was stirred under $H_2(g)$ (1 atm.) at 25° for 3.5 hours. The mixture was filtered, and the resulting solution concentrated in vacuo. Column chromatography (elution: 0-5% methanol/chloroform) furnished 0.33 g of 1-[(3'-carbomethoxybiphenyl-4-yl)methyl]-2-butyl-5-hydroxymethyl imidazole. NMR (200 MHz, DMSO-$d_6$) δ 8.20 (s, 1H); 7.98 (d, 2H); 7.65 (t, 1H); 7.41 ($A_2M_2$, 4H); 6.80 (s, 1H); 5.30 (s, 2H); 5.12 (t, 1H); 4.37 (d, 2H); 3.90 (s, 3H); 2.52 (t, 2H); 1.51 (quint., 2H); 1.27 (sext., 2H); 0.80 (t, 3H).

The following intermediates shown below were also prepared by the procedures described in Part C or Parts C and D above.

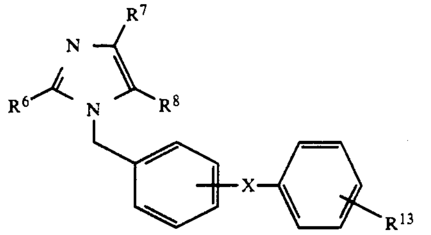

| $R^6$ | $R^7$ | $R^8$ | 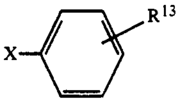 | MP(°C.) |
|---|---|---|---|---|
| n-butyl | Cl | $CH_2OH$ | 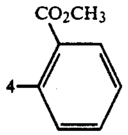 | 162-163 |
| n-butyl | Cl | $CH_2OH$ | 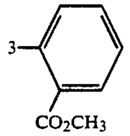 | (oil)[a] |
| n-butyl | H | $CH_2OH$ | 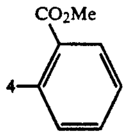 | 139-141 |
| n-butyl | I | $CH_2OH$ | 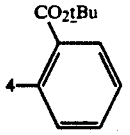 | 125-126 |
| n-butyl | $CH_2OH$ | Cl | 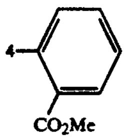 | 116-118 |
| n-butyl | $CH_2OH$ | Cl | 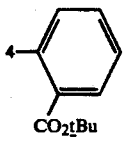 | 122-124 |
| n-butyl | I | $CH_2OH$ | 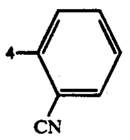 | 180-180.5 |

[a]NMR(200MHz, $CDCl_3$)δ7.82(d of d, 1H); 7.58(t of d, 1H); 7.44(t of d, 1H); 7.35(d of d, 1H); 7.11($A_2B_2$, 4H); 5.21(s, 2H); 4.46(s, 2H); 2.59(t, 2H); 1.60(quint, 2H); 1.29(sext., 2H); 0.82(t, 3H).

Part E: Preparation of 1-[(3'-Carboxybiphenyl-4-yl)methyl]-2-butyl-4-chloro-5-hydroxymethylimidazole A solution of 0.30 g of 1-[(3'-carbomethoxybiphenyl-4-yl)methyl]-2-butyl-4-chloro-5-hydroxymethylimidazole in 16 mL of ethanol and 8 mL of 10% aqueous sodium hydroxide was refluxed for 5 hours. After cooling, the reaction mixture was filtered, and the solvent was removed in vacuo. The residue was dissolved in water, and the solution was acidified to pH 3.5 using hydrochloric acid. The precipitated solid was recovered by filtration and recrystallized from aqueous ethanol to furnish 0.24 g of 1-[(3'-carboxybiphenyl-4-yl)methyl]-2-butyl-4-chloro-5-hydroxymethylimidazole (m.p. 180°-181°); NMR (200 MHz, DMSO-$d_6$): δ 8.26 (s, 1H); 8.04 (d, 1H); 7.77 (d, 1H); 7.52 (t, 1H); 7.36 ($A_2M_2$, 4H); 5.30 (s, 2H); 4.48 (s, 2H); 2.57 (t, 2H); 1.64 (quint., 2H); 1.34 (sext., 2H); 0.87 (t, 3H).

EXAMPLE 86

Part A: Preparation of 1-[(3'-Carbomethoxybiphenyl-4-yl)methyl]-2-butyl-4-chloro-5-methoxymethylimidazole A solution of 5.00 g of 1-[(3'-carbomethoxybiphenyl-4-yl)methyl]-2-butyl-4-chloro-5-hydroxymethylimidazole and 1.0 mL of conc. sulfuric acid in 200 mL of methanol was refluxed for 20 hours. After cooling, the solvent was removed in vacuo, and the residue was poured into saturated sodium bicarbonate solution. The resulting mixture was extracted with methylene chloride, and the combined organic phases were washed with water and brine, dried over anhydrous sodium sulfate, filtered, and concentrated in vacuo. Column chromatography on silica gel (elution: 0-20% ethyl acetate/benzene) furnished 5.35 g of 1-[(3'-carbomethoxybiphenyl-4-yl)methyl]-2-butyl-4-chloro-5-methoxymethylimidazole; NMR (200 MHz, $CDCl_3$): δ 8.26 (t, 1H); 8.03 (d of t, 1H); 7.76 (d of t, 1H); 7.51 (t, 1H); 7.33 ($A_2M_2$, 4H); 5.20 (s, 2H); 4.31 (s, 2H); 3.94 (s, 3H); 3.27 (s, 3H); 2.59 (t, 2H); 1.68 (quint., 2H); 1.34 (sext., 2H); 0.87 (t, 3H).

The following intermediates were prepared or could be prepared using the above described procedure.

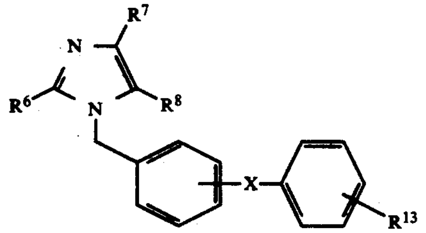

| $R^6$ | $R^7$ | $R^8$ | 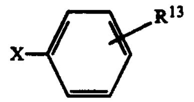 | MP(°C.) |
|---|---|---|---|---|
| n-butyl | Cl | $CH_2OCH_3$ | 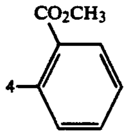 | oil[a] |
| n-butyl | Cl | $CH_2OCH_3$ | 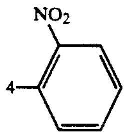 | oil[b] |

-continued

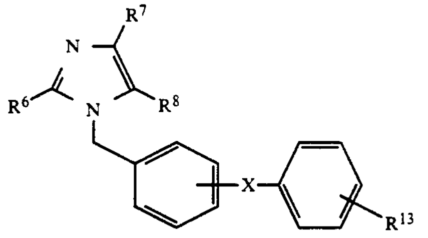

| $R^6$ | $R^7$ | $R^8$ | 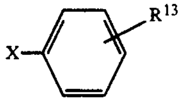 | MP(°C.) |
|---|---|---|---|---|
| n-butyl | Cl | 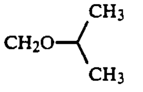 | 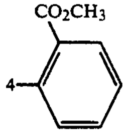 | oil[c] |

[a]NMR(200MHz, $CDCl_3$)δ7.82(d, 1H, J=7Hz); 7.50(t, 1H, J=7Hz); 7.38(t, 1H, J=7Hz); 7.30(d, 1H, J=7Hz); 7.26(d, 2H, J=10Hz); 7.00(d, 2H, J=10Hz); 5.14(s, 2H); 4.32(s, 2H); 3.63(s, 3H); 3.28(s, 3H); 2.60(t, 2H, J=7Hz); 1.70(t of t, 2H, J=7, 7Hz); 1.36(t of q, 2H, J=7, 7Hz); 0.89(t, 3H, J=7Hz).

[b]NMr(200MHz, $CDCl_3$)δ7.88(d of d, 1H); 7.63(t of d, 1H); 7.51(t of d, 1H); 7.41(d of d, 1H); 7.17($A_2B_2$, 4H); 5.20(s, 2H); 4.30(s, 2H); 3.27(s, 3H); 2.59(t, 2H); 1.67(quint., 2H); 1.35(sext., 2H); 0.87(t, 3H).

[c]NMR(200MHz, $CDCl_3$)δ7.84(d, 1H); 7.53(t, 1H), 7.40(t, 1H); 7.29(m, 3H); 7.04(d, 2H), 5.22(s, 2H); 4.36(s, 2H); 3.65(s, 3H); 3.61(sept., 1H), 2.59(t, 2H); 1.68(quint., 2H); 1.33(sext., 2H); 1.14(d, 6H); 0.88(t, 3H).

Part B: Preparation of 1-[(3'-Carboxybiphenyl-4-yl)methyl]-2-butyl-4-chloro-5-methoxymethylimidazole By the procedure described in Example 85, Part E, 3.35 g of the title compound was prepared from 5.35 g of 1-[(3'-carbomethoxy)biphenyl-4-yl)methyl]-2-butyl-4-chloro-5-methoxymethylimidazole; NMR (200 MHz, $CDCl_3$) δ 8.33 (s, 1H); 8.11 (d, 1H); 7.80 (d, 1H); 7.55 (t, 1H); 7.34 ($A_2M_2$, 4H); 5.21 (s, 2H); 4.32 (s, 2H); 3.27 (s, 3H); 2.63 (t, 2H); 1.68 (quint., 2H); 1.34 (sext., 2H); 0.86 (t, 3H).

EXAMPLE 87

Preparation of 1-[(3'-Carboxybiphenyl-4-yl)methyl]-2-butyl-4-chloro-5-acetoxymethylimidazole A solution of 0.10 g of 1-[(3'-carboxybiphenyl-4-yl)methyl]-2-butyl-4-chloro-5-hydroxymethylimidazole, 5 mg of N,N-dimethylaminopyridine, 0.10 mL of acetic anhydride, and 0.14 mL of triethylamine in 8 mL of tetrahydrofuran was stirred for 4.5 hours at 25°. The reaction mixture was poured into water, and dilute aqueous sodium hydroxide was added until the pH of the solution remained in the range of pH 8–9. The solution was then acidified to pH 3.5 using 10% aqueous hydrochloric acid and extracted with ethyl acetate. The combined organic phases were washed with brine, dried over anhydrous sodium sulfate and concentrated. Column chromatography on silica gel (elution: 0.5% i-propanol/chloroform) furnished 0.065 g of 1-[(3'-carboxybiphenyl-4-yl)methyl]-2-butyl-4-chloro-5-acetoxymethylimidazole, m.p. 172°–173°; NMR (200 MHz, DMSO-$d_6$): δ 8.17 (s, 1H); 7.93 (t, 2H); 7.61 (t, 1H); 7.43 ($A_2M_2$, 4H); 5.32 (s, 2H); 4.99 (s, 2H); 2.60 (t, 2H); 1.76 (s, 3H); 1.53 (quint., 2H); 1.28 (sext., 2H); 0.82 (t, 3H).

EXAMPLE 88

Preparation of 1-[(3'-Trimethylacetoxymethoxycarbonylbiphenyl-4-yl)methyl]-2-butyl-4-chloro-5-hydroxymethylimidazole To a solution of 1.25 g of 1-[(3'-carboxybiphenyl-4-yl)methyl]-2-butyl-4-chloro-5-hydroxymethylimidazole in 10 mL of dimethylformamide at 25° was added 0.17 g of sodium methoxide followed after 5 minutes by 0.45 g of chloromethyl trimethylacetate. The mixture was stirred at 25° for 4 days. The solvent was removed in vacuo and the residue was dissolved in ethyl acetate. This solution was washed with water and brine, dried over anhydrous sodium sulfate, filtered and concentrated. Column chromatography on silica gel afforded 1.38 g of the product as a glassy solid. NMR (200 MHz, $CDCl_3$) δ 7.87 (d, 1H); 7.54 (t, 1H); 7.43 (t, 1H); 7.29 (d, 1H); 7.11 ($A_2B_2$, 4H); 5.72 (s, 2H); 5.24 (s, 2H); 4.51 (s, 2H); 2.61 (t, 2H); 2.06 (br s, 1H); 1.68 (quint., 2H); 1.36 (sext., 2H); 1.17 (s, 9H); 0.88 (t, 3H).

EXAMPLE 89

Part A: Preparation of 4'-methylbiphenyl-2-carboxylic acid

Methyl 4'-methylbiphenyl-2-carboxylate (10.0 g, 44.2 mmol, 1 eq), 0.5N KOH in methanol (265.5 mL, 133 mmol, 3 eq), and water (50 mL) were mixed and refluxed under $N_2$. After 5 hours, the solvent was removed in vacuo and water (200 mL) and ethyl acetate (200 mL) added. The aqueous layer was acidified with concentrated hydrochloric acid to a pH of 3 and the layers were separated. The aqueous phase was extracted with ethyl acetate (2×200 mL), the organic layers collected, dried ($MgSO_4$) and the solvent removed in vacuo to yield 8.71 g of a white solid; m.p. 140.0–145.0. NMR (200 MHz, DMSO-$d_6$) δ 7.72 (d, 1H, J= 7 Hz); 7.56 (t, 1H, J=7 Hz); 7.45 (d, 1H, J=7 Hz); 7.40 (t, 1H, J=7 Hz); 7.25 (s, 4H); 2.36 (s, 3H). Anal. Calcd. for $C_{14}H_{12}O_2$; C, 79.23; H, 5.70. Found: C, 79.22; H, 5.47.

Part B: Preparation of 4'-Methyl-2-cyanobiphenyl

4'-Methylbiphenyl-2-carboxylic acid (8.71 g, 41 mmol, 1 eq) and thionyl chloride (30.0 mL, 411 mmol, 10 eq) were mixed and refluxed for 2 hours. The excess thionyl chloride was removed in vacuo and the residue was taken up in toluene. The toluene was removed by rotary evaporation and this toluene evaporation procedure was repeated to ensure that all of the thionyl chloride was removed. The crude acid chloride was then added slowly to cold (0° C.) concentrated $NH_4OH$ (50 mL) so that the temperature was kept below 15°. After 15 minutes of stirring, water (100 mL) was added and solids precipitated. These were collected, washed well with water and dried under high vacuum over $P_2O_5$ in a dessicator overnight to yield 7.45 g of a white solid; m.p. 126.0°–128.5°. NMR (200 MHz, DMSO-$d_6$) δ 7.65–7.14 (m, 10H); 2.32 (s, 3H). Anal. Calcd. for $C_{14}H_{13}NO$: C, 79.59; H, 6.20; N, 6.63. Found C, 79.29; H, 6.09; N, 6.52.

The above product amide (7.45 g, 35 mmol, 1 eq) and thionyl chloride (25.7 mL, 353 mmol, 10 eq) were mixed and refluxed for 3 hours. The thionyl chloride was removed using the same procedure as described above. The residue was washed with a little hexane which partly solubilized the product, but removed the impurity as well to yield 6.64 g of white solid; m.p. 44.0°–47.0°. NMR (200 MHz, DMSO-$d_6$) δ 7.95 (d, 1H, J=8 Hz); 7.78 (t, 1H, J=7 Hz); 7.69–7.32 (m, 6H); 2.39 (s, 3H). Anal. Calcd. for $C_{14}H_{11}N$: C, 87.01; H, 5.74. Found: C, 86.44; H, 5.88.

Part C: Preparation of 4'-bromomethyl-2-cyanobiphenyl

4'-methyl-2-cyanobiphenyl (5.59 g) was brominated in the benzylic position by the procedure in Example 85, Part B using benzoyl peroxide as an initiator. The product was recrystallized from ether to yield 4.7 g of product; m.p. 114.5°–120.0°. NMR (200 MHz, $CDCl_3$) δ 7.82–7.37 (m, 8H); 4.50 (s, 2H). Anal. Calcd. for $C_{14}H_{10}BrN$: C, 61.79; H, 3.70; N, 5.15. Found: C, 62.15; H, 3.45; N, 4.98.

Part D: Preparation of 2-n-butyl-4-chloro-1-[2'-cyanobiphenyl-4-yl)methyl]-5-(hydroxymethyl)imidazole 4'-Bromomethyl-2-cyanobiphenyl (4.6 g) was alkylated onto 2-n-butyl-4-chloro-5-(hydroxymethyl-)imidazole by the procedure described in Example 1, Part A. Work-up and flash chromatography in 1:1 hexane/ethyl acetate over silica gel to separate the regioisomeric products yielded 2.53 g of the faster eluting isomer. Recrystallization from acetonitrile yielded 1.57 g of analytically pure product; m.p. 153.5°–155.5°. NMR (200 MHz, $CDCl_3$) δ 7.82–7.43 (m, 6); 7.12 (d, 2, J=8 Hz); 5.32 (s, 2); 4.52 (s, 2); 2.62 (t, 2, J=7 Hz); 1.70 (t of t, 2, J=7,7 Hz); 1.39 (t of q, 2, J=7,7 Hz); 0.90 (t, 3, J=7 Hz). Anal. Calcd. for $C_{22}H_{22}ClN_3O$: C, 69.56; H, 5.84; N, 11.06. Found: C, 69.45; H, 5.89; N, 10.79.

Part E: Preparation of 2-n-butyl-4-chloro-5-hydroxymethyl-1-[(2'-(1H-tetrazol-5-yl)biphenyl-4-yl)methyl]imidazole 2-n-Butyl-4-chloro-1-[(2'-cyanobiphenyl-4-yl)methyl]-5-(hydroxymethyl)imidazole (11.93 g) was converted to the above product by the procedure described in Example 90, Part C. The product was purified by flash chromatography in 100% ethyl acetate to 100% ethanol over silica gel to yield 5.60 g of a light yellow solid. Recrystallization from acetonitrile yielded 4.36 g of light yellow crystals which still melted broadly. The crystals were taken up in 100 mL of hot acetonitrile. The solid that did not dissolve was filtered off to yield 1.04 g of product as a light yellow solid; m.p. 183.5°–184.5°. Upon cooling, the mother liquor yielded an additional 1.03 g of product as a light yellow solid; m.p. 179.0°–180.0°. NMR (200 MHz, DMSO-$d_6$) δ 7.75–7.48 (m, 4H); 7.07 (d, 2H, J=9 Hz); 7.04 (d, 2H, J=9 Hz); 5.24 (s, 2H); 5.24 (bs, 1H); 4.34 (s, 2H); 2.48 (t, 2H, J=7 Hz); 1.48 (t of t, 2H, J=7,7 Hz); 1.27 (t of q, 2H, J=7,7 Hz); 0.81 (t, 3H, J=7 Hz). Anal. Calcd. for $C_{22}H_{23}ClN_6O$: C, 62.48; H, 5.48; Cl, 8.38. Found for the solids which did not dissolve in 100 mL of acetonitrile: C, 62.73; H, 5.50; Cl, 8.26. Found for the solids obtained from the mother liquor: C, 62.40; H, 5.23; Cl, 8.35.

EXAMPLE 90

Part A: Preparation of 2-n-Butyl-4-chloro-5-chloromethyl-1-[(2'-cyanobiphenyl-4-yl)methyl]imidazole.HCl salt 2-n-Butyl-4-chloro-5-hydroxymethyl-1-[(2'-cyanobiphenyl-4-yl)methyl]imidazole (15.00 g, 39.3 mmol, 1 eq) was converted to the chloride by the procedure in Example 1, Part B. The reaction time was 5 hours. The crude solid product was washed with ether to remove the yellow color. The solid white powdery product was then dried under high vacuum, yield 10.02 g; m.p. 152.0°–154.0°. NMR (200 MHz, $CDCl_3$) δ 7.85–7.46 (m, 6H); 7.20 (d, 2H, J=10 Hz); 5.47 (s, 2H); 4.50 (s, 2H); 3.06 (t, 2H, J=7 Hz); 1.82 (t of t, 2H, J=7,7 Hz); 1.45 (t of q, 2H, J=7,7 Hz); 0.94 (t, 3H, J=7 Hz). Mass Calcd. for $C_{22}H_{21}Cl_2N_3$: 397.1113. Found: 397.1105.

Part B: Preparation of 2-n-Butyl-4-chloro-1-[(2'-cyanobiphenyl-4-yl)methyl]-5-(methoxymethyl)imidazole 2-n-Butyl-4-chloro-5-chloromethyl-1-[(2'-cyanobiphenyl-4-yl)methyl]imidazole.HCl salt (5.00 g, 11.5 mmol, 1 eq), sodium methoxide (1.37 g, 25.3 mmol, 2.2 eq) and methanol (100 mL) were mixed and stirred for 3 days. The solvent was removed in vacuo and ethyl acetate (200 mL) and water (200 mL) added. The layers were separated and the aqueous layer was extracted with ethyl acetate (2×200 mL). The organic layers were dried ($MgSO_4$), the solvent removed in vacuo and the residue flash chromatographed over silica gel in 1:1 hexane/ethyl acetate to yield 4.06 g of a clear light yellow oil. NMR (200 MHz, $CDCl_3$) δ 7.82–7.43 (m, 6); 7.10 (d, 2H, J=7 Hz); 5.23 (s, 2H); 4.32 (s, 2H); 3.30 (s, 3H); 2.60 (t, 2H, J=7 Hz); 1.70 (t of t, 2H, J=7,7 Hz); 1.38 (t of q, 2H, J=7,7 Hz); 0.89 (t, 3H, J=7 Hz). Anal. Calcd. for $C_{23}H_{24}ClN_3O$: C, 68.11; H, 6.54; Cl, 9.58. Found: C, 68.70; H, 6.11; Cl, 9.51. Mass Calcd. for $C_{23}H_{24}ClN_3O$: 393.1607. Found: 393.1616.

Part C: Preparation of 2-n-Butyl-4-chloro-5-methoxymethyl-1-[(2'-(1H-tetrazol-5-yl)biphenyl-4-methyl]imidazole 2-n-Butyl-4-chloro-1-[2'-cyanobiphenyl-4-yl)methyl]-5-methoxymethyl)imidazole (3.94 g, 10 mmol, 1 eq), sodium azide (1.95 g, 30 mmol, 3 eq), and ammonium chloride (1.60 g, 30 mmol, 3 eq) were mixed and stirred in DMF (150 mL) in a round bottom flask connected to a reflux condenser under $N_2$. An oil bath with a temperature controller was then used to heat the reaction at 100° C. for 2 days, after which the temperature was raised to 120° C. for 6 days. The reaction was cooled and 3 more equivalents each of ammonium chloride and sodium azide were added. The reaction was again heated for 5 more days at 120° C. The reaction was cooled, the inorganic salts filtered, and the filtrate solvent removed in vacuo. Water (200 mL) and ethyl acetate (200 mL) were added to the residue and the layers were separated. The aqueous layer was extracted with ethyl acetate (2×200 mL), the organic layers were collected, dried ($MgSO_4$) and the solvent removed in vacuo, to yield a dark yellow oil. Flash chromatography in 100% ethyl acetate yielded 3.54 g of a white glass. NMR (200 MHz, $CDCl_3$) δ 7.83 (d, 1H, J=7 Hz); 7.59 (t, 1H, J=7 Hz); 7.50 (t, 1H, J=7 Hz); 7.39 (d, 1H, J=7 Hz); 7.03 (d, 2H, J=8 Hz); 6.73 (d, 2H, J=8 Hz); 5.08 (s, 2H); 4.12 (s, 2H); 3.18 (s, 3H); 2.32 (t, 2H, J=7 Hz); 1.52 (t of t, 2H, J=7,7 Hz); 1.28 (t of q, 2H, J=7,7 Hz); 0.83 (t, 3H, J=7 Hz). Mass Calcd. for $C_{23}H_{25}ClN_6O$:436.1178. Found: 436.1750.

CAUTION! The above reaction although uneventful in our hands can be potentially explosive! Crystals that sublimed and collected in the reflux condenser during the reaction were not analyzed, but potentially could be ammonium azide. Hydrazoic acid, which is shock sensitive, could also be potentially produced during the reaction and work-up. Extreme care should be taken!

EXAMPLE 91

Part A: Preparation of 2-butyl-4(5)-hydroxymethyl-5(4)-nitroimidazole

To a solution of 5.75 g of 2-butyl-4(5)-hydroxymethylimidazole (prepared as described in U.S. Pat. No. 4,355,040) in 200 mL of aqueous methanol at 25° C. was added concentrated hydrochloric acid until the pH of the solution reached pH 3. The solvent was then removed in vacuo, and the residue was dissolved in 100 mL of chloroform. To this solution at 25° was added dropwise 15.0 mL of thionyl chloride, and the mixture was refluxed for 1 hour. After cooling, the solvent and excess thionyl chloride were removed in vacuo to provide a viscous yellow oil.

To a solution of 20 mL of concentrated sulfuric acid and 10 mL of concentrated nitric acid at −10° was added a solution of the yellow oil, prepared above, in 10 mL of concentrated sulfuric acid. The resulting mixture was heated on a steam bath for 2 hours. After cooling, the reaction mixture was poured onto water-ice, and the resulting emulsion was extracted with chloroform. The combined organic phases were washed with water and brine, dried over anhydrous sodium sulfate, filtered, and concentrated in vacuo. The residue was then dissolved in 100 mL of 1:12-propanol/water. The solution was then refluxed for 16 hours. Finally, after cooling, the solution was concentrated in vacuo. Column chromatography (elution: methanol/chloroform) afforded 2.64 g of 2-butyl-4(5)-hydroxymethyl-5(4)-nitroimidazole. NMR (200 MHz, DMSO-$d_6$): δ 12.92 (br s, 1H); 5.80 (br t, 1H); 4.82 (d, 2H); 2.60 (t, 2H); 1.61 (quint., 2H); 1.25 (sext., 2H); 0.84 (t, 3H).

Part B: Preparation of 1-[(2'-tert-butoxycarbonylbiphenyl-4-yl)methyl]-2-butyl-5-hydroxymethyl-4-nitroimidazole This compound was prepared according to the procedure described in Example 85, Part C. From 2.64 g of 2-butyl-4(5)-hydroxymethyl-5(4)-nitroimidazole and 5.55 g of tert-butyl 4'-bromomethylbiphenyl-2-carboxylate there was obtained 2.05 g of 1-[(2'-tertbutoxycarbonylbiphenyl-4-yl)methyl]-2-butyl-5-hydroxymethyl-4-nitroimidazole. NMR (200 MHz, $CDCl_3$): δ 7.79 (d, 1H); 7.45 (m, 2H); 7.33 (d, 1H); 7.28 (d, 1H); 7.03 (d, 2H); 5.34 (s, 2H); 4.87 (s, 2H); 2.81 (br s, 1H); 2.67 (t, 2H); 1.73 (quint., 2H); 1.37 (sext. 2H); 1.27 (s, 9H); 0.90 (t, 3H).

Part C: Preparation of 1-[(2'-carboxybiphenyl-4-yl)methyl]-2-butyl-5-hydroxymethyl-4-nitroimidazole A solution of 1.98 g of 1[(2'-tert-butoxycarbonylbiphenyl-4-yl)methyl]-2-butyl-5-hydroxymethyl-4-nitroimidazole, 20 mL of trifluoroacetic acid, and 20 mL of methylene chloride was stirred at 25° for 1 hour. At this point, the solution was poured into water. The resulting mixture was adjusted to pH 3 using 10% sodium hydroxide solution and then extracted with chloroform. The combined organic phases were washed with brine, dried over anhydrous magnesium sulfate, filtered, and concentrated in vacuo. Column chromatography (elution: methanol/chloroform) provided 1.49 g of 1-[(2'-carboxybiphenyl-4-yl)methyl]-2-butyl-5-hydroxymethyl-4-nitroimidazole; m.p. 204°–205.5°. NMR (200 MHz, DMSO-$d_6$): δ 7.71 (d, 1H); 7.56 (t, 1H); 7.43 (t, 1H); 7.32 (m, 3H); 7.15 (d, 2H); 5.63 (br s, 1H); 5.42 (s, 2H); 4.83 (s, 2H); 2.54 (t, 2H); 1.50 (quint., 2H); 1.24 (sext., 2H); 0.76 (t, 3H).

EXAMPLE 92

Part A: Preparation of 1-[(2'-tert-butoxycarbonylbiphenyl-4-yl)methyl]-2-butyl-4-iodo-5-(2-methoxyethoxymethoxymethyl-)imidazole To a solution of 5.56 mL of 1.6M n-butyllithium/hexane in 80 mL of tetrahydrofuran at 0° was added dropwise 1.15 mL of t-butanol. To the solution was added 3.28 g of 1-[(2'-tert-butoxycarbonylbiphenyl-4-yl)methyl]-2-butyl-5-hydroxymethyl-4-iodoimidazole followed by 1.15 mL of 2-methoxyethoxymethyl chloride. The resulting solution was stirred at 25° for 16 hours. The mixture was diluted with diethyl ether, washed with water and brine, dried over anhydrous sodium sulfate, filtered and concentrated. Column chromatography afforded 2.61 g of 1-[2'-tert-butoxycarbonylbiphenyl-4-yl)methyl]-2-butyl-4-iodo-5-(2-methoxyethoxymethoxymethyl)imidazole. NMR (200 MHz, $CDCl_3$): δ 7.78 (d, 1H); 7.43 (m, 2H); 7.28 (m, 3H); 6.98 (d, 2H); 5.26 (s, 2H); 4.69 (s, 2H); 4.45 (s, 2H); 3.68 (m, 2H); 3.57 (m, 2H); 3.37 (s, 3H); 2.58 (t, 2H); 1.67 (quint., 2H); 1.34 (sext., 2H); 1.26 (s, 9H); 0.87 (t, 3H).

Part B: Preparation of 1-[(2'-tert-butoxycarbonylbiphenyl-4-yl)methyl]-2-butyl-5-(2-methoxyethoxymethoxymethyl)-4-trifluoromethylimidazole To a suspension of 22.4 g of cadmium powder powder in 50 mL of dimethylformamide at 25° was added dropwise 8.60 mL of bromochlordifluoromethane. The resulting mixture was stirred at 25° for 2 hours and then was filtered through a medium-fritted Schlenk funnel under nitrogen pressure to provide a dark brown solution of the trifluoromethyl cadmium reagent.

To a mixture of 15 mL of the above solution and 20 mL of hexamethylphosphoric triamide at 0° was added 2.10 g of copper(I)bromide followed by 2.61 g of 1-[(2'-tert-butoxycarbonylbiphenyl-4-yl)methyl]-2-butyl-4-iodo-5-(2-methoxyethoxymethoxymethyl)imidazole in 5 mL of dimethylformamide. The reaction mixture was stirred at 70°–75° for 6 hours. After cooling, the mixture was diluted with water and then extracted with methylene chloride. The combined organic phases were washed with water and brine, dried over anhydrous sodium sulfate, filtered, and concentrated. Column chromatography (elution: ethyl acetate/hexane) afforded 2.30 g of 1-[(2'-tert-butoxycarbonylbiphenyl-4-yl)methyl]-2-butyl-5-(2-methoxyethoxymethoxymethyl)-4-trifluoromethylimidazole. NMR (200 MHz, $CDCl_3$): δ 7.79 (d, 1H); 7.46 (m, 2H); 7.28 (m, 3H); 7.00 (d, 2H); 5.28 (s, 2H); 4.71 (s, 2H); 4.58 (s, 2H); 3.66 (m, 2H); 3.54 (m, 2H); 3.38 (s, 3H); 2.62 (t, 2H); 1.70 (quint., 2H); 1.36 (sext., 2H); 1.27 (s, 9H); 0.88 (t, 3H).

Part C: Preparation of 1-[(2'-carboxybiphenyl-4-yl)methyl]-2-butyl-5-hydroxymethyl-4-trifluoromethylimidazole A solution of 2.30 g of 1-[(2'-tert-butoxycarbonylbiphenyl-4-yl)methyl]-2-butyl-5-(2-methoxyethoxymethoxymethyl)-5-trifluoromethylimidazole in 200 mL of 1.5M aqueous tetrafluoroboric acid/acetonitrile was stirred at 25° for 18 hours, and then the mixture was poured into water. The resulting aqueous solution was adjusted to pH 3 employing saturated sodium bicarbonate solution and then was extracted with chloroform. The combined organic phases were washed with brine, dried over anhydrous sodium sulfate, filtered, and concentrated. Column chromatography (elution: methanol/chloroform) provided 1.38 g of 1-[(2'-carboxybiphenyl-4-yl)methyl]-2-butyl-5-hydroxymethyl-4-trifluoromethylimidazole (m.p. 198°–199.5°). NMR (200 MHz, DMSO-$d_6$): δ 7.75 (d, 1H); 7.54 (t, 1H); 7.43 (t, 1H); 7.32 (m, 3H); 7.10 (d, 2H); 5.36 (s, 2H); 4.51 (s, 2H); 2.56 (t, 2H); 1.56 (quint., 2H); 1.30 (sext., 2H); 0.83 (t, 3H).

EXAMPLE 92A

Part A: Preparation of 1-[(2'-tert-butoxycarbonylbiphenyl-4-yl)methyl]-2-butyl-5-(2-methoxyethoxymethoxymethyl)-4-pentafluoroethylimidazole To 20 mL of the trifluoromethyl cadmium reagent prepared in Example 92, Part B was added 2.80 g of copper(I) bromide, and the resulting solution was stirred at 25° for 14 hours. At this point, 20 mL of hexamethylphosphoric triamide was added, followed by 1.90 g of 1-[(2'-tert-butoxycarbonylbiphenyl-4-yl)methyl]-2-butyl-4-iodo-5-(2-methoxyethoxymethoxymethyl)imidazole in 5 mL of dimethylformamide. The reaction mixture then was stirred at 70°–75° for 6 hours. After cooling, the mixture was diluted with water and then extracted with methylene chloride. The combined organic phases were washed with water and brine, dried over anhydrous sodium sulfate, filtered and concentrated. Column chromatography (elution: ethyl acetate/benzene) afforded 1.71 g of 1-[2'-tertbutoxycarbonylbiphenyl-4-yl)methyl]-2-butyl-5-(2-methoxyethoxymethoxymethyl)-4-pentafluoroethylimidazole. NMR (200 MHz, $CDCl_3$): δ 7.77 (d, 1H), 7.55–7.35 (m, 2H), 7.27 (m, 3H), 6.97 (d, 2H), 5.28 (s, 2H), 4.69 (s, 2H), 4.55 (s, 2H), 3.65 (m, 2H), 3.53 (m, 2H), 3.33 (s, 3H), 2.63 (t, 2H), 1.68 (quint., 2H), 1.35 (sext., 2H), 1.26 (s, 9H), 0.87 (t, 3H).

Part B: Preparation of 1-[(2'-carboxybiphenyl-4-yl)methyl]-2-butyl-5-hydroxymethyl-4-pentafluoroethylimidazole This compound was prepared according to the procedure described in Example 92, Part C. From 1.71 g of 1-[(2'-tert-butoxycarbonylbiphenyl-4-yl)methyl]-2-butyl-5-(2-methoxyethoxymethoxymethyl)-4-pentafluoroethylimidazole was obtained 0.72 g of 1-[(2'-carboxybiphenyl-4-yl)methyl]-2-butyl-5-hydroxymethyl-4-pentafluoroethylimidazole (mp 190°–191°). NMR (200 MHz, DMSO-$d_6$): δ 7.72 (d, 1H), 7.61–7.42 (m, 2H), 7.34 (m, 3H), 7.11 (d, 2H), 5.50 (br s, 2H), 5.39 (s, 2H), 4.50 (s, 2H), 2.55 (t, 2H), 1.50 (quint., 2H), 1.25 (sext, 2H), 0.80 (t, 3H).

EXAMPLE 92 B

Part A: Preparation of 2-butyl-1-[(2'-cyanobiphenyl-4-yl)methyl]-5-hydroxymethyl-4-trifluoromethylimidazole This compound was prepared according to the procedures described in Example 92, Parts A–C. From 2-butyl-1-[(2'-cyanobiphenyl-4-yl)methyl]-5-hydroxymethyl-4-iodoimidazole was obtained 2-butyl-1-[(2'-cyanobiphenyl-4-yl)methyl]-5-hydroxymethyl-4-trifluoromethylimidazole (mp 136.5°–137.5°). NMR (200 MHz, $CDCl_3$): δ 7.76 (d, 1H), 7.64 (t, 1H), 7.56–7.42 (m, 4H), 7.08 (d, 2H), 5.33 (s, 2H), 4.65 (d, 2H), 3.65 (t, 2H), 1.97 (br t, 1H), 1.69 (quint., 2H), 1.38 (sext., 2H), 0.89 (t, 3H).

Part B: Preparation of 2-butyl-5-hydroxymethyl-4-trifluoromethyl-1-[(2'-(triphenylmethyltetrazol 5-yl)biphenyl-4-yl)methyl]imidazole A solution of 6.45 g of 2-butyl-1-[(2'-cyanobiphenyl-4-yl)methyl]-5-hydroxymethyl-4-trifluoromethylimidazole and 4.00 g of trimethylstannylazide in 65 mL of xylene was stirred at 115°–120° C. At 24 hours and at 48 hours into the reaction, 1.00 g portions of trimethylstannylazide were added. After a total of 64 hours at 115°–120° C., the mixture was cooled to 80° C. and filtered to provide 10.22 g of an off-white solid.

To a suspension of this solid in 60 mL of methylene chloride and 10 mL of THF at 25° C. was added dropwise over several minutes 1.65 mL of 10N aqueous sodium hydroxide solution, and the mixture was stirred at 25° C. for 15 minutes. To the reaction mixture then was added 4.60 g of triphenylmethylchloride and the resulting mixture was stirred at 25° C. for 2 hours. Finally the mixture was poured into water and then extracted with methylene chloride. The combined organic phases were washed with water and brine, dried over anhydrous sodium sulfate, filtered and concentrated. Recrystallization of the crude product from toluene/hexane afforded 7.59 g of 2-butyl-5-hydroxymethyl-4-trifluoromethyl-1-[(2'-triphenylmethyltetrazol-5-yl)biphenyl-4-yl)methyl]imidazole.

NMR (200 MHz, $CDCl_3$): δ 7.93 (d of d, 1H), 7.46 (m, 2H), 7.35–7.08 (m, 12H), 6.90 (d, 6H), 6.71 (d, 2H), 5.13 (s, 2H), 4.39 (d, 2H), 2.53 (t, 2H), 1.63 (quint., 2H), 1.30 (sext., 2H), 0.85 (t, 3H).

Part C: Preparation of 2-butyl-5-hydroxymethyl-1-[(2'-(1H-tetrazol-5-yl)biphenyl-4-yl)methyl]-4-trifluoromethylimidazole A solution of 4.06 g of 2-butyl-5-hydroxymethyl-4-trifluoromethyl-1-[(2'-(triphenylmethyltetrazol-5-yl)biphenyl-4-yl)methyl]imidazole in 40 mL of 10% hydrochloric acid and 80 mL of tetrahydrofuran was stirred at 25° for 2 hours and then poured into water containing an excess of sodium hydroxide. The aqueous solution was washed with diethyl ether, adjusted to pH 3 with 10% hydrochloric acid, and then extracted with chloroform. The combined chloroform extracts were washed with brine, dried over anhydrous sodium sulfate, filtered, and concentrated. Column chromatography (elution: 10% methanol/chloroform) furnished 2.04 g of 2-butyl-5-hydroxymethyl-1-[(2'-(1H-tetrazol-5-yl)biphenyl-4-yl)methyl]-4-trifluoromethylimidazole as an amrphous solid.

NMR (200 MHz, DMSO-$d_6$): δ 7.68–7.47 (m, 4H), 7.02 ($A_2B_2$, 4H), 5.43 (br s, 1H), 5.27 (s, 2H), 4.44 (s, 2H), 2.47 (t, 2H), 1.47 (quint., 2H), 1.22 (sext., 2H), 0.77 (t, 3H).

EXAMPLE 93

Part A: Preparation of 4-azidomethyl-2'-methoxycarbonylbiphenyl

To a stirred solution of 4-bromomethyl-2'-methoxycarbonylbiphenyl (150 g, 0.49 mol) in dry DMF (500 ml) was added $NaN_3$ (80 g, 1.23 mol, 2.5 eq). The mixture was stirred at room temperature overnight (ca. 18 hours), filtered, and the filtrate was partitioned between ethyl acetate and $H_2O$ (500 ml each). The organic phase was washed twice more with $H_2O$, once with saturated aqueous NaCl solution and dried over anhydrous magnesium sulfate before being filtered and concentrated to leave 111.3 g (85%) of a yellow oil, used in the following step without further purification. NMR ($CDCl_3$, TMS, δ) 7.9-7.1 (m, 8H); 4.35 (s, 2H); 3.55 (s, 3H) IR $V_{max}$ 2487 $cm^{-1}$.

Part B: Preparation of 4-aminomethyl-2'-methoxycarbonylbiphenyl hydrochloride

The azido compound prepared above was dissolved in liter of methanol. The solution was divided into three equal volumes and placed in 500 ml Parr bottles. To each flask was added 6.7 g of 5% Pd on carbon (Caution: Pyrophoric! add under a $N_2$ atmosphere). The flasks were shaken on a Parr hydrogenator under 40-50 psi $H_2$ for 4-5 hours (overnight is also acceptable). The mixture was suction filtered through a bed of Celite * and the filtrate was concentrated to leave a viscous yellow residue (88 g). This was dissolved in EtOAc (500 ml) to which was added with stirring a solution of EtOAc saturated with anhydrous HCl (100-150 ml) until precipitation was complete. The amine hydrochloride as produced was suction filtered, washed with EtOAc and hexanes and dried under vacuum to afford 48.5 g (40% overall from the bromide) white solid; m.p. 204°-208°. NMR ($CDCl_3$, $CD_3OD$; TMS) δ 7.9-7.25 (m, 8H); 4.2 (s, 2H); 4.1-3.8 (br, 3H; shifts in $D_2O$); 3.6 (s, 3H). HRMS calcd. for $C_{15}H_{15}NO_2$ (free base); M/Z 241.1103; Found: M/Z: 241.1045.

Part C: Preparation of 1-[(2'-carboxybiphenyl-4-yl)methyl]-2-propylthio-5-hydroxymethylimidazole The title compound was prepared from methyl 4'-aminomethylbiphenyl-2-carboxylate by the procedures described in Examples 72, Parts A and B, and 85, Part E; m.p. 194°-195°.

The 4-biphenylmethyl compounds in Table 6 were prepared or could be prepared by the procedures illustrated in Examples 85-92B or by procedures previously described.

TABLE 6

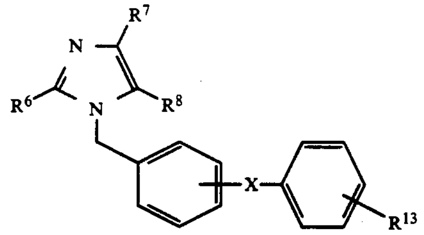

| Ex. No. | $R^6$ | $R^7$ | $R^8$ | 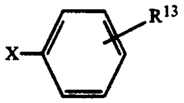 | MP (°C.) |
|---|---|---|---|---|---|
| 94 | n-butyl | Cl | $CH_2OH$ | 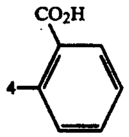 | 168-169.5 |
| 95 | n-butyl | $CH_2OH$ | Cl | 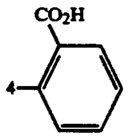 | 197-198 |
| 96 | n-butyl | H | $CH_2OH$ | 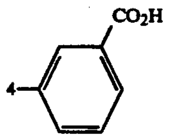 | 154-155 |
| 97 | n-butyl | H | $CH_2OH$ | 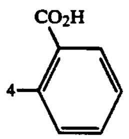 | (amorphous solid)[a] |
| 98 | n-butyl | Cl | $CH_2OCH_3$ | 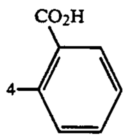 | 166.5-169.0 |

TABLE 6-continued
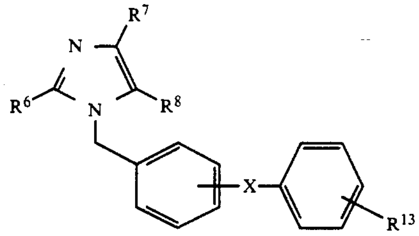
| | | | | | |
|---|---|---|---|---|---|
| 99 | n-butyl | Cl | $CH_2OCH(CH_3)_2$ | 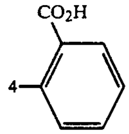 | 156-158 |
| 100 | n-butyl | Br | $CH_2OH$ | 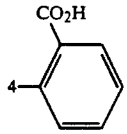 | 175-178 |
| 101 | n-butyl | F | $CH_2OH$ | 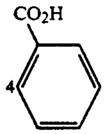 | |
| 102 | n-butyl | I | $CH_2OH$ | 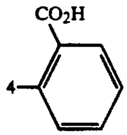 | 165 (dec) |
| 103 | 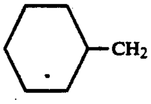 | Cl | $CH_2OH$ | 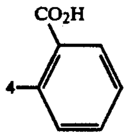 | |
| 104 | 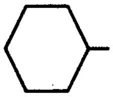 | Cl | $CH_2OH$ | 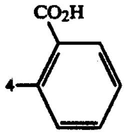 | |
| 105 | n-butyl | $CH_2OH$ | I | 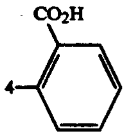 | 205 (dec) |
| 106 | n-butyl | Cl | $CH_2OH$ | 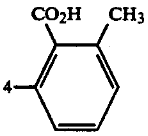 | 185-186 |
| 107 | ethyl | Cl | $CH_2OH$ | 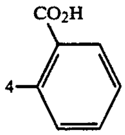 | 153-156 |

TABLE 6-continued
| 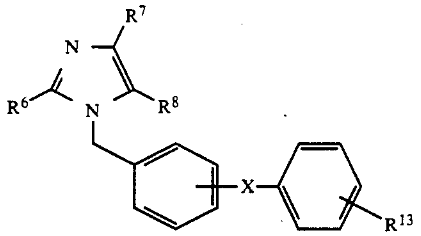 | | | | | |
|---|---|---|---|---|---|
| 108 | n-propyl | Cl | $CH_2OH$ | 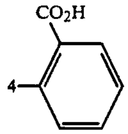 | 198-200 |
| 109 | n-pentyl | Cl | $CH_2OH$ | 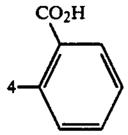 | (amorphous solid)[b] |
| 110 | n-hexyl | Cl | $CH_2OH$ | 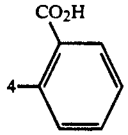 | 84-88 |
| 111 | n-butyl | Cl | $CH_2SH$ | 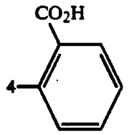 | |
| 112 | n-butyl | Cl | 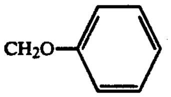 | 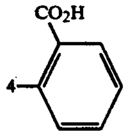 | |
| 113 | n-propyl | Cl | $CH_2OH$ | 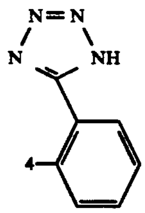 | (amorphous solid)[c] |
| 114 | n-propyl | Cl | CHO | 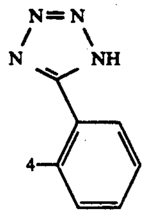 | (amorphous solid)[d] |
| 115 | n-butyl | Cl | $CH_2CO_2H$ | 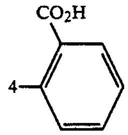 | 221-222 |

TABLE 6-continued
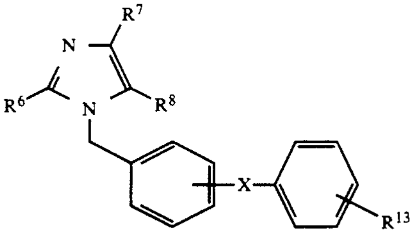
| | | | | | |
|---|---|---|---|---|---|
| 116 | n-butyl | Cl | $CH(CH_3)CO_2H$ | 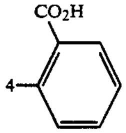 | 118–120 |
| 117 | n-butyl | $CH_2OH$ | $NO_2$ | 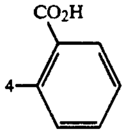 | 154–157 |
| 118 | n-butyl | $CH_2OH$ | Cl | 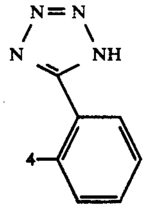 | (white powder)[e] |
| 119 | n-butyl | $NO_2$ | $CH_2OH$ | 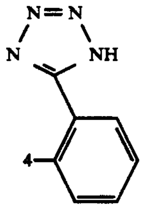 | |
| 120 | n-butyl | Cl | 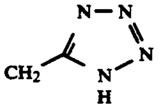 | 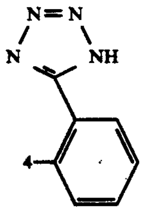 | |
| 121 | n-butyl | Cl | $CH_2OCOCH_3$ | 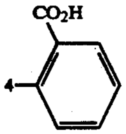 | 157–159 |
| 122 | n-butyl | Cl | $CH_2OCOCH_2CH_2$- 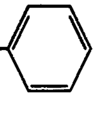 | 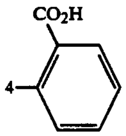 | |
| 123 | n-$C_4H_9S$ | H | $CH_2OH$ | 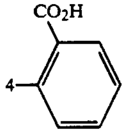 | 190–191 |

TABLE 6-continued
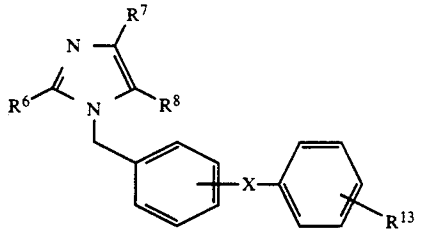
| Ex. No. | $R^6$ | $R^7$ | $R^8$ | 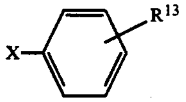 | MP (°C.) |
|---|---|---|---|---|---|
| 124 | 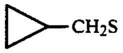 | H | $CH_2OH$ | 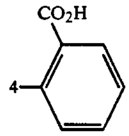 | 194.5–195.5 |
| 124A | n-propyl | $CF_3$ | $CH_2OH$ | 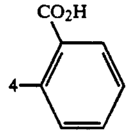 | 229–230.5 |
| 124B | n-propyl | $CF_2CF_3$ | $CH_2OH$ | 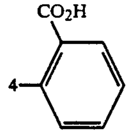 | 197–198 |
| 124C | n-butyl | Br | $CH_2OH$ | 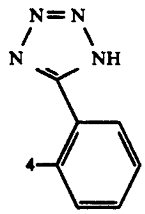 | (amorphous solid)[f] |
| 124D | n-propyl | $CF_3$ | $CH_2OH$ | 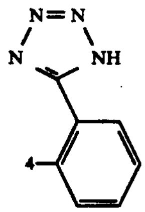 | (amorphous solid)[g] |
| 124E | n-butyl | $CF_2CF_3$ | $CH_2OH$ | 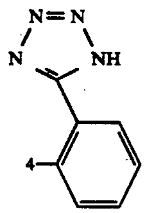 | (amorphous solid)[h] |
| 124F | n-propyl | $CF_2CF_3$ | $CH_2OH$ | 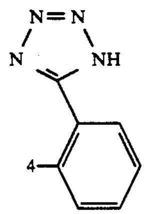 | (amorphous solid)[i] |

TABLE 6-continued
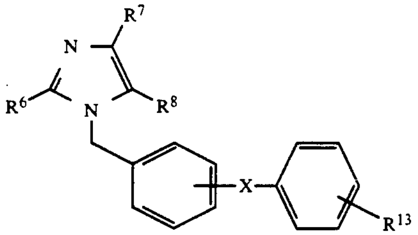
| | | | | | |
|---|---|---|---|---|---|
| 124G | n-propyl | $(CF_2)_2CF_3$ | $CH_2OH$ | 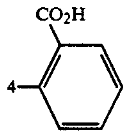 | 169–170.5 |
| 124H | n-propyl | $(CF_2)_3CF_3$ | $CH_2OH$ | 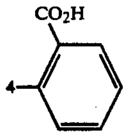 | 154–157° |
| 124I | n-propyl | $(CF_2)_5CF_3$ | $CH_2OH$ | 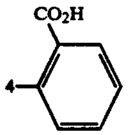 | (amorphous solid)[j] |
| 124J | n-propyl | $C_6F_5$ | $CH_2OH$ | 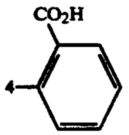 | (amorphous solid)[k] |
| 124K | n-propyl | $(CF_2)_2CF_3$ | $CH_2OH$ | 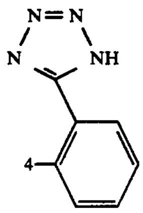 | (amorphous solid)[l] |

TABLE 6-continued

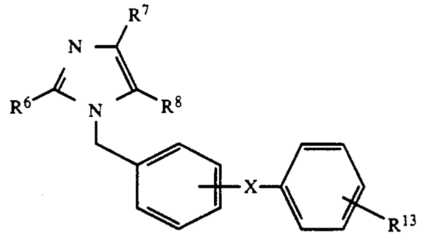

| | | | | | |
|---|---|---|---|---|---|
| 124L | n-butyl | I | $CH_2OH$ | 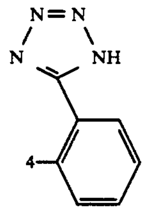 | (amorphous solid)[m] |

[a]NMR(200MHz, DMSO-$d_6$)δ7.69(dd, 1H); 7.54(d of t, 1H); 7.43(d of t, 1H); 7.33(d, 1H); 7.16($A_2B_2$, 4H); 6.76(s, 1H); 5.24(s, 2H); 4.34(s, 2H); 2.50(t, 2H); 1.49(quint, 2H); 1.25(sext, 2H); 0.80(t, 3H).

[b]NMR(200MHz, DMSO-$d_6$)δ7.70(d, 1H), 7.55(t, 1H), 7.42(t, 1H), 7.28(m, 3H), 7.10(d, 2H), 5.28(s, 2H), 4.34(s, 2H), 2.49(t, 2H), 1.49(m, 2H), 1.18(m, 4H), 0.79(t, 3H).

[c]NMR(200MHz, $CDCl_3/CD_3OD$): δ7.82–6.93(m, 8H); 5.21(s, 2H); 4.47(s, 2H); 2.55(t, J=7.5hz, 2H); 1.70–1.59(m, 2H); 0.92(t, J=7.5hz, 3H).

[d]NMR(200MHz, $CDC_3$)9.65(s, 1H); 7.95–6.96(m, 8H); 5.51(s, 2H); 2.59(t, J=7.5hz, 2H); 1.70–1.63(m, 2H); 0.92(t, J=7.5hz, 3H).

[e]NMR(200MHz, $CDCl_3$)δ7.76(d, 1H, J=7Hz); 7.57(t, 1H, J=7Hz); 7.49(t, 1H, J=7Hz); 7.40(d, 1H, J=7Hz); 7.02(d, 2H, J=8Hz); 6.81(d, 2H, J=8Hz); 5.03(s, 2H); 4.28(s, 2H); 2.46(t, 2H, J=7Hz); 1.47(t of t, 2H, J=7,7Hz); 1.17(t of q, 2H, J=7,7Hz); 0.73(t, 3H, J=7Hz).

[f]NMR(200MHz, DMSO-$d_6$): δ7.71–7.50(m, 4H), 7.04($A_2B_2$, 4H), 5.26(s, 2H), 4.32(s, 2H), 2.46(t, 2H), 1.45(quint., 2H), 1.24(sext., 2H), 0.81(t, 3H).

[g]NMR(200MHz, DMSO-$d_6$): δ16.25(br s, 1H), 7.72–7.50(m, 4H), 7.05($A_2B_2$, 4H), 5.44(br s, 1H), 5.30(s, 2H), 4.46(s, 2H), 2.47(t, 2H), 1.52(sext., 2H), 0.83(t, 3H).

[h]NMR(200MHz, DMSO-$d_6$): δ7.72–7.50(m, 4H), 7.05($A_2B_2$, 4H), 5.45(br s, 1H), 5.32(s, 2H), 4.45(s, 2H), 2.49(t, 2H), 1.44(quint., 2H), 1.22(sext., 2H), 0.78(t, 3H).

[i]NMR(200MHz, DMSO-$d_6$): δ7.73–7.53(m, 4H), 7.04($A_2B_2$, 4H), 5.48(brs, 1H), 5.32(s, 2H), 4.46(s, 2H), 2.47(t, 2H), 1.51(sext., 2H), 0.82(t, 3H).

[j]NMR(200MHz, DMSO-$d_6$): δ12.74(br s, 1H), 7.71(d, 1H), 7.56(t, 1H), 7.44(t, 1H), 7.34(m, 3H), 7.08(d, 2H), 5.47(br s; 1H), 5.40(s, 2H), 4.46(s, 2H), 2.53(t, 2H), 1.55(sext., 2H), 0.84(t, 3H).

[k]NMR(200MHz, DMSO-$d_6$): δ7.73(d, 1H), 7.62–7.32(m, 5H), 7.14(d, 2H), 5.39(s, 2H), 5.23(br s, 1H), 4.34(s, 2H), 2.56(t, 2H), 1.57(sext., 2H), 0.87(t, 3H).

[l]NMR(200MHz, DMSO-$d_6$): δ16.25(br s, 1H), 7.71–7.52(m, 4H), 7.04($A_2B_2$, 4H), 5.45(br s, 1H), 5.34(s, 2H), 4.44(s, 2H), 2.48(t, 2H), 1.50(sext., 2H), 0.82(t, 3H).

[m]NMR(200MHz, DMSO-$d_6$): δ16.30(br s, 1H), 7.67–7.52(m, 4H), 7.07($A_2B_2$, 4H), 5.33(br s, 3H), 4.33(s, 2H), 2.52(t, 2H), 1.45(quint., 2H), 1.23(sext., 2H), 0.80(t, 3H).

EXAMPLE 125

Preparation of 1-[(2'-Carboxybiphenyl-4-yl)methyl]-2-butyl-4-chloroimidazole-5-carboxaldehyde A mixture of 1.46 g of 1-[2'-carboxybiphenyl-4-yl)methyl]-2-butyl-4-chloro-5-hydroxymethylimidazole and 7.30 g of activated manganese dioxide in 40 ml of tetrahydrofuran was stirred at 25° C. for 5 days. The mixture was filtered through Celite®, and the filtrate was concentrated in vacuo. Column chromatography on silica gel (elution: 2–10% methanol/chloroform) followed by recrystallization from ethyl acetate afforded 0.71 g of 1-[(2'-carboxybiphenyl-4-yl)methyl]-2-butyl-4-chloroimidazole-5-carboxaldehyde (m.p. 154°–158° C. (dec.)). NMR (200 MHz, DMSO-$d_6$) δ 12.85 (br s, 1H), 9.77 (s, 1H), 7.77 (d, 1H), 7.62 (t, 1H), 7.50 (t, 1H), 7.40 (d, 1H), 7.26 ($A_2B_2$, 4H), 5.67 (s, 2H), 2.70 (t, 2H), 1.56 (quint., 2H), 1.28 (sext., 2H), 0.83 (t, 3H).

EXAMPLE 126

Preparation of Methyl 1-[(2'-carboxybiphenyl-4-yl)methyl]-2-butyl-4-chloroimidazole-5-carboxylate To a mixture of 1.45 g of 1-[(2'-carboxybiphenyl-4-yl)methyl]-2-butyl-4-chloroimidazole-5-carboxaldehyde and 0.91 g of sodium cyanide in 20 mL of methanol at 25° C. was added 0.32 mL of acetic acid followed by 7.25 g of manganese dioxide. The resulting mixture was stirred at 25° C. for 40 hours. The reaction mixture was filtered through Celite®, and the filtrate diluted with water. The aqueous solution was adjusted to pH 3 using hydrochloric acid and extracted with methylene chloride. The combined organic phases were washed with brine, dried over anhydrous sodium sulfate, filtered, and concentrated. The crude product was recrystallized from diethyl ether to afford 0.90 g of methyl 1-[(2'-carboxybiphenyl-4-yl)methyl]-2-butyl-4-chloroimidazole-5-carboxylate (m.p. 154°–155° C.). NMR (200 MHz, DMSO-$d_6$); δ 12.75 (br s, 1H), 7.73 (d, 1H) 7.58 (t, 1H), 7.46 (t, 1H), 7.34 (m, 3H), 7.07 (d, 2H), 5.63 (s, 2H), 3.78 (s, 3H), 2.67 (t, 2H), 1.56 (quint., 2H), 1.29 (sext., 2H), 0.83 (t, 3H).

EXAMPLE 127

Preparation of 1-[(2'-Carboxybiphenyl-4-yl)methyl]-2-butyl-4-chloroimidazole-5-carboxamide Anhydrous ammonia was bubbled into 40 mL of i-propanol until the solvent was saturated. To this solution at 25° C. was added 0.49 g of powdered sodium cyanide, then 0.80 g of 1-[(2'-carboxybiphenyl-4-yl)methyl]-2-butyl-4-chloroimidazole-5-carboxaldehyde, and finally 3.48 g of manganese dioxide. This mixture was stirred at 25° C. for 65 hours. The reaction mixture was filtered through Celite®, and the filtrate concentrated in vacuo. The residue was dissolved in water, and the aqueous solution was adjusted to pH 3 using hydrochloric acid and then extracted with methylene chloride. The combined organic phases were washed with brine, dried over anhydrous sodium sulfate, filtered, and concentrated. Column chromatography on silica gel (elution: 0–10% i-propanol (chloroform) provided 0.22 g of 1-[(2'-carboxybiphenyl-4-yl)methyl]-2-butyl-4- chloroimidazole-5-carboxamide as a white solid (m.p. 200°-202° C.). NMR (200 MHz, DMSO-$d_6$): δ 12.74 (br s, 1H); 7.71 (d, 2H); 7.56 (t, 1H), 7.48-7.30 (m, 6H); 7.09 (s, 2H); 5.57 (s, 2H); 2.59 (t, 2H); 1.51 (quint., 2H); 1.26 (sext. 2H); 0.80 (s, 3H).

EXAMPLE 128

Part A: Preparation of 1-[(2'-Carbomethoxybiphenyl-4-yl)methyl]-2-butyl-4-chloroimidazole-5-carboxaldehyde A mixture of 2.06 g of 1-[(2'-carbomethoxybiphenyl-4-yl)methyl]-2-butyl-4-chloro-5-hydroxymethylimidazole and 3.08 g of activated manganese dioxide in 20 mL of methylene chloride at 25° C. was stirred for 40 hours. The reaction mixture was filtered through Celite®, and the filtrate concentrated in vacuo. Column chromatography (elution: ethyl acetate/benzene) provided 1.15 g of 1-[(2'-carbomethoxybiphenyl-4-yl)methyl]-2-butyl-4-chloroimidazole-5-carboxaldehyde. NMR (200 MHz, $CDCl_3$) δ 9.76 (s, 1H); 7.83 (d of d, 1H); 7.52 (t of d, 1H); 7.40 (t of d, 1H); 7.31 (d of d, 1H); 7.17 ($A_2B_2$, 4H); 5.58 (s, 2H); 3.63 (s, 3H); 2.67 (t, 2H); 1.70 (quint., 2H); 1.38 (sext., 2H); 0.90 (t, 3H).

Part B: Preparation of 1-[(2-Carbomethoxybiphenyl-4-yl)methyl]-2-(1-bromobutyl)-4-chloroimidazole-5-carboxaldehyde A mixture of 1.12 g of 1-[(2'-carbomethoxybiphenyl-4-yl)methyl]-2-butyl-4-chloroimidazole-5-carboxaldehyde and 0.49 g of N-bromosuccinimide in 40 mL of $CCl_4$ was irradiated (UV-lamp, pyrex filter) for 0.5 hours. The reaction mixture was filtered, and the filtrate was concentrated in vacuo. Column chromatography (elution: ethyl acetate/benzene) afforded 0.54 g of 1-[(2'-carbomethoxybiphenyl-4-yl)methyl]-2-(1-bromobutyl)-4-chloroimidazole-5-carboxaldehyde. NMR (200 MHz, $CDCl_3$) δ 9.87 (s, 1H); 7.86 (d, 1H); 7.54 (t, 1H); 7.46 (t, 1H); 7.30 (m, 3H); 7.11 (d, 2H); 6.16 (d, 1H); 5.32 (d, 1H); 4.79 (t, 1H); 3.65 (s, 3H); 2.32 (m, 2H); 1.34 (sext., 2H); 0.83 (t, 3H).

Part C: Preparation of 1-[(2'-Carbomethoxybiphenyl-4-yl)methyl]-2-(1-trans-butenyl)-4-chloroimidazole-5-carboxaldehyde A solution of 0.54 g of 1-[(2'-carbomethoxybiphenyl-4-yl)methyl]-2-(1-bromobutyl)-4-chloroimidazole-5-carboxaldehyde and 0.33 mL of 1,8-diazabicyclo[4.5.0]undec-7-ene in 10 mL of tetrahydrofuran was stirred at 25° C. for 18 hours. the reaction mixture was diluted with diethyl ether, washed with dilute hydrochloric acid, water, and brine, dried over anhydrous sodium sulfate, filtered, and concentrated in vacuo. Column chromatography (elution:ethyl acetate/benzene) furnished 0.26 g of 1-[(2'-carbomethoxybiphenyl-4-yl)methyl]-2-(1-trans-butenyl)-4-chloroimidazole-5-carboxaldehyde. NMR (200 MHz, $CDCl_3$) δ 9.75 (s, 1H); 7.82 (d, 1H); 7.51 (t, 1H); 7.40 (t, 1H); 7.33-7.07 (m, 6H); 6.27 (d, 1H); 5.62 (s, 2H); 3.62 (s, 3H); 2.30 (quint., 2H); 1.09 (t, 3H).

Part D: Preparation of 1-[(2'-Carbomethoxybiphenyl-4-yl)methyl]-2-(1-trans-butenyl)-4-chloro-5-hydroxymethylimidazole To a solution of 0.26 g of 1-[(2'-carbomethoxybiphenyl-4-yl)methyl]-2-(1-trans-butenyl)-4-chloroimidazole-5-carboxaldehyde in 10 mL of methanol at 0° C. was added 0.24 g of sodium borohydride portionwise over 0.5 hours. The mixture was stirred for an additional 0.5 hours at 0° C. and then poured into a solution at 10% sodium hydroxide in water. The resulting mixture was extracted with ethyl acetate, and the combined organic phases were washed with brine, dried over anhydrous sodium sulfate, filtered, and concentrated in vacuo. Column chromatography (elution:ethyl acetate/benzene) provided 0.23 g of 1-[2'-carbomethoxybiphenyl-4-yl)methyl-2-(1-transbutenyl)-4-chloro-5-hydroxymethylimidazole. NMR (200 MHz, $CDCl_3$) δ 7.84 (d, 1H); 7.53 (t, 1H); 7.40 (t, 1H); 7.29 (m, 3H); 7.08 (d, 2H); 6.86 (d of t, 1H); 6.17 (d, 1H); 5.30 (s, 2H); 4.54 (br s, 2H); 3.63 (s, 3H); 2.23 (quint., 2H); 1.04 (t, 3H).

Part E: Preparation of 1-[(2'-Carboxybiphenyl-4-yl)methyl]-2-(1-trans-butenyl)-4-chloro-5-hydroxymethylimidazole This compound was prepared according to the procedure described in Example 85, Part E. From 0.23 g of 1-[(2'-carbomethoxybiphenyl-4-yl)methyl]-2-(1-trans-butenyl)-4-chloro-5-hydroxymethylimidazole there was obtained 0.16 g of 1-[(2'-carboxybiphenyl)-4-yl)methyl]-2-(1-trans-butenyl)-4-chloro-5-hydroxymethylimidazole (m.p. 198.5°-199.5° C.). NMR (200 MHz, DMSO-$d_6$) δ 7.71 (d, 1H); 7.56 (t, 1H); 7.44 (t, 1H); 7.32 (m, 3H); 7.11 (d, 2H); 6.62 (d of t, 1H); 6.39 (d, 1H); 5.38 (s, 2H); 5.33 (br s, 1H); 4.35 (br s, 2H); 2.18 (quint., 2H); 0.99 (t, 3H).

EXAMPLE 129

Preparation of 1-[(2'-Carboxybiphenyl-4-yl)methyl]-2-(1-trans-butenyl)-4-chloroimidazole-5-carboxaldehyde This compound was prepared according to the procedure of Example 125. From 0.50 g of 1-[(2'-carboxybiphenyl-4-yl)methyl]-2-(1-trans-butenyl)-4-chloro-5-hydroxymethylimidazole and 2.50 g of manganese dioxide was obtained 0.24 g of 1-[(2'-carboxybiphenyl-4-yl)methyl]-2-(1-trans-butenyl)-4-chloroimidazole-5-carboxaldehyde (m.p. 164°-166° C.). NMR (200 MHz, DMSO-$d_6$) δ 12.79 (br s, 1H); 9.70 (s, 1H); 7.72 (d, 1H); 7.57 (t, 1H); 7.46 (t, 1H); 7.33 (m, 3H); 7.15 (d, 2H); 7.01 (d of t, 1H); 6.65 (d, 1H); 5.71 (s, 2H); 2.28 (quint., 2H); 1.04 (t, 3H).

The compounds in Table 7 were prepared or could be prepared employing the procedures described in Examples 125-129 or by procedures described previously.

TABLE 7
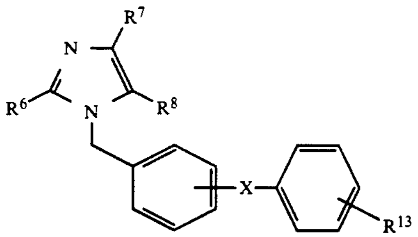
| Ex. No. | $R^6$ | $R^7$ | $R^8$ | 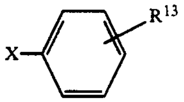 | MP (°C.) |
|---|---|---|---|---|---|
| 130 | n-butyl | H | CHO | 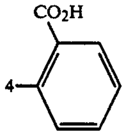 | (amorphous solid)[a] |
| 131 | n-butyl | $CF_3$ | CHO | 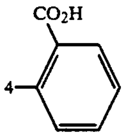 | 132–134 |
| 132 | n-butyl | Cl | CHO | 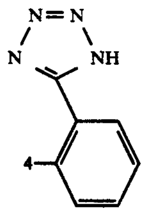 | 127.5–131.5° C. |
| 133 | n-butyl | $CF_3$ | CHO | 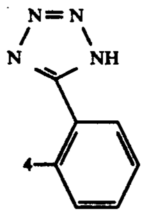 | (amorphous solid)[b] |
| 134 | n-butyl | Cl | $CONHCH_3$ | 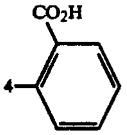 | (amorphous solid)[c] |
| 135 | n-butyl | Cl | $CON(CH_3)_2$ | 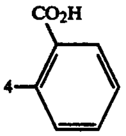 | (amorphous solid)[d] |
| 136 | $CH_3CH{=}CH-$ | Cl | $CH_2OH$ | 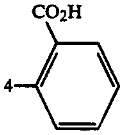 | |
| 137 | $CH_3CH_2CH{=}CH-$ | $CF_3$ | $CH_2OH$ | 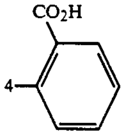 | 217–219 |

TABLE 7-continued
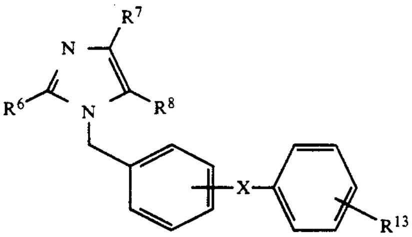
| Ex. No. | $R^6$ | $R^7$ | $R^8$ | 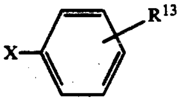 | MP (°C.) |
|---|---|---|---|---|---|
| 138 | $CH_3CH{=}CH-$ | Cl | CHO | 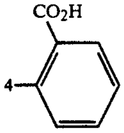 | |
| 139 | $CH_3CH_2CH{=}CH-$ | Cl | $CH_2OH$ | 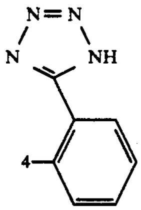 | (amorphous solid)[e] |
| 140 | $CH_3CH_2CH{=}CH-$ | Cl | CHO | 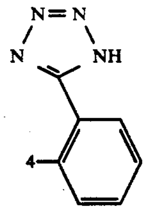 | |
| 140A | n-propyl | $CF_3$ | CHO | 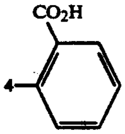 | (amorphous solid)[f] |
| 140B | n-propyl | $CF_2CF_3$ | CHO | 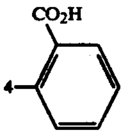 | (amorphous solid)[g] |
| 140C | n-propyl | $CF_3$ | CHO | 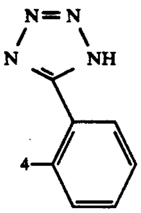 | (amorphous solid)[h] |
| 140D | n-butyl | Br | CHO | 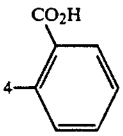 | 169.5–171 |

TABLE 7-continued
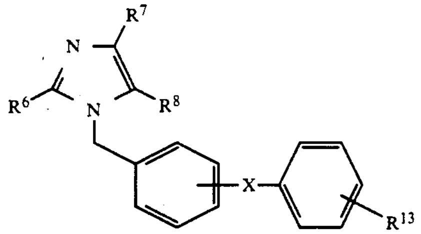
| | | | | | |
|---|---|---|---|---|---|
| 140E | n-butyl | Br | CHO | 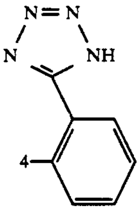 | (amorphous solid)[i] |
| 140F | $CH_3CH_2CH{=}CH-$ | $CF_3$ | CHO | 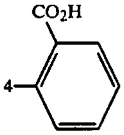 | 134–135.5 |
| 140G | n-propyl | $CF_2CF_3$ | CHO | 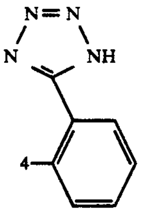 | (amorphous solid)[j] |
| 140H | n-butyl | $CF_3$ | $CO_2CH_3$ | 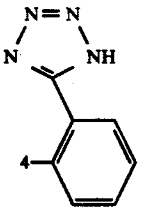 | (amorphous solid)[k] |
| 140I | n-butyl | $CF_3$ | $CO_2CH_2CH_3$ | 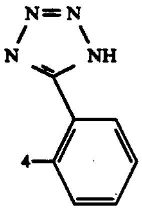 | (amorphous solid)[i] |
| 140J | n-butyl | $CF_3$ | $CONH_2$ | 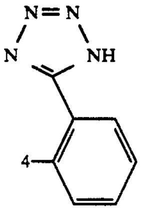 | 224.5–225.5 |

TABLE 7-continued

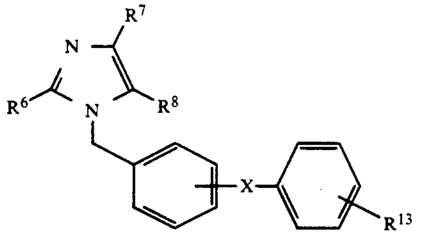

| | | | | | |
|---|---|---|---|---|---|
| 140K | n-butyl | I | CHO | 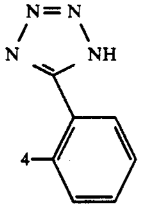 | (amorphous solid)[m] |
| 140L | n-butyl | Cl | CHO | 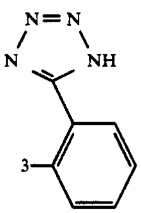 | 184.5-187.5 |

[a]NMR(200MHz, DMSO-$d_6$)δ12.76(br s, 1H); 9.67(s, 1H); 7.93(s, 1H); 7.71(d, 1H); 7.55(t, 1H); 7.43(t, 1H); 7.30(m, 3H); 7.06(d, 2H); 5.63(s, 2H); 2.67(t, 2H); 2.57(quint., 2H); 2.27(sext. 2H); 0.81(t, 3H).
[b]NMR(200MHz, DMSO-$d_6$): δ9.87(s, 1H), 7.67-7.47(m, 4H), 7.01($A_2B_2$, 4H), 5.63(s, 2H), 2.66(t, 2H), 1.53(quint., 2H), 1.25(sext., 2H), 0.78(t, 3H).
[c]NMR(200MHz, DMSO-$d_6$)δ12.75(br s, 1H); 8.10(br quart., 1H); 7.72(d, 1H); 7.57(t, 1H); 7.45(t, 1H); 7.32(m, 3H); 7.10(d, 2H); 5.51(s, 2H); 2.75(d, 3H); 2.58(t, 2H); 1.52(quint., 2H); 1.27(sext., 2H); 0.81(t, 3H).
[d]NMR(200MHz, DMSO-$d_6$)δ12.77(br s, 1H); 7.73(d, 1H); 7.57(t, 1H); 7.45(t, 1H); 7.45(t, 1H); 7.33(m, 3H); 7.09(d, 2H); 5.20(br s, 2H); 2.83(s, 3H); 2.73(t, 2H); 2.66(s, 3H); 1.63(quint., 2H); 1.36(sext., 2H); 0.89(t, 3H).
[e]NMR(200MHz, DMSO-$D_6$): δ7.51-7.71(m, 4H); 6.94-7.23(m, 4H); 6.53-6.76(m, 1H); 6.32(d, 1H, J=7Hz); 5.34(s, 2H); 4.34(s, 2H); 2.10-2.30(m, 2H); 0.98(t, 3H, J=7Hz).
[f]NMR(200MHz, DMSO-$D_6$): δ12.79(br s, 1H), 9,95(s, 1H), 7.69(d, 1H), 7.57(t, 1H), 7.45(t, 1H), 7.35(m, 3H), 7.12(d, 2H), 5.72(s, 2H), 2.72(t, 2H), 1.64(sext. 2H), 0.88(t, 3H).
[g]NMR(200MHz, DMSO-$D_6$): δ12.79(br s, 1H), 9.93(s, 1H), 7.72(d, 1H), 7.57(t, 2H), 7.45(t, 2H), 7.33(m, 3H), 7.08(d, 2H), 5.70(s, 2H), 2.73(t, 2H), 1.63(sext., 2H), 0.86(t, 3H).
[h]NMR(200MHz, DMSO-$D_6$): δ9.90(s, 1H), 7.72-7.50(m, 4H), 7.04($A_2B_2$, 4H), 5.64(s, 2H), 2.66(t, 2H), 1.59(sext., 2H), 0.84(t, 3H).
[i]NMR(200MHz, DMSO-$D_6$): δ9.57(s, 1H), 7.69-7.47(m, 4H), 7.01($A_2B_2$, 4H), 5.56(s, 2H), 2.59(t, 2H), 1.50(quint., 2H), 1.24(sext., 2H), 0.78(t, 3H).
[j]NMR(200MHz, DMSO-$D_6$): δ9.92(s, 1H), 7.73-7.52(m, 4H), 7.05($A_2B_2$, 4H), 5.67(s, 2H), 2.68(t, 2H), 1.57(sext., 2H), 0.84(t, 3H).
[k]NMR(200MHz, DMSO-$D_6$): δ16.35(br s, 1H), 7.73-7.51(m, 4H), 7.03($A_2B_2$, 4H), 5.57(s, 2H), 3.78(s, 3H), 2.67(t, 2H), 1.56(quint., 2H), 1.28(sext., 2H), 0.83(t, 3H).
[l]NMR(200MHz, DMSO-$D_6$): δ7.73-7.50(m, 4H), 7.03($A_2B_2$, 4H), 5.57(s, 2H), 4.24(quart., 2H), 2.66(t, 2H), 1.56(quint., 2H), 1.28(sext., 2H), 1.19(t, 3H), 0.82(t, 3H).
[m]NMR(200MHz, DMSO-$D_6$): δ16.25(br s, 1H), 9.47(s, 1H), 7.71-7.49(m, 4H), 7.03($A_2B_2$, 4H), 5.58(s, 2H), 2.61(t, 2H), 1.51(quint., 2H), 1.25(sext., 2H), 0.81(t, 3H).

EXAMPLE 141

Part A: Preparation of 1-[2'-Aminobiphenyl-4-yl)methyl]-2-butyl-4-chloro-5-methoxymethylimidazole A solution of 4.40 g of 1-[(2'-nitrobiphenyl-4-yl)methyl]-2-butyl-4-chloro-5-methoxymethylimidazole, 2.10 g of iron powder, 4.25 mL of glacial acetic acid, and 200 mL of methanol was refluxed for 5 hours. After cooling, the solvent was removed in vacuo, and the residue was dissolved in ethyl acetate. The precipitated iron salts were removed by filtration through Celite®, and the resulting solution was washed with water and brine, dried over anhydrous sodium sulfate and concentrated. Column chromatography on silica gel (elution: 10-30% ethyl acetate/benzene) furnished 2.95 g of 1-[2'-aminobiphenyl-4-yl)methyl]-2-butyl-4-chloro-5-methoxymethylimidazole; NMR (200 MHz, $CDCl_3$): δ 7.43 (d, 2H); 7.19-7.04 (m, 4H); 6.80 (m, 2H); 5.19 (s, 2H); 4.33 (s, 2H); 3.70 (br s, 1H); 3.28 (s, 3H); 2.59 (t, 2H); 1.67 (quint., 2H); 1.34 (sext., 2H); 0.87 (t, 3H).

Part B: Preparation of 1-[2'-Trifluoromethanesulfonamidobiphenyl-4-yl)methyl]-2-butyl-4-chloro-5-methoxymethylimidazole To a solution of 2.95 g of 1-[(2'-aminobiphenyl-4-yl)methyl]-2-butyl-4-chloro-5-methoxymethylimidazole and 1.07 mL of triethylamine in 30 mL of methylene chloride at −78° was added 2.59 mL of trifluoromethanesulfonic anhydride dropwise at such rate that the reaction temperature remains below −50°. Following the addition, the reaction mixture was allowed to warm slowly to 25°. At the point the mixture was poured into dilute aqueous acetic acid. The resulting suspension was stirred vigorously for several minutes and then extracted with methylene chloride. The combined organic phases were washed with water and brine, dried over anhydrous sodium sulfate, filtered and concentrated. Column chromatography on silica gel (elution: 20-50% ethyl acetate/benzene) afforded 0.80 g of 1-[(2'-trifluoromethanesulfonamidobiphenyl-4-yl)methyl]-2-butyl-4-chloro-5-methoxymethylimidazole, m.p.

148°-150°; NMR (200 MHz, $CDCl_3$): δ 7.60 (d, 1H); 7.44-7.27 (m, 5H); 7.07 (d, 2H); 5.20 (s, 2H); 4.29 (s, 2H); 3.27 (s, 3H); 2.57 (t, 2H); 1.65 (quint., 2H); 1.35 (sext., 2H); 0.88 (t, 3H).

Examples 142 to 147 can or could be prepared by the procedures described in Example 141 using the appropriate starting material.

TABLE 8

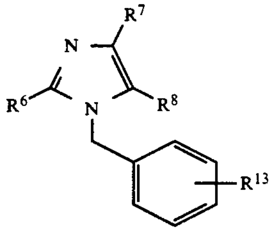

| Ex. No. | $R^6$ | $R^7$ | $R^8$ | $R^{13}$ | MP(°C.) |
|---|---|---|---|---|---|
| 142 | n-butyl | H | $CH_2OCH_3$ | 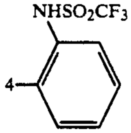 | |
| 143 | n-hexyl | Cl | $CH_2OCH_3$ | 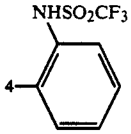 | |
| 144 | n-butyl | Cl | $CH_2OH$ | 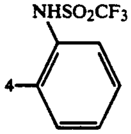 | 171-172 |
| 145 | $FCH_2CH_2CH_2CH_2—$ | Cl | $CH_2OH$ | 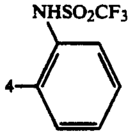 | |
| 146 | $HO_2CCH_2CH_2CH_2CH_2—$ | Cl | $CH_2OH$ | 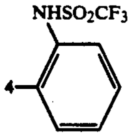 | |
| 147 | $CH_3O_2CCH_2CH_2—$ | Cl | $CH_2OH$ | 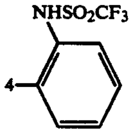 | |

EXAMPLE 148

Part A: Preparation of 2-Butyl-1-[(2'-carbomethoxybiphenyl-4-yl)methyl]-4-chloro-5-(chloromethyl)imidazole.HCl salt 2-Butyl-1-[(2'-carbomethoxybiphenyl-4-yl)methyl]-4-chloro-5-(chloromethyl)imidazole.HCl salt was prepared from 2-butyl-1-[(2'-carbomethoxybiphenyl-4-yl)methyl]-4-chloro-5-(hydroxymethyl)imidazole using the procedure of Example 1, Part B; m.p. 156.0°-161.0°. NMR (200 MHz, $CDCl_3$) δ 7.90 (d, 1H, 7 Hz); 7.56 (t, 1H, J=7 Hz); 7.45 (t, 1H, J=7 Hz); 7.43-7.26 (m, 3H); 7.12 (d, 2H, J=8 Hz); 5.47 (s, 2H); 4.48 (s, 2H); 3.70 (s, 3H); 3.14 (t, 2H, J=7 Hz); 1.80 (t of t, 2H, J=7,7 Hz); 1.44 (t of q, 2H, J=7,7 Hz); 0.92 (t, 3H, J=7 Hz). Anal. Calcd. for $C_{23}H_{24}Cl_2N_2O_2$.HCl: C, 59.05; H, 5.39; N, 5.99. Found: C, 58.80; H, 5.48; N, 5.69. Mass Calcd. for $C_{23}H_{24}Cl_2N_2O_2$: 430.1215. Found 430.1215.

Part B: Preparation of 5-Azidomethyl-2-n-butyl-1-[(2'-carbomethoxybiphenyl-4-yl)methyl]-4-chloroimidazole 2-Butyl-1-[(2'-carbomethoxybiphenyl-4-yl)methyl]-4-chloro-5-(chloromethyl)imidazole.HCl salt (3.31 g, 7.67 mmol, 1 eq), sodium azide (1.50 g, 23.0 mmol, 3 eq) and DMSO (100 mL) were mixed and stirred overnight. Water was then added (500 mL) and the aqueous extracted with ethyl acetate (3×300 mL). The organic layers were dried ($MgSO_4$) and concentrated to yield 3.48 g of product as an oil. NMR (200 MHz, $CDCl_3$) δ 7.85 (d, 1H, J=7 Hz); 7.54 (t, 1H, J=7 Hz); 7.40 (t, 1H, J=7 Hz); 7.28 (d, 2H, J=8 Hz); 7.00 (d, 2H, J=8 Hz); 5.20 (s, 2H); 4.23 (s, 2H); 3.67 (s, 3H); 2.63 (t, 2H, J=7 Hz); 1.73 (t of t, 2H, J=7,7 Hz); 1.39 (t of q, 2H, J=7,7 Hz); 0.91 (t, 3H, J=7 Hz). Mass Calcd. for $C_{23}H_{24}ClN_5O_2$: 438.1697. Found: 438.1669.

Part C: Preparation of 5-Aminomethyl-2-butyl-1-[(2'-carbomethoxybiphenyl-4-yl)methyl]-4-chloroimidazole 5-Azidomethyl-2-butyl-1-[(2'-carbomethoxybiphenyl-4-yl)methyl]-4-chloroimidazole (3.48 g) was hydrogenated at 1 atm in methanol (100 mL) over 10% palladium/carbon (0.5 g). After 1 hour, the mixture was filtered through Celite® and the solvent removed in vacuo to give product (2.80 g) as an oil. NMR (200 MHz, $CDCl_3$) δ 7.84 (d, 1H, J=7 Hz); 7.52 (t, 1H, J=7 Hz); 7.40 (t, 1H, J=7 Hz); 7.30 (d, 1H, J=7 Hz); 7.26 (d, 2H, J=8 Hz); 7.02 (d, 2H, J=8 Hz); 5.27 (s, 2H); 3.74 (s, 2H); 3.65 (s, 3H); 2.60 (t, 2H, J=7 Hz); 1.67 (t of t, 2H, J=7,7 Hz); 1.36 (t of q, 2H, J=7,7 Hz); 0.86 (t, 3H, J=7 Hz). Anal. Calcd. for $C_{23}H_{26}ClN_3O_2.(DMSO)_{0.5}$: C, 63.91; H, 6.48; N, 9.32. Found: C, 63.78; H, 6.30; N, 9.14.

Part D: Preparation of 5-Aminomethyl-2-butyl-1-[(2'-carboxybiphenyl-4-yl)methyl]-4-chloroimidazole 5-Aminomethyl-2-butyl-1-[(2'-carbomethoxybiphenyl-4-yl)methyl]-4-chloroimidazole (1.64 g. 3.98 mmol, 1 eq), 0.5N KOH in methanol (11.96 mL, 5.98 mmol, 1.5 eq), water (1.0 mL) and methanol (20 mL) were mixed and refluxed under $N_2$ overnight. The solution was then brought to neutrality with 1N HCl and the solvents removed in vacuo. The residue was taken up in DMF and the salts filtered off. The DMF was then removed in vacuo to yield 1.76 g of a glass. NMR (200 MHz, DMSO-$d_6$) δ 7.50 (d, 1H, J=7 Hz); 7.40-7.18 (m, 5H); 6.92 (d, 2H, J=8 Hz); 6.50 (bm, 3H); 5.26 (s, 2H); 3.60 (s, 2H); 2.55 (t, 2H, J=7 Hz); 1.51 (t of t, 2H, J=7,7 Hz); 1.27 (t of q, 2H, J=7,7 Hz); 0.81 (t, 3H, J=7 Hz).

Part E: Preparation of 2-Butyl-1-[(2'-carboxybiphenyl-4-yl)methyl]-4-chloro-5-(ethoxycarbonylaminomethyl)imidazole 2-Butyl-1-[(2'-carboxybiphenyl-4-yl)methyl]-4-chloro-5-(ethoxycarbonylaminomethyl)imidazole was prepared from 5-aminomethyl-2-n-butyl-1-[(2'-carboxybiphenyl-4-yl)methyl]-4-chloroimidazole using ethyl chloroformate and the Schotten-Baumann procedure described in Example 209, Part B: m.p. 144.0°-147.0°. NMR (200 MHz, DMSO-$d_6$) δ 12.74 (s, 1H); 7.73 (d, 1H, J=7 Hz); 7.63-7.27 (m, 5H); 7.03 (d, 2H, J=10 Hz); 5.27 (s, 2H); 4.60 (bd, 2H, J=7 Hz); 3.90 (q, 2H, J=7 Hz); 3.34 (s, 2H); 2.47 (t, 2H, J=7 Hz); 1.48 (t of t, 2H, J=7,7 Hz); 1.24 (t of q, 2H, J=7,7 Hz); 1.06 (t, 3H, J=7 Hz); 0.78 (t, 3H, J=7 Hz). Anal. Calcd. for $C_{25}H_{28}ClN_3O_4.(H_2O)_{0.33}$: C, 63.17; H, 6.06; N, 8.83. Found: C, 63.30; H, 6.35; N, 8.44.

Examples 149-159 in Table 9 were prepared or could be prepared using the appropriate chloroformate by the procedure described in Example 148, Parts D and E (the order of which may be interchanged by one skilled in the art) i.e., starting with the amino ester from Part C, reacting it with a chloroformate under Schotten-Baumann type conditions followed by hydrolyzing the ester if necessary.

TABLE 9

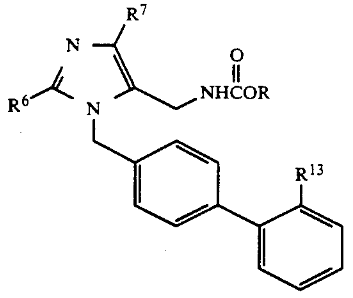

| Ex. No. | $R^6$ | $R^7$ | R | $R^{13}$ | MP(°C.) |
|---|---|---|---|---|---|
| 149 | n-butyl | Cl | $C_6H_5$ | $CO_2H$ | 198.0-200.0 |
| 150 | n-butyl | Cl | $CH_3$ | $CO_2H$ | 151.0-155.0 |
| 151 | n-butyl | Cl | $CH_2CH_2CH_3$ | $CO_2H$ | 115.5-117.0 |
| 152 | n-butyl | Cl | $CH_2(CH_3)_2$ | $CO_2H$ | 135.5-138.0 |
| 153 | n-butyl | Cl | $CH_2CH_2CH_2CH_3$ | $CO_2H$ | 123.0-125.0 |
| 154 | n-butyl | Cl | 1-adamantyl | $CO_2H$ | 170.0-172.0 |
| 155 | n-propyl | Cl | $CH_3$ | $CO_2H$ | |
| 156 | n-butyl | Cl | $CH_3$ | 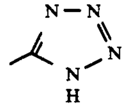 | 202.0-204.5 |
| 157 | n-butyl | Cl | $(CH_2)_2CH_3$ | 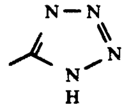 | |
| 158 | n-propyl | Cl | $CH_3$ | 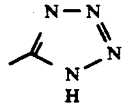 | |
| 159 | n-propyl | H | $CH_2CH_3$ | 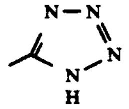 | |

Examples 160-164 in Table 10 were prepared or could be prepared from 2-n-butyl-1-[(2'-carbomethoxybiphenyl-4-yl)methyl]-5-chloro-4-(hydroxymethyl)imidazole using the procedures in Example 148.

TABLE 10

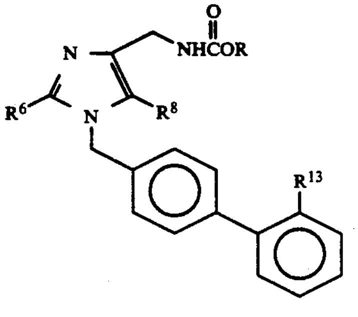

| Ex. No. | $R^6$ | $R^8$ | R | $R^{13}$ | MP(°C.) |
|---|---|---|---|---|---|
| 160 | n-butyl | Cl | $CH_3$ | COOH | 200-205 |
| 161 | n-butyl | Cl | $CH_2CH_3$ | COOH | |
| 162 | n-butyl | Cl | $CH_2CH_2CH_3$ | COOH | 166.5-169.5 |
| 163 | n-butyl | Cl | $CH_2CH_2CH_2CH_3$ | COOH | |

TABLE 10-continued

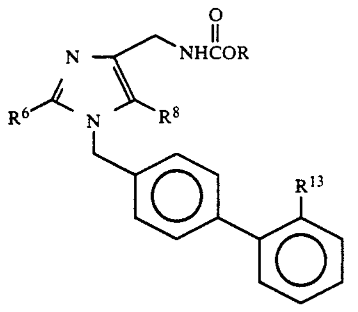

| Ex. No. | $R^6$ | $R^8$ | R | $R^{13}$ | MP(°C.) |
|---|---|---|---|---|---|
| 164 | n-butyl | Cl | $CH(CH_3)_2$ | COOH | |

EXAMPLE 165

Part A: Preparation of 2-n-Butyl-1-[(2'-carbomethoxybiphenyl-4-yl)methyl]-4-chloro-5-(1-naphthylaminocarbonylaminomethyl-)imidazole 5-Aminomethyl-2-butyl-1-[(2'-carbomethoxybiphenyl-4-yl)methyl]-4-chloroimidazole (1.00 g, 2.4 mmol, 1 eq) and 1-naphthyl isocyanate (0.35 mL, 2.4 mmol, 1 eq), were mixed and stirred in chloroform at room temperature for 3 days. The solvent was removed in vacuo and the residue was purified by flash chromatography over silica gel in 1:1 hexane/ethyl acetate to yield 770 mg of a white glass. NMR (200 MHz, $CDCl_3$) δ 7.83 (d, 3H, J=6 Hz); 7.67 (d, 1H, J=6 Hz); 7.56–7.18 (m, 9H); 6.97 (d, 2H, J=7 Hz); 6.74 (s, 1H); 5.27 (s, 2H); 4.74 (s, 1H); 4.39 (d, 2H, J=7 Hz); 3.58 (s, 3H); 2.60 (t, 2H, J=7 Hz); 1.43–1.21 (m, 4H); 0.85 (t, 3H, J=7 Hz).

Part B: Preparation of 2-n-Butyl-1-[(2'-carboxybiphenyl-4-yl)methyl]-4-chloro-5-(1-naphthylaminocarbonylaminomethyl-)imidazole The title compound was prepared from 2-n-butyl-1-[(2'-carbomethoxybiphenyl-4-yl)methyl]-4-chloro-5-(1-naphthylaminocarbonylaminomethyl)imidazole by the hydrolysis procedure described in Example 148, Part D. Work-up yielded 380 mg of white crystalline solid; m.p. 169°–175°. NMR (200 MHz, DMSO-$d_6$) δ 8.45 (s, 1H); 8.05–7.03 (m, 15H); 6.97 (s, 1H); 5.34 (s, 2H); 4.30 (d, 2H, J=5 Hz); 2.52 (t, 2H, J=7 Hz); 1.48 (t of t, 2H, J=7,7 Hz); 1.21 (t of q, 2H, J=7,7 Hz); 0.85 (t, 3H, J=7 Hz). Anal. Calcd. for $C_{33}H_{31}ClN_4O_3.(H_2O)_{0.5}$: C, 68.77; H, 5.60; N, 9.70. Found: C, 68.88; H, 5.67; N, 9.70.

Examples 166–172 in Table 11 were prepared or could be prepared using the appropriate isocyanate by the procedure described in Example 165.

TABLE 11

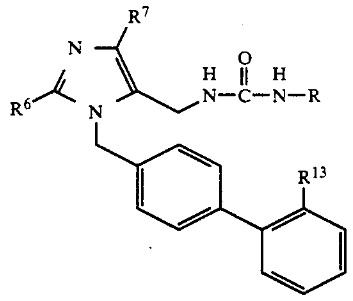

| Ex. No. | $R^6$ | $R^8$ | R | $R^{13}$ | MP (°C.) |
|---|---|---|---|---|---|
| 166 | n-Bu | Cl | $CH_3$ | $CO_2H$ | 187–193 |
| 167 | n-Bu | Cl | $CH_2CH_3$ | $CO_2H$ | |
| 168 | n-Bu | Cl | $CH_2CH_2CH_3$ | CO H | |
| 169 | n-Bu | Cl | $CH_2CH_2CH_2CH_3$ | $CO_2H$ | |
| 170 | n-Bu | Cl | $CH(CH_3)_2$ | CO H | |
| 171 | n-Bu | Cl | 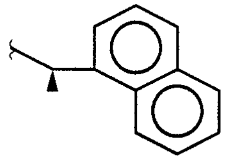 | $CO_2H$ | 163–166 |
| 172 | n-Bu | Cl | 1-adamantyl | 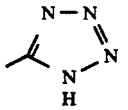 | |

EXAMPLE 173

Preparation of 2-n-Butyl-4-chloro-5-methoxymethyl-1-[(2'-((tetrazol-5-yl)aminocarbonyl)biphenyl-4-yl)methyl]imidazole 2-n-Butyl-1-[(2'-carboxybiphenyl-4-yl)methyl]-4-chloro-5-(methoxymethyl)imidazole (1.0 g) was first converted to the corresponding acid chloride and then coupled to 5-aminotetrazole by the procedure in Example 78, Part C to yield 0.87 g of a yellow glass. Flash chromatography in 100% ethyl acetate over silica gel yielded 77.1 mg of a white solid; m.p. 169°–173°. NMR (200 MHz, $CDCl_3$, DMSO-$d_6$) δ 12.0 (br s, 1H); 7.73–7.30 (m, 6H); 7.00 (d, 2H, J=7 Hz); 5.18 (s, 2H); 4.23 (s, 2H); 2.55 (t, 2H, J=7 Hz) 1.63 (t of t, 2H, J=7,7 Hz); 1.31 (t of q, 2H, J=7,7 Hz); 0.84 (t, 3H, J=7 Hz). Anal. Calcd. for $C_{24}H_{26}ClN_7O_2.(H_2O)_2$: C, 55.87; H, 5.86. Found: C, 56.01; H, 6.01.

EXAMPLE 174

Part A: Preparation of 2-n-Butyl-4-chloro-1-[(2'-(hydroxymethyl)biphenyl-4-yl)methyl]-5-(methoxymethyl)imidazole 2-n-Butyl-1-[2'-carbomethoxybiphenyl-4-yl)methyl]4-chloro-5-(methoxymethyl)imidazole (5.62 g, 13 mmol, 1 eq) was dissolved in THF (50 mL) and to it was slowly added a 1M lithium aluminum hydride solution in THF (39.5 mL, 39 mmol, 3 eq). The resultant mixture was refluxed under $N_2$ for 2 hours and worked up according to Fieser and Fieser, V.1, p. 584 (Steinhardt procedure) to yield 4.68 g of a light yellow oil which slowly crystallized. NMR (200 MHz, $CDCl_3$) δ 7.57

(bd, 1H, J=7 Hz); 7.47-7.20 (m, 5H); 7.03 (d, 2H, J=9 Hz); 5.18 (s, 2H); 4.58 (s, 2H); 4.32 (s, 2H); 3.28 (s, 3H); 2.60 (t, 2H, J=7 Hz); 1.67 (t of t, 2H, J=7,7 Hz); 1.35 (t of q, 2H, J=7,7 Hz); 0.86 (t, 3H, J=7 Hz). Anal. Calcd. for $C_{23}H_{27}ClN_2O_2$: C, 69.25; H, 6.82; Cl, 8.89. Found: C, 69.42; H, 6.87; Cl, 8.65.

Part B: Preparation of 2-n-Butyl-4-chloro-1-[(2'-(cyanomethyl)biphenyl-4-yl)methyl]-5-(methoxymethyl)imidazole 2-n-Butyl-4-chloro-1-[(2'-(hydroxymethyl)biphenyl-4-yl)methyl-5-(methoxymethyl)imidazole (4.68 g) was converted to the title cyanomethyl compound by the procedure described in Example 1, Part B. Work up yielded 5.20 g of a brown oil which was further reacted with purification. NMR (200 MHz, $CDCl_3$) δ 7.54 (m, 1H); 7.40 (m, 2H); 7.28 (m, 3H); 7.08 (d, 2H, J=10 Hz); 5.23 (s, 2H); 4.33 (s, 2H); 3.63 (s, 2H); 3.30 (s, 3H); 2.60 (t, 2H, J=7 Hz); 1.70 (t of t, 2H, J=7,7 Hz); 1.37 (t of q, 2H, J=7,7 Hz); 0.90 (t, 3H, J=7 Hz). Mass Calcd. for $C_{24}H_{26}ClN_3O$: 407.1764. Found: 407.1778.

Part C: Preparation of 2-n-Butyl-4-chloro-5-methoxymethyl-1-[(2'-((tetrazol-5-yl)methyl)biphenyl-4-yl)methyl]imidazole 2-n-Butyl-4-chloro-1-[(2'-(cyanomethyl)biphenyl-4-yl)methyl]-5-(methoxymethyl)imidazole (5.20 g) was converted to the above tetrazole in 2 days using the procedure of Example 90, Part C. Work-up and flash chromatography over silica gel eluting with a gradient solvent system of 1:1 hexane/ethyl acetate to 1:1 ethyl acetate/isopropanol yielded 3.13 g of a light yellow solid; m.p. 149.0°-152.5°. NMR (200 MHz, $CDCl_3$) δ 7.37-7.15 (m, 6H); 6.96 (d, 2H, J=9 Hz); 5.18 (s, 2H); 4.30 (s, 2H); 4.24 (s, 2H); 3.27 (s, 3H); 2.57 (t, 2H, J=7 Hz); 1.56 (t of t, 2H, J=7,7 Hz); 1.28 (t of q, 2H, J=7,7 Hz); 0.77 (t, 3H, J=7 Hz). Anal. Calcd. for $C_{24}H_{27}ClN_6O$: C, 63.97, H, 6.03; Cl, 7.86. Found: C, 63.79; H, 6.04; Cl, 7.70.

EXAMPLE 175

Preparation of 2-n-Butyl-1-[(2'-(carboxymethyl)biphenyl-4-yl)methyl]-4-chloro-5-(hydroxymethyl)imidazole.dicyclohexylamine salt 2-n-Butyl-4-chloro-1-[(2'-(cyanomethyl)biphenyl-4-yl)methyl]-5-(methoxymethyl)imidazole (2.60 g) and a 1:1 mixture of concentrated aqueous HCl and glacial acetic acid (50 mL) were mixed together and then refluxed for 6 hours. The solvents were removed in vacuo and water (200 mL) was added to the residue. The pH was adjusted to 3 with concentrated $NH_4OH$ and this aqueous mixture was extracted with ethyl acetate (3×200 mL). The organic layers were combined, dried ($MgSO_4$) and the solvent removed in vacuo to yield an oil. Subsequent flash chromatography in 60:40 ethyl acetate/hexane to 100% isopropanol yielded 1.07 g of a glass. This product was dissolved in acetone and dicyclohexylamine was added (1 eq). A gum precipitated which was redissolved with more acetone (total of 75 mL) and heat. Upon cooling, solid precipitate was obtained (291 mg); m.p. 135.0-137.0. NMR shows $—OCH_3$ to be missing. NMR (200 MHz, $CDCl_3$) δ 7.43-7.13 (m, 6H); 6.95 (d, 2H, J=8 Hz); 5.20 (s, 2H) 4.46 (s, 2H); 3.45 (s, 2H); 2.76 (m, 2H); 2.60 (t, 2H, J=7 Hz); 2.00-1.03 (m, 24H); 0.87 (t, 3H, J=7 Hz). Mass Calcd. for $C_{23}H_{25}ClN_2O_3$: 412.1554. Found: 412.1544.

EXAMPLE 176

Part A: Preparation of 2-n-Butyl-4-chloro-1-[(2'-(hydrazido)biphenyl-4-yl)methyl]-5-(methoxymethyl)imidazole 2-n-Butyl-1-[(2'-carbomethoxybiphenyl-4-yl)methyl]-4-chloro-5-(methoxymethyl)imidazole (2.00 g, 4.7 mmol, 1 eq), hydrazine (1.5 mL, 46.8 mmol, 10 eq) and methanol (30 mL) were mixed together and then refluxed for 3 days after which 1.5 mL more of hydrazine was added and the reaction refluxed for another day. More hydrazine (1.5 mL) was again added and the reaction was refluxed for an additional day. The reaction was worked up by first removing the hydrazine and methanol in vacuo, following by taking up the residue in ethyl acetate (200 mL) and washing it with water (3×100 mL). The organic layer was dried ($MgSO_4$) and the solvent removed in vacuo to yield 1.37 g of a white glass. NMR ($CDCl_3$, 200 MHz,) δ 7.67-7.31 (m, 4H); 7.40 (d, 2H, J=9 Hz); 7.03 (d, 2H, J=9 Hz); 7.56 (bs, 1H); 5.17 (s, 2H); 4.27 (s, 2H); 3.25 (s, 3H); 2.57 (t, 2H, J=7 Hz); 1.70 (t of t, 2H, 7,7 Hz); 1.34 (t of q, 2H), J=7,7 Hz); 0.86 (t, 3H, J=7 Hz). Anal. Calcd. for $C_{23}H_{27}ClN_4O_2$: C, 64.70; H, 6.37; N, 13.12. Found: C, 64.47; H, 6.35; N, 12.85.

Part B: Preparation of 2-n-Butyl-4-chloro-5-methoxymethyl-1-[4-(2-(trifluoromethylsulfonylhydrazido)biphenyl-4-yl)methyl-]imidazole A solution of triflic anhydride (0.42 mL, 2.5 mmol, 1.5 eq) in methylene chloride (2 mL) was slowly dripped into a stirred solution at −78° C. of 2-n-butyl-4-chloro-1-[(2'-(hydrazido)biphenyl-4-yl)methyl]-5-(methoxymethyl)imidazole (0.71 g, 1.7 mmol, 1.0 eq) and triethylamine (0.35 mL, 2.5 mmol, 1.5 eq) in methylene chloride (5 mL). The solution was stirred at −78° C. for 1 hour and then allowed to warm to room temperature. After 2 hours at room temperature, water (100 mL) was added, the pH adjusted to 5 and the aqueous layer extracted with ethyl acetate (3×100 mL). The organic layers were dried ($MgSO_4$), the solvent removed in vacuo, and the residue flash chromatographed over silica gel beginning in 1:1 hexane/ethyl acetate and finishing in 100% ethyl acetate to yield 380 mg of a light yellow glass. NMR (200 MHz, $CDCl_3$) δ 7.82-7.15 (m, 8H); 6.94 (d, 2H, J=8 Hz); 5.13 (s, 2H); 4.25 (s, 2H); 3.17 (s, 3H); 2.53 (t, 2H, J=7 Hz); 1.69 (t of t, 2H, J=7,7 Hz); 1.27 (t of q, 2H, J=7,7 Hz); 0.81 (t, 3H, J=7 Hz). Fast Atom Bombardment Mass Spectrum: Mass Calcd. for $C_{24}H_{26}ClF_3N_4O_4S$: 559.15. Found: 559.12.

EXAMPLE 177

Part A: Preparation of 4'-Methylbiphenyl-2-carboxaldehyde

Methyl 4'-methylbiphenyl-2-carboxylate (20.00 g, 88 mmol, 1 eq) was dissolved in dry toluene (250 mL) and cooled to −78°: Diisobutylaluminum hydride (1.0M in toluene, 220.0 mL, 220 mmol, 2.2 eq) was then dripped in slowly over 25 minutes keeping the temperature under −70°. When the addition was complete, the mixture was stirred at −78° for 15 minutes and then methanol (10 mL) was added cautiously. When gas evolution was complete, the mixture was poured into a solution of Rochelle salt (100 mL of saturated solution plus 600 mL water). The mixture was stirred or shaken until an extractable solution was obtained. The layers were separated and the aqueous layer extracted with ether ($2\times200$ mL). The organic layers were combined, dried ($MgSO_4$) and the solvent removed in vacuo to yield 16.7 g of a light yellow oil. NMR (200 MHz, $CDCl_3$) δ 7.56–7.16 (m, 8H); 4.59 (s, 2H); 2.40 (s, 3H); 1.74 (s, 1H). This oil (16.7 g, 84 mmol, 1 eq) was subsequently oxidized by dissolving in methylene chloride (100 mL) and stirring with manganese dioxide (7.34 g, 84 mmol, 1 eq). After stirring for one day at room temperature, more manganese dioxide (14.68 g, 168 mmol, 2 eq) was added. The next day, 14.68 g more of manganese dioxide was again added. After another day of stirring, the reaction was filtered through Celite® and the filtrate evaporated to an oil. The oil was chromatographed in 9:1 hexane/ethyl acetate over silica gel to yield 13.4 g of a light yellow opaque oil. The above oxidation can also be performed using pyridinium chlorochromate. NMR ($CDCl_3$, 200 MHz) δ 9.98 (s, 1H); 8.01 (d, 1H, J=7 Hz); 7.64 (t, 1H, J=7 Hz); 7.53–7.38 (m, 2H); 7.28–7.17 (m, 4H); 2.43 (s, 3H). Mass Calcd. for $C_{14}H_{12}O$: 196.0888. Found: 196.0881.

Part B: Preparation of 4'-Methyl-2-(2-nitroethen-1-yl)biphenyl

4'-Methylbiphenyl-2-carboxaldehyde (13.21 g, 67.3 mmol (1.0 eq), nitromethane (4.74 mL, 87.5 mmol, 1.3 eq), ammonium acetate (2.07 g, 26.0 mmol, 0.4 eq) and glacial acetic acid (30 mL) were mixed and refluxed for 2 days, at which time more nitromethane (4.74 mL) and ammonium acetate (2.07 g) were added and the reaction was refluxed for an additional 5 hours. The reaction mixture was poured into ice water (300 mL) and extracted with ethyl acetate (300 mL). The ethyl acetate layer was washed with water ($3\times200$ mL), the organic layer dried ($MgSO_4$), the solvent removed in vacuo and the residue chromatographed in 1:1 hexane/toluene to yield 11.22 g of a light yellow oil which crystallized. The product was recrystallized from methylcyclohexane to yield 8.47 g of yellow crystals; m.p. 64.0°–65.0°. NMR (200 MHz, $CDCl_3$) δ 8.04 (d, 1H, J=13 Hz); 7.69 (d, 1H, J=9 Hz) 7.59–7.37 (m, 4H); 7.50 (d, 1H, J=13 Hz); 7.27 (d, 2H, J=7 Hz); 7.19 (d, 2H, J=7 Hz); 2.41 (s, 3H). Anal. Calcd. for $C_{15}H_{13}NO_2$: C, 75.30; H, 5.48; N, 5.85. Found: C, 75.32; H, 5.56; N, 5.58.

Part C: Preparation of 4'-methyl-2-(1,2,3-triazol-4-yl)biphenyl

4'-Methyl-2-(2-nitroethen-1-yl)biphenyl (6.58 g, 27.5 mmol, 1 eq), sodium azide (5.40 g, 82.3 mmol, 3 eq), and dimethylsulfoxide (minimum to dissolve everything) were mixed together and stirred at room temperature for 4.5 hours. Ethyl acetate (500 mL) was then added and the organic phase washed with water ($3\times400$ mL). The organic layer was dried ($MgSO_4$) and the solvent removed in vacuo to yield 6.54 g of an orange glass. Chromatography in 75:25 hexane/ethyl acetate yielded 2.87 g of of a yellow glass. NMR (200 MHz, $CDCl_3$) δ 7.83 (m, 1H); 7.51–7.32 (m, 3H); 7.18 (d, 2H, J=8 Hz); 7.13 (d, 2H, J=8 Hz); 7.03 (s, 1H); 2.38 (s, 3H). Mass Calcd. for $C_{15}H_{13}N_3$: 235.1110. Found: 235.1111.

Part D: Preparation of 4'-Methyl-2-(N-(triphenylmethyl)-1,2,3-triazol-4-yl)biphenyl 4'-Methyl-2-(1,2,3-triazol-4-yl)biphenyl (2.61 g, 11 mmol, 1.0 eq), triethylamine (1.69 mL, 12 mmol, 1 eq), tritylbromide (3.88 g, 12 mmol, 1 eq) and methylene chloride (30 mL) were mixed and stirred at 0° C. and then allowed to warm to room temperature. After 1 hour, ethyl acetate was added (200 mL) and the organic phase was washed with water ($3\times200$ mL). The organic layer was dried ($MgSO_4$) and the solvent removed in vacuo to yield 5.15 g of a yellow solid. This product was recrystallized from methylcyclohexane to give 3.26 g of off-white crystals; m.p. 181.0°–182.5°. NMR (200 MHz, $CDCl_3$) δ 8.18 (d, 1H, J=7 Hz); 7.50–7.16 (m, 12H); 7.05–6.89 (m, 10 Hz); 6.47 (s, 1H); 2.54 (s, 3H). Anal. Calcd. for $C_{34}H_{27}N_3$: C, 85.50; H, 5.70; N, 8.80. Found: C, 86.60; H, 5.80; N, 8.94.

Part E: Preparation of 2-n-Butyl-4-chloro-5-hydroxymethyl-1-[(2'-(N-(triphenylmethyl)-1,2,3-triazol-4-yl)biphenyl-4-yl)methyl-]imidazole 4'-Methyl-2-(N-triphenylmethyl)-1,2,3-triazol-4-yl)biphenyl (3.14 g, 6.57 mmoles) was brominated in the benzylic position by the procedure in Example 85, Part B, using benzoylperoxide instead of AIBN as radical initiator. Filtration of succinimide and evaporation yielded 4.45 g of a crude oil which was used as is. NMR (200 MHz, $CDCl_3$) δ $CH_2Br$, 4.41. This bromide (4.33 g, approx. 7.8 mmol, 1 eq) was alkylated onto 2-n-butyl-4-chloro-5-(hydroxymethyl)imidazole by the procedure described in Example 1, Part A. Flash chromatography in 75:25 hexane/ethyl acetate over silica gel yielded a yellow solid (0.67 g) which was recrystallized from carbon tetrachloride to yield 447 mg of white crystals; m.p. 173.0°–176.5°. NMR ($CDCl_3$, 200 MHz) δ 8.03 (d, 1H, J=9 Hz); 7.51–7.14 (m, 14H); 6.98 (m, 6H); 6.86 (d, 2H, J=9 Hz); 6.63 (s, 1H); 5.15 (s, 2H); 4.33 (s, 2H); 2.53 (t, 2H, J=7 Hz); 1.15 (t of t, 2H, J=7,7 Hz); 1.32 (t of q, 2H, J=7,7 Hz); 0.87 (t, 3H, J=7 Hz). Mass Calcd. for $C_{42}H_{38}ClN_5O$: 663.2765. Found: 663.2762.

Part F: Preparation of 2-n-Butyl-4-chloro-5-hydroxymethyl-1-[(2'-1,2,3-triazol-4-yl)biphenyl-4-yl)methyl]imidazole 2-n-Butyl-4-chloro-5-hydroxymethyl-1-[(2'-(N-(triphenylmethyl)triazol-4-yl)biphenyl-4-yl)methyl-]imidazole (408 mg, 0.6 mmol, 1 eq), 1,4-dioxane (5 mL), water (1 mL) and 4.0N HCl in dioxane (0.46 mL, 1.8 mmol, 3 eq) were mixed and stirred at room temperature. After 2 hours, water was added (200 mL), and the aqueous layer extracted with ethyl acetate ($3\times200$ mL). The organic layers were dried ($MgSO_4$) and the solvent removed in vacuo to yield 260 mg of an off-white glass. Flash chromatography of the product in 100% ethyl acetate over silica gel yielded 140 mg of a white glass. NMR (200 MHz, $CDCl_3$) δ 7.82 (m, 1H); 7.50–7.25 (m, 3H); 7.17 (d, 2H, J=9 Hz); 6.98 (d, 2H, J=9 Hz); 6.95 (s, 1H); 5.23 (s, 2H); 4.52 (s, 2H); 2.58 (t, 2H, J=7 Hz); 1.63 (t of t, 2H, J=7,7 Hz); 1.30 (t of q, 2H, J=7,7 Hz); 0.82 (t, 3H, J=7 Hz). Mass Calcd. for $C_{23}H_{24}ClN_5O$: 421.1669. Found: 421.1670.

EXAMPLES 178 AND 179

Part A: Preparation of Ethyl 3-(4-methylphenyl)-3-oxo-2-(allyl)propanoate

Ethyl 3-(4-methylphenyl)-3-oxopropanoate (prepared as described in W. Wierenga and H. I. Skulnick, *J. Org. Chem.* (1979), 44, 310) (63.66 g, 309 mmol, 1 eq) was added to a freshly prepared sodium ethoxide solution (Na, 7.43 g, 323 mmol, 1.05 eq; EtOH, 250 mL). The ethanol was removed in vacuo and the residue was dissolved in DMF (250 mL). Allyl bromide (29.3 mL, 338 mmol, 1.1 eq) followed by sodium iodide (4.56 g, 304 mmol, 1 eq) were then added and the contents stirred overnight at room temperature. The DMF was removed in vacuo, water (250 mL) was added and the aqueous layer extracted with ethyl acetate (3×200 mL). The organic layers were dried ($MgSO_4$) and the solvent removed in vacuo to yield 74.21 g of an amber oil. NMR (200 MHz, $CDCl_3$) δ 7.81 (d, 2H, J=10 Hz); 7.30 (d, 2H, J=10 Hz); 5.96–5.72 (m, 1H); 5.21–5.00 (m, 2H); 4.41 (t, 1H, J=7 Hz); 4.16 (q, 2H, J=7 Hz); 2.78 (t, 2H, J=7 Hz); 2.42 (s, 3H); 1.18 (t, 3H, J=7 Hz). Anal. Calcd. for $C_{15}H_{18}O_3$: C, 73.15; H, 7.37. Found: C, 73.10; H, 7.38.

Part B: Preparation of 3-Carboethoxy-4-(4-methylphenyl)-4-(oxo)butanal

Ethyl 3-(4-methylphenyl)-3-oxo-2-(allyl)propanoate (74.21 g, 301 mmol, 1.0 eq), osmium tetroxide (100 mg, cat.), sodium metaperiodate (141.8 g, 663 mmol, 2.2 eq), ether (500 mL) and water (1 L) were mixed and stirred at room temperature. After 24 hours, an additional 110 mg of $OsO_4$ was added and after another 24 hours, 200 mg more of $OsO_4$ was added together with sodium metaperiodate (190 g, 888 mmol, 3.0 eq). After 4 days, the layers were separated and the ether layer washed with aqueous sodium bisulfite (1×500 mL) followed by brine (1×300 mL). The ether layer was dried ($MgSO_4$) and the solvent removed in vacuo to yield 64.99 g of a dark brown oil. This oil was flash chromatographed over silica gel in 4:1 hexane/ethyl acetate to yield 37.5 g of an amber oil. NMR (200 MHz, $CDCl_3$) δ 9.79 (s, 1H); 7.93 (d, 2H, J=9 Hz); 7.27 (d, 2H, J=9Hz); 4.87 (t, 1H, J=7 Hz); 4.13 (q, 2H, J=7 Hz); 3.37–3.08 (AB multiplet, 2H); 2.40 (s, 3H); 1.14 (t, 3H, J=7 Hz). Anal. Calcd. for $C_{14}H_{16}O_4$: C, 67.73; H, 6.50. Found: C, 67.53; H, 6.54.

Part C: Preparation of 3-Carboethoxy-2-(4-methylphenyl)furan

Ethyl 3-Carboethoxy-4-(4-methylphenyl)-4-(oxo)-butanal (10.00 g), trifluoroacetic anhydride (50 mL) and trifluoroacetic acid (2 drops) were mixed and stirred at 0° over ice and allowed to warm to room temperature. After 3 hours, more trifluoroacetic anhydride (50 mL) together with trifluoroacetic acid (2 drops) were added at room temperature. The next day, the solvent was removed in vacuo and the residue partitioned between 1N NaOH (200 mL) and ethyl acetate (200 mL). The layers were separated and the organic layer washed with 1N NaOH (2×200 mL). The organic layer was dried ($MgSO_4$) and the solvent removed in vacuo to yield a brown oil (9.95 g) which was flash chromatographed in 99:1 hexane/ethyl acetate to yield 2.57 g of an off-white solid; m.p. 79.0°–80.5°. NMR (200 MHz, $CDCl_3$) δ 7.88 (d, 2H, J=9 Hz); 7.42 (d, 1H, J=2 Hz); 7.26 (d, 2H, J=9 Hz); 6.83 (d, 1H, J=2 Hz); 4.34 (q, 2H, J=7 Hz); 2.40 (s, 3H); 1.34 (t, 3H, J=7 Hz). Anal. Calcd. for $C_{14}H_{14}O_3$: C, 73.03; H, 6.13. Found: C, 73.52; H, 6.30.

Part D: Preparation of 2-n-Butyl-1-[4-(3-carboxyfuran-2-yl)benzyl]-4-chloro-5-(hydroymethyl)imidazole (isomer A) and 2-n-butyl-1-[4-(3-carboxyfuran-2-yl)benzyl]-5-chloro-4-(hydroxymethyl)imidazole (isomer B)

3-Carboethoxy-2-(4-methylphenyl)furan was brominated, alkylated, and saponified by the procedures described in Example 85, Parts B, C, and E.

Isomer A, the faster eluting isomer, was recrystallized from acetonitrile; m.p. 158.5°–160.0°. NMR (200 MHz, DMSO-$d_6$) δ 12.80 (bm, 1H); 7.92 (d, 2H, J=9H); 7.82 (d, 1H, J=2 Hz); 7.17 (d, 2H, J=9 Hz); 6.84 (d, 1H, J=2 Hz); 5.30 (s, 2H), 5.30 (m, 1H); 4.34 (s, 2H); 2.47 (t, 2H, J=7 Hz); 1.47 (t of t, 2H, J=7,7 Hz); 1.24 (t of q, 2H, J=7,7 Hz); 0.74 (t, 3H, J=7 Hz). Anal. Calcd. for $C_{20}H_{21}ClN_2O_4$: C, 61.78; H, 5.44; N, 9.12. Found: C, 61.66; H, 5.39; N, 9.09.

Isomer B was recrystallized from nitromethane/acetonitrile; m.p. 118.5°–120.5°. NMR (200 MHz, DMSO-$d_6$) δ 12.89 (bm, 1H); 7.92 (d, 2H, J=9 Hz); 7.82 (d, 1H, J=2 Hz); 7.13 (d, 2H, J=9 Hz); 6.83 (d, 1H, J=2 Hz); 5.23 (s, 2H); 4.93 (m, 1H) 4.29 (d, 2H, J=7 Hz); 2.57 (t, 2H, J=7 Hz); 1.53 (t of t, 2H, J=7,7 Hz); 2.57 (t of q, 2H, J=7,7 Hz); 0.77 (t, 3H, J=7 Hz). Mass Calcd. for $C_{20}H_{21}ClN_2O_4$: 388.1190. Found: 388.1171.

EXAMPLE 180

Part A: Preparation of 1-[(2'-Carbomethoxybiphenyl-4-yl)methyl]-2-butyl-4-chloro-5-(2-methoxyethoxymethoxymethyl)imidazole To a solution of 7.50 mL of 1.6M n-butyllithium/hexane in 50 mL of tetrahydrofuran at 0° was added dropwise 1.50 mL of t-butanol. To this solution was added 4.52 g of 1-[(2'-carbomethoxybiphenyl-4-yl)methyl]-2-butyl-4-chloro-5-hydroxymethylimidazole followed by 1.50 ml of 2-methoxyethoxymethyl chloride. The resulting solution was stirred at 25° for 16 hours. The mixture was diluted with diethyl ether, washed with water and brine, dried over anhydrous sodium sulfate, filtered and concentrated. Column chromatography afforded 3.50 g of 1-[(2'-carbomethoxybiphenyl-4-yl)methyl]-2-butyl-4-chloro-5-(2-methoxyethoxymethoxymethyl)imidazole. NMR (200 MHz, $CDCl_3$) δ 7.83 (d, 1H); 7.52 (t, 1H); 7.40 (t, 1H), 7.28 (m, 3H); 7.00 (d, 1H); 5.19 (s, 2H); 4.68 (s, 2H); 4.48 (s, 2H); 3.67 (m, 2H); 3.64 (s, 3H); 3.54 (m, 2H); 3.37 (s, 3H); 2.58 (t, 2H); 1.67 (quint., 2H); 1.34 (sext., 2H); 0.88 (t, 3H).

Part B: Preparation of 1-[(2'-Carboxybiphenyl-4-yl)methyl]-2-butyl-4-chloro-5-(2-methoxyethoxymethoxymethyl)imidazole A solution of 3.15 g of 1-[(2'-carbomethoxybiphenyl-4-yl)methyl]-2-butyl-4-chloro-5-(2-methoxyethoxymethoxymethyl)imidazole and 2.77 g of potassium methanethiolate in 125 mL of dimethylformamide was stirred at 125° for 4 hours. After cooling the solvent was removed in vacuo, and the residue was dissolved in water. The resulting aqueous solution was washed with diethyl ether, adjusted to pH 3 employing 10% hydrochloric acid, and extracted with methylene chloride. The combined organic layers were washed with brine, dried over anhydrous sodium sulfate, filtered, and concentrated. The crude product was recrystallized from chlorobutane to afford 2.45 g of 1-[(2'-carboxybiphenyl-4-yl)methyl]-2-butyl-4-chloro-5-(2-methoxyethoxymethoxymethyl)imidazole. NMR (200 MHz, $CDCl_3$) δ 7.95 (d, 1H); 7.57 (t, 1H); 7.46 (t, 1H); 7.38 (m, 3H); 7.05 (d, 2H); 5.22 (s, 2H); 4.64 (s, 2H); 4.48 (s, 2H); 3.58 (m, 4H); 3.40 (s, 3H); 2.54 (t, 2H); 1.60 (quint., 2H); 1.32 (sext., 2H); 0.84 (t, 3H).

Part C: Preparation of 1-[(2'-Methoxyaminocarbonylbiphenyl-4-yl)methyl]-2-butyl-4-chloro-5-(2-methoxyethoxymethoxymethyl-)imidazole A solution of 0.24 ml of oxalyl chloride in 5 mL of chloroform was added dropwise to a solution of 1 mL of dimethylformamide in 4 mL of chloroform at −20°. After this solution had been stirred at −20° for 20 minutes, 0.28 mL of N-methylmorpholine was added followed by 1.21 g of 1-[(2'-carboxybiphenyl-4-yl)methyl]-2-butyl-4-chloro-5-(2-methoxyethoxymethoxymethyl-)imidazole. After another 20 minutes at −20°, 0.55 ml of mixture was extracted with diethyl ether. The combined organic phases were washed with brine, dried over anhydrous sodium sulfate, filtered, and concentrated. Column chromatography (elution: methanol/-chloroform) provided 0.11 g of 1-[(2'-methoxyaminocarbonylbiphenyl-4-yl)methyl]-2-butyl-4-chloro-5-hydroxymethylimidazole. NMR (200 MHz, $CDCl_3$) δ 11.31 (br s, 1H); 7.48 (m, 1H); 7.41–7.33 (m, 5H); 7.09 (d, 2H); 5.27 (br s, 3H); 4.32 (d, 2H); 3.44 (s, 3H); 2.49 (t, 2H); 1.48 (quint., 2H); 1.25 (sext., 2H); 0.80 (t, 3H).

The following compounds were prepared according to the procedures described in the above example.

| | | NMR (200 MHz, DMSO-$d_6$) |
|---|---|---|
| Example 181 | 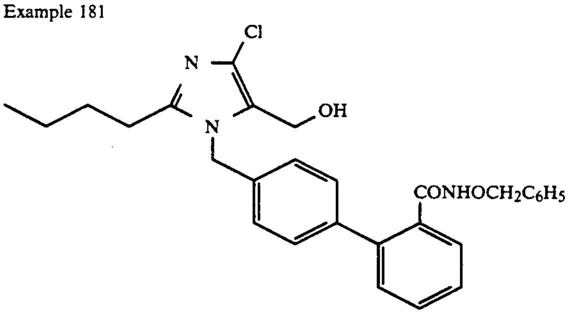 | δ 11.29(brs, 1H), 7.48(m, 1H), 7.33(m, 10H), 7.09(d, 2H), 5.27(d, 2H), 4.67(s, 2H), 4.31 (s, 2H), 2.47(t, 2H), 1.46(quint., 2H), 1.21 (sext., 2H), 0.76(t, 3H). |
| Example 182 | 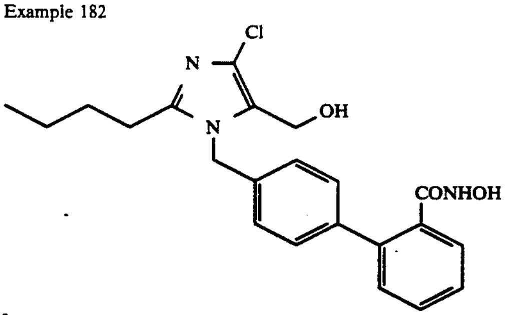 | δ 10.81(brs, 1H), 9.02(brs, 1H), 7.55–7.35(m, 6H), 7.11(d, 2H), 5.28(brs, 3H), 4.34(d, 2H), 2.50(t, 2H), 1.49(quint., 2H), 1.25 (sext., 2H), 0.78(t, 3H). |

N-methylmorpholine and 1.35 mL of methoxylamine were added to the mixture. The reaction mixture was warmed slowly to 25°, stirred at 25° for 4 hours, and finally refluxed for 40 hours. After cooling the mixture was diluted with ethyl acetate. The resulting solution was washed with 10% hydrochloric acid, water, 10% sodium bicarbonate solution and brine. Finally the solution was dried over anhydrous sodium sulfate, filtered, and concentrated in vacuo. Column chromatography (elution: methanol/chloroform) furnished 0.21 g of 1-[(2'-methoxyaminocarbonylbiphenyl-4-yl)methyl]-2-butyl-4-chloro-5-(2-methoxyethoxymethoxymethyl-)imidazole. NMR (200 MHz, $CDCl_3$) δ 7.85 (s, 1H); 7.63 (d, 1H); 7.53–7.33 (m, 5H); 7.05 (d, 2H); 5.20 (s, 2H); 4.67 (s, 2H); 4.47 (s, 2H); 3.63 (m, 5H); 3.55 (m, 2H); 3.36 (s, 3H); 2.56 (t, 2H); 1.67 (m, 2H); 1.32 (m, 2H); 0.87 (t, 3H).

Part D: Preparation of 1-[(2'-Methoxyaminocarbonylbiphenyl-4-yl)methyl]-2-butyl-4-chloro-5-hydroxymethylimidazole A solution of 0.20 g of 1-[(2'-methoxyaminocarbonylbiphenyl-4-yl)methyl]-2-butyl-4-chloro-5-(2-methoxyethoxymethoxymethyl)imidazole in 60 ml of 1.5M aqueous tetrafluoroboric acid/acetonitrile was stirred for 20 hours at 25°. The reaction mixture was poured into dilute sodium bicarbonate solution, and the resulting

EXAMPLE 183

Part A: Preparation of 1-[(2'-Aminobiphenyl-4-yl)methyl]-2-butyl-4-chloro-5-hydroxymethylimidazole

This compound was prepared according to the procedure described in Example 141, Part A. From 3.30 g of 1-[(2'-nitrobiphenyl-4-yl)methyl]-2-butyl-4-chloro-5-hydroxymethylimidazole, 1.60 g of iron powder, 3.20 ml of acetic acid, and 160 mL of methanol there was obtained 2.05 g of 1-[(2'-aminobiphenyl-4-yl)methyl]-2-butyl-4-chloro-5-hydroxymethylimidazole. NMR (200 MHz, $CDCl_3$) δ 7.45 (d, 2H); 7.23–7.08 (m, 4H); 6.89–6.77 (m, 2H); 5.27 (s, 2H); 4.55 (br s, 2H); 2.62 (t, 2H); 1.69 (quint., 2H); 1.37 (sext., 2H); 0.88 (t, 3H).

Part B: Preparation of 1-[(2'-Aminobiphenyl-4-yl)methyl]-2-butyl-4-chloro-5-(2-methoxyethoxymethoxymethyl)imidazole This compound was prepared according to the procedure described in Example 180, Part A. From 2.03 g of 1-[(2'-aminobiphenyl-4-yl)methyl]-2-butyl-4-chloro-5-hydroxymethylimidazole, 3.75 mL of 1.6M n-butyllithium/hexane, 0.75 ml of t-butanol, 0.75 ml of 2-methoxyethoxymethyl chloride, and 25 mL of tetrahydrofuran there was obtained 0.84 g of 1-[(2'-aminobiphenyl-4-yl)methyl]-2-butyl-4-chloro-5-(2-methoxyethoxymethoxymethyl)imidazole. NMR (200 MHz, $CDCl_3$) δ 7.42 (d, 2H); 7.19–7.03 (m, 4H); 6.86 (m, 2H); 5.20 (s, 2H); 4.69 (m, 2H); 4.49 (m, 2H); 3.67 (m, 2H), 3.54 (m, 2H); 3.37 (s, 3H); 2.59 (t, 2H); 1.67 (quint., 2H); 1.34 (sext., 2H); 0.87 (t, 3H).

Part C: Preparation of 1-[(2'-Trifluoroacetamidobiphenyl-4-yl)methyl[-2-butyl-4-chloro-5-(2-methoxyethoxymethoxymethyl-)imidazole To a solution of 0.84 g of 1-[(2'-aminobiphenyl-4-yl)methyl]-2-butyl-4-chloro-5-(2-methoxyethoxymethoxymethyl)imidazole, 0.23 g of 4-dimethylaminopyridine, 1.28 mL of triethylamine, and 10 mL of tetrahydrofuran at 25° was added dropwise 1.30 mL of trifluoroacetic anhydride. The reaction mixture was stirred at 25° for 4 hours and then was poured into water. The resulting solution was adjusted to pH 4 using 10% hydrochloric acid and extracted with diethyl ether. The combined organic phases were washed with water and brine, dried over anhydrous sodium sulfate, filtered, and concentrated in vacuo. Column chromatography afforded 0.96 g of 1-[(2'-trifluoroacetamidobiphenyl-4-yl)methyl]-2-butyl-4-chloro-5-(2-methoxyethoxymethoxymethyl)-imidazole. NMR (200 MHz, $CDCl_3$) δ 8.22 (d, 1H); 7.89 (br s, 1H); 7.44 (m, 1H); 7.36–7.29 (m, 4H); 7.12 (d, 2H); 5.23 (s, 2H); 4.68 (s, 2H); 4.49 (s, 2H); 3.65 (m, 2H); 3.54 (m, 2H); 3.37 (s, 3H); 2.56 (t, 2H); 1.67 (quint., 2H); 1.34 (sext., 2H); 0.87 (t, 3H).

Part D: Preparation of 1-[(2'-Trifluoroacetamidobiphenyl-4-yl)methyl]-2-butyl-4-chloro-5-hydroxymethylimidazole This compound was prepared according to the procedure described in Example 180, Part D. From 0.96 g of 1-[(2'-trifluoroacetamidobiphenyl-4-yl)methyl-2-butyl-4-chloro-5-(2-methoxyethoxymethoxymethyl-)imidazole there was obtained 0.35 g of 1-[(2'-trifluoroacetamidobiphenyl-4-yl)methyl]-2-butyl-4-chloro-5-hydroxymethylimidazole. NMR (200 MHz, $CDCl_3$) δ 8.24 (d, 1H); 7.89 (br s, 1H); 7.46 (m, 1H); 7.32 (m, 4H); 7.15 (d, 2H); 5.30 (s, 2H); 4.55 (d, 2H); 2.60 (t, 2H); 1.67 (br t, 1H), 1.70 (quint., 2H); 1.36 (sext., 2H); 0.88 (t, 3H).

EXAMPLE 184

Part A: Preparation of 2-(4-Methylphenoxy)benzoic acid

To a solution of 5.95 g of p-cresol and 7.83 g of 2-chlorobenzoic in 50 mL of dimethylformamide at 25° was added, in portions, 14.50 g of anhydrous potassium carbonate. The resulting mixture was heated to 80°, and 0.10 g of copper(I) iodide was added. The reaction mixture then was refluxed for 16 hours. While still hot the mixture was poured onto water-ice. The resulting suspension was filtered, and the filtrate was adjusted to pH 3.0 using aqueous hydrochloric acid. The precipitate was recovered by filtration. The crude solid was dissolved in an aqueous sodium hydroxide solution. This solution was acidified to pH 6.0 using hydrochloric acid, filtered, and then acidified to pH 3.0. Filtration provided 5.67 g of 2-(4-methylphenoxy)benzoic acid which was employed in the following reaction without further purification. NMR (200 MHz, $CDCl_3$): δ 8.15 (d of d, 1H); 7.42 (d of d of d, 1H); 7.23–7.12 (m, 3H); 6.97 (d, 2H); 6.80 (d, 1H); 2.37 (s, 3H).

Part B: Preparation of Methyl 2-(4-methylphenoxy)benzoate

A solution of 37.70 g of 2-(4-methylphenoxy)benzoic acid was 12.0 mL of concentrated sulfuric acid in 500 mL of methanol was refluxed for 14 hours. After cooling, the reaction mixture was concentrated in vacuo and the residue was added to a mixture of methylene chloride and water. The organic phase was separated, washed with saturated sodium bicarbonate solution and brine, dried over anhydrous sodium sulfate, filtered, and concentrated. The crude product was kugelrohr distilled (120°–135°/0.025 torr) to furnish 35.08 g of methyl 2-(4-methylphenoxyl)benzoate, m.p. 31°–34°. NMR (200 MHz, $CDCl_3$) δ 7.87 (d of d, 1H); 7.39 (t of d, 1H); 7.11 (m, 3H); 6.88 (m, 3H); 3.81 (s, 3H); 2.30 (s, 3H).

Part C: Preparation of Methyl 2-(4-bromomethylphenoxy)benzoate

A solution of 35.08 g of methyl 2-(4-methylphenoxy)-benzoate, 25.7 g of N-bromosuccinimide, 0.57 g of azobisisobutyronitrile, and 1200 mL of carbon tetrachloride was refluxed for 3 hours. After cooling to room temperature the resulting suspension was filtered and then concentrated in vacuo to provide 4.51 g of crude methyl 2-(4-bromomethylphenoxy)benzoate which was used in a subsequent reaction without further purification; NMR (200 MHz, $CDCl_3$): δ 7.92 (d of d, 1H); 7.45 (t of d, 1H); 7.16 (m, 3H); 6.90 (m, 3H); 4.49 (s, 2H); 3.83 (s, 3H).

Part D: Preparation of 2-Butyl-4-chloro-1-[4-(2-carbomethoxyphenoxy)benzyl]-5-hydroxymethylimidazole To a suspension of 7.51 g of sodium methoxide in 100 mL of dimethylformamide at 25° was added a solution of 26.50 g of 2-butyl-4(5)-chloro-5(4)-hydroxymethylimidazole in 100 mL of DMF. The resulting mixture was stirred at 25° for 0.25 hours; to this mixture was added dropwise a solution of 45.1 g of methyl 2-(4-bromomethylphenoxy)benzoate in 100 mL of DMF. Finally, the reaction mixture was stirred at 40° for 4 hours. After cooling to 25°, the solvent was removed in vacuo. The residue was dissolved in ethyl acetate, and this solution was washed with water and brine, dried over anhydrous sodium sulfate, filtered, and concentrated. Column chromatography on silica gel (elution: 10–25% ethyl acetate/benzene) afforded 7.80 g of 2-butyl-4-chloro-1-[4-(2-carbomethoxyphenoxy)benzyl]-5-hydroxymethylimidazole. NMR (200 MHz, $CDCl_3$) δ 7.92 (d, 1H); 7.48 (t, 1H); 7.21 (t, 1H); 6.93 (m, 5H); 5.21 (s, 2H); 4.48 (s, 2H); 3.79 (s, 3H); 2.56 (t, 2H); 1.65 (quint., 2H); 1.34 (sext., 2H); 0.88 (t, 3H).

Part E: Preparation of 2-Butyl-4-chloro-1-[4-(2-carboxyphenoxy)benzyl]-5-hydroxymethylimidazole A solution of 7.70 g of 1-[4-(2-carbomethoxyphenoxy)benzyl]-2-butyl-4-chloro-5-hydroxymethyl imidazole in 250 mL of ethanol and 125 mL of 10% aqueous sodium hydroxide was refluxed for 5 hours. After cooling, the reaction mixture was filtered, and the solvent was removed in vacuo. The residue was dissolved in water, and the solution was acidified to pH 3.5 using hydrochloric acid. The precipitated solid was recovered by filtration and recrystallized from acetone to furnish 6.52 g of 2-butyl-4-chloro-1-[4-(2-carboxyphenoxy)benzyl]-5-hydroxymethylimidazole, m.p. 178°-180°. NMR (200 MHz, DMSO) δ 7.79 (d, 1H); 7.53 (t, 1H); 7.23 (t, 1H); 7.07 (d, 2H); 6.94 (d, 1H); 6.87 (d, 2H); 5.18 (s, 2H); 4.32 (s, 2H); 2.47 (t, 2H); 1.46 (quint., 2H); 1.23 (sext., 2H); 0.78 (t, 3H).

The following compounds have been or could be prepared by the above procedures.

TABLE 12

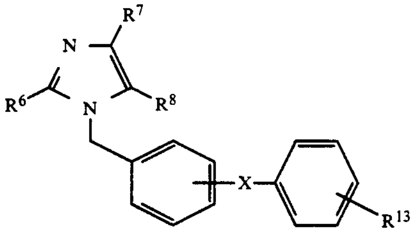

| Ex. No. | $R^6$ | $R^7$ | $R^8$ | 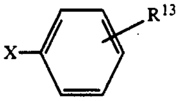 | MP(°C.) |
|---|---|---|---|---|---|
| 185 | n-butyl | Cl | $CH_2OH$ | 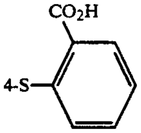 | 166-167 |
| 186 | n-butyl | Cl | $CH_2OH$ | 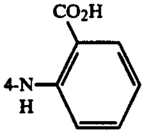 | |
| 187 | n-butyl | Cl | $CH_2OH$ | 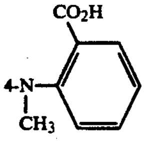 | |
| 188 | n-propyl | H | $CH_2OH$ | 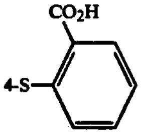 | |
| 189 | n-propyl | Cl | $CH_2OH$ | 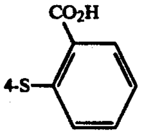 | |
| 190 | $CH_2OCH_2CH_2CH_2$ | Cl | $CH_2OH$ | 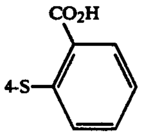 | |
| 191 | n-butyl | Cl | $CH_2OH$ | 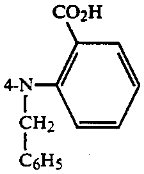 | |

EXAMPLE 192

Part A: Preparation of 1-(4-Benzyloxybenzyl)-2-butyl-4-chloro-5-hydroxymethylimidazole To a suspension of 1.43 g of sodium methoxide in 20 mL of dimethylformamide at 25° was added a solution of 5.00 g of 2-butyl-4(5)-chloro-5(4)-hydroxymethylimidazole in 15 mL of dimethylformamide (DMF). The resulting mixture was stirred at 25° for 0.25 hours, and then to this mixture was added dropwise a solution of 4-benzyloxybenzyl chloride in 15 mL of DMF. Finally, the reaction mixture was stirred at 40°, the solvent was removed in vacuo. The residue was dissolved in ethyl acetate, and this solution was washed with water and brine, dried over anhydrous sodium sulfate, filtered, and concentrated. Column chromatography on silica gel (elution: 10–25% ethyl acetate/benzene) afforded 3.27 g of 1-(4-benzyloxybenzyl)-2-butyl-4-chloro-5-hydroxymethylimidazole; m.p. 115°–116°; NMR (200 MHz, $CDCl_3$): δ 7.39 (m, 5H); 6.94 (s, 4H); 5.15 (s, 2H); 5.04 (s, 2H); 4.47 (bs, 2H); 2.56 (t, 2H); 2.07 (bs, 1H); 1.63 (quint., 2H); 1.32 (sext., 2H); 0.87 (t, 3H).

Part B: Preparation of 1-(4-Hydroxybenzyl)-2-butyl-4-chloro-5-hydroxymethylimidazole A mixture of 0.50 g of 1-(4-benzyloxybenzyl)-2-butyl-4-chloro-5-hydroxymethylimidazole, 0.50 g of 10% palladium/carbon and 40 mL of tetrahydrofuran was stirred at room temperature under hydrogen gas (1 atm.) for 6 hours. The mixture was filtered through Celite ® under nitrogen, and the resulting solution was concentrated in vacuo. The crude product was extracted with hot chloroform. After cooling, the chloroform mixture was concentrated in vacuo, and the resulting solid was washed with hexane to afford 0.16 g of 1-(4-hydroxybenzyl)-2-butyl-4-chloro-5-hydroxymethylimidazole; NMR (200 MHz, DMSO-$d_6$): δ 9.43 (s, 1H); 6.81 ($A_2B_2$, 4H); 5.21 (t, 1H); 5.10 (s, 2H); 4.33 (d, 2H); 2.47 (t, 2H); 1.44 (quint 2H); 1.23 (sext., 2H); 0.79 (t, 3H).

Part C: Preparation of 1-[4-(2-Cyanobenzyloxy)benzyl]-2-butyl-4-chloro-5-hydroxymethylimidazole To a solution of 1.00 g of 1-(4-hydroxybenzyl)-2-butyl-4-chloro-5-hydroxymethylimidazole in 15 mL of DMF at 25° was added 0.185 g of sodium methylate, and the resulting mixture was stirred at 25° for 0.25 hours. To this mixture was then added a solution of 0.80 g of α-bromo-o-tolunitrile in 5 mL of DMF. The reaction mixture was stirred at 25° for 16 hours. The solvent was removed in vacuo, and the residue dissolved in ethyl acetate. This solution was washed with water and brine, dried over anhydrous sodium sulfate, filtered, and concentrated in vacuo. Column chromatography on silica gel (elution: 10–25% ethyl acetate/benzene) provided 0.76 g of 1-[4-(2-cyanobenzyloxy)benzyl]-2-butyl-4-chloro-5-hydroxymethylimidazole; NMR (200 MHz, $CDCl_3$): δ 7.73–7.59 (m, 3H); 7.44 (m, 1H); 6.96 (s, 4H); 5.23 (s, 2H); 5.14 (s, 2H); 4.50 (d, 2H); 2.57 (t, 2H); 1.66 (quint., 2H); 1.33 (sext., 2H); 0.87 (t, 3H).

Part D: 1-[4-(2-Cyanobenzyloxy)benzyl]-2-butyl-4-chloro-5-cyanomethylimidazole

To a solution of 0.76 g of 1-[4-(2-cyanobenzyloxy)-benzyl]-2-butyl-4-chloro-5-hydroxymethylimidazole in 20 mL of chloroform at 25° was added dropwise 0.95 mL of thionyl chloride and the mixture was stirred at 25° for 2 hours. The solvent was removed in vacuo. The residue was dissolved in 20 mL of toluene, and then the toluene was removed in vacuo. Finally, the residue was dissolved in 10 mL of dimethyl sulfoxide, and the resulting solution was added to a solution of 0.71 g of sodium cyanide in 10 mL of dimethylsulfoxide. The mixture was stirred at 25° for 1 hour and then poured into water. This emulsion was extracted with ethyl acetate; and the combined organic phases were washed with water and brine, dried over anhydrous sodium sulfate, filtered, and concentrated. Column chromatography on silica gel (elution 0–25% ethyl acetate/benzene) afforded 0.67 g of 1-[4-(2-cyanobenzyloxy)benzyl]-2-butyl-4-chloro-5-cyanomethylimidazole; NMR (200 MHz, $CDCl_3$): δ 7.79–7.60 (m, 3H); 7.47 (m, 1H); 7.00 (s, 4H); 5.24 (s, 2H); 5.14 (s, 2H); 3.46 (s, 2H); 2.66 (t, 2H); 1.71 (quint., 2H); 1.40 (sext., 2H); 0.92 (t, 3H).

Part E: 1-[4-(2-Carboxybenzyloxy)benzyl]-2-butyl-4-chloroimidazole-5-acetic acid A solution of 0.65 g of 1-[4-(2-cyanobenzyloxy)benzyl]-2-butyl-4-chloro-5-cyanomethylimidazole in 20 mL of ethylene glycol and 10 mL of 10% aqueous sodium hydroxide was refluxed for 14 hours. After cooling, the reaction mixture was filtered, and the solvent was removed in vacuo. The residue was dissolved in water, and the solution was acidified to pH 3.5 using hydrochloric acid. The precipitated solid was recovered by filtration and recrystallized from aqueous ethanol to furnish 0.21 g of 1-[4-(2-carboxybenzyloxy)benzyl]-2-butyl-4-chloroimidazole-5-acetic acid, m.p. 170°–172°; NMR (200 MHz, DMSO-$d_6$): δ 12.9 (bs, 2H); 7.94 (d, 1H); 7.61 (d, 1H); 7.60 (t, 1H); 7.46 (t, 1H); 6.99 (s, 4H); 5.45 (s, 2H); 5.11 (s, 2H); 3.49 (s, 2H); 2.52 (t, 2H); 1.48 (quint., 2H); 1.24 (sext., 2H); 0.82 (t, 3H).

EXAMPLE 193

Part A: Preparation of 1-(4-Hydroxybenzyl)-2-butyl-5-hydroxymethylimidazole

A mixture of 1.00 g of 10% palladium/carbon and 1.00 g of 1-(4-benzyloxybenzyl)-2-butyl-4-chloro-5-hydroxymethyl imidazole in 20 mL of methanol was stirred at 25° for five minutes. Hydrogen gas was bubbled into the solution, and the mixture was stirred under hydrogen gas (1 atm.) at 25° for 2 hours. The mixture was filtered, and the resulting solution concentrated in vacuo to furnish 0.75 g of 1-(4-hydroxybenzyl)-2-butyl-5-hydroxymethylimidazole; NMR (200 MHz, DMSO-$d_6$): δ 9.75 (bs, 1H); 7.55 (s, 1H); 6.91 ($A_2B_2$, 4H); 5.80 (bs, 1H); 5.35 (s, 2H); 4.45 (s, 2H); 2.89 (t, 2H); 1.44 (quint, 2H); 1.21 (sext., 2H); 0.80 (t, 3H).

Part B: Preparation of 1-[4-(2-Carboxybenzyloxy)benzyl]-2-butyl-5-hydroxymethylimidazole The title compound was prepared from 1-(4-hydroxybenzyl)-2-butyl-5-hydroxymethylimidazole using the alkylation and hydrolysis procedures described in Example 192, Parts C and E, m.p. 115°–116°; NMR (200 MHz, DMSO-$d_6$): δ 7.92 (d, 1H); 7.59 (m, 2H); 7.43 (m, 1H); 6.95 ($A_2B_2$, 4H); 6.74 (s, 1H); 5.40 (s, 2H); 5.11 (s, 2H); 4.31 (s, 2H); 2.48 (t, 2H); 1.47 (quint., 2H); 1.23 (sext., 2H); 0.77 (t, 3H).

EXAMPLE 194

Part A: Preparation of 1-[4-(2-Cyanobenzyloxy)benzyl]-2-butyl-4-chloro-5-methoxymethylimidazole To a solution of 0.29 g of 1-[4-(2-cyanobenzyloxy)-benzyl]-2-butyl-4-chloro-5-hydroxymethylimidazole in 8.0 mL of dimethyl sulfoxide at 25° was added 0.93 g of potassium t-butoxide followed by 0.060 mL of methyl iodide. The reaction mixture was stirred at 25° for 2.5 hours and then was poured into water. The aqueous emulsion was extracted with ethyl acetate; the organic phases were combined and washed with water and brine, dried over anhydrous sodium sulfate, filtered, and concentrated in vacuo. Column chromatography on silica gel (elution: 5-25% ethyl acetate/benzene) furnished 0.17 g of 1-[4-(2-cyanobenzyloxy)benzyl]-2-butyl-4-chloro-5-methoxymethylimidazole; NMR (200 MHz, $CDCl_3$): δ 7.72-7.57 (m, 3H); 7.43 (m, 1H); 6.94 (s, 4H); 5.22 (s, 2H); 5.04 (s, 2H); 4.27 (s, 2H); 3.26 (s, 3H); 2.56 (t, 2H); 1.65 (quint., 2H); 1.33 (sext., 2H); 0.88 (t, 3H).

Part B: Preparation of 1-[4-(2-Carboxybenzyloxy)benzyl]-2-butyl-4-chloro-5-methoxymethylimidazole The title compound was prepared from 1-[4-(2-cyanobenzyloxy)benzyl]-2-butyl-4-chloro-5-methoxymethylimidazole via the hydrolysis procedure described in Example 192, Part E; NMR (200 MHz, DMSO-$d_6$): δ 7.91 (d, 1H); 7.57 (m, 2H); 7.42 (m, 1H); 6.97 ($A_2B_2$, 4H); 5.41 (s, 2H); 5.09 (s, 2H); 4.27 (3, 2H); 3.17 (s, 3H); 2.49 (t, 2H); 1.44 (quint, 2H); 1.21 (sext., 2H); 0.79 (t, 3H).

The compounds shown in Table 13 where X=—$OCH_2$— were prepared or could be prepared employing the above procedures of Examples 192-194 and procedures previously described.

TABLE 13

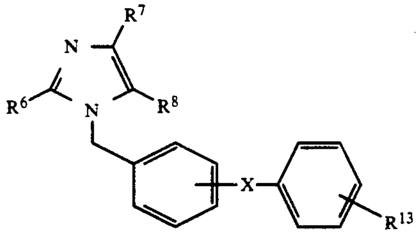

| Ex. No. | $R^6$ | $R^7$ | $R^8$ | 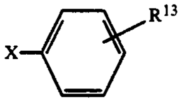 | MP(°C.) |
|---|---|---|---|---|---|
| 195 | n-butyl | Cl | $CH_2OH$ | 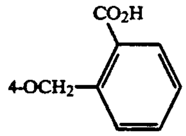 | (oil)[a] |
| 196 | n-butyl | Cl | $CH_2OH$ | 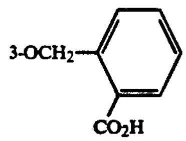 | |
| 197 | n-butyl | Cl | $CH_2OCH_2CH_3$ | 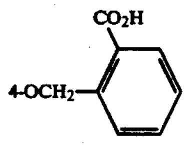 | |
| 198 | n-butyl | Cl | $CH_2OCH_2C_6H_5$ | 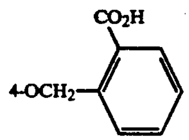 | |
| 199 | n-butyl | Cl | $CH_2O\overset{O}{\overset{\|}{C}}CH_3$ | 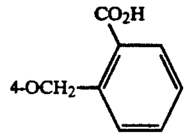 | (oil)[b] |
| 200 | $CH_3OCH_2CH_2$— F F | Cl | $CH_2OH$ | 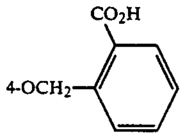 | |

TABLE 13-continued

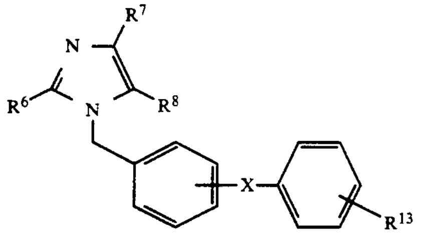

| Ex. No. | $R^6$ | $R^7$ | $R^8$ | 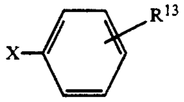 | MP(°C.) |
|---|---|---|---|---|---|
| 201 | n-propyl | $CF_3$ | $CH_2OH$ | 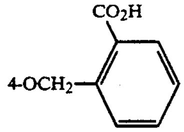 | |

[a]NMR(200 MHz, DMSO-$d_6$): δ7.91(d, 1H); 7.58(m, 2H); 7.42(m, 1H); 6.98($A_2B_2$, 4H); 5.42(s, 2H); 5.15(s, 2H); 4.32(s, 2H); 2.48(t, 2H); 1.44(quint., 2H); 1.23(sext., 2H); 0.79(t, 3H).

[b]NMR(200 MHz, $CDCl_3$): δ8.13(d, 1H); 7.75(d, 1H); 7.58(t, 1H); 7.39(t, 1H); 6.88($A_2B_2$, 4H); 5.51(s, 2H); 5.04(s, 2H); 4.95(s, 2H); 2.60(t, 2H); 1.83(s, 3H); 1.65(quint., 2H); 1.32(sext., 2H); 0.85(t, 3H).

EXAMPLE 202

Part A: Methyl 2-[4-(Bromomethyl)benzoyl]benzoate

Methyl 2-toluylbenzoate (CA reg. #6424-25-5: available by simple esterification of commercially available 2-toluylbenzoic acid) (10.00 g, 39.3 mmol, 1 eq), N-bromosuccinimide (7.00 g, 39.3 mmol, 1 eq), benzoyl peroxide (1.0 g) and 100 mL carbon tetrachloride were mixed and refluxed overnight (peroxide added last). The mixture was filtered and 250 mL of a 100 g/l aqueous solution of sodium bisulfite solution was added. The layers were separated and the organic layer was dried ($MgSO_4$) and concentrated. The brown solid residue was recrystallized from ether/hexane to give 6.47 g of product; m.p. 88.2°-91.5°. NMR (200 MHz, $CDCl_3$) δ 8.07 (d, 1H, J=7 Hz); 7.82-7.07 (m, 7H); 4.50 (s, 2H); 3.67 (s, 3H). Anal. Calcd. for $C_{16}H_{13}O_3Br$: C, 57.68; H, 3.93; Br, 23.98. Found: C, 57.84; H, 4.04; Br 23.99. Mass Calcd. for $C_{16}H_{13}O_3Br$: 332.0048. Found: 332.0033.

Part B: Preparation of 2-Butyl-1-[4-(2-carbomethoxybenzoyl)benzyl]-4-chloro-5-hydroxymethylimidazole To a solution of 2-butyl-4-chloro-5-(hydroxymethyl-)imidazole (11.12 g, 54 mmol, 1 eq) in 200 mL methanol was added dropwise a freshly prepared sodium methoxide solution (1.36 g Na, 59 mmol, 1.1 eq in 50 mL MeOH). After stirring for 0.5 hours, the methanol was removed in vacuo and the resultant glass was dissolved in 200 mL DMF. To this mixture was added a solution of methyl 2-[4-(bromomethyl)benzoyl]benzoate (18.00 g, 59 mmol, 1.1 eq) in DMF and the entire contents was stirred overnight under $N_2$ at room temperature. The solvent was then removed in vacuo and the residue dissolved in 500 mL ethyl acetate and 500 mL $H_2O$. The layers were separated and the aqueous layer was extracted twice with 500 mL portions of ethyl acetate. The organic layers were dried and concentrated and the crude product flash chromatographed to separate the two regioisomers in 60:40 hexane/ethyl acetate over silica gel. The faster moving isomer was isolated to yield 14.72 g of a glassy solid. NMR (200 MHz, $CDCl_3$) δ 8.03 (d, 1H, J=7 Hz); 7.67 (m, 4H); 7.36 (d, 1H, J=7 Hz); 7.05 (d, 2H, J=7 Hz); 5.28 (s, 2H); 4.43 (s, 2H); 3.63 (s, 3H); 2.53 (t, 2H, J=7 Hz); 1.60 (t of t, 2H, J=7,7 Hz); 1.30 (t of q, 2H, J=7,7 Hz); 0.87 (t, 3H, J=7 Hz). Mass Calcd. for $C_{25}H_{26}ClF_3N_4O_5S$: 586.1264. Found: 586.1285.

Part C: 2-Butyl-1-[4-(2-Carboxybenzoyl)benzyl]-4-chloro-5-(hydroxymethyl)imidazole 2-Butyl-1-[4-(2-carbomethoxybenzoyl)benzyl]-4-chloro-5-hydroxymethylimidazole (500 mg, 1.13 mmol, 1 eq), 0.5N KOH in methanol (2.27 mL, 1.14 mmol, 1 eq), and 0.5 mL of $H_2O$ were mixed and stirred. After 6 hours, water (50 mL) was added and the pH was lowered to 3-5 with conc. HCl. The aqueous mixture was extracted with ethyl acetate (3×50 mL) and the organic layers were dried ($MgSO_4$) and concentrated to give 200 mg of product; m.p. 90.0°-95.0°. NMR (200 MHz, $CDCl_3$) δ 8.05 (d, 1H, J=7 Hz); 7.48-7.75 (m, 4H); 7.37 (d, 1H, J=7 Hz); 7.00 (d, 2H, J=7 Hz); 5.20 (s, 2H); 4.40 (s, 2H); 2.45 (t, 2H, J=7 Hz); 1.50 (t of t, 2H, J=7 Hz); 1.25 (t of q, 2H, J=7 Hz); 0.79 (t, 3H, J=7 Hz). Anal. Calcd. for $C_{23}H_{23}ClN_2O_4.(CH_3OH)$: C, 62.81; H, 5.93; Found: C, 62.95; H, 5.99. Mass spectrum shows $M-H_2O$. Mass Calcd. for $C_{23}H_{23}ClN_2O_4-H_2O$: 408,1235. Found: 408.1228.

EXAMPLE 203

Preparation of 2-n-Butyl-1-[4-(2-carboxybenzoyl)benzyl]-4-hydroxymethyl-5-chlorimidazole Using the procedure of Example 202, 2-n-butyl-1-[4-(2-carboxybenzoyl)benzyl]-4-hydroxymethyl-5-chloroimidazole was prepared from 2-n-butyl-1-[4-(2-carbomethoxybenzoyl)benzyl]-4-hydroxymethyl-5-chloroimidazole, m.p. 214.0°-216.0°. NMR (200 MHz, $CDCl_3$+DMSO-$d_6$) δ 8.07 (d, 1H, J=7,7 Hz); 7.32 (d, 1H, J=7 Hz); 7.10 (d, 2H, J=7 Hz); 5.19 (s, 2H); 4.50 (s, 2H); 2.61 (t, 2H, J=7 Hz); 1.63 (t of t, 2H, J=7,7 Hz); 1.33 (t of q, 2H, J=7,7 Hz); 0.87 (t, 3H, J=7 Hz). Titration of the product with 1.000N NaOH showed the presence of exactly one acidic functionality. Anal.

Calcd. for $C_{23}H_{23}ClN_2O_4$: C, 64.71; H, 5.43; N, 6.56. Found: C, 64.75; H, 5.30; N, 6.65.

EXAMPLE 204

Part A: Preparation of 2-Butyl-1-[4-(2-carbomethoxybenzoyl)benzyl]-4-chloro-5-(chloromethyl)imidazole, hydrochloride salt 2-Butyl-1-[4-(2-carbomethoxybenzoyl)benzyl]-4-chloro-5-hydroxymethylimidazole (5.00 g, 11.3 mmol, 1 eq) was dissolved in 50 mL chloroform and to this solution was dropwise added thionyl chloride (4.13 mL, 56.6 mmol, 5 eq) with stirring at room temperature. After 4 hours, the solvent and excess thionyl chloride were removed by rotary evaporation. Toluene (100 mL) was added to the residue and the solvent again removed by rotary evaporation. Toluene was again added and while evaporating the second time, product crystallized from solution yielding 2.91 g of a white solid; m.p. 139.0°-143.5°. NMR (200 MHz, $CDCl_3$) δ 8.07 (d, 1H, J=7 Hz); 7.80 (d, 2H, J=10 Hz); 7.68 (t, 1H, J=7 Hz); 7.58 (t, 1H, J=7 Hz); 7.35 (d, 1H, J=7 Hz); 7.13 (d, 2H, J=10 Hz); 5.43 (s, 2H); 4.42 (s, 2H); 3.67 (s, 3H); 2.96 (m, 2H); 1.75 (m, 2H); 1.39 (m, 2H); 0.88 (t, 2H, J=7 Hz). Mass Calcd. for $C_{24}H_{24}Cl_2N_2O_3$: 458.1162. Found: 458.1160.

Part B: 2-Butyl-1-[4-(2-Carbomethoxybenzoyl)benzyl]-4-chloro-5-((1,2,4-triazol-1-yl)methyl)imidazole 2-Butyl-1-[4-(2-carbomethoxybenzoyl)benzyl]-4-chloro-5-chloromethylimidazole.HCl salt (1.00 g, 2.06 mmol, 1.0 eq), potassium triazolide (0.26 g, 2.39 mmol, 1.1 eq) and DMF (50 mL) were mixed and heated at 90° under $N_2$ overnight. The reaction was worked up by removing the solvent in vacuo, taking up the residue in water (200 mL) and ethyl acetate (200 mL), separating the layers and extracting the aqueous with ethyl acetate (2×200 mL). The organic layers were dried ($MgSO_4$) and concentrated; the residue was flash chromatographed over silica gel in 100% ethyl acetate to give 780 mg of a white glassy solid. NMR (200 MHz, $CDCl_3$) δ 8.05 (s, 1H); 8.05 (d, 1H, J=7 Hz); 7.83 (s, 1H); 7.74 (d, 2H, J=10 Hz); 7.66 (t, 1H, J=7 Hz); 7.58 (t, 1H, J=7 Hz); 7.33 (d, 1H, J=7 Hz); 6.98 (d, 2H, J=7 Hz); 5.37 (s, 2H); 5.15 (s, 2H); 3.69 (s, 3H); 2.56 (t, 2H, J=7 Hz); 1.73 (m, 2H); 1.36 (t of q, 2H, J=7,7 Hz); 0.87 (t, 3H, J=7 Hz). Mass Calcd. for $C_{26}H_{26}ClN_5O_3$: 491.1722. Found: 491.1816.

The following intermediates were prepared by the above procedure using the appropriate nucleophile, imidazole starting material, and solvent.

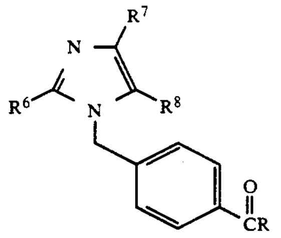

| $R^6$ | $R^7$ | $R^8$ | R | MP(°C.) |
|---|---|---|---|---|
| n-butyl | Cl | 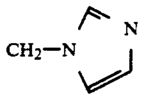 | 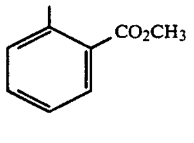 | (oil)[a] |
| n-butyl | Cl | $CH_2N_3$ | 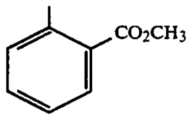 | 127.0–129.5 |
| n-butyl | Cl | $CH_2CN$ | 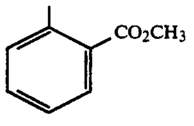 | (oil)[b] |
| n-butyl | Cl | $CH_2OCH_3$ | 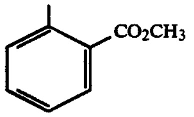 | (solid)[c] |

[a]NMR(200 MHz, $CDCl_3$) δ 8.05(d, 1H, J=7Hz); 7.72(d, 2H, J=8Hz); 7.65(t, 1H, J=7Hz); 7.56(t, 1H, J=7Hz); 7.36(d, 1H, J=7Hz); 7.33(bs, 1H); 7.00(bs, 1H); 6.89(d, 2H, J=8Hz); 6.78(bs, 1H); 4.91(s, 2H); 4.88(s, 2H); 3.67(s, 3H); 2.54(t, 2H, J=7Hz); 1.65(t of t, 2H, J=7,7Hz); 1.33(t of q, 2H, J=7,7Hz); 0.85(t, 3H, J=7Hz).

[b]NMR(200 MHz, $CDCl_3$) δ 8.05(d, 1H, J=7Hz); 7.76(d, 2H, J=10Hz); 7.64(t, 1H, J=7Hz); 7.56(t, 1H, J=7Hz); 7.36(d, 1H, J=7Hz); 7.06(d, 2H, J=10Hz); 5.24(s, 2H); 3.66(s, 3H); 3.47(s, 2H); 2.63(t, 2H, J=7Hz); 1.70(t, of t, 2H, J=7,7Hz); 1.37(t of q, 2H, J=7,7Hz); 0.89(t, 3H, J=7Hz).

[c]NMR(200 MHz, $CDCl_3$) δ 8.05(d, 1H, J=8Hz); 7.72(d, 2H, J=8Hz); 7.61(m, 2H); 7.38(d, 1H, J=7Hz); 7.04(d, 2H, J=7Hz); 5.20(s, 2H); 4.26(s, 2H); 3.63(s, 3H); 3.21(s, 3H); 2.50(t, 2H, J=7Hz); 1.65(m, 2H); 1.29(m, 2H); 0.84(t, 3H, J=7Hz).

Part C: 2-Butyl-1-[4-(2-Carboxybenzoyl)benzyl]-4-chloro-5-((1,2,4-triazol-1-yl)methyl)imidazole 2-Butyl-1-[4-(2-carbomethoxybenzoyl)benzyl]-4-chloro-5-((1,2,4-triazol-1-yl)methyl)imidazole (780 mg, 1.59 mmol, 1 eq), 0.5N KOH in MeOH (6.34 mL, 3.17 mmol, 2 eq) and methanol (20 mL) were mixed and stirred at 20° under $N_2$. After 2.5 hours, one more equivalent of 0.5N KOH in MeOH was added. After seven hours, the solution was acidified to a pH of 4 with 1N HCl, and 200 mL each of ethyl acetate and water was added. The layers were separated and the aqueous layer was extracted with ethyl acetate (2×200 mL). The organic layers were dried ($MgSO_4$) and concentrated to give 640 mg of a white glassy solid; m.p. 180.0°-188.0°. NMR (200 MHz, $CDCl_3$) δ 7.94 (d, 1H, J=7 Hz); 7.74 (s, 1H); 7.65 (s, 1H); 7.55 (d, 2H, J=7 Hz); 7.70-7.50 (m, 3H); 6.67 (d, 2H, J=7 Hz); 5.34 (s, 2H); 5.14 (s, 2H); 2.64 (t, 2H, J=7 Hz); 1.74 (t of t, 2H, J=7,7 Hz); 1.36 (t of q, 2H, J=7,7 Hz); 0.89 (t, 3H, J=7 Hz). Anal. Calcd. for $C_{25}H_{24}ClN_5O_3.EtOAc$: C, 61.53; H, 5.70; N, 12.37. Found: C, 61.72; H, 5.19, N, 12.27.

Examples 205–207 in Table 14 were prepared by the procedure described in Example 203, Part C using the appropriate imidazole starting materials.

TABLE 14

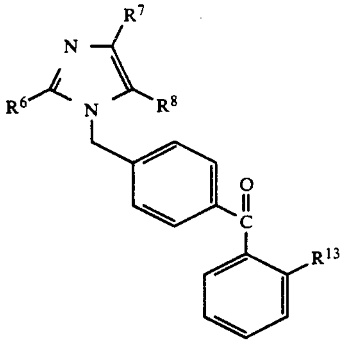

| Ex. No. | $R^6$ | $R^7$ | $R^8$ | $R^{13}$ | MP(°C.) |
|---|---|---|---|---|---|
| 205 | n-butyl | Cl | 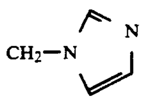 | $CO_2H$ | (oil)[a] |
| 206 | n-butyl | Cl | $CH_2N_3$ | $CO_2H$ | 188.0–190.0 |
| 207 | n-butyl | Cl | $CH_2OCH_3$ | $CO_2H$ | 210.0–211.5 |

[a]NMR(200MHz, $CDCl_3/D_2O$ exchange)δ9.67(s, 1H); 7.98(d, 1H, J=7Hz); 7.63(t, 1H, J=7Hz); 7.55(t, 2H, J=7Hz); 7.41(d, 2H, J=10Hz); 7.41(d, 1H, J=7Hz); 7.09(s, 1H); 7.08(s, 1H); 6.70(d, 2H, J=10Hz); 5.65(s, 2H); 5.58(s, 2H); 2.59(t, 2H, J=7Hz); 1.71(t of t, 2H, J=7.7Hz); 1.36(t of q, 2H, J=7.7Hz); 0.87(t, 3H, J=7Hz).

EXAMPLE 208

Part A: Preparation of 2-Butyl-1-[4-(2-carbomethoxybenzoyl)benzyl]-4-chloro-5-[(1H-tetrazol-5-yl)methyl]imidazole The title compound was prepared from 2-butyl-1-[4-(2-carbomethoxybenzoyl)benzyl]-4-chloro-5-(cyanomethyl)imidazole by the procedure described in Example 26; NMR (200 MHz, DMSO-$d_6$) δ 8.00 (d, 1H, J=7 Hz); 7.78 (t, 1H, J=7 Hz); 7.70 (t, 1H, J=7 Hz); 7.50 (d, 2H, J= 8 Hz); 7.46 (d, 1H, J=7 Hz); 7.05 (d, 2H, J=8 Hz); 5.35 (s, 2H); 4.20 (s, 2H); 3.57 (s, 3H); 2.52 (t, 2H, J=7 Hz); 1.52 (t of t, 2H, J=7,7 Hz); 1.27 (t of q, 2H, J=7,7 Hz); 0.70 (t, 3H, J=7 Hz). Anal. Calcd. for $C_{25}H_{25}ClN_6O_3$: C, 60.91; H, 5.11; N, 17.05. Found: C, 60.84; H, 5.12; N, 16.71. Mass Calcd. for $C_{25}H_{25}ClN_6O_3$: 492.1686. Found: 492.1614.

Part B: Preparation of 2-Butyl-1-[4-(2-carboxybenzoyl)benzyl]-4-chloro-5-[(1H-tetrazol-5-yl)methyl]imidazole The title compound was prepared from 2-butyl-1-[4-(2-carbomethoxybenzoyl)benzyl]-4-chloro-5-[(1H-tetrazol-5-yl)methyl]imidazole by the procedure described in Example 202, Part C; m.p. 228.0°–229.5°. NMR (200 MHz, DMSO-$d_6$) δ 7.98 (d, 1H, J=7 Hz); 7.73 (t, 1H, J=7 Hz); 7.69 (t, 1H, J=7 Hz); 7.55 (d, 2H, J=8 Hz); 7.38 (d, 1H, J=7 Hz); 7.05 (d, 2H, J=8 Hz); 5.32 (s, 2H); 4.16 (s, 2H); 2.50 (t, 2H, J=7 Hz); 1.50 (t of t, 2H, J=7,7 Hz); 1.24 (t of q, 2H, J=7,7 Hz); 0.80 (t, 3H, J=7 Hz).

Anal. Calcd. for $C_{24}H_{23}ClN_6O_3$: C, 60.19; H, 4.84; N, 17.55. Found: C, 59.73; H, 4.61; N, 17.82.

EXAMPLE 209

Part A: Preparation of 5-Aminomethyl-2-n-butyl-1-[4-(2-carbomethoxybenzoyl)benzyl]-4-chloroimidazole, chromium salt 5-Azidomethyl-2-n-butyl-1-[4-(2-carbomethoxybenzoyl)benzyl]-4-chloroimidazole (4.24 g, 9.1 mmol, 1 eq), chromium (II) chloride (6.75 g, 54.7 mmol, 6 eq), acetone (40 mL) and water (13 mL) were mixed and stirred (the chromium (II) chloride being added last). After $N_2$ evolution had stopped, the reaction mixture was diluted with saturated aqueous sodium bicarbonate (250 mL) and extracted with ethyl acetate (3×250 mL). The organic layers were dried ($MgSO_4$) and concentrated to give solids which after washing with ether gave 2.92 g of white solid (chromium salt of the product); m.p. 178.5°–181.0°. NMR (200 MHz, $CDCl_3$/DMSO-$d_6$) δ 8.85 (bs, 1H); 8.05 (d, 1H, J=7 Hz); 7.57–7.25 (m, 4H); 7.36 (d, 1H, J=7 Hz); 7.06 (bd, 2H, J=7 Hz); 5.67 (bs, 2H); 3.85 (bs, 2H); 3.67 (s, 3H); 2.60 (t, 2H, J=7 Hz); 1.68 (m, 2H); 1.37 (t of q, 2H, J=7,7 Hz); 0.89 (t, 3H, J=7 Hz). Mass Calcd. for $C_{24}H_{26}ClN_3O_3$: 439.1663. Found: 439.1663. Anal. Calcd. for $Cr(C_{24}H_{26}ClN_3O_3)_2$: C, 61.87; H, 5.62; N, 9.02. Found: C, 61.46; H, 5.59; N, 8.54.

Part B: Preparation of 2-Butyl-4-chloro-1-[4-(2-carbomethoxybenzoyl)benzyl]-5-(methoxycarbonylaminomethyl)imidazole 5-Aminomethyl-2-butyl-1-[4-(2-carbomethoxybenzoyl)benzyl]-4-chloroimidazole (chromium salt) (500 mg, 1.14 mmol, 1 eq) was dissolved in a mixture of 1.00N NaOH (1.14 mL, 1.14 mmol, 1 eq) and $H_2O$ (10 mL). Tetrahydrofuran may be added to assist solvation. The solution was cooled to 0° when methyl chloroformate (0.176 mL, 2.28 mmol, 2 eq) in THF (5 mL) was slowly dripped in, in five equal portions, alternating with five portions of 1.00N NaOH (total of 1.14 mL, 1.14 mmol, 1 eq). When the addition was complete, the mixture was stirred at room temperature for 4 hours. Water (100 mL) was added and the pH adjusted to 5 with 1N HCl. The aqueous was extracted with ethyl acetate (3×100 mL), the organic layers dried ($MgSO_4$) and stripped to give a white glass (560 mg). Flash chromatography in 100% ethyl acetate to 100% isopropanol yielded 280 mg of product as an oil. NMR (200 MHz, $CDCl_3$) δ 8.10 (d, 1H, J=7 Hz); 7.75 (d, 2H, J=7 Hz); 7.75–7.56 (m, 2H), 7.39 (d, 1H, J=7 Hz); 7.02 (d, 2H, J=7 Hz); 5.32 (s, 2H); 4.83 (m, 1H); 4.28 (d, 2H, J=7 Hz); 3.70 (s, 3H); 3.57 (s, 3H); 2.58 (t, 2H, J=7 Hz); 1.72 (t of t, 2H, J=7,7 Hz); 1.37 (t of q, 2H, J=7,7 Hz); 0.92 (t, 3H, J=7 Hz). Mass Calcd. for $C_{26}H_{28}ClN_3O_5$: 497.1717. Found: 497.1699.

The following intermediates were prepared or could be prepared by the procedure described in Example 209, Part B from the corresponding 5-(aminoalkyl)imidazole intermediate and the appropriate chloroformate or sulfonyl chloride.

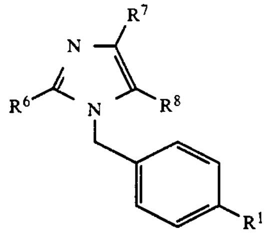

| $R^1$ | $R^6$ | $R^7$ | $R^8$ | MP(°C.) |
|---|---|---|---|---|
| 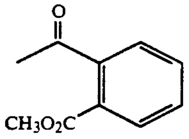 | n-butyl | Cl | $CH_2NHCOCH_2CH_3$ | |
| 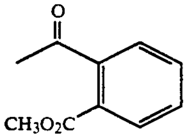 | n-butyl | Cl | $CH_2NHCOCH_2CH_2CH_3$ | |
| 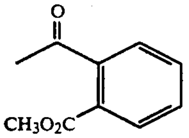 | n-butyl | Cl | $CH_2NHCOCH(CH_3)_2$ | |
| 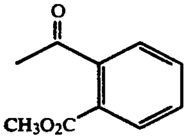 | n-butyl | Cl | $CH_2NHCOCH_2CH_2CH_2CH_3$ | |
| 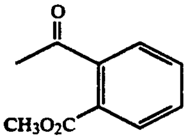 | n-butyl | Cl | $CH_2NHCOC_6H_5$ | |
| 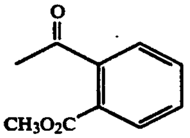 | n-butyl | Cl | $CH_2NHCOCH_2C_6H_5$ | |
| 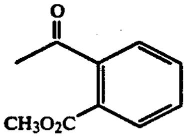 | n-butyl | Cl | $CH_2NHSO_2CH_3$ | 163.0-168.0 |

Part C: Preparation of 2-Butyl-4-chloro-1-[4-(2-carboxybenzoyl)benzyl]-5-(methoxycarbonylaminomethyl)imidazole Using the procedure of Example 202, Part C (with or without refluxing), 2-butyl-1-[4-(2-carboxybenzoyl)benzyl]-4-chloro-5-(methoxycarbonylaminomethyl)imidazole was prepared from 2-butyl-1-[4-(2-carbomethoxybenzoyl)benzyl]-4-chloro-5-(methoxycarbonylaminomethyl)imidazole; mp=sublimes. NMR (200 MHz, DMSO-$d_6$) δ 13.17 (bm, 1H); 7.97 (d, 1H, J=7 Hz); 7.71 (t, 1H, J=7 Hz); 7.63 (t, 1H, J=7 Hz); 7.56 (d, 2H, J=10 Hz); 7.50 (m, 1H); 7.36 (d, 1H, J=7 Hz); 7.03 (d, 2H, J=10 Hz); 5.31 (s, 2H); 4.06 (d, 2H, J=7 Hz); 2.46 (t, 2H, J=7 Hz); 1.48 (t of t, 2H, J=7,7 Hz); 1.22 (t of q, 2H, J=7,7 Hz); 0.78 (t, 3H, J=7 Hz). Anal. Calcd. for $C_{25}H_{26}ClN_3O_5$: C, 62.05; H, 5.42; N, 8.68. Found: C, 61.97; H, 5.58; N, 8.40. Mass Calcd. for $C_{25}H_{26}ClN_3O_5$: 483.1561. Found: 483.1560.

Examples 210-216 in Table 15 were prepared or could be prepared by the procedure described in Example 209, Part C using the appropriate starting material.

TABLE 15

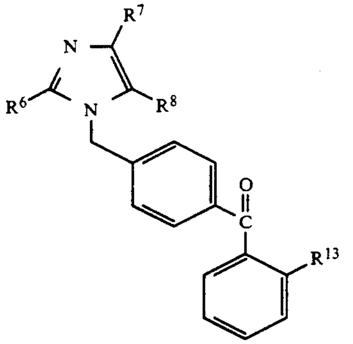

| Ex. No. | $R^{13}$ | $R^6$ | $R^7$ | $R^8$ | MP (°C.) |
|---|---|---|---|---|---|
| 210 | $CO_2H$ | n-butyl | Cl | O<br>‖<br>$CH_2NHCOCH_2CH_3$ | |
| 211 | $CO_2H$ | n-butyl | Cl | O<br>‖<br>$CH_2NHCOCH_2CH_2CH_3$ | |
| 212 | $CO_2H$ | n-butyl | Cl | 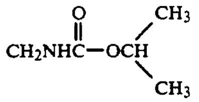 | |
| 213 | $CO_2H$ | n-butyl | Cl | O<br>‖<br>$CH_2NHCOCH_2CH_2CH_2CH_3$ | |
| 214 | $CO_2H$ | n-butyl | Cl | O<br>‖<br>$CH_2NHCOC_6H_5$ | |
| 215 | $CO_2H$ | n-butyl | Cl | O<br>‖<br>$CH_2NHSCH_3$<br>‖<br>O | (oil)[a] |
| 216 | $CO_2H$ | n-butyl | Cl | O<br>‖<br>$CH_2NHCOCH_2C_6H_5$ | |

[a]NMR(200MHz, $CDCl_3$)δ7.97(d, 1H, J=7Hz); 7.71–7.50(m, 4H); 7.45(d, 1H, J=7Hz); 6.95(d, 2H, J=8Hz); 5.23(s, 2H); 4.15(s, 2H); 2.57(t, 2H, J=7Hz); 1.67(t of t, 2H, J=7.7Hz); 1.36(t of q, 2H, J=7.7Hz); 0.87(t, 3H, J=7Hz).

EXAMPLE 217

Part A: Preparation of 2-Butyl-1-[4-(2-carbomethoxybenzoyl)benzyl]-4-chloro-5-[(trifluoromethylsulfonamido)methyl-]imidazole Triflic anhydride (0.21 mL, 1.25 mmol, 1.1 eq) was slowly added to a pyridine (20 mL) solution of the chromium salt of 5-aminomethyl-2-butyl-1-[4-(2-carbomethoxybenzoyl)benzyl]-4-chloroimidazole (0.50 g, 1.1 mmol, 1.0 eq) at 0° C. The solution was allowed to warm to room temperature. After 1.5 hour, 1.5 equivalents of triflic anhydride were added at 0°. After an additional 4 hours at room temperature, water (200 mL) was added and the pH adjusted to 5. The aqueous was extracted with ethyl acetate (3×100 mL) and the organic layers dried ($MgSO_4$) and concentrated to yield 150 mg of a yellow oil which was used as is for the subsequent hydrolysis step. NMR (200 MHz, $CDCl_3$) δ 8.33 (bm, 1H); 7.96 (d, 1H, J=7 Hz); 7.64 (d, 2H, J=10 Hz); 7.56 (t, 1H, J=7 Hz); 7.48 (t, 1H, J=7 Hz); 7.28 (d, 1H, J=7 Hz); 6.92 (d, 2H, J=10 Hz); 5.21 (s, 2H); 4.14 (s, 2H); 3.17 (s, 3H); 2.48 (t, 2H, J=7 Hz); 1.55 (t of t, 2H, J=7,7 Hz); 1.24 (m, 2H); 0.79 (t, 3H, J=7 Hz).

Part B: Preparation of 2-Butyl-1-[4-(2-carboxybenzoyl)benzyl]-4-chloro-5-[(trifluoromethylsulfonamido)methyl]imidazole 2-Butyl-1-[4-(2-carbomethoxybenzoyl)benzyl]-4-chloro-5-[(trifluoromethylsulfonamido)methyl-]imidazole (150 mg, 0.26 mmol, 1 eq), 1.000N NaOH (0.55 mL, 0.55 mmol, 2.1 eq), methanol (20 mL), and water (0.5 mL) were mixed and stirred for 5 hours at room temperature under $N_2$. The solvent was removed in vacuo. Water (50 mL) was added and the pH was adjusted to 4 with 1N HCl. Tan solids precipitated. These were collected and dried to yield 89 mg. NMR (200 MHz, DMSO-$d_6$) δ 7.98 (d, 1H, J=7 Hz); 7.70 (t, 1H, J=7 Hz); 7.68 (t, 1H, J=7 Hz); 7.63 (d, 2H, J=10 Hz); 7.37 (d, 1H, J=7 Hz); 7.10 (d, 2H, J=10 Hz); 5.34 (s, 2H); 4.20 (s, 2H); 2.50 (t, 2H, J=7 Hz); 1.49 (t of t, 2H, J=7,7 Hz); 1.27 (t of q, 2H, J=7,7 Hz); 0.80 (t, 3H, J=7 Hz). Mass calcd. for $C_{24}H_{23}ClF_3N_3O_5S$: 557.0999. Found: 557.0988

EXAMPLE 218

Part A: Preparation of 2-Butyl-1-[4-(2-carbomethoxybenzoyl)benzyl]-5-[(4-carbomethoxy-1,2,3-triazol-1-yl)methyl]-4-chloroimidazole and 2-butyl-1-[4-(2-carbomethoxybenzoyl)benzyl]-5-[(5-carbomethoxy-1,2,3-triazol-1-yl)methyl]-4-chloroimidazole 5-Azidomethyl-2-butyl-4-chloro-1-[4-(2-carbomethoxybenzoyl)benzyl]imidazole (0.50 g, 1.07 mmol, 1 eq), methyl propiolate (0.95 mL, 10.7 mmol, 10 eq) and toluene (20 mL) were mixed and refluxed under $N_2$ for 3 hours. The reaction mixture was concentrated and the residue flash chromatographed over silica gel in 75:25 hexane/ethyl acetate. The two regioisomers were separated to give 10 mg of the faster eluting isomer as a glass and 330 mg of the slower as a solid. The slower isomer could be further purified by washing with ethyl acetate to give 190 mg of white crystalline solid. Faster eluting isomer: NMR (200 MHz, $CDCl_3$) δ 8.06 (d, 1H, J=8 Hz); 7.96 (s, 1H); 7.73–7.54 (m, 4H); 7.37 (d, 1H, J=8 Hz); 6.86 (d, 2H, J=8 Hz); 5.76 (s, 2H); 5.41 (s, 2H); 3.90 (s, 3H); 3.68 (s, 3H); 2.56 (t, 2H, J=7 Hz); 1.67 (t of t, 2H, J=7,7 Hz); 1.35 (t of q, 2H, J=7,7 Hz); 0.86 (t, 2H, J=7 Hz). Mass calcd. for $C_{28}H_{28}N_5O_5Cl$: 549.1778. Found: 549.1860. Slower eluting isomer: m.p. 163.5°–167.0°; NMR (200 MHz, $CDCl_3$) δ 8.06 (d, 1H, J=8 Hz); 8.00 (s, 1H); 7.72 (d, 2H, J=8 Hz); 7.72–7.55 (m, 2H); 7.41 (d, 1H, J=7 Hz); 6.96 (d, 2H, J=8 Hz); 5.40 (s, 2H); 5.23 (s, 2H); 3.95 (s, 3H); 3.69 (s, 3H); 2.58 (t, 2H, J=7 Hz); 1.70 (t of t, 2H, J=7,7 Hz); 1.38 (t of q, 2H, J=7,7 Hz); 0.89 (t, 3H, J=7 Hz). Mass calcd. for $C_{28}H_{28}N_5O_5Cl$: 549.1778. Found: 549.1763.

The intermediates shown below were prepared or could be prepared by the procedure described in Example 218, Part A using the appropriate starting materials.

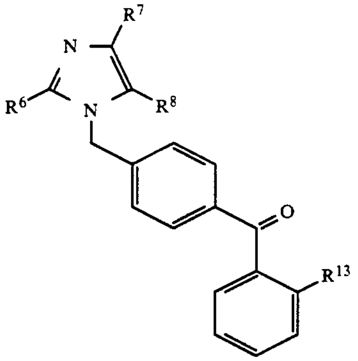

| $R^6$ | $R^7$ | $R^8$ | $R^{13}$ | MP(°C.) |
|---|---|---|---|---|
| n-butyl | Cl | 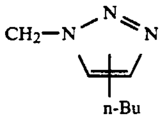 | $CO_2CH_3$ | (oil)[a] (mixture of 2 regioisomers) |
| n-butyl | Cl | 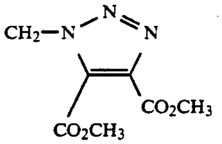 | $CO_2CH_3$ | |
| n-butyl | Cl | 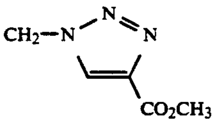 | $NHSO_2CF_3$ | |
| n-butyl | Cl | 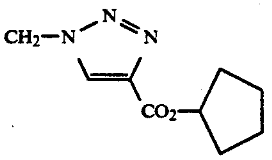 | $NHSO_2CF_3$ | |
| n-butyl | Cl | 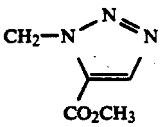 | $NHSO_2CF_3$ | |
| n-propyl | H | 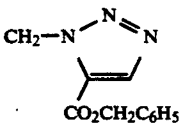 | $NHSO_2CF_3$ | |
| n-propyl | H | 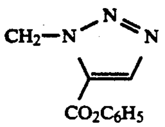 | $NHSO_2CF_3$ | |

[a]NMR(200MHz, $CDCl_3$) shows a mixture of 2 regioisomers; δ8.08(d, 1H, J=8Hz); 7.80–7.55(m, 4H); 7.44–7.34(m, 1H); 7.28(s, 1H); 7.00–6.88(m, 2H); 5.40(s, 0.5×2H); 5.32(s, 0.5×4H); 5.29(s, 0.5×2H); 3.71(s, 0.5×3H); 3.69(s, 0.5×3H); 2.75–2.48(m, 4H); 1.80–1.21(m, 8H); 1.00–0.81(m, 6H).

Part B: Preparation of 2-Butyl-1-[4-(2-carboxybenzoyl)benzyl]-5-[(4-carboxy-1,2,3-triazol-1-yl)methyl]-4-chloroimidazole and 2-butyl-1-[4-(2-carboxybenzoyl)benzyl]-5-[(5-carboxy-1,2,3-triazol-1-yl)methyl]-4-chloroimidazole The slower eluting isomer in Example 218, Part A (190 mg, 0.35 mmol, 1 eq), 0.5N KOH in methanol (2.76 mL, 1.39 mmol, 4 eq) and 5 mL of water were mixed and refluxed overnight under $N_2$. Water (50 mL) was added and the pH adjusted to 5. The aqueous mixture was extracted with ethyl acetate (3×50 mL), the organic fractions dried ($MgSO_4$) and concentrated to give a residue which was triturated with ether yielding 160 mg of solid product. NMR (200 MHz, DMSO-$d_6$+py-$d_5$) δ 8.20 (d, 1H, J=8 Hz); 7.86–7.63 (m, 4H); 7.57 (d, 1H, J=8 Hz); 7.43 (s, 1H); 7.04 (d, 2H, J=10 Hz); 6.84 (s, 2H); 6.63 (s, 2H); 2.62 (t, 2H, J=7 Hz); 1.65 (t of t, 2H, J=7,7 Hz); 1.30 (t of q, 2H, J=7,7 Hz); 0.81 (t, 3H, J=7 Hz). Mass calcd. for $C_{26}H_{24}N_5O_5Cl$-$CO_2$: 477.1567. Found: 477.1593.

The faster eluting isomer in Example 218, Part A was hydrolyzed in a similar fashion except that upon acidification in the work-up, solid product precipitated, m.p. 149.0°-152.5°. NMR (200 MHz, DMSO-$d_6$) δ 8.02 (s, 1H); 8.02 (d, 2H, J=7 Hz); 7.74 (t, 1H, J=7 Hz); 7.66 (t, 1H, J=7 Hz); 7.50 (d, 2H, J=7 Hz); 7.37 (d, 1H, J=7 Hz); 6.92 (d, 2H, J=7 Hz); 5.83 (s, 2H); 5.42 (s, 2H); 2.52 (t, 2H, J=7 Hz); 1.55 (t of t, 2H, J=7 Hz); 1.28 (t of q, 2H, J=7,7 Hz); 0.78 (t, 3H, J=7 Hz). Mass calcd. for $C_{26}H_{24}N_5O_5Cl$-$CO_2$: 477.1567. Found: 477.1479.

Examples in Table 16 were prepared or could be prepared by the procedure described in Example 218, Part B.

TABLE 16

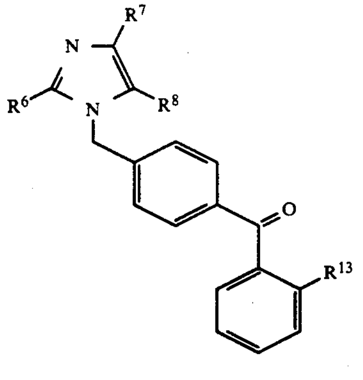

| Ex. No. | $R^6$ | $R^7$ | $R^8$ | $R^{13}$ | MP(°C.) |
|---|---|---|---|---|---|
| 219 | n-butyl | Cl | 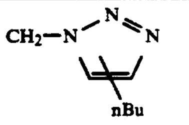 | $CO_2H$ | (oil)[a] (2 regio-isomers) |
| 220 | n-butyl | Cl | 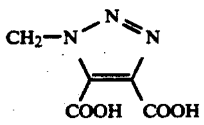 | $CO_2H$ | |
| 221 | n-butyl | Cl | 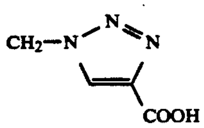 | $NHSO_2CF_3$ | |
| 222 | n-butyl | Cl | 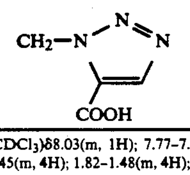 | $NHSO_2CF_3$ | |

[a]NMR(200MHz, $CDCl_3$)δ8.03(m, 1H); 7.77–7.42(m, 5H); 7.33(s, 1H); 5.36(s, 2H); 5.26(s, 2H); 2.68–2.45(m, 4H); 1.82–1.48(m, 4H); 1.42–1.20(m, 4H); 1.00–0.80(m, 6H).

Part A: Preparation of 1-(4-Formylbenzyl)-2-butyl-4-chloro-5-hydroxymethylimidazole To a solution of 5.05 g of 1-(4-cyanobenzyl)-2-butyl-4-chloro-5-hydroxymethylimidazole in 350 mL of benzene at 25° was added dropwise 22.8 mL of diisobutylaluminum hydride (0.15M in toluene). The mixture was warmed to 45° and stirred for 16 hours. After cooling, the reaction mixture was poured in ice-cold 20% aqueous sulfuric acid. This solution was allowed to warm to 25° and then stirred for 2 hours. The solution was cooled to 0°, neutralized using aqueous sodium hydroxide and extracted with ethyl acetate. The combined organic phases were washed with water and brine, dried over anhydrous sodium sulfate, filtered, and concentrated. Column chromatography on silica gel (elution: 0–20% ethyl acetate/benzene) provided 3.60 g of 1-(4-formyl-benzyl)-2-butyl-4-chloro-5-hydroxymethylimidazole; NMR (200 MHz, $CDCl_3$) δ : 9.96 (s, 1H); 7.47 ($A_2M_2$, 4H); 5.26 (s, 2H); 4.42 (s, 2H); 2.54 (t, 2H); 1.64 (quint., 2H); 1.32 (sext., 2H); 0.86 (t, 3H).

Part B: Preparation of 1-[(2'-Cyano-trans-stilben-4-yl)methyl]-2-butyl-4-chloro-5-hydroxymethylimidazole To a solution of 0.98 g of α-bromo-o-tolunitrile in 25 mL of dimethylformamide at 25° was added 1.40 g of triphenylphosphine. The mixture was stirred at 80° for 3 hours, then treated with 1.53 g of 1-(4-formylbenzyl)-2-butyl-4-chloro-5-hydroxymethylimidazole, followed immediately by 0.54 g of sodium methoxide, and the mixture was diluted with water and extracted with benzene. The organic phases were combined and washed with water and brine, dried over anhydrous sodium sulfate, filtered, and concentrated. Column chromatography on silica gel (elution: 0–20% ethyl acetate/benzene) afforded 0.45 g of 1-[(2'-cyano-trans-stilben-4-yl)methyl]-2-butyl-4-chloro-5-hydroxymethylimidazole; NMR (200 MHz, $CDCl_3$): δ 8.01 (d, 1 h); 7.85 (d, 1 h); 7.73 (t, 1 h); 7.47 (t, 1 h); 7.44 (AB, 2H, J=16.3); 7.38 ($A_2B_2$, 4H); 5.28 (s, 2H); 5.24 (t, 1H); 4.34 (d, 2H); 2.49 (t, 2H); 1.47 (quint., 2H); 1.24 (sext., 2H); 0.79 (t, 3H).

Part C: 1-[(2'-Carboxy-trans-stilben-4-yl)methyl]-2-butyl-4-chloro-5-hydroxymethylimidazole A solution of 0.40 g of 1-[2'-cyano-trans-stilben-4-yl)methyl]-2-butyl-4-chloro-5-hydroxymethylimidazole in 20 mL of ethylene glycol and 12 mL of 10% aqueous sodium hydroxide was refluxed for 5.5 hours. After cooling, the reaction mixture was filtered, and the solvent was removed in vacuo. The residue was dissolved in water, and the solution was acidified to pH 3.5 using hydrochloric acid and the resulting emulsion was extracted with chloroform. The combined organic phases were washed with saturated aqueous sodium chloride solution, dried over anhydrous sodium sulfate, filtered and concentrated. Column chromatography on silica gel (elution: 5% methanol/chloroform) afforded 0.12 g of 1-[(2'-carboxy-trans-stilben-4-yl)methyl]-2-butyl-4-chloro-5-hydroxymethylimidazole; NMR (200 MHz, $CDCl_3$): δ 8.08–8.00 (m, 2H); 7.71 (d, 1 h); 7.57–7.47 (m, 3H); 7.34 (t, 1 h); 7.01–6.92 (m, 3H); 5.21 (s, 2H); 4.50 (s, 2H); 2.60 (t, 2H); 1.62 (quint, 2H); 1.31 (sext., 2H); 0.03 (t, 3H).

EXAMPLE 224

Part A: Preparation of N-(4-Benzyloxybenzyl)glycine ethyl ester

To a suspension of 11.0 g of glycine ethyl ester hydrochloride in 100 mL of dimethylformamide at 25° was added 22.0 mL of triethylamine. To the resulting milky suspension was added 9.08 g of 4-benzyloxybenzyl chloride in 50 mL of DMF dropwise over 0.5 hour. The mixture was stirred for 16 hours at 25°. The reaction mixture was diluted with diethyl ether and then filtered to remove the precipitated triethylamine hydrochloride. The resulting solution was concentrated in vacuo, and the residue was dissolved in ethyl acetate. The solution was washed with water and brine, dried over anhydrous sodium sulfate, filtered, and concentrated. Kugelrohr distillation provided 5.90 g of N-(4-benzyloxybenzyl)glycine ethyl ester [bp 160°-180° (0.015 torr.)]; NMR (200 MHz, $CDCl_3$): δ 7.43-7.27 (m, 5H); 7.06 ($A_2B_2$, 4H); 5.01 (s, 2H); 4.14 (quart., 2H); 3.71 (s, 2H); 3.36 (s, 3H); 2.01 (bs, 1h); 1.24 (t, 3H).

Part B: Preparation of N-(4-Benzyloxybenzyl)-N-formylglycine ethyl ester

A solution of 5.83 g of N-(4-benzyloxybenzyl)glycine ethyl ester, 0.86 mL of formic acid, and 20 mL of xylene was refluxed for 2 hours using a Dean-Stark trap to remove the water produced in the reaction. After cooling, the reaction mixture was washed with 20% aqueous formic acid, water, saturated sodium bicarbonate solution, water, and brine. Finally the mixture was dried over anhydrous sodium sulfate, filtered, and the filtrate was concentrated to furnish 6.23 g of crude N-(4-benzyloxybenzyl)-N-formyl glycine ethyl ester, used in the following reaction without further purification.

Part C: Preparation of 1-(4-Benzyloxybenzyl)-5-carbomethoxy-2-(3H)-imidazolethione To a suspension of 1.10 g of sodium methoxide in 35 mL of tetrahydrofuran at 10° there was added in one portion, a solution of 6.23 g of N-(4-benzyloxybenzyl)-N-formyl glycine ethyl ester and 3.46 mL of methyl formate in 15 mL of THF. The mixture was stirred at 10° for 1 hour and then at 25° for 16 hours. The solvent was removed in vacuo and the residue dissolved in 36 mL of methanol. To this solution was added 3.57 mL of conc. hydrochloric acid, and the mixture was stirred at 40° for 0.5 hour. A solution of 2.80 g of potassium thiocyanate in 6 mL of water was added, and the resulting mixture was stirred for 16 hours at 40°. Finally, 40 mL of water was added, and the mixture was allowed to cool to 25°. The precipitated solid was recovered by filtration to afford 3.60 g of 1-(4-benzyloxybenzyl)-5-carbomethoxy-2(3H)-imidazolethione; NMR (200 MHz, $CDCl_3$): δ 11.25 (bs, 1 h); 8.05 (s, 1 h); 7.39 (m, 5H); 7.03 ($A_2B_2$, 4H); 5.06 (s, 2H); 4.56 (s, 2H); 3.81 (s, 3H).

Part D: Preparation of 1-(4-Benzyloxybenzyl)-2-propylthio-5-carboethoxyimidazole To 60 mL of ethanol at 25° was added portionwise 0.30 g of sodium metal. After the sodium metal has reacted 3.54 g of 1-(4-benzyloxybenzyl)-5-carbomethoxy-2-(3H)-imidazolethione was added followed immediately by 2.24 mL of 1-iodopropane, and the mixture was stirred at 24° for 3 hours. At this point, the solvent was removed in vacuo, and the residue was dissolved in methylene chloride. This solution was washed with water and brine, dried over anhydrous sodium sulfate, filtered, and concentrated to furnish 3.46 g of crude 1-(4-benzyloxybenzyl)-2-propylthio-5-carboethoxyimidazole, used in a subsequent reaction without further purification; NMR (200 MHz, $CDCl_3$): δ 7.77 (s, 1 h); 7.45-7.32 (m, 5H); 7.03 ($A_2B_2$, 4H); 5.49 (s, 2H); 5.03 (s, 2H); 4.28 (quart., 2H); 3.20 (t, 2H); 1.32 (t, 3H); 1.02 (t, 3H).

The following intermediates were prepared or could be prepared employing the above procedure.

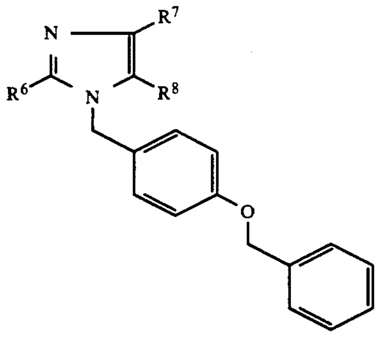

| $R^6$ | $R^7$ | $R^8$ |
|---|---|---|
| n-$C_6H_{13}S$— | H | $CO_2CH_2CH_3$ |
| n-$C_4H_9S$— | H | $CO_2CH_2CH_3$ |

Part E: Preparation of 1-(4-Benzyloxybenzyl)-2-propylthio-5-hydroxymethylimidazole A solution of 2.05 g of 1-(4-benzyloxybenzyl)-2-propylthio-5-carboethoxyimidazole in 10 mL of tetrahydrofuran was added dropwise to 10 mL of 1M lithium aluminum hydride in THF at 0° such that the reaction temperature remained below 5°. The resulting solution then was stirred at 0° for 1 hour. At this point, the reaction mixture was quenched by sequential dropwise addition of 0.40 mL of water, 0.40 mL of 15% aqueous sodium hydride, and 1.20 mL of water. The resulting suspension was filtered employing diethyl ether, and the filtrate was concentrated to furnish 1.55 g of 1-(4-benzyloxybenzyl)-2-propylthio-5-hydroxymethylimidazole; NMR (200 MHz, $CDCl_3$): δ 7.41-7.29 (m, 5H); 7.03-6.86 (m, 5H); 5.22 (s, 2H); 5.01 (s, 2H); 4.45 (s, 2H); 3.01 (t, 2H); 2.32 (bs, 1 h); 1.66 (sext., 2H); 0.97 (t, 3H).

The intermediates shown below were prepared or could be prepared employing the above procedure.

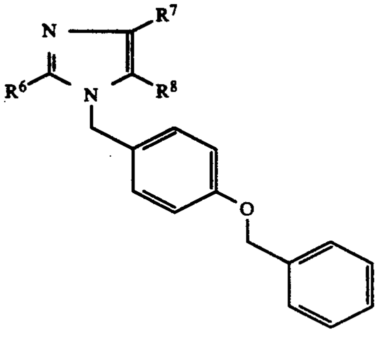

| $R^6$ | $R^7$ | $R^8$ |
|---|---|---|
| n-$C_6H_{13}S$— | H | $CH_2OH$ |
| n-$C_4H_9S$— | H | $CH_2OH$ |

Part F: Preparation of 1-(4-Hydroxybenzyl)-2-propylthio-5-hydroxymethylimidazole A solution of 1.40 g of 1-(4-benzyloxybenzyl)-2-propylthio-5-hydroxymethylimidazole in 15 mL of trifluoroacetic acid was refluxed for 0.25 hour. After cooling, the reaction was poured into water containing an excess of sodium bicarbonate, and the resulting emulsion was extracted with ethyl acetate. The combined organic phases were washed with brine, dried over anhydrous sodium sulfate, filtered, and concentrated. Column chromatography on silica gel (elution: 0–5% methanol/chloroform) afforded 0.28 g of 1-(4-hydroxybenzyl)-2-propylthio-5-hydroxymethylimidazole; NMR (200 MHz, DMSO-$d_6$): δ 9.41 (s, 1 h); 6.88 (s, 1 h); 6.79 ($A_2B_2$, 4H); 5.14 (t, 1 h); 5.07 (s, 2H); 4.33 (d, 2H); 2.89 (t, 2H); 1.54 (sext., 2H); 0.88 (t, 3H).

These intermediates were prepared or could be prepared employing the above procedure.

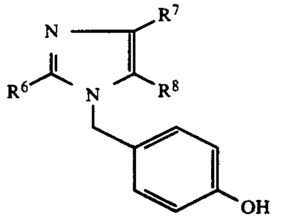

| $R^6$ | $R^7$ | $R^8$ |
|---|---|---|
| n-$C_6H_{13}S$— | H | $CH_2OH$ |
| n-$C_4H_9S$— | H | $CH_2OH$ |

Step G: Preparation of 1-[4-(2-Cyanobenzyloxy)benzyl]-2-propylthio-5-hydroxymethylimidazole The title compound was prepared from 1-(4-hydroxybenzyl)-2-propylthio-5-hydroxymethylimidazole using the procedure described in Example 192, Part C; NMR (200 MHz, $CDCl_3$): δ 7.66 (m, 3H); 7.43 (m, 1 h); 7.03 (s, 1 h); 6.99 ($A_2B_2$, 4H); 5.23 (s, 2H); 5.22 (s, 2H); 4.47 (s, 2H); 3.04 (t, 2H); 1.69 (sext., 2H); 0.98 (t, 3H).

The following 2-mercaptoimidazoles shown below were prepared by the procedure illustrated above.

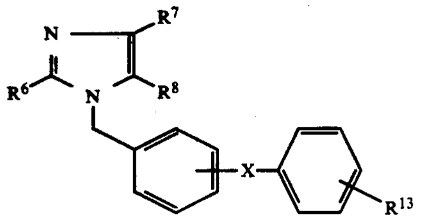

| $R^6$ | $R^7$ | $R^8$ | 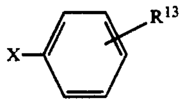 |
|---|---|---|---|
| n-$C_6H_{13}S$— | H | $CH_2OH$ | 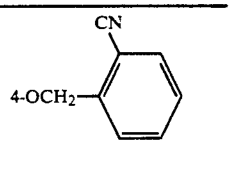 |

-continued

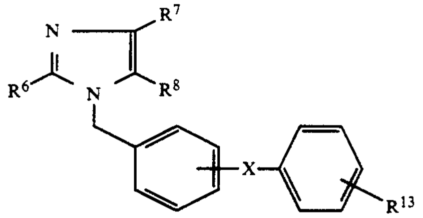

| $R^6$ | $R^7$ | $R^8$ | 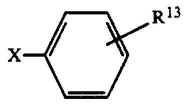 |
|---|---|---|---|
| n-$C_4H_9S$— | H | $CH_2OH$ | 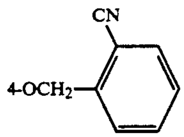 |

Step H: Preparation of 1-[4-(2-Carboxybenzyloxy)benzyl]-2-propylthio-5-hydroxymethylimidazole A solution of 0.23 g of 1[4-(2-cyanobenzyloxy)benzyl]-2-propylthio-5-hydroxymethylimidazole in 17 mL of ethylene glycol and 7 mL of 10% aqueous sodium hydroxide was refluxed for 14 hours. After cooling, the reaction mixture was filtered, and the solvent was removed in vacuo. The residue was dissolved in water, and the solution was acidified to pH 3.5 using hydrochloric acid. The precipitated solid was recovered by filtration and recrystallized from aqueous ethanol to furnish 0.094 g of 1-[4-(2-carboxybenzyloxy)benzyl]-2-propylthio-5-hydroxymethylimidazole; NMR (200 MHz, DMSO-$d_6$): δ 13.12 (bs, 1 h); 7.93 (d, 1 h); 7.58 (m, 2H); 7.45 (m, 1 h); 6.99 ($A_2B_2$, 4H); 6.98 (s, 1 h); 5.42 (s, 2H); 5.25 (bs, 1 h); 5.17 (s, 2H); 4.35 (s, 2H); 2.92 (t, 2H); 1.54 (sext., 2H); 0.89 (t, 3H).

The following 2-mercaptoimidazoles of Table 17 were prepared or could be prepared by the procedure illustrated above.

TABLE 17

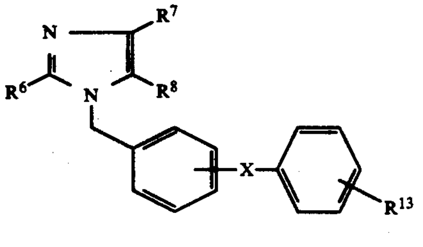

| Ex. NO. | $R^6$ | $R^7$ | $R^8$ | 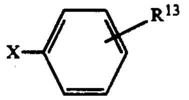 |
|---|---|---|---|---|
| 225 | n-$C_6H_{13}S$— | H | $CH_2OH$ | 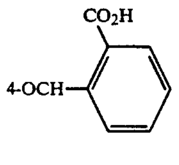 |

TABLE 17-continued

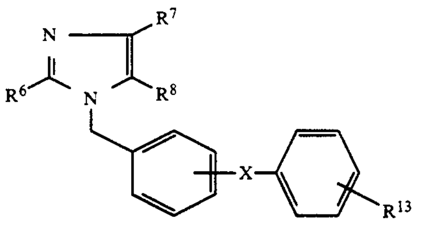

| Ex. NO. | $R^6$ | $R^7$ | $R^8$ | 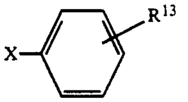 |
|---|---|---|---|---|
| 226 | n-$C_4H_9S$— | H | $CH_2OH$ | 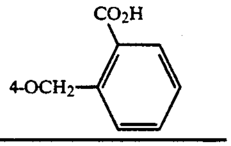 |

EXAMPLE 227

Part A: Preparation of 1-(4-Nitrobenzyl)-2-butyl-4-chloroimidazole-5-aldehyde A mixture of 1 g of 1-(4-nitrobenzyl)-2-butyl-4-chloro-5-hydroxymethyl imidazole and 5 g of activated $MnO_2$ in $CH_2Cl_2$ was stirred at room temperature for 16 hours. The reaction mixture was filtered through celite and the filtrate was concentrated to give a thick oil which was purified by flash column chromatography on silica gel (Hexane:ethyl acetate=1.5:1 elution). The desired compound was obtained as a colorless solid, 0.76 g; m.p. 88°-89°; NMR (200 MHz, $CDCl_3$): δ 9.74 (2, 1 h); 5.64 (s, 2H); 2.63 (t, 3H, J=7.4 Hz); 1.68 (m, 2H); 1.34 (m, 2H); 0.89 (t, 3H, J=7.3 Hz).

Part B: Preparation of 3-[1-(4-Nitrobenzyl)-2-butyl-4-chloroimidazol-5-yl]propenoic acid, ethyl ester, E and Z isomers A mixture of 1.2 g of 1-(4-nitrobenzyl)-2-butyl-4-chloroimidazole-5-aldehyde and 1.5 g of (carboxymethylene)triphenylphosphorane in 50 mL of benzene was refluxed for 2 hours. The reaction mixture was concentrated and the residue was purified by flash column chromatography on silica gel (Hexane: EtOAc=3:1 elution). The major product, the E isomer, was eluted first and was obtained as a thick oil initially which solidified to give an amorphous solid, 1.2 g. The minor product, the Z isomer was eluted next and was isolated as a thick liquid, 85 mg. E isomer: NMR (200 MHz, $CDCl_3$): 7.3 and 6.53 (d, 2H, 5=16 Hz); 5.3 (s, 2H); 2.62 (t, 2H, J=7.3 Hz); 1.69 (m, 2H); 1.28 (m, 5H); 0.89 (t, 3H, J=7.3 Hz). Z isomer: NMR (200 MHz, $CDCl_3$): (key peaks only) δ 6.45 and 6.02 (d, 2H, J=11.8 Hz); 5.17 (s, 2H).

Part C: Preparation of 3-[1-(4-Nitrobenzyl)-2-butyl-4-chloroimidazol-5-yl]propen-1-ol, E isomer A solution of 0.5 g of 3-[1-(4-nitrobenzyl)-2-butyl-4-chloroimidazol-5-yl]propenoic acid, ethyl ester, E isomer in 20 mL of THF was cooled with an ice bath, 1.7 mL of 1.5M diisopropylaluminum hydride (in toluene) was added slowly. The cooling bath was removed and the reaction mixture was stirred at room temperature for 1 hour. The reaction mixture was then quenched with 3 mL of conc. $NH_4Cl$ solution and the mixture was stirred for an additional 30 minutes. During this period an extensive gel-like material formed. The reaction mixture was further diluted with ether and filtered through celite. The filtrate was concentrated and the crude product was purified by flash column chromatography on silica gel (Hexane: EtOAc=1:1 elution). The desired compound was obtained as a thick liquid; NMR (200 MHz, $CDCl_3$): δ 6.5-6.15 (m, 2H); 5.21 (s, 2H); 4.25 (d, 2H, J=4.5 Hz); 2.35 (t, 3H, J=7.4 Hz); 1.68 (m, 2H); 1.34 (m, 2H); 0.86 (t, 3H, J=7.4 Hz).

Part D: Preparation of 3-[1-(4-Aminobenzyl)-2-butyl-4-chloroimidazol-5-yl]propen-1-ol, E isomer A mixture of 0.2 g of 3-[1-(4-nitrobenzyl)-2-butyl-4-chloroimidazol-5-yl]propen-1-ol, 0.15 g of iron and 0.3 mL of glacial acetic acid in 10 mL of absolute ethanol was refluxed for 1 hour. The reaction mixture was concentrated to dryness and the residue was dissolved in 20 mL of water and the solution was made basic to pH 8 by adding $K_2CO_3$. The mixture was then extracted with ethyl acetate and the ethyl acetate layer was washed with water. The organic layer was concentrated to give a crude product which was purified by flash silica gel column chromatography (ethyl acetate elution). A pure product was obtained as an amorphous solid; NMR (200 MHz, $CDCl_3$): δ 6.76 and 6.62 (dd, 4H, J=8.5 Hz); 6.42-6.22 (m, 2H); 2.57 (t, 2H, J=7.3 Hz); 1.65 (m, 2H); 1.33 (m, 2H); 0.87 (t, 2H, J=7.3 Hz).

Part E: Preparation of 3-[1-(4-(2-Carboxybenzamido)benzyl)-2-butyl-4-chloroimidazol-5-yl]propen-1-ol, E isomer To a solution of 95 mg of 3-[1-(4-aminobenzyl)-2-butyl-4-chloroimidazol-5-yl]propen-1-ol in 2 mL of $CHCl_3$ was added 45 mg of phthalic anhydride and the mixture was stirred at room temperature for 1 hour. During this period of time the initially clear solution became turbid and produced solid. The reaction mixture was diluted with 2 mL of ether and the solid was collected by filtration and washed with ether. The desired product was obtained as a tan solid, 115 mg, m.p. 150°-151°; NMR (10% DMSO-$d_6$/$CDCl_3$): δ 9.94 (s, 1 h); 7.71 and 6.93 (d, 4H, J=8.3 Hz); 6.36 (m, 2H); 5.1 (s, 2H); 4.18 (d, 2H, J=3.9 Hz); 2.6 (t, 3H, J=7.4 Hz); 1.68 (m, 2H); 1.34 (m, 2H); 0.89 (t, 3H, J=7.4 Hz).

EXAMPLE 228

Part A: Preparation of 3-[2-Butyl-4-chloro-1-(4-aminobenzyl)imidazol-5-yl]propenoic acid ethyl ester, E isomer A mixture of 0.5 g of 3-[2-butyl-4-chloro-1-(4-nitrobenzyl)imidazol-5-yl]propenoic acid ethyl ester (E isomer) prepared from Part B of Example 227, 1 g of iron and 2 mL of glacial acetic acid in 30 mL of absolute ethanol was refluxed for 1 hour. The reaction mixture was concentrated to dryness and the residue was dissolved in 50 mL of $H_2O$. The aqueous solution was adjusted to pH 8 by $K_2CO_3$ and was extracted with ethyl acetate. The crude product obtained upon concentration of the ethyl acetate extract was purified by flash silica gel column chromatography (hexane:ethyl acetate=1:1 elution). The desired compound was obtained as a thick colorless oil, 0.35 g.

Part B: Preparation of 3-[2-Butyl-4-chloro-1-(4-(2-carboxybenzamido)benzyl-)imidazol-5-yl]propenoic acid ethyl ester, E isomer A mixture of 361 mg of the aniline derivative obtained from Part A and 150 mg of phthalic anhydride in 3 mL of chloroform was stirred at room temperature for 1 hour. The reaction mixture was concentrated and the residue was triturated in ethyl ether. The resulting solid was collected and dried to give a colorless solid, 450 mg, m.p. 180°-181°. NMR ($CDCl_3$, 5% DMSO-$d_6$) δ 0.91 (t, 3H, J=7,1 Hz); 1.1-1.4 (m, 5H); 1.60 (q, 2H, J=7,3 Hz); 2.71 (t, 2H, J=8,4 Hz); 4.17 (q, 2H, J=7,3 Hz); 5.23 (s, 2H); 6.46+7.38 (d each, 2H, J=16,1 Hz); 6.0-8.0 (m, 8H), 10.2 (s, 1H).

EXAMPLE 229

Part A: Preparation of 1-(2'-Carbomethoxybiphenyl-4-yl)methyl-2-butyl-4-chloro-imidazole-5-carboxaldehyde A mixture of 0.68 g of the hydroxymethyl precursor prepared in Example 85, Part C and 3.4 g of activated $MnO_2$ in 30 mL of $CHCl_3$ was stirred at room temperature for 4 hours. The reaction mixture was then filtered through celite and the filtrate was concentrated to give a thick oily residue which was purified by flash chromatography on silica gel (hexane:ethyl acetate=2:1 elution). The desired aldehyde was obtained as a thick colorless oil, 0.5 g; NMR ($CDCl_3$): 9.78 (s, 1H); 5.6 (s, 2H); 3.63 (s, 3H); 2.63 (t, 3H, J=7.4 Hz); 1.68 (m, 2H); 1.34 (m, 2H); 0.89 (t, 3H, J=7.4 Hz).

Part B: 4-[1-(2'-Carbomethoxybiphenyl-4-yl)methyl-2-butyl-4-chloroimidazol-5-yl]-3-buten-2-one, E isomer A mixture of 0.5 g of 1-(2'-carbomethoxybi-phenyl-4-yl)methyl-2butyl-4-chloroimidazole-5-carboxaldehyde and 0.04 g of 1-triphenylphosphoran-ylidene-2-propanone in 20 mL of benzene was refluxed for 16 hours. The reaction mixture was concentrated to give an oily residue which was purified by flash chromatography on silica gel (hexane:ethyl acetate=1:1 elution). The desired compound was obtained as a thick yellowish liquid, 0.46 g; NMR (200 MHz, $CDCl_3$): δ 7.9-6.8 (m, 10H); 5.24 (s, 2H); 3.62 (s, 3H); 3.62 (s, 3H); 2.69 (t, 2H, J=7.4 Hz); 2.26 (s, 3H); 1.72 (m, 2H); 1.38 (m, 2H); 0.91 (t, 3H, J=7.4 Hz).

Part C: Preparation of 4-[1-(2'-Carbomethoxybiphenyl-4-yl)methyl-2-butyl-4-chloroimidazol-5-yl]-3-buten-2-ol, E isomer A solution of 0.45 g of the compound prepared in Part B in 5 mL of methanol was cooled with ice and 0.2 g of $NaBH_4$ was added portionwise. After all the $NaBH_4$ was added the reaction mixture was stirred for 10 minutes. The reaction mixture was concentrated to dryness and the residue was treated with 3 mL of satd. $NH_4Cl$ and the mixture was stirred at room temperature for 10 min. The mixture was then extracted with ethyl acetate and the ethyl acetate extract was concentrated to give a thick liquid, 0.45 g; NMR (200 MHz, $CDCl_3$): 6.45-6.15 (m, 2H,); 5.16 (s, 2H); 4.34 (m, 1H,); 3.67 (s, 3H).

EXAMPLE 230

Part A: Preparation of 1-(4-nitrobenzyl)-2-butyl-4-chloro-5-(2-phenylethen-1-yl)imidazole, E isomer A solution of 0.4 g of benzyltriphenylphosphonium chloride in 20 mL of dried THF was cooled to −30°. To the above solution was added 0.65 mL of 1.6M n-BuLi dropwise. As the BuLi was added the solution turned to deep orange color. After stirring for 10 min. at −30°, 0.32 g of 1-(4-nitrobenzyl)-2-butyl-4-chloroimidazole-5-aldehyde was added and the reaction mixture was allowed to warm up to room temperature and stirred at room temperature for 2 hours. The reaction mixture was quenched with 2 mL of saturated $NH_4Cl$ solution and diluted with ethyl acetate, and the ethyl acetate solution was washed with water and a brine solution. Evaporation gave a thick oily residue which was purified by the flash silica gel column chromatography (hexane:ethyl acetate=3:1 elution) to give a thick yellow oil, 0.39 g.

Part B: Preparation of 1-[4-(2-Carboxybenzamido)benzyl]-2-butyl-4-chloro-5-(2-phenylethen-1-yl)imidazole, E isomer The compound was prepared from the compound of Part A by the procedure described in Example 227, Parts D and E; m.p. 111°-113° (dec).

EXAMPLE 231

Part A: Preparation of 3-[2-Butyl-4-chloro-1-(4-nitrobenzyl)imidazol-5-yl]-3-propen-1-ol acetate, E isomer A mixture of 1 g of 3-[1-(4-nitrobenzyl)-2-butyl-4-chloroimidazol-5-yl]propen-1-ol obtained from Part C of Example 227, 1 mL of acetic anhydride and 2 mL of pyridine in 20 mL of $CH_2Cl_2$ was stirred at room temperature for 16 hours. The reaction mixture was diluted with 100 mL of ethyl acetate and the organic layer was washed with $H_2O$. The crude product obtained upon concentration of the organic layer was purified by flash silica gel chromatography (hexane:ethyl acetate=1:1 elution) to give the desired acetate as a thick colorless oil, 0.95 g.

Part B: Preparation of 3-[2-Butyl-4-chloro-1-(4-aminobenzyl)imidazol-5-yl]-3-propen-1-ol acetate, E isomer The nitro compound obtained from Part A was reduced to the amino compound by the conditions described in Part D of Example 227. The desired compound was obtained as a colorless thick oil.

Part C: Preparation of 3-[2-Butyl-4-chloro-1-(4-(2-carboxybenzamido)benzyl-)imidazol-5-yl]-3-propen-1-ol acetate, E isomer The phthalamic acid derivative was obtained from the aniline derivative obtained from Part B and phthalic anhydride by the method described in Part E of Example 227. The desired compound was obtained as a colorless solid, m.p. 84°-87°.

NMR ($CDCl_3$) δ 0.91 (t, 3H, J=7,1 Hz); 1.2 (m, 2H); 1.7 (m, 2H); 2.0 (s, 3H); 2.7 (t, 2H, J=7,4 Hz); 4.57 (d, 2H, J=5,4 Hz); 5.06 (s, 2H); 6.24 (m, 2H); 6.9-8.0 (m, 8H); 8.8 (s, 1H).

EXAMPLE 232

Preparation of 3-[1-(4-((N-Trifluoromethanesulfonyl)anthranilamido)-benzyl)-2-butyl-4-chloroimidazol-5-yl]-3-propen-1-ol acetate, E isomer A mixture of 0.72 g of 3-[2-butyl-4-chloro-1-(4-aminobenzyl)imidazol-5-yl]-3-propen-1-ol acetate obtained from Example 231, Part B and 0.6 mL of triethylamine in 20 mL of $CH_2Cl_2$ was cooled with an ice bath. To this solution was added 0.6 g of o-(trifluoromethanesulfonamido)benzoyl chloride dropwise and the reaction mixture was stirred at room temperature for 2 hours. The reaction mixture was then diluted with 100 mL of ethyl acetate, and the ethyl acetate solution was washed with water, dried over $Na_2SO_4$ and concentrated to give a crude product which was purified by a flash silica gel column chromatography (3% aceto-nitrile in ethyl acetate) to give the desired compound as a solid, 1.05 g, m.p. 156°-158°; NMR (200 mHz, $CDCl_3$): δ 12.9 (bs, 1H); 8.12-6.91 (m); 6.3 (s); 5.09 (s); 4.61 (d, 2H, J=4.5 Hz); 2.04 (s, 3H).

EXAMPLE 233

Preparation of 3-[1-(4-((N-trifluoromethanesulfonyl)anthranilamido)-benzyl)-2-butyl-4-chloroimidazol-5-yl]propen-1-ol, E isomer A mixture of 0.9 g of the compound of Example 232 and 3 mL of 1N NaOH in 6 mL of methanol was stirred at room temperature for 16 hours. The reaction mixture was diluted with 50 mL of water and the aqueous solution was acidified to a pH of 3 with 1N HCl to produce extensive solids which were collected and washed with water. The solids were then dried in vacuo to give 0.85 g of the desired product, m.p. 129°-131°; NMR (200 MHz, 5% DMSO-$d_6$/CDCL$_3$): 11.15 (bs, 1H); 8.02-6.95 (m, 8H); 6.5-6.3 (m, 2H); 5.13 (s, 2H); 4.19 (d, 2H, J=3.5 Hz).

EXAMPLE 234

Part A: Preparation of 3-[2-Butyl-4-chloro-1-(4-nitrobenzyl)imidazol-5-yl]-2-(carboethoxy)propanoic acid, ethyl ester The sodium salt of diethyl malonate was generated from 2.5 g of NaH (50% oil dispersion) and 8 mL of diethyl malonate in 100 mL of dried DMF with ice cooling. To the above solution was added 5 g of the chloromethyl compound and the mixture was stirred at room temperature for 3 hours. The reaction mixture was stirred at room temperature for 3 hours. The reaction mixture was concentrated and the residue was diluted with 100 mL of water. The aqueous layer was acidified to a pH of 6 by 1N HCl and the product was extracted with ethyl acetate. The crude product was purified by column chromatography (Hexane: EtOAc=2:1 elution) which afforded the product as a thick yellow oil, 2.8 g.

Part B: Preparation of 3-[2-Butyl-4-chloro-1-(4-nitrobenzyl)imidazol-5-yl]propanoic acid methyl ester A mixture of 0.5 g of the compound from Part A in 20 mL of 3N HCl was refluxed for 2 hours. The reaction mixture was cooled and neutralized to a pH of 6 with 4N NaOH solution. The resulting gummy solids were extracted into ethyl acetate and concentrated to give a thick yellow oil, 0.5 g. The propionic acid derivative was dissolved in ethyl ether and was treated with diazomethane in ethyl ether to give a crude methyl ester which was purified by column chromatography (hexane:ethyl acetate=1:1) which afforded the product as a waxy solid, 0.34 g.

Part C: Preparation of 3-[2-Butyl-4-chloro-1-(4-(2-carboxybenzamido)benzyl-)imidazol-5-yl]propanoic acid methyl ester The nitro compound of Part B was reduced to the corresponding amino compound by methods previously described. A mixture of 17 mg of the amino compound and 7.5 g of phthalic anhydride in 1 mL of $CHCl_3$ was stirred at room temperature for 1 hour. The reaction mixture was concentrated to dryness and the residue was triturated with ether. The resulting solids were collected and washed with ether. The pure product was obtained as a colorless solid, 20 mg, m.p. 150.5°-151.5° (dec.).

EXAMPLE 235

Preparation of 3-[2-Butyl-4-chloro-1-(4-((N-trifluoromethanesulfonyl-)anthranilamido)benzyl)imidazol-5-yl]propanoic acid methyl ester Reaction between the amino compound of Example 234, Part C and o-(trifluoromethanesulfonamido)benzoyl chloride using the conditions described in Example 232 produced the title compound as a solid, m.p. 168°-172°.

EXAMPLE 236

Part A: Preparation of 3-[1-(4-Nitrobenzyl)-2-butyl-4-chloroimidazol-5-yl]propanoic acid, N,N-dimethylamide To a solution of 0.7 g of propionic acid from Part B of Example 234 in 20 mL of methylene chloride was added 0.5 mL of pyridine, 0.16 g of dimethylamine HCl salt and 0.42 g of dicyclohexylcarbodiimide. The mixture was then stirred at room temperature for 16 hours. At the end of the reaction the mixture was filtered through celite and the filtrate was concentrated to give a thick oily product. Thus obtained crude product was purified by flash column chromatography (100% elution) to give a pure product as a thick colorless oil, 0.68 g; NMR (200 MHz, $CDCl_3$) δ 2.89 (s, 3H); 2.93 (s, 3H); 5.43 (s, 2H).

Part B: Preparation of 3-[1-(4-Aminobenzyl)-2-butyl-4-chloroimidazol-5-yl]propanoic acid, N,N-dimethylamide The nitro compound from Part A was reduced by the same method described in Part D of Example 227 to give the amino compound as a solid, m.p. 146°-148°.

Part C: Preparation of 3-[2-Butyl-4-chloro-1-(4-((N-trifluoromethanesulfonyl-)anthranilamido)benzyl)imidazol-5-yl]propanoic acid, N,N-dimethylamine amide The amino compound from Part B was treated with o-(trifluoromethanesulfonamido)benzoyl chloride as described in Example 232 to give the trifluoromethylsulfonamide product, m.p. 106°-108°.

Part D: Preparation of 3-[2-Butyl-4-chloro-1-(4-(2-carboxybenzamido)benzyl-)imidazol-5-yl]-propanoic acid, N,N-dimethylamine amide The amino compound from Part B was reacted with phthalic anhydride as described in Part E of Example 227 to give the phthalamic acid derivative, m.p. 139°-142°.

EXAMPLE 237

Part A: Preparation of 3-[1-(4-Nitrobenzyl-2-butyl-4-chloroimidazol-5-yl]-2-carboethoxy-2-methylpropanoic acid, ethyl ester A solution of 2 g of the malonate derivative obtained from Part A of Example 234 in 10 mL of dried DMF was cooled with ice. To the solution was added 0.22 g of NaH (50% oil dispersion) and the solution was stirred for 5 minutes before adding 0.3 mL of methyl iodide. The reaction mixture then stirred at room temperature for 2 hours. The reaction mixture was diluted with 400 mL of ethyl acetate and the organic layer was washed with $H_2O$ and brine. The crude product obtained upon concentration of the organic layer was purified by flash silica gel column chromatography (hexane:ethyl acetate=1:1 elution) to give a pure compound as a thick colorless oil, 1.8 g.

Part B: Preparation of 3-[1-(4-Nitrobenzyl)-2-butyl-4-chloroimidazol-5-yl]-2-methylpropanoic acid The malonate derivative from Part A was subjected to the hydrolysis-decarboxylation condition as described in Part B of Example 234. The desired compound was obtained as a thick yellowish liquid.

Part C: Preparation of 3-[1-(4-Nitrobenzyl)-2-butyl-4-chloroimidazol-5-yl]-2-methylpropanoic acid, isopropyl ester A mixture of 0.38 g of the acid from Part B, 1 mL of isopropyl alcohol and 0.22 g of dicyclohexylcarbodiimide in 10 mL of $CH_2Cl_2$ was stirred at room temperature for 16 hours. The reaction mixture was concentrated and the residue was taken into ethyl acetate. Insoluble material was filtered off and the filtrate was concentrated to give a crude product which was purified by column chromatography (hexane:ethyl acetate=2:1 elution) to give the desired compound as a thick colorless oil, 0.36 g.

Part D: Preparation of 3-[1-(4-((N-trifluoromethanesulfonyl)anthranilamido)-benzyl)-2-methylpropanoic acid, isopropyl ester The title compound was prepared from the ester of Part C by the methods described in Parts B and C of Example 236; m.p. 132°-135°.

EXAMPLES 238 AND 239

Part A: Preparation of d and l 3-[1-(4-Nitrobenzyl)-2-butyl-4-chloroimidazol-5-yl]-2-methylpropanoic acid d-(+)-α-methylbenzylamide A mixture of 0.71 g of the propionic acid derivative from Part B of Example 237, 0.25 mL of d-(+)-α-methylbenzylamine and 0.4 g of dicyclohexylcarbodiimide in 50 mL of $CH_2Cl_2$ was stirred at room temperature for 16 hours. The reaction mixture was concentrated and residue was dissolved in 100 mL of ethyl acetate. Insoluble material was filtered off through celite and the filtrate was concentrated to give a crude product which was purified by silica gel column chromatography (hexane:ethyl acetate=2:1 elution). Two diastereoisomers were separated as a thick colorless oil, 0.37 g each.

Part B: Preparation of d and l 3-[1-(4-Aminobenzyl)-2-butyl-4-chloroimidazol-5-yl]-2-methylpropanoic acid, d-(+)-α-methylbenzylamide The nitro compound from Part A was reduced by the same method described in Part D of Example 227 to give the amino compound as a thick colorless oil.

Part C: Preparation of d and l 3-[1-(4-(2-Carboxybenzamido)benzyl-2-butyl-4-chloroimidazol-5-yl]-2methylpropanoic acid, d-(+)-α-methylbenzylamide Each diasteroisomer of the amino compound from Part B was reacted with phthalic anhydride separately as described in Part E of Example 227, to give the phthalamic acid derivatives, m.p. 188°-189.5° and 201°-202°, respectively.

EXAMPLE 240

Preparation of 1-[(2'-Carboxybiphenyl-4-yl)methyl]-2-butyl-4-chloroimidazole-5-carboxylic acid To a solution of 1.03 g of 1-[(2'-carbomethoxybiphenyl-4-yl)methyl]-2-butyl-4-chloro-5-hydroxymethylimidazole in 10 mL of anhydrous acetic acid at 25° was added a solution of 0.62 g of chromium trioxide in 10 mL of water. The mixture was stirred at 25° for 15 minutes and then poured into water. The precipitated solids were recovered by filtration and then dissolved in 50 mL of 1.0N aqueous sodium hydroxide solution. The alkaline solution was allowed to stand at 25° overnight and then was acidified to pH 3 with 10% aqueous hydrochloric acid. The precipitated solid was recovered by filtration and recrystallized from ethyl acetate to afford 0.10 g of 1-[(2'-carboxybiphenyl-4-yl)methyl]-2-butyl-4-chloroimidazole-5-carboxylic acid (m.p. 186°-187° (decomp.)). NMR (DMSO-$d_6$) δ 12.97 (br s, 2H); 7.68 (d, 1H); 7.53 (t, 1H); 7.41 (t, 1H); 7.34 (d, 1H); 7.28 (d, 2H); 7.02 (d, 2H); 5.61 (s, 2H); 2.60 (t, 2H); 1.53 (quint., 2H); 1.27 (sext., 2H); 0.81 (t, 3H).

EXAMPLE 240A

Preparation of 2-butyl-1-[(2'-(1H-tetrazol-5-yl)biphenyl-4-yl)methyl]-4-trifluoromethylimidazole-5carboxylic acid A mixture of 4.00 g of 2-butyl-5-hydroxymethyl-4trifluoromethyl-1-[(2'-triphenylmethyltetrazol-5-yl)biphenyl-4-yl)methyl]imidazole and 8.00 g of activated manganese dioxide in 50 mL of methylene chloride was stirred at 25° C. At 24 hours into the reaction 2.00 g of manganese dioxide was added. After a total of 100 hours the reaction mixture was filtered with methylene chloride. The solids then were washed with methanol, and the methanol filtrate concentrated. The residue was dissolved in water. The resulting aqueous solution was adjusted to pH 3 using 10% hydrochloric acid and then extracted with 4:1 chloroform/i-propanol. The combined organic phases were washed with brine, dried over anhydrous sodium sulfate, filtered, and concentrated. Column chromatography (elution: 95:5:0.5 chloroform/methanol/acetic acid) furnished 0.25 g of 2- butyl-1-[(2'-(1H-tetrazol-5-yl)-biphenyl-4-yl)methyl]-4-trifluoromethylimidazole-5-carboxylic acid as an amorphous solid.

NMR (200 MHz, DMSO-$d_6$): δ 7.70–7.48 (m, 4H), 7.00 ($A_2B_2$, 4H), 5.58 (s, 2H), 2.59 (t, 2H), 1.51 (quint., 2H), 1.25 (sext., 2H), 0.79 (t, 3H).

Examples 241–265E were prepared using procedures illustrated in Examples 227–240A.

TABLE 18

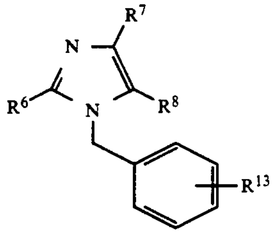

| Ex. No. | $R^6$ | $R^7$ | $R^8$ | $R^{13}$ | MP(°C.) |
|---|---|---|---|---|---|
| 241 | n-butyl | Cl | 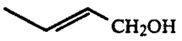 | 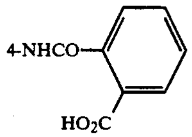 | 115–120 |
| 242 | n-butyl | Cl | 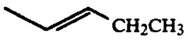 | 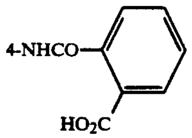 | 171.5–172.5 |
| 243 | n-butyl | Cl | 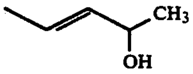 | 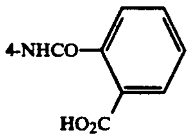 | 160–162 |
| 244 | n-butyl | Cl | $(CH_2)_2COCH_3$ | 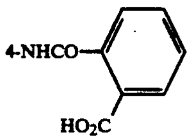 | 164–162 |
| 245 | n-propyl | Cl | $CH_2CH_2CO_2CH_3$ | 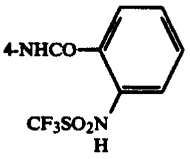 | |
| 246 | n-butyl | Cl | $CH_2CH(CH_3)CO_2CH(CH_3)_2$ | 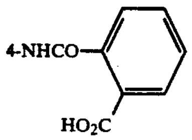 | 123–125 |
| 247 | n-butyl | Cl | $(CH_2)_3OAc$ | 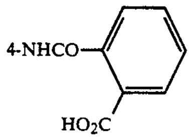 | 124–127 |

TABLE 18-continued
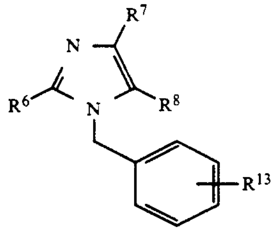
| Ex. No. | $R^6$ | $R^7$ | $R^8$ | $R^{13}$ | MP(°C.) |
|---|---|---|---|---|---|
| 248 | n-butyl | Cl | $(CH_2)_3OAc$ | 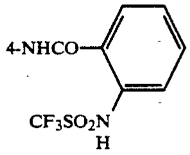 | 64-67 |
| 249 | n-butyl | Cl | 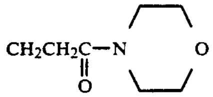 | 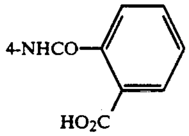 | 142-144 |
| 250 | n-butyl | Cl | 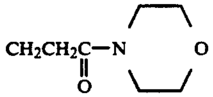 | 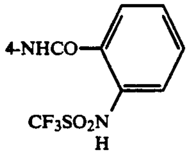 | 63-64.5 |
| 251 | n-butyl | Cl | 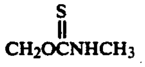 | 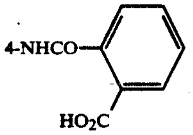 | |
| 251A | n-propyl | Cl | $CO_2H$ | 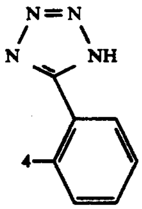 | (amorphous solid)[a] |
| 252 | n-butyl | Cl | $CO_2H$ | 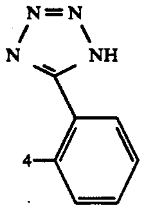 | (amorphous solid)[b] |
| 253 | n-pentyl | H | $CO_2H$ | 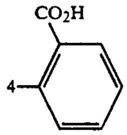 | |

TABLE 18-continued
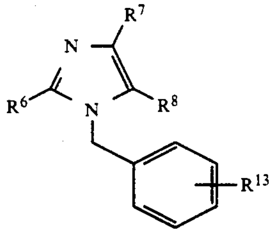
| Ex. No. | $R^6$ | $R^7$ | $R^8$ | $R^{13}$ | MP(°C.) |
|---|---|---|---|---|---|
| 254 | n-propyl | H | 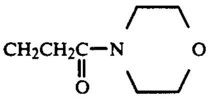 | 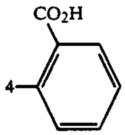 | |
| 255 | n-propyl | Cl | 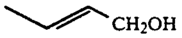 | 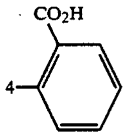 | |
| 256 | n-propyl | Cl | 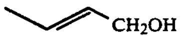 | 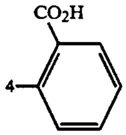 | |
| 257 | n-butyl | Cl | 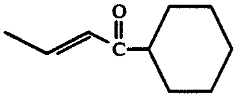 | 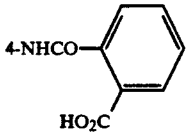 | |
| 258 | n-butyl | Cl | 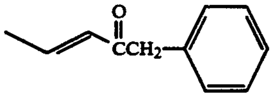 | 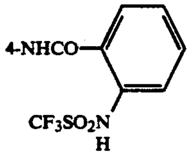 | |
| 259 | n-butyl | Cl | 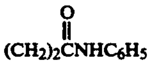 | 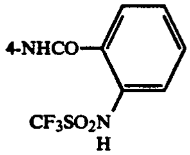 | |
| 260 | n-butyl | Cl | 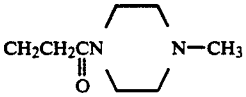 | 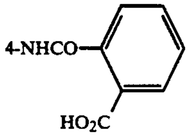 | |
| 261 | n-butyl | Cl | 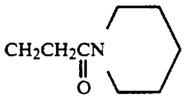 | 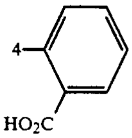 | |

TABLE 18-continued
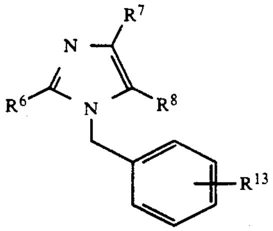
| Ex. No. | $R^6$ | $R^7$ | $R^8$ | $R^{13}$ | MP(°C.) |
|---|---|---|---|---|---|
| 262 | n-butyl | Cl | 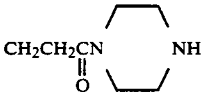 | 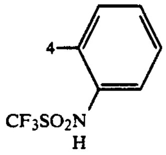 | |
| 263 | n-butyl | Cl | 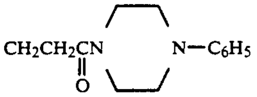 | 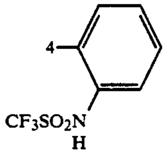 | |
| 264 | n-butyl | Cl | $CH_2CH_2CO_2H$ | 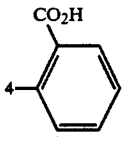 | 75-76.5 |
| 265 | n-butyl | Cl | $CH_2CH_2CH_2CO_2H$ | 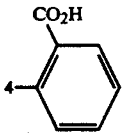 | 83-85 |
| 265A | n-propyl | $CF_3$ | $CO_2H$ | 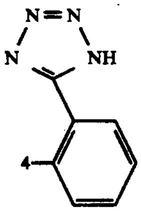 | (amorphous solid)[c] |
| 265B | n-butyl | $CF_2CF_3$ | $CO_2H$ | 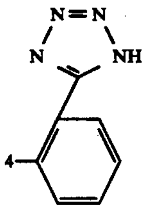 | (amorphous solid)[d] |
| 265C | n-propyl | $CF_2CF_3$ | $CO_2H$ | 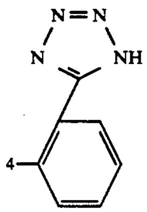 | (amorphous solid)[e] |

TABLE 18-continued

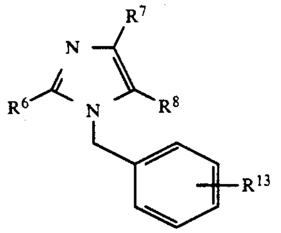

| Ex. No. | $R^6$ | $R^7$ | $R^8$ | $R^{13}$ | MP(°C.) |
|---|---|---|---|---|---|
| 265D | n-propyl | $CF_3$ | $CO_2H$ | 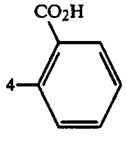 | (amorphous solid)[f] |
| 265E | n-propyl | $CF_2CF_3$ | $CO_2H$ | 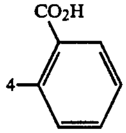 | (amorphous solid)[g] |

[a]NMR(200MHz; $CDCl_3$), $CD_3OD$, TMS): δ7.88–6.90(m, 8H), 5.52(s, 2H), 2.63(t, J=7.5Hz, 2H); 1.77–1.66(m, 2H), 0.95(t, J=7Hz, 3H).
[b]NMR(200MHz, DMSO-$d_6$): δ7.46–7.63(m, 4H), 7.05(d, 2H, J=8Hz), 6.93(d, 2H, J=8Hz), 5.56(s, 2H); 4.10(s, 12H); 2.55(t, 2H, J=7.5(Hz), 1.44–1.52(m, 2H), 1.17–1.28(m, 2H), 0.78(t, 3H, J=7Hz).
[c]NMR(200MHz, DMSO-$d_6$): δ7.71–7.50(m, 4H), 7.02($A_2B_2$, 4H), 5.60(s, 2H), 2.59(t, 2H), 1.57(sext., 2H), 0.84(t, 3H).
[d]NMR(200MHz, DMSO-$d_6$): δ7.74–7.52(m, 4H), 7.05($A_2B_2$, 4H), 5.58(s, 2H), 2.62(t, 2H), 1.51(quint., 2H), 1.25(sext., 2H), 0.80(t, 3H).
[e]NMR(200MHz, DMSO-$d_6$): δ7.73–7.53(m, 4H), 7.04($A_2B_2$, 4H), 5.58(s, 2H), 2.60(t, 2H), 1.56(sext., 2H), 0.84(t, 3H).
[f]NMR(200MHz, DMSO-$d_6$): δ13.78(brs, 1H), 12.82(brs, 1H), 7.75(d, 1H), 7.59(t, 1H), 7.47(t, 1H), 7.35(m, 3H), 7.08(d, 2H), 5.63(s, 2H), 2.66(t, 2H), 1.61(sext., 2H), 0.86(t, 3H).
[g]NMR(200MHz, DMSO-$d_6$): δ13.73(brs, 1H), 12.80(brs, 1H), 7.74(d, 1H), 7.59(t, 1H), 7.46(t, 1H), 7.33(m, 3H), 7.07(d, 2H), 5.65(s, 2H), 2.65(t, 2H), 1.62(sext., 2H), 0.85(t, 3H).

EXAMPLE 266

Part A: Preparation of 2-(But-1-en-1-yl)-5-t-butyldimethylsilyloxymethyl-1-[(2'-carbomethoxybiphenyl-4-yl)methyl]-4-chloroimidazole 2-(But-1-en-1-yl)-1-[(2'-carbomethoxybiphenyl-4-yl)methyl]-4-chloro-5-(hydroxymethyl)imidazole (1.4 g), t-butyldimethylsilyl chloride (0.55 g), and imidazole (0.5 g) were mixed and stirred in DMF (5 mL) for 18 hours at room temperature. Dilution with ethyl acetate and washing the organic phase with water followed by drying ($MgSO_4$), evaporation of the solvent in vacuo, and flash chromatography in 3:1 hexane/ethyl acetate yielded 1.5 g of a clear oil. NMR (200 MHz, $CDCl_3$) δ 7.83 (d, 1H); 7.52 (t, 1H); 7.40 (t, 1H); 7.33–7.24 (m, 3H); 7.08 (d, 2H); 6.83 (d of t, 1H); 6.13 (d, 1H); 5.30 (s, 2H); 4.57 (s, 2H); 3.64 (s, 3H); 2.21 (quint., 2H); 1.04 (t, 3H); 0.86 (s, 9H); 0.05 (s, 6H).

Part B: Preparation of 5-t-Butyldimethylsilyloxymethyl-1-[(2'-carbomethoxybiphenyl-4-yl)methyl]-4-chloroimidazole-2-carboxaldehyde 2-(But-1-en-1-yl)-5-(t-butyldimethylsilyloxymethyl)-1-[(2-carbomethoxybiphenyl-4-yl)methyl-4-chlorimidazole (262 mg) was reacted with osmium tetroxide and sodium periodate by the procedure described in Example 178, Part B for 1.5 hours at room temperature. Work-up and flash chromatography in 3:1 hexane/ethyl acetate yielded 200 mg of an amorphous solid. NMR (200 MHz, $CDCl_3$) δ 9.74 (s, 1H); 7.84 (d, 1H), 7.54 (t, 1H), 7.43 (t, 1H), 7.34–7.25 (m, 3H), 7.16 (d, 2H) 5.83 (s, 2H), 4.65 (s, 2H), 3.64 (s, 3H), 0.90 (s, 9H), 0.09 (s, 6H).

Part C: Preparation of 5-t-Butyldimethylsilyloxymethyl-1-[(2'-carbomethoxybiphenyl-4-yl)methyl]-4-chloro-2-(cis-pent-1-en-1-yl)imidazole 5-t-Butyldimethylsilyloxymethyl-1-[(2'-carbomethoxybiphenyl-4-yl)methyl]-4-chloroimidazole-2-carboxaldehyde (200 mg) was added all at once to a solution of n-butyltriphenylphosphonium bromide (0.26 g) and potassium t-butoxide (70 mg) in THF at 0° C. The reaction mixture was stirred at room temperature for 15 minutes when it was quenched with saturated aqueous ammonium chloride solution. The mixture was extracted with ethyl acetate, the organic layers washed with water, dried ($MgSO_4$) and the solvent removed in vacuo. The residue was flash chromatographed in hexane/ethyl acetate (5:1) to yield 100 mg of an oil. NMR (200 MHz, $CDCl_3$) δ 7.85 (d, 1H), 7.54 (t, 1H), 7.42 (t, 1H), 7.35–7.24 (m, 3H), 7.07 (d, 2H), 6.07 (d, 1H), 5.87 (d of t, 1H), 5.28 (s, 2H), 4.59 (s, 2H), 3.64 (s, 3H), 2.69 (quart., 2H), 1.46 (sext., 2H), 0.91 (t, 3H), 0.86 (s, 9H), 0.05 (s, 6H).

Part D: Preparation of 1-[(2'-Carbomethoxybiphenyl-4-yl)methyl]-4-chloro-5-hydroxymethyl-2-(cis-pent-1-en-1-yl)imidazole 5-t-Butyldimethylsilyloxymethyl-1-[(2'-carbomethoxybiphenyl-4-yl)methyl]-4-chloro-2-(cis-pent-1-en-1-yl)imidazole (100 mg) was desilylated with fluoride by procedures familiar to one skilled in the art. Flash chromatography in 1:1 hexane/ethyl acetate yielded 65 mg of a viscous, colorless oil. NMR (200 MHz, $CDCl_3$) δ 7.85 (d, 1H), 7.55 (t, 1H), 7.42 (t, 1H), 7.28 (m, 3H), 7.05 (d, 2H), 6.11 (d, 1H), 5.92 (d of t, 1H), 5.30 (s, 2H), 4.57 (d, 2H), 3.64 (s, 3H), 2.69 (quart., 2H), 1.62 (t, 1H), 1.47 (sext., 2H), 0.92 (t, 1H).

Part E: Preparation of 1-[(2-Carboxybiphenyl-4-yl)methyl]-4-chloro-5-hydroxymethyl-2-(cis-pent-1-en-1-yl)imidazole 1-[2'-Carbomethoxybiphenyl-4-yl)methyl]-4-chloro-5-hydroxymethyl-2-(cis-pent-1-en-1-yl)imidazole (65 mg) was hydrolyzed by a procedure similar to that found in Example 85, Part E. Work-up yielded 45 mg of colorless solids; m.p. 148°-150°. NMR (200 MHz, DMSO-$d_6$) δ 7.77 (d, 1H); 7.50 (t, 1H); 7.38 (t, 1H); 7.33 (m, 3H); 7.08 (d, 2H); 6.10 (d, 1H): 5.84 (d of t, 1H); 5.32 (s, 2H); 4.47 (s, 2H); 2.65 (quart., 2H), 1.45 (sext., 2H); 0.92 (t, 3H).

Table 19 further illustrates compounds which were made or could be made by the methods described in the specification.

TABLE 19

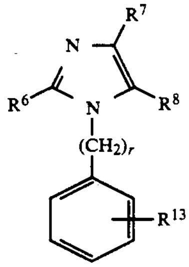

| Ex. No. | r | $R^6$ | $R^7$ | $R^8$ | $R^{13}$ | MP(°C.) |
|---|---|---|---|---|---|---|
| 267 | 1 | n-butyl | Cl | $CH_2OH$ | 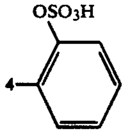 | |
| 268 | 1 | n-propyl | H | $CH_2OH$ | 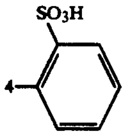 | |
| 269 | 1 | n-butyl | Cl | $CH_2CO_2CH_3$ | 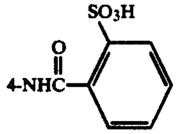 | |
| 270 | 1 | n-pentyl | Cl | $CH_2OH$ | 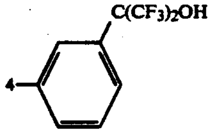 | |
| 271 | 1 | n-butyl | Cl | $CH_2NHC(=O)C_3H_7$ | 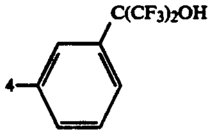 | |
| 272 | 2 | n-butyl | Cl | $CH_2OH$ | 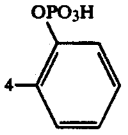 | |
| 273 | 1 | n-propyl | H | $CH_2OH$ | 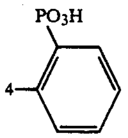 | |

TABLE 19-continued
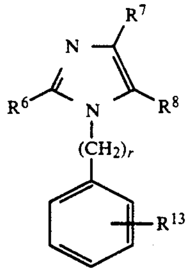
| Ex. No. | r | $R^6$ | $R^7$ | $R^8$ | $R^{13}$ | MP(°C.) |
|---|---|---|---|---|---|---|
| 274 | 1 | n-butyl | $CF_3$ | $CH_2OH$ | 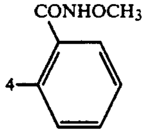 | |
| 275 | 1 | n-butyl | Cl | $CH_2OH$ | 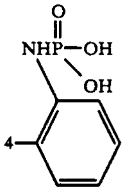 | |
| 276 | 1 | n-butyl | H | $CH_2OH$ | 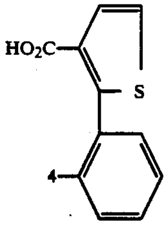 | |
| 276 | 1 | n-hexyl | Cl | $CH_2NHCO_2CH_3$ | 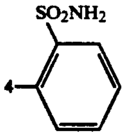 | |
| 278 | 1 | n-butyl | Cl | $CH_2OH$ | 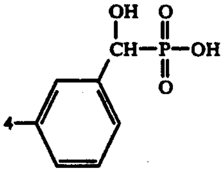 | |
| 279 | 1 | n-butyl | Cl | $CH_2OH$ | 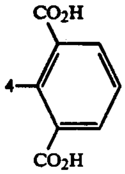 | |
| 280 | 0 | n-butyl | Cl | $CH_2OH$ | 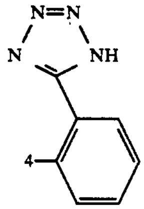 | |

TABLE 19-continued
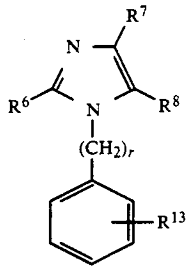
| Ex. No. | r | $R^6$ | $R^7$ | $R^8$ | $R^{13}$ | MP(°C.) |
|---|---|---|---|---|---|---|
| 281 | 1 | n-propyl | Cl | $CH_2OH$ | 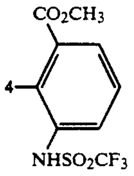 | |
| 282 | 1 | n-butyl | Cl | $CH_2OH$ | 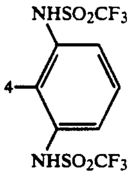 | |
| 283 | 1 | n-butyl | Cl | $CH_2OH$ | 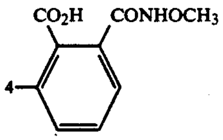 | |
| 284 | 1 | n-hexyl | H | $CH_2OH$ | 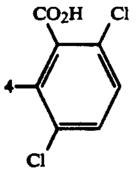 | |
| 285 | 1 | n-butyl | Cl | $CH_2OH$ | 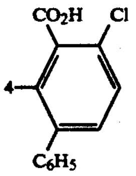 | |
| 286 | 1 | n-propyl | H | $CH_2OH$ | 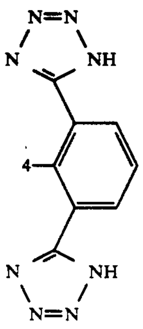 | |

TABLE 19-continued
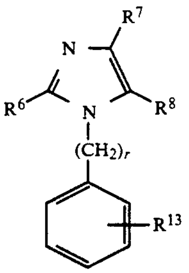
| Ex. No. | r | $R^6$ | $R^7$ | $R^8$ | $R^{13}$ | MP(°C.) |
|---|---|---|---|---|---|---|
| 287 | 1 | n-butyl | Cl | $(CH_2)_2F$ | 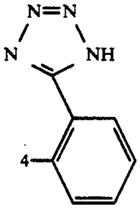 | |
| 288 | 1 | n-butyl | Cl | O<br>‖<br>$CH_2OCNHCH_3$ | 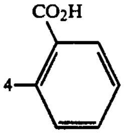 | |
| 289 | 1 | n-butyl | Cl | S<br>‖<br>$CH_2OCNHCH_3$ | 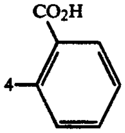 | |
| 290 | 1 | n-propyl | H | S<br>‖<br>$CH_2NHCOCH_2CH_2CH_3$ | 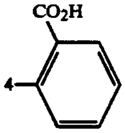 | |
| 291 | 1 | n-pentyl | H | O<br>‖<br>$CH_2NHCNHCH_3$ | 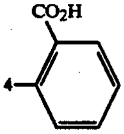 | |
| 292 | 1 | n-butyl | Cl | $(CH_2)_3F$ | 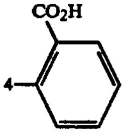 | 181-182.5 |
| 293 | 1 | n-butyl | Cl | $CH_2ONO_2$ | 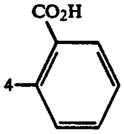 | |
| 293 | 1 | n-butyl | Cl | 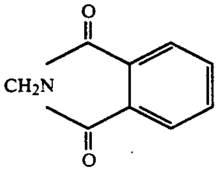 | 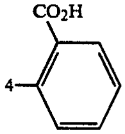 | |

TABLE 19-continued
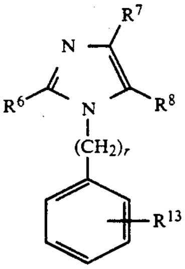
| Ex. No. | r | $R^6$ | $R^7$ | $R^8$ | $R^{13}$ | MP(°C.) |
|---|---|---|---|---|---|---|
| 295 | 1 | n-butyl | Cl | $CH_2OH$ | 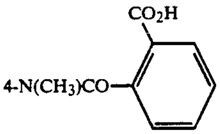 | |
| 296 | 1 | n-butyl | Cl | $CH_2OH$ | 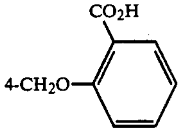 | |
| 297 | 1 | n-butyl | Cl | $CH_2OH$ | 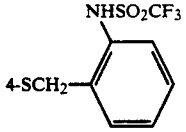 | |
| 298 | 1 | n-butyl | Cl | $CH_2OH$ | 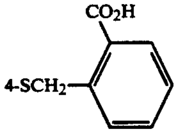 | |
| 299 | 1 | n-butyl | Cl | $CH_2OH$ | 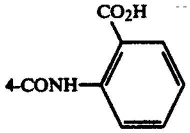 | |
| 300 | 1 | n-butyl | Cl | $CH_2OH$ | 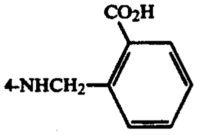 | |
| 301 | 1 | n-butyl | Cl | $CH_2OH$ | 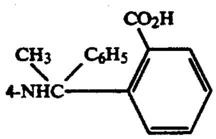 | |
| 302 | 1 | n-propyl | Cl | $CH_2OH$ | 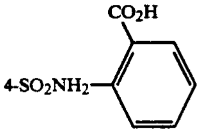 | |
| 303 | 1 | n-pentyl | Cl | $CH_2OH$ | 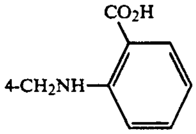 | |

TABLE 19-continued
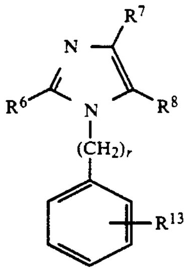
| Ex. No. | r | $R^6$ | $R^7$ | $R^8$ | $R^{13}$ | MP(°C.) |
|---|---|---|---|---|---|---|
| 304 | 1 | n-hexyl | Cl | $CH_2OH$ | 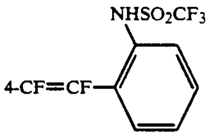 | |
| 305 | 1 | n-butyl | Cl | $CH_2OH$ | 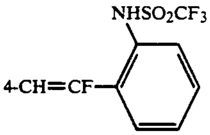 | |
| 306 | 1 | n-butyl | H | $CH_2OH$ | 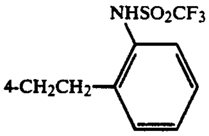 | |
| 307 | 1 | n-butyl | Cl | $CH_2OH$ | 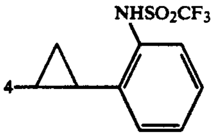 | |
| 308 | 1 | n-butyl | Cl | $CH_2OH$ | 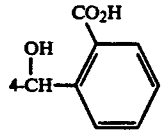 | |
| 309 | 1 | n-butyl | Cl | $CH_2OH$ | 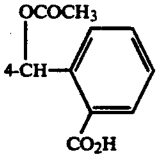 | |
| 310 | 1 | n-butyl | Cl | $CH_2OH$ | 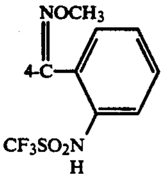 | |
| 311 | 1 | n-butyl | Cl | $CH_2OH$ | 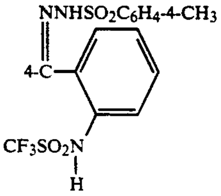 | |

TABLE 19-continued

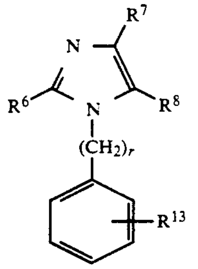

| Ex. No. | r | $R^6$ | $R^7$ | $R^8$ | $R^{13}$ | MP(°C.) |
|---|---|---|---|---|---|---|
| 312 | 1 | n-propyl | Cl | $CH_2OH$ | 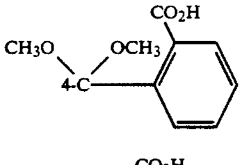 | |
| 313 | 1 | n-pentyl | Cl | $CH_2OH$ | 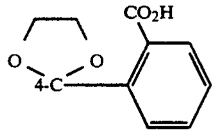 | |
| 314 | 1 | n-butyl | Cl | $CH{=}CHCH_2OH$ | 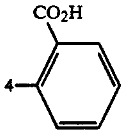 | 103-104.5 |
| 314A | 1 | n-butyl | $CF_3$ | $CO_2CH_2OOCC(CH_3)_3$ | 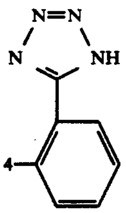 | 204-205 |

EXAMPLE 315

Part A: Preparation of 2-Propyl-4-chloroimidazole-5-carboxaldehyde

This example illustrates the preferred procedure for preparing the compound of Example 114.

To a solution of 2-propyl-4-chloro-5-hydroxymethylimidazole (prepared according to U.S. Pat. No. 4,355,040; m.p. 110.5°-114° C.; 32.0 g, 0.18 mol) in dichloromethane (1 L) was added activated manganese dioxide (207 g, 2.38 mol, 13 eq.). The mixture was stirred for 4-18 hours at room temperature and subsequently filtered through Celite®. The Celite® was washed with 500 ml of a dichloromethane/methanol solution (1/1, V/V) and the filtrate was concentrated in vacuo to give 24.7 g of a pale yellow solid. Recrystallization from ethyl acetate gave 16.6 g (53%) of pure product; m.p., 139°-141.5° C.

NMR (200 MHz; $CDCl_3$, $CD_3OD$, TMS): δ 9.61 (s, 1H), 2.66 (t, J=7.5 Hz, 2H), 1.83-1.67 (m, 2H), 0.98 (t, J=7 Hz, 3H).

Part B: Preparation of 2-Propyl-4-chloro-1[(2'-(1-triphenylmethyltetrazol-5-yl)biphenyl-4-yl-methyl]imidazole-5-carboxaldehyde To a mixture of 2-propyl-4-chloroimidazole-5-carboxaldehyde (15.0 g, 86.9 mmol) and potassium carbonate (13.2 g, 95.6 mmol) in N,N-dimethylformamide (800 ml) was added 4'-bromomethyl-2-(1-triphenylmethyltetrazol-5-yl)biphenyl (prepared according to Example 317, Part B; 53.3 g, 95.6 mmol). The mixture was warmed to 75°-80° C. for 4-18 hours, cooled to room temperature and poured into a separatory funnel containing 1 liter each of water and ethyl acetate. The aqueous phase was extracted twice more with ethyl acetate (250 ml) and the combined organic phase was washed with water (4×500 ml) and saturated aqueous sodium chloride (500 ml), dried over anhydrous magnesium sulfate, filtered and concentrated in vacuo to give the crude product. Flash chromatography on silica gel (1 kg, 10-20% EtOAc/hexanes) gave 27.5 g (49%) of the title compound as a pale yellow solid; m.p. 55°-62° C.

NMR (200 MHZ, $CDCL_3$, TMS): δ 9.73 (s, 1H), 7.95-6.81 (m, 23H), 5.45 (s, 2H), 2.49 (t, J=7.5 Hz, 2H), 1.75-1.64 (m, 2H), 0.89 (t, J=7 Hz, 3H).

Part C: Preparation of 2-Propyl-4-chloro-1-[(2'-(1H-tetrazol-5-yl)biphenyl-4-yl)methyl]imidazole-5-carboxaldehyde To a slurry of 2-propyl-4-chloro-1-[(2'-(1-triphenylmethyletrazol-5-yl)biphenyl-4-yl)methyl]-imidazole-5-carboxaldehyde (26.5 g, 40.8 mmol) in water (100 ml) was added dropwise over 15 minutes 50% aqueous trifluoroacetic acid (V/V, 200 ml). After an additional 15 minutes the mixture was made alkaline with 4N NaOH (350 ml). The resulting mixture was extracted with ether (2×100 ml) and the aqueous phase was acidified to pH 4–5 with 4N HCl and the resulting precipitate was extracted into ethyl acetate (2×100 ml). The combined ethyl acetate layers were dried over anhydrous magnesium sulfate before being filtered and concentrated in vacuo to afford 16 g of the crude product. Flash chromatography on silica gel (100 g, 50% EtOAc/hexanes) provided 13.7 g (83%) of the purified title compound; m.p. 165°-167° C.

NMR (200 MHz, $CDCl_3$, TMS): δ 9.65 (s, 1H), 7.95–6.96 (m, 8H), 5.51 (s, 2H), 2.59 (t, J=7.5 Hz, 2H), 1.70–1.63 (m, 2H), 0.92 (t, J=7 Hz, 3H).

EXAMPLE 316

This example illustrates preferred procedure for preparing the compound of Example 89, Part E, and its potassium salt, which is a preferred compound of this invention.

Part A: Preparation of 1-[(2'-(Trimethylstannyltetrazol-5-yl)biphenyl-4-yl)methyl]-2-butyl-4-chloro-5-hydroxymethylimidazole 1-[(2'-Cyanobiphenyl-4-yl)methyl]-2-butyl-4-chloro-5-hydroxymethylimidazole (766 g), trimethyl tin azide (766 g) and xylenes (7.90 L) were charged to a 12 liter round-bottomed flask equipped with mechanical stirrer, condenser with $N_2$ inlet and thermometer contained in a heating mantle. The slurry was heated to 115° C., giving a clear solution, and held for 41 hours. The resulting slurry was cooled to room temperature and the crude product isolated by vacuum filtration, washed with toluene (800 ml) and dried in vacuo at ~50° C. overnight. The crude product (1202 g) was charged to a 12 liter round-bottomed flask and slurried at 105° C. with toluene (70 L). The slurry was cooled to 50° C. and the product isolated by vacuum filtration, washed with one liter of toluene and dried in vacuo at 50° C. overnight. Yield: 1071 g, 94%. M.P.: 211°-214° C.

Part B: Preparation of 1-[(2'-(Triphenylmethyltetrazol-5-yl)biphenyl-4-yl)methyl]-2-butyl-4-chloro-5-hydroxymethylimidazole 1-[(2'-(Trimethylstannyltetrazol-5-yl)-biphenyl-4-yl)methyl]-2-butyl-4-chloro-5-hydroxymethylimidazole (1.046 Kg), methylene chloride (5.00 L), tetrahydrofuran (0.85 L) and 10N sodium hydroxide (192 ml) were charged to a 12 liter round-bottomed flask equipped with mechanical stirrer, condenser with $N_2$ inlet, and thermometer. After stirring five minutes at room temperature, triphenylmethyl chloride (0.530 Kg) was added and the mixture stirred three hours. 10N Sodium hydroxide (20 ml) and additional triphenylmethyl chloride (50 g) were added and the mixture stirred overnight. Deionized (D.I.) water (3.70 L) and 10N sodium hydroxide (30 ml) were added and the phases allowed to separate. The organic phase was washed twice with 2.0 L portions of water, dried with sodium sulfate (100 g) and filtered into a 12 L round-bottomed flask equipped for distillation. Methylene chloride (~2.0 L) was distilled. Heating was discontinued and heptane (5.0 L) was added. The resulting slurry was stirred at ambient temperature over the weekend (~68 hours). The mixture was cooled to ~5° C. and the product isolated by vacuum filtration, washed with heptane (1.0 L) and dried 48 hours in in vacuo at 40°-50° C. Yield: 959.5 g, 80%. M.P.: 167°-169° C. Purity by HPLC: 99.8%.

Part C: Preparation of 2-butyl-4-chloro-5-hydroxymethyl-1-[(2'-(1H-tetrazol-5-yl)biphenyl-4-yl)methyl]imidazole 1-[(2'-(Triphenylmethyltetrazol-5-yl)biphenyl-4-yl)methyl]-2-butyl-4-chloro-5-hydroxymethylimidazole (920 g), and methanol (2.10 L) were charged to a 12-liter round-bottomed flask, equipped with mechanical stirrer, condenser with $N_2$ inlet and thermometer. The slurry was cooled to ~10° C. and 3.4N hydrochloric acid (700 ml) was added over 10 minutes. After stirring two hours at 10°-20° C., the thick slurry was diluted with methanol (500 ml) and warmed to 30° C. After one hour at 30° C., the reaction was neutralized to pH 13 with 10N sodium hydroxide (420 ml). Solvent (largely methanol, 2.3 L) was distilled while 2.3 L D.I. water was added. Heating was discontinued and D.I. water (700 ml) and toluene (1.40 L) was added. After cooling to ~30° C., the organic phase was removed. The aqueous phase was reextracted with toluene (700 ml). Ethyl acetate (1.20 L) was added to the pot containing the aqueous phase. After stirring 10 minutes, acetic acid (130 ml) was added. The mixture was stirred one hour, then let stand overnight. Agitation was restarted and the slurry cooled to ~5° C. The product was isolated by vacuum filtration, reslurried with 1.50 L D.I. water and sucked semi-dry. The wet cake was charged to a 12 L round bottomed flask and reslurried ½ hour at ambient temperature with ethyl acetate (4.0 L). The product was isolated by vacuum filtration, washed with 200 ml ethyl acetate and dried in vacuo overnight at 50° C. Yield: 518 g, 88.5%. M.P.: 184°-185° C. Purity by HPLC: 98.8%.

NMR (200 MHz, DMSO-$d_6$): δ 7.61 (m, 4H), 7.05 (m, 4H); 5.24 (s, 2H); 4.32 (s, 2H); 3.35 (br s, 1H); 2.46 (t, 2H, J=7.8 Hz); 1.44 (m, 2H); 1.23 (m, 2H); 0.79 (t, 3H, J=7.2 Hz).

Part D: Preparation of 2-butyl-4-chloro-5-hyroxymethyl-1-[(2'-(1H-tetrazol-5-yl)-biphenyl-4-yl)methyl]imidazole; potassium salt The product of Part C (11.00 g) and isopropanol (30 ml) were charged to a 100 ml round-bottomed flask equipped with magnetic stirrer, thermometer and Dean Stark Trap under nitrogen. The slurry was heated to 40° C. A solution of 87% potassium hydroxide (2.00 g)/isopropanol (20 ml/water (1.0 ml) was added to pH 11 (18.5 ml). Most of the water was removed by azeotropic distillation of isopropanol (20 ml distilled). Heptane (25 ml) was added and the slurry cooled to room temperature. Additional heptane (15 ml) was added and the mixture stirred for ½ hr. The product was isolated by vacuum filtration, washed 1×20 ml heptane and dried overnight at 60° C. in vacuo. Yield: 10.33 g, 86%. M.P.: >250° C.

EXAMPLE 317

This example illustrates another preferred method for making the compound of Example 89, Part E.

Part A: Preparation of 2-(Triphenylmethyltetrazol-5-yl)-4'-methylbiphenyl 2-(p-Tolyl)benzonitrile (9.00 g), sodium azide (3.00 g), toluene (35 ml) and tributyltin chloride (16.4 g) were charged to a 250 ml round-bottomed flask equipped with mechanical stirrer, condenser with $N_2$ inlet and thermometer, in a heating mantle. The mixture was heated to 110° C. and held for 70 hours. The mixture was diluted with 35 ml toluene and cooled to room temperature. 10N Sodium hydroxide (5.5 ml) and triphenylmethylchloride (13.5 g) were added and the mixture stirred 3 hours at room temperature. D.I. water (35 ml) and heptane (70 ml) were added and the resulting slurry cooled in an ice bath 1½ hours. The mixture was vacuum filtered, washed 2×50 ml water and once with 50 ml (3/2, V/V) heptane/toluene, and dried in vacuo overnight at 40° C. Crude Yield=18.32 g, 82.2%. The crude product was dissolved in methylene chloride (200 ml) and washed 1×52 ml 0.4N sodium hydroxide. The organic phase was gravity filtered, stripped on a rotary evaporator and the product reslurried with heptane (100 ml), filtered and dried in vacuo at 40° C. overnight. Overall Yield: 15.1 g, 68%. M.P.: 161°-162° C.

Part B: Preparation of 4'-Bromomethyl-2-(triphenylmethyltetrazol-5-yl)biphenyl)

Into a 100 mL round-bottomed flask equipped with thermometer, condenser, and nitrogen is entered 9.0 g 2-[(triphenylmethyltetrazo-5-yl)]-4'-methyl(1,1'-biphenyl (0.0188 mole), 4.0 g N-bromosuccinimide (0.0225 mole), 0.1 g azo(bisisobutyronitrile) (0.00061 mole), and 40 mL carbon tetrachloride. The reaction mass is brought to reflux and held for ~3 hours or until complete by NMR. Upon reaction completion, the reaction mass is cooled to room temperature, diluted with 30 mL methylene chloride, and washed with 30 mL water. The aqueous phase is discarded.

Part C: Preparation of 2-n-Butyl-4-chloroimidazole-5-carboxaldehyde 2-n-Butyl-4-chloro-5-hydroxymethylimidazole (50.0 g, 265 mmol, 1 eq.) was dissolved in glacial acetic acid (150 mL). A 1N cerricammonium nitrate (CAN) solution (575.0 mL, 595 mmol, 2.25 eq.) was then added dropwise to the stirred imidazole solution maintaining the temperature at 20°-30° C. After the addition was complete, an additional 10 mL of 1N CAN solution was added so that the mixture remained orange. After 3 hours, the reaction was cooled on ice and 50% NaOH (210 mL) was added to neutralize the acetic acid. The product precipitated. The pH was adjusted to 6 and the solids were filtered, washed with water (3×500 mL) and dried under high vacuum to yield 38.13 g of a white powder; M.P. 92.5°-93.5° C. NMR (200 MHz, $CDCl_3$): δ 11.83 (m, 1H); 9.64 (s, 1H); 2.85 (t, 2H, J=7 Hz); 1.78 (t of t, 2H, J=7,7 Hz); 1.38 (t of q, 2H, J=7,7 Hz); 0.93 (t, 3H, J=7 Hz). Anal. calcd. for $C_8H_{11}ClN_2O$: C, 51.48; H, 5.94; Cl, 19.00; N, 15.01. Found: C, 51.75; H, 5.82; Cl, 18.73; N, 14.87.

Part D: Preparation of 1-[(2'-(Triphenylmethyltetrazol-5-yl)biphenyl-4-yl)methyl]-2-butyl-4-chloro-5-hydroxymethylimidzole The organic phase is charged to a 100 mL round bottomed flask equipped with condenser, thermometer, and nitrogen. Also charged to the flask is 2.56 g 2-butyl-4-chloroimidazole-5-carboxaldehyde (0.0137 mole), 9.5 mL water, 2.8 mL 10N NaOH, and 1.2 mL aliquot 336. The two-phase system is stirred overnight at room temperature. To the completed reaction mass is added 0.48 g $NaBH_4$ (0.0127 mole) and the reaction mass is again stirred overnight at room temperature. Upon completion, the reaction mass is washed with 30 mL water and the aqueous phase discarded.

The organic phase is entered into a 100 mL round-bottomed flask equipped with thermometer, distillation head-condenser, receiver and addition flask. Methylene chloride and carbon tetrachloride are distilled and reaction volume replaced with 25 mL toluene. Distillation is continued until the pot temperature reaches ~110° C. The reaction mass is cooled to ~40° C. and then diluted with 15 mL ethyl acetate and 20 mL n-heptane. A seed crystal is added and the reaction mass is further cooled to 0°-10° C. and stirred for 1.0-2.0 hours. The slurry is filtered through a Buchner funnel, and solids are rinsed with small amount of cold toluene/ethyl acetate. Solids are dried in a vacuum oven overnight to give 5.91 grams; 51.7% yield (based on 2-butyl-4-chloroimidazole-5-carboxaldehyde or 47.2% yield (based on 2-(triphenylmethyltetrazol-5-yl)-4'-methylbiphenyl.

Crude material was recrystallized from 30 mL toluene to give 4.57 grams product (77.33% recovery) with M.P.=161°-162.5° C.

Part E: Preparation of 2-Butyl-4-chloro-5-hydroxymethyl-1-[(2'-(1H-tetrazol-5-yl)biphenyl-4-yl)methyl]imidazole and its potassium salt The product of Part C is converted to the title compound and its potassium salt by the procedures of Example 316, Parts C and D.

EXAMPLE 317A

Part A: Preparation of 2-Butyl-4-chloro-1-[(2'-N-triphenylmethyl(1H-tetrazol-5-yl)biphenyl-4-yl)methyl]imidazole-5-carboxaldehyde 2-n-Butyl-4-chloroimidazole-5-carboxaldehyde (26.78 g, 143.0 mmol, 1 eq.) was alkylated with 4'-bromomethyl-2-(N-triphenylmethyl(1H-tetrazol-5-yl)biphenyl (80.0 g, 143.0 mmol, 1 eq.) (isolated from Example 317, Part B) by the procedure described in Example 1, Part A. Chromatography and recrystallization from hexane/THF of one-third of the crude material yielded 19.63 g of a white powder; m.p. 86.0°-88.0° C. NMR ($CDCl_3$) of 9.76 (s, 1H); 7.96 (d, 1H, J=8 Hz); 7.56-6.80 (m, 22H); 5.47 (s, 2H); 2.53 (t, 2H),; 1.65 (t of t, 2H, J=7,7 Hz); 1.30 (t of q, 2H, J=7,7 Hz); 0.83 (t, 3H, J=7 Hz). Anal. calcd. for $C_{41}H_{35}ClN_6O.THF$; C, 73.5; H, 5.89; N, 11.43. Found: C, 73.32; H, 5.88; N, 11.84.

Part B: Preparation of α-[2-n-butyl-4-chloro-1-[(2'-(1H-tetrazol-5-yl)biphenyl-4-yl)methyl]imidazol-5-yl]-α-phenylmethanol Phenylmagnesium chloride (2M, 6.8 mmol, 1.5 eq.) was slowly added to a stirred solution of the aldehyde from Part A (3.00 g, 4.5 mmol, 1.0 eq.) in dioxane (25 mL) at 0° C. After 1 h, the reaction was quenched with methanol (5 mL), followed by water (25 mL). Trifluoroacetic acid (25 mL) was then added, and the mixture stirred at room temperature for 1 h. 10N NaOH was added to adjust the pH to 10 and the organic solvents removed in vacuo leaving solid triphenylmethanol and an aqueous phase behind. The triphenylmethanol was filtered and the aqueous was acidified to pH=3 with conc. HCl producing a precipitate. The solids were filtered, dried, and recrystallized from hexane/ethyl acetate yielding 532 mg of a white solid; m.p. 137.0°-145.0° C. NMR (DMSO-$d_6$): δ 7.77-7.46 (m, 4H); 7.46-7.30 (m, 5H); 6.94 (d, 2H, J=9 Hz); 6.76 (d, 2H, J=9 Hz); 6.37 (d, 1H, J=5 Hz); 5.97 (d, 1H, J=5 Hz); 5.09 (s, 2H); 2.25 (t, 2H, J=7 Hz); 1.34 (t of t, 2H, J=7,7 Hz); 1.17 (t of q, 2H, J=7,7H); 0.74 (t, 3H, J=7 Hz). Anal. calcd. for $C_{28}H_{27}ClN_6O.(H_2O)_{0.5}$: C, 66.20: H, 5.56; Cl, 6.98. Found: 66.12; H, 5.51; Cl, 7.25.

The following examples can be prepared by the procedure described in Example 317A and by other methods familiar to one skilled in the art.

TABLE 20

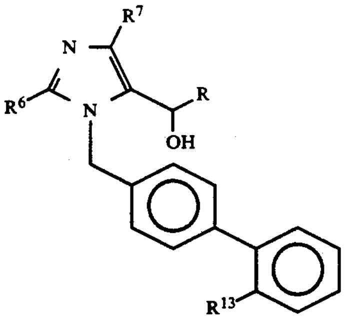

| Ex. No. | $R^6$ | $R^7$ | R | $R^{13}$ | MP(°C.) |
|---|---|---|---|---|---|
| 317B | n-butyl | Cl | $CH_3$ | 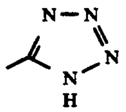 | |
| 317C | n-propyl | Cl | $CH_3$ | 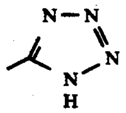 | |
| 317D | n-propyl | Cl | $C_2H_5$ | 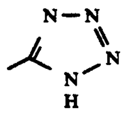 | |
| 317E | n-propyl | Cl | 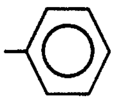 | 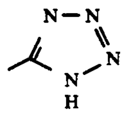 | |
| 317F | n-butyl | Cl | $C_2H_5$ | 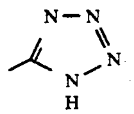 | |
| 317G | n-propyl | Cl | $CH_3$ | COOH | |
| 317H | n-propyl | Cl | $C_2H_5$ | COOH | |

TABLE 20-continued

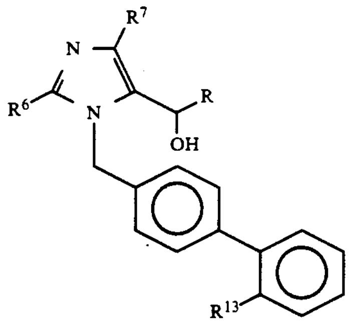

| Ex. No. | $R^6$ | $R^7$ | R | $R^{13}$ | MP(°C.) |
|---|---|---|---|---|---|
| 317I | n-propyl | Cl | 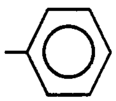 | COOH | |

EXAMPLE 318

Part A: Preparation of 2-butyl-4-chloro-1-[(2'-(N,N-diphenylcarbamoyloxycarbonyl)biphenyl-4-yl)methyl]-5-hydroxymethyl imidazole A solution of 3.99 g of 2-butyl-1-[(2'-carboxybiphenyl-4-yl)methyl]-4-chloro-5-hydroxymethylimidazole (Example 94) and 10 mL of 1.00 N aqueous sodium hydroxide in 60 mL of methanol was added dropwise over 0.25 hour to a solution of 3.73 g of N-(N,N-diphenylcarbomoyl)pyridinium chloride in 30 mL of methanol at 25° C. The resulting mixture was stirred at 25° C. for 0.75 hour and then was diluted with ethyl acetate. This organic solution was washed with water and brine, dried over anhydrous sodium sulfate, filtered, and concentrated to afford 6.55 g of crude 2-butyl-4-chloro-1-[(2'-(N,N-diphenylcarbamoyloxycarbonyl)-biphenyl-4-yl)methyl]-5-hydroxymethylimidazole which was used in the following step without further purification.

Part B: Preparation of 1-[(2'-(Benzenesulfonamidocarbonyl)biphenyl-4-yl)methyl]-2-butyl-4-chloro-5-hydroxymethylimidazole A solution of 9.53 g of benzenesulfonamide in 25 mL of dimethylformamide was added dropwise over 0.25 hour to a suspension of 1.32 g of oil-free sodium hydride in 30 mL of dimethylformamide at 25° C. The resulting mixture was stirred at 25° C. for 1.0 hour. To the mixture then was added a solution of 6.55 g of 2-butyl-4-chloro-1-[(2'-(N,N-diphenylcarbamoyloxycarbonyl)-biphenyl-4-yl)methyl]-5-hydroxymethylimidazole in 15 mL of dimethylformamide. Finally the reaction mixture was stirred at 25° C. for 16 hours. At this point the mixture was diluted with water, acidified to pH 5 employing 10% hydrochloric acid, and extracted with ethyl acetate. The combined organic phases were washed with water and brine, dried over anhydrous sodium sulfate, filtered, and concentrated. Column chromatography (elution: 10% methanol/chloroform) furnished 1.54 g of 1-[(2'-(benzenesulfomamidocarbonyl)biphenyl-4-yl)methyl]-2-butyl-4-chloro-5-hydroxymethylimidazole (mp 172°-174° C.).

NMR (200 MHz, DMSO-$d_6$): δ 12.55 (br s, 1H), 7.82 (d, 2H), 7.62–7.33 (m, 7H), 7.03 (d, 2H), 6.77 (d, 2H), 5.30 (br t, 1H), 5.23 (s, 2H), 4.38 g (d, 2H), 2.50 (t, 2H), 1.51 (quint., 2H), 1.27 (sext., 2H), 0.82 (t, 3H).

The following compound has also been prepared by the procedures of Example 318, Parts A–B.

EXAMPLE 319

| | MP(°C.) |
|---|---|
| 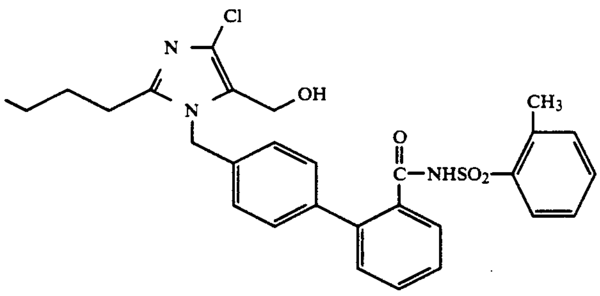 | 152–154 |

EXAMPLE 320

Part A: Preparation of 4(5)-Methyl-2-propylimidazole

To a well-stirred mixture of 72.0 ml of butyraldehyde, and 240 g of copper(II)acetate monohydrate in 1000 mL of 25% aqueous ammonia at 0° C. was added 32.8 mL of acetol dropwise over 0.25 hour. The mixture then was heated to 80°–100° C. for 0.5 hour. After allowing the reaction mixture to cool, the resulting gray-green solid was recovered by filtration.

Into a suspension of this solid in water at 80° C. was bubbled hydrogen sulfide gas for 0.5 hour. The mixture then was filtered, while still hot, to remove solid copper(I) sulfide. After cooling to 25° C. the mixture was extracted with methylene chloride. The combined organic phases were then washed with brine, dried over anhydrous sodium sulfate, filtered, and concentrated to provide 26.4 g of 4(5)-methyl-2-propylimidazole as a viscous orange oil.

NMR (200 MHz, $CDCl_3$): δ 10.15 (br s, 1H), 6.61 (s, 1H), 2.64 (t, 2H), 2.20 (s, 3H), 1.72 (sext., 2H), 0.92 (t, 3H).

Part B: Preparation of 4(5)-Hydroxymethyl-5(4)-methyl-2-propylimidazole

A solution of 21.0 g of 4(5)-methyl-2-propylimidazole, 14.0 g of 37% aqueous formaldehyde 76.0 g of concentrated hydrochloric acid, and 100 mL of water was refluxed for 62 hours. After cooling the mixture was diluted with water. The resulting aqueous solution was adjusted to pH 10 employing 10% aqueous sodium hydroxide and then was extracted with 4:1 chloroform/isopropanol. The combined organic phases were washed with brine, dried over anhydrous sodium sulfate, filtered, and concentrated. Column chromatography (elution: 10% methanol/chloroform with 0.2% conc. ammonia) followed by recrystallization from ethyl acetate furnished 13.9 g of 4(5)-hydroxymethyl-5(4)-methyl-2-propylimidazole (mp 138.5°–139.5° C.).

NMR (200 MHz, DMSO-$d_6$): δ 11.30 (br s, 1H), 4.68 (br s, 1H), 4.26 (s, 2H), 2.46 (t, 2H), 2.06 (s, 3H), 1.60 (sext., 2H), 0.88 (t, 3H).

Part C: Preparation of 4(5)-Methyl-2-propylimidazole-5(4)-carboxaldehyde

To solution of 12.1 g of 4(5)-hydroxymethyl-5(4)-methyl-2-propylimidazole in 200 mL of acetic acid at 25° C. was added 170 mL of 1.0N cericammonium nitrate in water dropwise over 1.0 hour. The resulting solution was stirred for 1.0 hour at 25° C. and then was poured into water. This solution was adjusted to pH 4 employing 10% aqueous sodium hydroxide and then was extracted with chloroform. The combined organic phases were washed with water and brine, dried over anhydrous sodium sulfate, filtered, and concentrated. The crude product was recrystallized to afford 9.66 g of 4(5)-methyl-2-propylimidazole-5(4)-carboxaldehyde (mp 128°–128.5° C.).

NMR (200 MHz, DMSO-$d_6$): δ 12.49 (br s, 1H), 9.69 (s, 1H), 2.53 (t, 2H), 2.38 (s, 3H), 1.65 (sext., 2H), 0.87 (t, 3H).

Part D: Preparation of 1-[(2'-Tert-butoxycarbonylbiphenyl-4-yl)methyl]-4-methyl-2-propylimidazole-2-carboxaldehyde A solution of 3.60 g of 4(5)-methyl-2-propylimidazole-5(4)-carboxaldehyde, 8.64 g of tert-butyl 4'-bromomethylbiphenyl-2-carboxylate, 6.54 g of anhydrous potassium carbonate, and 60 mL of dimethylformamide was stirred at 25° C. for 18 hours. The reaction mixture was filtered, and the filtrate was diluted with water and then extracted with ethyl acetate. The combined organic sulfate, filtered, and concentrated. Column chromatography (elution: ethyl acetate/benzene) provided 6.31 g of 1-[(2'-tertbutoxycarbonylbiphenyl-4-yl)methyl]-4-methyl-2-propylimidazole-5-carboxaldehyde.

NMR (200 MHz, $CDCl_3$): δ 9.77 (s, 1H), 7.78 (d, 1H), 7.51–7.35 (m, 2H), 7.27 (m, 3H), 7.05 (d, 2H), 5.59 (s, 2H), 2.64 (t, 2H), 2.50 (s, 3H), 1.78 (sext., 2H), 1.20 (s, 9H), 0.97 (t, 3H).

Part E: Preparation of 1-[(2'-Carboxybiphenyl-4-yl)methyl]-4-methyl-2-propylimidazole-5-carboxaldehyde This compound was prepared according to the procedure described in Example 92, Part C. From 4.20 g of 1-[(2'-tert-butoxycarbonylbiphenyl-4-yl)methyl]-4-methyl-2-propyl-imidazole-5-carboxaldehyde was obtained 0.92 g of 1-[(2'-carboxybiphenyl-4-yl)methyl]-4-methyl-2-propyl imidazole-5-carboxaldehyde (mp 243°–245°).

NMR (200 MHz, DMSO-$d_6$): δ 12.77 (br s, 1H), 9.75 (s, 1H), 7.71 (d, 2H), 7.55 (t, 1H), 7.43 (t, 1H), 7.36–7.27

(m, 3H), 7.06 (d, 2H), 5.59 (s, 2H), 2.60 (t, 2H), 2.41 (s, 3H), 1.62 (sext., 2H), 0.86 (t, 3H).

EXAMPLE 321

Part A: Preparation of 1-[(2'-Tert-butoxycarbonylbiphenyl-4-yl)methyl]-5-hydroxymethyl-4-methyl-2-propylimidazole To a solution of 3.43 g of 1-[(2'-tert-butoxycarbonylbiphenyl-4-yl)methyl]-4-methyl-2-propylimidazole-5-carboxaldehyde (from Example 320, Part D) in 22 mL of methanol and 22 mL of tetrahydrofuran at 25° C. was added in several portions, 3.09 g of sodium borohydride. The reaction mixture was stirred at 25° C. for 1.5 hours and then was poured into dilute aqueous sodium hydroxide solution. After stirring for 0.2 hour at 25° C. this solution was extracted with chloroform. The combined organic phases were washed with water and brine, dried over anhydrous sodium sulfate, filtered, and concentrated. Column chromatography (elution: ethyl acetate/benzene) furnished 3.32 g of 1-[(2'-tert-butoxycarbonylbiphenyl-4-yl)methyl]-5-hydroxymethyl-4-methyl-2-propylimidazole.

NMR (200 MHz, $CDCl_3$): δ 7.76 (d, 1H), 7.42 (m, 2H), 7.28–7.24 (m, 3H), 6.96 (d, 2H), 5.24 (s, 2H), 4.47 (s, 2H), 2.56 (t, 2H), 2.21 (s, 3H), 1.71 (sext., 2H), 1.25 (s, 9H), 0.95 (t, 3H).

Part B: Preparation of 1-[(2'-Carboxybiphenyl-4-yl)methyl]-5-hydroxymethyl-4-methyl-2-propylimidazole.hydrochloride A solution of 3.32 g of 1-[(2'-tertbutoxycarbonylbiphenyl-4-yl)methyl]-5-hydroxymethyl-4-methyl-2-propylimidazole in 100 mL of 10% aqueous hydrochloride acid was stirred at 25° C. for 16 hours. The solvent and excess hydrochloric acid then were removed under vacuum to provide 2.22 g of 1-[(2'-carboxybiphenyl-4-yl)methyl]-5-hydroxymethyl-4-methyl-2-propylimidazole.hydrochloride (mp 208°–210° C. (dec.)).

NMR (200 MHz, DMSO-$d_6$): δ 12.92 (br s, 1H), 7.74 (d, 1H), 7.58 (t, 1H), 7.47 (t, 1H), 7.34 (m, 3H), 7.26 (d, 2H), 5.67 (br s, 1H), 5.53 (s, 2H), 4.42 (s, 2H), 2.86 (t, 2H), 2.30 (s, 3H), 1.54 (sext., 2H), 0.83 (t, 3H).

The compounds of Table 21 have been or could be prepared by the procedures of Examples 320–321.

TABLE 21

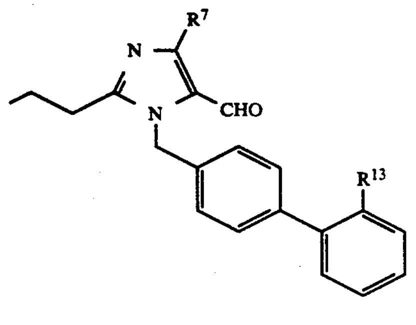

| Ex. No. | $R^7$ | $R^{13}$ | m.p. °C. |
|---|---|---|---|
| 322 | $C_6H_5$ | $CO_2H$ | 224–225.5° C. |
| 323 | $C(CH_3)_3$ | $CO_2H$ | |
| 324 | $CH_2C_6H_5$ | $CO_2H$ | |

TABLE 21-continued

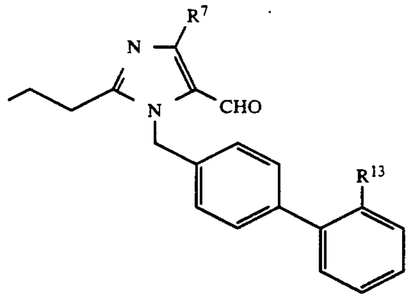

| Ex. No. | $R^7$ | $R^{13}$ | m.p. °C. |
|---|---|---|---|
| 324A | $C_6H_5$ | 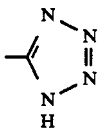 | (amorphous solid)[a] |

[a]NMR(200MHz, DMSO-$d_6$): δ9.77(s, 1H), 7.79–7.47(m, 9H), 7.08(s, 4H), 5.67(s, 2H), 2.65(t, 2H), 1.63(sext., 2H), 0.88(t, 3H).

EXAMPLES 325 AND 326

Part A: Preparation of 2-n-Butyl-4-chloro-1-(4-nitrophenyl)imidazole-5-carboxaldehyde 2-n-Butyl-4-chloroimidazole-5-carboxaldehyde (10.00 g, 53.6 mmol, 1 eq.) was dissolved in a freshly prepared solution of sodium methoxide (1.23 g Na, 53.6 mmol, 1 eq.) in methanol (175 mL). The methanol was removed in vacuo and replaced with DMF (100 mL). 4-Fluoro-1-nitrobenzene (11.37 mL, 107.0 mmol, 2 eq.) was then added. The mixture was heated at 100° C. for 36 h. Two more equivalents of 4-fluoro-1-nitrobenzene were then added and the mixture heated at 100° C. for an additional 48 hours. The DMF was removed in vacuo and the residue partitioned between ethyl acetate and water. The aqueous phase was extracted twice more with ethyl acetate, the organic layers combined, dried ($MgSO_4$) and the solvent removed in vacuo. Flash chromatography of the residue over silica gel in 9:1 toluene/ethyl acetate yielded 4.92 g (30%) of an amber oil. NMR ($CDCl_3$): δ 9.74 (s, 1H); 8.42 (d, 2H, J=9 Hz); 7.46 (d, 2H, J=9 Hz); 2.51 (t, 2H, J=7 Hz); 1.67 (t of t, 2H, J=7,7 Hz); 1.30 (t of q, 2H, J=7,7 Hz); 0.84 (t, 3H, J=7 Hz). Anal. calcd. for $C_{14}H_{14}ClN_3O_3$: C, 54.64; H, 4.59; Cl, 11.52, N, 13.65. Found: C, 54.91; H, 4.67; Cl, 11.20; N, 13.62.

Part B: Preparation of 1-(4-Aminophenyl)-2-n-butyl-4-chloro-5-(hydroxymethyl)imidazole and 1-(4-aminophenyl)-2-n-butyl-5-(hydroxymethyl-)imidazole Sodium borohydride (1.70 g, 44.4 mmol, 3 eq.) in water (74 mL) was added to a suspension of 10% Pd on C (0.5 g) in methanol (74 mL). Nitrogen was then slowly bubbled through the mixture while a solution of 2-n-butyl-4-chloro-1-(4-nitrophenyl)imidazole-5-carboxaldehyde (4.56 g, 14.8 mmol, 1 eq.) in methanol (74 mL) was added dropwise. The introduction of $N_2$ was stopped and the mixture allowed to stir for 2.5 h. The mixture was filtered through Celite® and water (500 mL) added to the filtrate. The pH was adjusted to 1-2 with conc. HCl and then to 7 with 6N NaOH. The product is extracted with ethyl acetate (3×), the organic layers combined, dried ($MgSO_4$) and the solvent removed in vacuo to yield 3.63 g of a yellow glass. NMR shows a 2:1 ratio of chloro/des-chloro product. The material was suitable for further transformation. NMR (chloro-product) (DMSO-$d_6$): δ 7.03 (d, 2H, J=9 Hz); 6.68 (d, 2H, J=9 Hz); 5.50 (bm 2H); 4.68 (bm, 1H); 4.15 (bs, 2H); 2.49 (t, 2H, J=7 Hz); 1.50 (t of t, 2H, J=7,7 Hz); 1.24 (t of q, 2H, J=7,7 Hz); 0.80 (t, 2H, J=7 Hz). NMR (des-chloro product) shows imidazole ring H at δ 6.82 and 6.98 (d, 2H, J=9 Hz). All other peaks match those of the chloro-product. MS: $(M+H)^+$ detected at 280 and 246.

Part C: Preparation of 2-n-Butyl-4-chloro-5-hydroxymethyl-1-[4-((N-trifluoromethanesulfonyl)anthranilamido)phenyl-]imidazole and 2-n-butyl-5-hydroxymethyl-1-[4-((N-trifluoromethanesulfonyl)anthranilamido)phenyl]imidazole The product in Part B was reacted with N-(trifluoromethanesulfonyl)anthranoyl chloride by the procedure described in Example 30. Flash chromatography over silica gel in 100% ethyl acetate to 1:1 ethyl acetate/isopropanol yielded the above titled products as white amorphous solids. NMR (chloro-product) (DMSO-$d_6$): δ 12.50 (bs, 1H); 8.30 (m, 3H); 8.00–7.54 (m, 5H); 4.62 (s, 2H); 2.89 (t, 2H, J=7 Hz) 1.93 (t of t, 2H, J=7,7 Hz); 1.64 (t of q, 2H, J=7,7 Hz); 1.20 (t, 3H, J=7 Hz).

NMR (des-chloro-product) (DMSO-$d_6$): δ 14.34 (bs, 1H); 13.67 (bs, 1H); 8.10 (d, 1H, J=9 Hz); 7.90 (d, 2H, J=9 Hz); 7.73 (s, 1H); 7.60 (d, 2H, J=9 Hz); 7.55 (d, 1H, J=9 Hz), 7.37 (t, 1H, J=9 Hz); 7.00 (t, 1H, J=9 Hz); 4.28 (s, 2H); 2.76 (t, 2H, J=7 Hz); 1.54 (t of t, 2H, J=7,7 Hz); 1.23 (t of q, 2H, J=7,7 Hz); 0.77 (t, 3H, J=7 Hz).

EXAMPLE 327

Preparation of 2-n-Butyl-4-chloro-1-[(2'-(1H-tetrazol-5-yl)biphenyl-4-yl)methyl]imidazole-5-carboxaldehyde, benzenesulfonylhydrazone 2-n-Butyl-4-chloro-1-[(2'-(1H-Tetrazol-5-yl)biphenyl-4-yl)methyl]imidazole-5-carboxaldehyde (Example 132) (1.00 g, 2.4 mmol, 1 eq.) was dissolved in 1.000N NaOH (4.76 mL, 4.8 mmol, 1 eq.) and water (10 mL). Benzenesulfonylhydrazide (0.41 g, 2.4 mmol, 1 eq.) was added and the solution was stirred overnight at 25° C. The solution was acidified to pH=2.5 with conc. HCl. The resultant precipitate was filtered, dried and recrystallized from ethyl acetate yielding 0.85 g of a solid; m.p. 227.5–230.0 (dec.). NMR (DMSO-$d_6$): δ 16.31 (bm, 1H); 11.48 (bm, 1H); 7.96 (s, 1H); 7.78–7.39 (m, 9H); 7.04 (d, 2H, J=7 Hz); 6.87 (d, 2H, J=7 Hz); 5.52 (s, 2H); 2.51 (t, 2H, J=7 Hz); 1.45 (t of t, 2H, J=7,7 Hz); 1.24 (t of q, 2H, J=7,7 Hz); 0.79 (t, 3H, J=7 Hz). Anal. calcd. for $C_{28}H_{27}ClN_8O_2S$: C, 58.48; H, 4.73; Cl, 6.16. Found: C, 58.67; H, 4.87; Cl, 6.19.

The compounds of Table 22 can be made by the procedure described in Example 327 from the appropriate aldehyde precursor:

TABLE 22

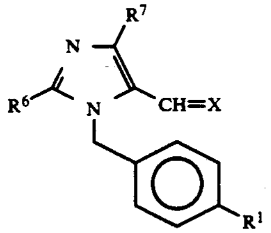

| Ex. No. | $R^6$ | $R^7$ | X | $R^1$ | MP(°C.) |
|---|---|---|---|---|---|
| 327A | n-butyl | Cl | 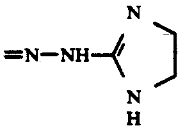 | 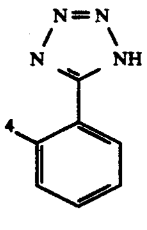 | 224.0–227.0 |
| 327B | n-propyl | $CF_3$ | $=N-\underset{H}{N}-SO_2-Ph$ | 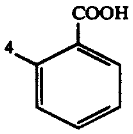 | |
| 327C | n-propyl | $C_2F_5$ | 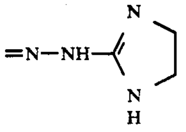 | 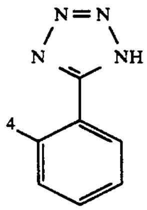 | |

TABLE 22-continued

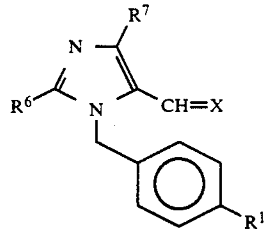

| Ex. No. | $R^6$ | $R^7$ | X | $R^1$ | MP(°C.) |
|---|---|---|---|---|---|
| 327D | n-butyl | Cl | 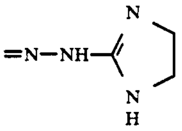 | 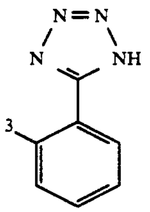 | >275[a] |

[a]NMR(DMSO-$d_6$): δ7.95(s, 1H); 7.73(bm, 2H); 7.68(d, 1H, J=9Hz); 7.56(t, 1H, J=9Hz); 7.49(t, 1H, J=9Hz); 7.37(d, 1H, J=9Hz); 7.25(t, 1H, J=9Hz); 7.05(d, 1H, J=9Hz); 6.88(s, 1H); 6.83(d, 1H, J=9Hz); 5.53(s, 2H); 3.57(s, 2H); 2.65(t, 2H, J=Hz); 1.60(t of t, 2H, J=7,7Hz); 1.35(t of q, 2H=7,7Hz); 0.87(t, 3H, J=7Hz).

EXAMPLE 328

Part A: Preparation of 2-n-Propyl-4,5-dicarbomethoxyimidazole 2-n-Propylimidazole-4,5-dicarboxylic acid [prepared by the method of R. G. Fargher and F. L. Pyman (*J. Chem. Soc.* (1919) 115, 217); m.p. 257 (dec.) °C.] (17.14 g, 86.6 mmol, 1 eq.), methanol (400 mL) and acetyl chloride (38.1 mL, 534 mmol, 6 eq.) were cautiously mixed (acetyl chloride addition to methanol is very exothermic) and refluxed overnight. The solvent was removed in vacuo and water (100 mL) and 10N NaOH were added until pH=7. The aqueous mixture was extracted with ethyl acetate (3×), the organic layers combined, dried ($MgSO_4$) and the solvent removed in vacuo to yield 12.00 g of a white solid. Recrystallization from hexane/ethyl acetate yielded 11.41 g of a white solid; m.p. 162.0°-164.5° C. NMR ($CDCl_3$): δ 3.95 (s, 6H); 2.78 (t, 2H); 1.83 (t of t, 2H, J=7,7 Hz); 0.97 (t, 3H, J=7 Hz). Anal. Calcd. for $C_{10}H_{14}N_2O_4.(H_2O)_{0.25}$: C, 52.06; H, 6.28; N, 12.14. Found: C, 52.06; H, 6.17; N, 12.49.

Part B: Preparation of 1-[(2'-Carbomethoxybiphenyl-4-yl)methyl]-4,5-dicarbomethoxy-2-n-propylimidazole 2-n-Propyl-4,5-dicarbomethoxyimidazole (2.00 g, 8.8 mmol, 1 eq.) was alkylated with 4'-bromomethyl-2-carbomethoxybiphenyl (2.70 g, 8.8 mmol, 1 eq.) by the procedure described in Example 1, Part A. Obtained 3.87 g of a yellow oil which was suitable for further transformation. NMR (DMSO-$d_6$): δ 7.84-7.22 (m, 4H); 7.22 (d, 2H, J=9 Hz); 7.13 (d, 2H, J=9 Hz); 5.50 (s, 2H); 3.77 (s, 3H); 3.75 (s, 3H); 3.55 (s, 3H); 2.67 (t, 2H, J=7 Hz); 1.67 (t of q, 2H, J=7,7 Hz); 0.88 (t, 3H, J=7 Hz).

Part C: Preparation of 1-[(2'-Carboxybiphenyl-4-yl)methyl]imidazole-4,5-dicarboxylic acid The triester from Part B was saponified by the procedure described in Example 202, Part C. The resultant glass was crystallized from chloroform; m.p. 143 (shrink), 152.0 (dec.)°C. NMR (DMSO-$d_6$): δ 12.74 (m, 1H); 7.72 (d, 1H, J=9 Hz); 7.56 (t, 1H, J=9 Hz); 7.46 (t, 1H, J=9 Hz); 7.36 (d, 1H, J=9 Hz); 7.30 (d, 2H, J=9 Hz); 7.20 (d, 2H, J=9 Hz); 5.99 (s, 2H); 2.89 (t, 2H, J=7 Hz); 1.48 (t of q, 2H, J=7,7 Hz); 0.80 (t, 3H, J=7 Hz). Anal. calcd. for $C_{22}H_{20}N_2O_6.(H_2O)_{1.5}$: C, 60.68; H, 5.32; N, 6.43. Found: C, 60.99; H, 5.71; N, 6.50.

The compounds of Table 23 can be prepared by the method described in Example 328 and by other procedures familiar to one skilled in the art.

TABLE 23

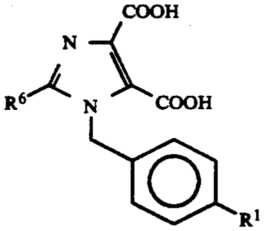

| Ex. No. | $R^6$ | $R^1$ | MP(°C.) |
|---|---|---|---|
| 329 | n-propyl | 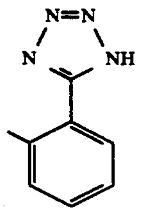 | 269.0-270.5 (dec.) (di Na+ salt) |
| 330 | n-butyl | 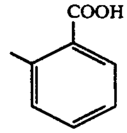 | |

TABLE 23-continued

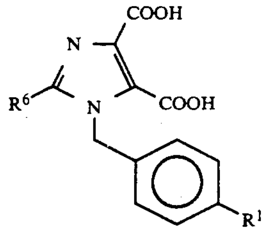

| Ex. No. | $R^6$ | $R^1$ | MP(°C.) |
|---|---|---|---|
| 331 | n-butyl | 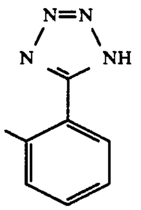 | |
| 332 | n-propyl | 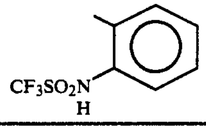 | |

EXAMPLE 333

Preparation of 4,5-Dicarbomethoxy-2-n-propyl-1-[(2'-(1H-tetrazol-5-yl)biphenyl-4-yl)methyl]imidazole 4,5-Dicarbomethoxy-2-n-propyl-1-[(2'-N-triphenylmethyl(1H-tetrazol-5-yl)biphenyl-4-yl)methyl-]imidazole (prepared by the procedure in Example 328, Part B, m.p. 124.0°-125.5° C. from 4'-bromomethyl-2-[N-triphenylmethyl(1H-tetrazol-5-yl)]biphenyl) (3.00 g) was mixed and refluxed in methanol (50 mL) for 4 h. The solvent was removed in vacuo and the residue immediately flash chromatographed over silica gel in 1:1 hexane/ethyl acetate to 100% ethanol. Obtained 1.30 g of a white glass which when stirred with ether yielded 0.92 g of a white solid; m.p. 100° C. (slow decomposition). NMR (DMSO-$d_6$): δ 7.68-7.43 (m, 4H); 7.08 (d, 2H, J=9 Hz); 6.96 (d, 2H, J=9 Hz); 5.41 (s, 2H); 3.80 (s, 3H); 3.74 (s, 3H); 2.63 (t, 2H, J=7 Hz); 1.62 (t of q, 2H, J=7,7 Hz); 0.88 (t, 3H, J=7 Hz). Anal. calcd. for $C_{24}H_{24}N_6O_4(H_2O)_{1.5}$: C, 59.13; H, 5.58; N, 17.23. Found: C, 59.27; H, 5.31; N, 17.11.

EXAMPLE 334

Part A: Preparation of 4-Carbomethoxy-5-hydroxymethyl-2-n-propyl-1-[(2'-N-triphenylmethyl(1H-tetrazol-5-yl)biphenyl-4-yl)methyl]imidazole 4,5-Dicarbomethoxy-2-n-propyl-1-[(2'-N-triphenylmethyl(1H-tetrazol-5-yl)biphenyl-4-yl)methyl-]imidazole (see Example 333) (10.00 g, 14.0 mmol, 1 eq.) was dissolved in THF (50 mL) and a THF solution of lithium tri-t-butoxy aluminumhydride (7.2 g, 28.0 mmol, 2 eq.) was added thereto. After 24 h, another 0.5 eq. of reducing agent was added. After another 24 h, the reaction was quenched by the addition of methanol (10 mL) and the solvent removed in vacuo. Chromatography in 1:1 hexane/ethyl acetate to 9:1 ethyl acetate/isopropanol yielded 2.16 g of a white glass. NMR shows a 6:1 mixture of regioisomers at the imidazole 4,5-positions. NMR ($CDCl_3$) (major isomer) δ 7.96 (m, 1H); 7.80 (m, 2H); 7.39-7.18 (m, 10H); 7.13 (d, 2H, J=9 Hz); 6.95 (m, 6H); 6.71 (d, 2H, J=9 Hz); 5.08 (s, 2H); 4.57 (d, 2H, J=6 Hz); 3.95 (s, 3H); 3.50 (m, 1H); 2.55 (t, 2H, J=7 Hz); 1.65 (t of q, 2H, J=7,7 Hz); 1.62 ($H_2O$); 0.89 (t, 3H, J=7 Hz). NMR minor isomer key peaks: δ 5.45 (s, 2H); 4.84 (m, 2H); 3.84 (m, 1H); 3.72 (s, 3H). Anal. calcd. for $C_{42}H_{38}N_6O_3.(H_2O)_{0.5}$: C, 73.77; H, 5.74; N, 12.29. Found: C, 73.54; H, 5.76; N, 12.59.

Part B: Preparation of 4-Carbomethoxy-5-hydroxymethyl-2-n-propyl-1-[(2'(1H-tetrazol-5-yl)biphenyl)methyl]imidazole The product from Part A was detritylated by the procedure in Example 333 yielding a glass. Crystallization was effected by stirring in ethyl acetate; m.p. 113-210 show decomposition. NMR (DMSO-$d_6$): δ 7.54 (m, 1H); 7.43-7.28 (m, 3H); 7.08 (d, 2H, J=9 Hz); 6.88 (d, 2H, J=9 Hz); 5.30 (s, 2H); 4.72 (s, 2H); 3.73 (s, 3H); 2.48 (t, 2H, J=7 Hz); 1.56 (t of q, 2H, J=7,7 Hz); 0.87 (t, 2H, J=7 Hz). IR(Nujol) 3206 (br); 1702; 761 $cm^{-1}$. Anal. calcd. for $C_{23}H_{24}N_6O_3.(H_2O)_{3.5}$: C, 55.75; H, 6.30; N, 16.96. Found: C, 55.83; H, 5.71; N, 16.86.

EXAMPLE 335

Preparation of 5-Hydroxymethyl-2-n-propyl-1-[(2'-(1H-tetrazol-5-yl)biphenyl)methyl]imidazole-4-carboxylic acid The product from Example 334, Part A was reacted with trifluoroacetic acid as described in Example 315, Part C. After the aqueous was acidified with HCl, the resulting gummy solids were stirred in the aqueous mixture to which ethyl acetate had been added. White crystalline product insoluble in both phases formed. This product was filtered and dried: m.p. 250 (dark), >275° C. NMR (DMSO-$d_6$): δ 7.73-7.47 (m, 4H); 7.07 (d, 2H, J=9 Hz); 6.98 (d, 2H, J=9 Hz); 5.30 (s, 2H); 4.72 (s, 2H); 3.5 ($H_2O$); 2.44 (t, 2H, J=7 Hz); 1.52 (t of q, 2H, J=7,7 Hz); 0.85 (t, 3H, J=7 Hz). Anal. calcd. for $C_{22}H_{22}N_6O_3.(H_2O)_{0.25}$: C, 62.47; H, 5.36; N, 19.87. Found: C, 62.63; H, 5.25; N, 19.51.

EXAMPLE 336

Part A: Preparation of 2-(4'-Methylbiphenyl-2-yl)-1-benzenesulfonylacrylonitrile 4'-Methylbiphenyl-2-carboxaldehyde (6.00 g, 30.6 g mmol, 1 eq.), benzenesulfonylacetonitrile (G. Beck, et al., *Chem. Ber.*, 106 (1973), p. 2758) (5.54 g, 30.6 mmol, 1 eq.), piperidine (0.5 mL), DMF (20 mL), and benzene (40 mL) were mixed and refluxed in a Dean-Stark apparatus overnight. The solvents were removed in vacuo and the residue chromatographed in 3:1 hexane/ethyl acetate on silica gel to yield 9.86 g of a light yellow solid; m.p. 91.0°-93.0° C. NMR (200 MHz, $CDCl_3$): δ 8.20 (s, 1H); 8.08 (d, 1H, J=9 Hz); 7.95 (d, 2H, J=9 Hz); 7.77-7.17 (m, 8H); 7.08 (d, 2H, J=9 Hz); 2.42 (s, 3H). Anal. calcd. for $C_{22}H_{17}NO_2S$: C, 73.51; H, 4.77; S, 8.92. Found: C, 73.25; H, 4.82; S, 8.82.

Part B: Preparation of 5-Cyano-4-(4'-methylbiphenyl-2-yl)-1,2,3-triazole 2-(4'-Methylbiphenyl-2-yl)-1-benzenesulfonylacrylonitrile (8.51 g, 23.7 mmol, 1 eq.), sodium azide (1.53 g, 23.7 mmol, 1 eq.) and DMF were mixed and stirred at 100° for 2.5 h. The reaction mixture was poured into water and extracted three times with ethyl acetate. The aqueous layer was saturated with sodium chloride and re-extracted twice more with ethyl acetate. The ethyl acetate layers were combined, dried ($MgSO_4$) and the solvent removed in vacuo. The residue was chromatographed in 100% ethyl acetate over silica gel to yield 6.21 g of a clear, colorless oil which subsequently crystallized. Recrystallization from acetonitrile yielded 3.59 g of white crystals; m.p. 170.5°-172.0° C. NMR (200 MHz, DMSO-$d_6$): δ 7.72-7.49 (m, 4H); 7.15 (d, 2H, J=9 Hz); 6.98 (d, 2H, J=9 Hz); 2.29 (s, 3H). Anal. calcd. for $C_{16}H_{12}N_4$: C, 73.83; H, 4.65; N, 21.52. Found: C, 73.84; H, 4.80; N, 21.24.

Part C: Preparation of
2-n-Butyl-4-chloro-1-[(2'-(5-cyano-1,2,3-triazol-4-yl)biphenyl-4-yl)methyl]-5-hydroxymethylimidazole The title compound was prepared from 5-cyano-4-(4'-methylbiphenyl-2-yl)-1,2,3-triazole using the procedures in Example 177, Parts D, E and F. NMR (200 MHz, $CDCl_3$): δ 7.66-7.44 (m, 4H); 7.15 (d, 2H, J=9 Hz); 6.95 (d, 2H, J=9 Hz); 5.25 (s, 2H); 4.50 (s, 2H); 2.55 (t, 2H, J=7 Hz); 1.55 (t of t, 2H, J=7,7 Hz); 1.27 (t of q, J=7,7 Hz); 0.80 (t, 3H, J=7 Hz). Titrated 260 mg with 1.000N NaoH. Theoretical=0.58 mL. Actual=0.58 mL. Anal. calcd. for $C_{24}H_{23}ClN_6O$: C, 64.50; H, 5.19. Found: C, 64.71; H, 5.52.

EXAMPLE 337

Preparation of
2-n-Butyl-5-chloro-1-[(2'-(5-cyano-1,2,3-triazol-4-yl)biphenyl-4-yl)methyl]-4-hydroxymethylimidazole The title compound is the other regioisomer isolated from the alkylation of 2-butyl-4-chloro-5-hydroxymethylimidazole in Example 336.

NMR (200 MHz, $CDCl_3$): δ 7.62-7.38 (m, 4H), 7.11 (d, 2H, J=9 Hz); 6.94 (d, 2H, J=9 Hz); 5.09 (s, 2H); 4.52 (s, 2H); 2.57 (t, 2H, J=7 Hz); 1.60 (t of t, 2H, J=7,7 Hz); 1.34 (t of q, 2H, J=7,7 Hz); 0.85 (t, 3H, J=7 Hz). Mass calcd. for $C_{24}H_{23}ClN_6O$: 446.1622. Found: 446.1601.

EXAMPLE 338

Preparation of
2-n-Butyl-4-chloro-1-[(2'-(5-carbomethoxy-1,2,3-triazol-4-yl)biphenyl-4-yl)methyl]-5-hydroxymethylimidazole The title compound was prepared from methyl benzenesulfonylacetate (G. Beck, et al., *Chem. Ber.* 106 (1973) p. 2758) by the procedures described in Example 336, Parts A, B, and C. NMR (200 MHz, $CDCl_3$): δ 7.57-7.37 (m, 4H); 7.00 (d, 2H, J=9 Hz); 6.83 (d, 2H, J=9 Hz); 5.15 (s, 2H); 4.45 (s, 2H); 3.65 (s, 3H); 2.50 (t, 2H, J=7 Hz); 1.55 (t of t, 2H, J=7,7 Hz); 1.26 (t of q, 2H, J=7,7 Hz); 0.80 (t, 3H, J=7 Hz). Titrated 320 mg with 1.000N NaOH. Theoretical=0.66 mL. Actual=0.60 mL. Anal. calcd. for $C_{25}H_{26}ClN_5O_3$: C, 62.56; H, 5.46. Found: C, 62.39; H, 5.75.

EXAMPLE 339

Preparation of
2-n-Butyl-5-chloro-1[(2'-(5-carbomethoxy-1,2,3-triazol-4-yl)biphenyl-4-yl)-methyl]-5-hydroxymethylimidazole The title compound is the other regioisomer isolated from the alkylation of 2-butyl-4-chloro-5-hydroxymethylimidazole in Example 338. NMR (200 MHz, $CDCl_3$+DMSO-$D_6$): δ 7.44 (d, 2H, J=6 Hz); 7.42 (d, 2H, J=6 Hz); 5.05 (s, 2H); 4.48 (s, 2H); 3.58 (s, 3H); 2.56 (t, 2H, J=7 Hz); 1.62 (t of t, 2H, J=7,7 Hz); 1.33 (t of q, J=7,7 Hz); 0.85 (t, 3H, J=7 Hz). Mass calcd. for $C_{25}H_{26}ClN_5O_3$: 479.1724. Found: 479.1724.

EXAMPLE 340

Part A: Preparation of
N-(2-Cyanoethyl)-4'-methylbiphenyl-2-carboxamide

4'-Methylbiphenyl-2-carboxylic acid (50.0 g, 0.24 mmol) was converted into the corresponding acid chloride as described in Example 89, Part B using thionyl chloride. This acid chloride was subsequently reacted with 3-aminopropionitrile fumarate (30.25 g, 0.24 mmol) under Schotten-Baumann reaction conditions described in Example 209, Part B to yield 53.50 g of white powder after recrystallization from methylcyclohexane/butylchloride; m.p. 102.0°-103.5° C.; NMR (200 MHz, $CDCl_3$): δ 7.68 (d, 1H, J=7 Hz); 7.56-7.19 (m, 7H); 5.65 (bm, 1H); 3.43 (d of t, 2H, J=7,7 Hz); 2.39 (t, 2H, J=7 Hz). Anal. calcd. for $C_{17}H_{16}N_2O$: C, 77.25; H, 6.10; N, 10.60. Found: C, 77.42; H, 6.40; N, 10.68.

Part B: Preparation of
$N^3$-(2-cyanoethyl)-4'-methylbiphenyl-2-yl-amidrazone

N-(2-cyanoethyl)-4'-methylbiphenyl-2-carboxamide (35.5 g, 126.7 mmol, 1 eq.) and phosphorous pentachloride (29.01 g, 139.3 mmol, 1.1 eq.) were mixed and gently heated under aspirator vacuum with a heat gun to maintain a slow but constant evolution of gas. After gas evolution had stopped (15-30 min.), the resultant oil was dissolved in 300 mL of dioxane and hydrazine was slowly added thereto (20.09 mL, 633.7 mmol, 5 eq.). The resultant biphasic mixture was stirred overnight at room temperature. The solvent was removed in vacuo and the residue partitioned between water and ethyl acetate. The layers were separated and the aqueous phase reextracted twice more with ethyl acetate. The organic layers were combined, dried ($MgSO_4$) and the solvent removed in vacuo to yield an orange glass. Slurrying this glass in 1:1 hexane/ethyl acetate yielded 16.14 g of a light pink solid; m.p. 146.5°-147.0° C.; NMR (200 MHz, $CDCl_3$): δ 7.60-7.16 (m, 10H); 6.15 (m, 1H); 2.98 (d of t, 2H, J=7,7 Hz); 2.40 (s, 3H); 1.93 (t, 2H, J=7 Hz). Anal. calcd. for $C_{17}H_{18}N_4.(N_2H_4)_{0.1}$: C, 72.52; H, 6.44; N, 20.89. Found: C, 72.50; H, 6.54; N, 21.13.

Part C: Preparation
3-(4'-Methylbiphenyl-2-yl)-5-trifluoromethyl-1,2,4-triazole $N^3$-(2-cyanoethyl)-4'-methylbiphenyl-2-yl amidrazone (14.91 g) was added to trifluoromethylacetic anhydride (600 mL) at 0° C. The mixture was allowed to warm to room temperature and stirred overnight. The solvent was removed in vacuo and the residue taken up in ethyl acetate and washed three times with 1N NaOH followed by once with brine. The organic layer was dried ($MgSO_4$) and the solvent removed in vacuo to yield 18.01 g of a pink solid. This solid without purification was dissolved in THF (300 mL) to which was added 1.000N NaOH (55.58 mL). The mixture was allowed to stir for 5 hours. The solvents were removed in vacuo and water was added. This mixture was then extracted three times with ethyl acetate. The organic layers were combined, dried ($MgSO_4$) and the solvent removed in vacuo to yield 15.80 g of an orange oil which subsequently crystallized. These solids were dissolved in 1N NaOH, the insoluble matter filtered, and the clear filtrate acidified to pH=1. The filtrate was extracted three times with ethyl acetate. The organic layers were combined, dried ($MgSO_4$) and the solvent removed in vacuo to yield 13.52 g of a clear, colorless oil which subsequently crystallized; m.p. 113.5°-115.5° C.; NMR (200 MHz, $CDCl_3$): δ 9.86 (m, 1H); 8.53 (m, 2H); 8.28 (m, 1H); 7.37 (m, 1H); 7.34 (d, 2H, J=9 Hz); 7.23 (d, 2H, J=9 Hz): 2.42 (s, 3H). Mass calcd. for $C_{16}H_{12}F_3N_3$: 303.0983. Found: 303.0972. Anal. calcd. for $C_{16}H_{12}F_3N_3$: C, 63.36; H, 3.99; N, 13.86. Found: C, 63.24; H, 4.17; N, 13.98.

Part D: Preparation of 2-n-Butyl-4-chloro-5-hydroxymethyl-1-[(2'-(5-trifluoromethyl-1,2,4-triazol-3-yl)biphenyl-4-yl)methyl]imidazole The title compound was prepared from 3-(4'-methylbiphenyl-2-yl)-5-trifluoromethyl-1,2,4-triazole using the procedures in Example 177, Parts D, E, and F.

NMR (200 MHz, $CDCl_3$): δ 12.67 (bs, 1H); 7.88 (d, 1H, J=9 Hz); 7.55 (t, 1H, J=9 Hz); 7.47 (t, 1H, J=9 Hz); 7.37 (d, 1H, J=9 Hz); 7.10 (d, 2H, J=9 Hz); 6.92 (d, 2H, J=9 Hz); 5.16 (s, 2H); 4.39 (s, 2H); 2.45 (t, 2H, J=7 Hz); 1.53 (t of t, 2H, J=7,7 Hz); 1.25 (t of q, 2H, J=7,7 Hz); 0.82 (t, 3H, J=7 Hz). Mass calcd. for $C_{24}H_{23}ClF_3N_5O$: 489.1543. Found: 489.1534.

EXAMPLE 341

Preparation of 2-n-Butyl-5-chloro-4-hydroxymethyl-1-[(2'-(5-trifluoromethyl-1,2,4-triazol-3-yl)biphenyl-4-yl)methyl]imidazole The title compound is the other regioisomer isolated from the alkylation of 2-butyl-4-chloro-5-hydroxymethylimidazole in Example 340. NMR (200 MHz, $CDCl_3$): δ 7.68 (d, 1H, J=9 Hz); 7.59-7.39 (m, 3H); 7.13 (d, 2H, J=9 Hz); 6.97 (d, 2H, J=9 Hz); 5.08 (s, 2H); 4.48 (s, 2H); 2.57 (t, 2H, J=7 Hz); 1.57 (t of t, 2H, J=7,7 Hz); 1.28 (t of q, 2H, J=7,7 Hz); 0.83 (t, 3H, J=7 Hz). Mass calcd. for $C_{24}H_{23}ClF_3N_5O$: 489.1543. Found: 489.1539.

EXAMPLE 342

Part A: Preparation of 2-n-Butyl-4,5-dicyano-1-[(2'-(N-triphenylmethyl(1H-tetrazol-5-yl))biphenyl-4-yl)methyl]imidazole Alkylation of 2-n-butyl-4,5-dicyanoimidazole (Example 75, Part A) with 2'-(N-triphenylmethyl(1H-tetrazol-5-yl))-4-(bromomethyl)biphenyl (isolated from Example 317, Part B) yielded the titled product as a light yellow solid; m.p. 152.5°-154.0° C. NMR ($CDCl_3$): δ 7.98 (m, 1H); 7.57-7.46 (m, 2H); 7.40-7.15 (m, 12H); 6.96-6.84 (m, 8H); 5.10 (2H); 2.57 (t, 2H, J=7 Hz); 1.63 (t of t, 2H, J=7,7 Hz); 1.30 (t of q, 2H, J=7,7 Hz); 0.85 (t, 3H, J=7 Hz). Anal. calcd. for $C_{42}H_{34}N_8$: C, 77.52; H, 5.27; N, 17.22. Found: C, 77.82; H, 5.28; N, 17.16.

Part B: Preparation of 2-n-Butyl-5-carboxamido-4-cyano-1-[(2'-(1H-tetrazol-5-yl)biphenyl-4-yl)methyl]imidazole The intermediate from Part A (4.80 g) was dissolved in THF (70 mL). Water (30 mL) followed by trifluoroacetic acid (30 mL) were then added and the mixture stirred for 1 h at 25° C. The pH was adjusted to 10 with 10 NaOH, and the organic solvent was removed in vacuo. The trityl alcohol was filtered and the aqueous filtrate was acidified to pH=4 with conc. HCl. The resultant precipitate was filtered and dried under high vacuum. Recrystallization from hexane/ethyl acetate yielded 1.18 g of a white powder; m.p. 192.5°-197.0° C. The compound titrates for one acidic functionality. NMR (DMSO-$d_6$): δ 8.30 (bs, 1H); 8.05 (bs, 1H); 7.76-7.50 (m, 4H); 7.11 (d, 2H, J=8 Hz); 7.01 (d, 2H, J=8 Hz); 5.48 (s, 2H); 2.57 (t, 2H, J=7 Hz); 1.48 (t of t, 2H, J=7,7 Hz); 1.22 (t of q, 2H, J=7,7 Hz); 0.77 (t, 3H, J=7 Hz). Anal. calcd. for $C_{23}H_{20}N_8(H_2O)_{1.5}$: C, 63.43; H, 5.32; N, 25.73. Found: C, 63.22; H, 5.25; N, 25.43.

EXAMPLE 343

Part A: Preparation of 2,6-Dicyano-4'-methylbiphenyl

4-Bromotoluene (10.44 mL, 84.9 mmol, 1.2 eq.) was converted to the Grignard reagent (Mg: 3.10 g, 127 mmol, 1.9 eq.) in THF (50 mL) and then added to a stirred mixture of freshly fused zinc (II) chloride (9.34 g, 68.5 mmol, 1 eq.) in THF (50 mL) at such a rate as to maintain the temperature at 18° C. In another flash, bis(triphenylphosphine)nickel (II)-chloride (1.10 g, 1.7 mmol, 0.025 eq.) and THF (5 mL) were mixed and cooled to 0° C. Diisobutylaluminum hydride (1M in THF, 3.37 mL, 3.4 mmol, 0.049 eq.) was added to the black mixture of Ni catalyst and THF. After warming to 20° C., 1-bromo-2,6-dicyanobenzene (T. D. Krizan, J. C. Martin *J. Org. Chem.*, (1982) 47, 2681) (0.95 g or 6.7% of the total amount to be coupled, 4.6 mmol, 0.067 eq.) in a minimum of THF was added to the Ni catalyst and stirred for 15 min. The Grignard solution was cooled to 6° C. and then to it the Ni catalyst mixture was transferred via cannula. The remaining 1-bromo-2,6-dicyanobenzene (13.16 g, 63.9 mmol, 0.933 eq.) in a minimum of THF was finally added to the Grignard+Ni catalyst mixture. After stirring overnight at 25° C., the mixture was diluted with ethyl acetate (400 mL) and washed with water (2×200 mL) and brine (1×200 mL). The ethyl acetate layer was dried ($MgSO_4$) and the solvent removed in vacuo to yield a yellow solid. Chromatography in 75:25 hexane/ethyl acetate to 100% ethyl acetate followed by recrystallization from hexane/ethyl acetate yielded 8.46 g of a white solid; m.p. 184.0°-186.0° C. NMR ($CDCl_3$): δ 7.98 (d, 2H, J=9 Hz); 7.58 (t, 1H, J=9 Hz); 7.45 (d, 2H, J=9 Hz); 7.37 (d, 2H, J=9 Hz); 2.44 (s, 3H). Anal. calcd. for $C_{15}H_{10}N_2$: C, 82.55; H, 4.62; N, 12.84. Found: C, 82.34; H, 4.78; N, 12.87.

Part B: Preparation of 2-n-Butyl-4-chloro-1-[(2'-cyano-6'-(1H-tetrazol-5-yl)biphenyl-4-yl)methyl]-5-hydroxymethylimidazole The product from Part A was converted to the above entitled compound by the procedure described in Example 317 to yield a glass. NMR (DMSO-$d_6$): δ 8.17 (d, 1H, J=9 Hz); 8.02 (d, 1H, J=9 Hz); 7.79 (t, 1H, J=9 Hz), 7.19 (d, 2H, J=9 Hz); 7.10 (d, 2H, J=9 Hz); 5.27 (s, 2H); 4.32 (s, 2H); 2.41 (t, 2H, J=9 Hz); 1.39 (t of t, 2H, J=7,7 Hz); 1.20 (t of q, 2H, J=7,7 Hz); 0.76 (t, 3H, J=7 Hz). Anal. calcd. for $C_{23}H_{22}ClN_7O.(H_2O)_{0.5}$: C, 60.46; H, 5.07; Cl, 7.75. Found: C, 60.51; H, 4.91; Cl, 7.78.

EXAMPLE 344

Part A: Preparation of 2-n-Butyl-4-chloro-1-[(2'-cyanobiphenyl-4-yl)methyl]imidazole-5-carboxaldehyde 2-n-Butyl-4-chloroimidazole-5-carboxaldehyde (6.34 g, 34.0 mmol, 1 eq.), 4-bromomethyl-2'-cyanobiphenyl (9.25 g, 34.0 mmol, 1 eq.), potassium carbonate (5.17 g, 37.4 mmol, 1.1 eq.) and DMF (100 mL) were mixed and stirred at 25° C. overnight. The solids were filtered and the filtrate evaporated. The residue was chromatographed over silica gel in 9:1 to 1:1 hexane/ethyl acetate and crystallized from methylcyclohexane/n-butyl chloride yielding 9.70 g of a solid; m.p. 96.0°-97.0° C. NMR ($CDCl_3$): δ 9.78 (s, 1H); 7.83-7.40 (m, 6H); 7.19 (d, 2H, J=9 Hz); 5.63 (s, 2H); 2.71 (t, 2H, J=7 Hz); 1.72 (t of t, 2H, J=7,7 Hz); 1.38 (t of q, 2H, J=7,7 Hz); 0.90 (t, 3H, J=7 Hz). Anal. calcd. for $C_{22}H_{20}ClN_3O$: C, 69.93; H, 5.34; N, 11.12. Found: C, 69.64; H, 5.37; N, 11.21.

Part B: Preparation of 2-n-Butyl-4-chloro-5-cyano-1-[(2'-cyanobiphenyl-4-yl)methyl]imidazole The aldehyde from Part A (8.37 g, 22.2 mmol, 1 eq.), hydroxylamine hydrochloride (1.67 g, 24.4 mmol, 1.1 eq.), pyridine (33.5 mL) and ethanol (33.5 mL) were mixed and stirred at room temperature. After 10 min., white precipitate began to form. After 24 h, the product was filtered, washed with ether and dried under high vacuum to yield 7.25 g of a white solid: m.p. 223.0°-224.5° C. NMR (DMSO-$d_6$): δ 11.38 (s, 1H); 8.03 (s, 1H); 7.97 (d, 1H, J=9 Hz); 7.80 (t, 1H, J=9 Hz); 7.69-7.52 (m, 4H); 7.18 (d, 2H, J=9 Hz); 5.67 (s, 2H); 2.62 (t, 2H, J=7 Hz); 1.52 (t of t, 2H, J=7,7 Hz); 1.27 (t of q, 2H, J=7,7 Hz); 0.80 (t, 3H, J=7 Hz). Anal. calcd. for $C_{22}H_{21}ClN_4O$: C, 67.26; H, 5.39; N, 14.26. Found: C, 67.21; H, 5.25; N, 14.29.

The oxime (5.13 g, 13.0 mmol, 1 eq.) was suspended in a solution of 1,2-dichloroethane (51.3 mL) and triethylamine (3.90 mL, 27.7 mmol, 2.1 eq.). The mixture was cooled to 0° C. and triflic anhydride (2.15 mL, 13.0 mmol, 1 eq.) was added. After 1.5 h, 0.2 mL of triethylamine followed by 0.22 mL of triflic anhydride were added at 25° C. After 5 hours, added ethyl acetate (200 mL) and washed with water 3×100 mL). The organic layer was dried ($MgSO_4$), the solvent removed in vacuo, and the residue chromatographed in 9:1 toluene/ethyl acetate yielding 3.56 g of a light tan solid: m.p. 96.0°-97.5° C. NMR ($CDCl_3$): δ 7.82 (d, 1H, J=9 Hz); 7.76-7.45 (m, 5H); 7.33-7.13 (m, 2H); 5.25 (s, 2H); 2.72 (t, 2H, J=7 Hz); 1.75 (t of t, 2H, J=7,7 Hz); 1.39 (t of q, 2H, J=7,7 Hz); 0.94 (t, 3H, J=7 Hz). Anal. calcd. for $C_{22}H_{19}ClN_4$: C, 70.49; H, 5.11; Cl, 9.46. Found: C, 70.57; H, 5.10; Cl, 9.30.

Part C: 2-n-Butyl-4-chloro-5-(1H-tetrazol-5-yl)-1-[(2'-(1H-tetrazol-5-yl)biphenyl-4-yl)methyl]imidazole The bisnitrile from Part B was converted to the above titled product by the method described in Example 316, Parts A, B and Example 342, Part B using the appropriate reagent stoichiometries to yield a light yellow amorphous solid: titration of compound with 1.000N NaOH showed the presence of exactly two acidic functionalities. NMR (DMSO-$d_6$): δ 7.75-7.47 (m, 4H); 7.06 (d, 2H, J=9 Hz); 6.98 (d, 2H, J=9 Hz); 5.55 (s, 2H); 2.65 (t, 2H, J=7 Hz); 1.53 (t of t, 2H, J=7,7 Hz); 1.30 (t of q, 2H, J=7,7 Hz); 0.82 (t, 3H, J=7 Hz). Anal. calcd. for $C_{22}H_{21}ClN_{10}\cdot(H_2O)_{0.5}$: C, 56.22; H, 4.72; Cl, 7.54. Found: C, 56.46; H, 4.61; Cl, 7.37.

EXAMPLE 345

Preparation of 2-n-Butyl-5-(4-carboxy-1,2,3-triazol-5-yl)-4-chloro-1-[(2'-(1H-tetrazol-5-yl)biphenyl-4-yl)methyl]imidazole The titled compound was prepared from 2-n-butyl-4-chloro-1-[(2'-(N-triphenylmethyl-1H-tetrazol-5-yl)biphenyl-4-yl)methyl]imidazole-5-carboxaldehyde using the procedures described in Example 338 and deprotecting both the methyl ester and trityl groups using trifluoroacetic acid by the procedure described in Example 342, Part B: white amorphous solid. NMR (DMSO-$d_6$): δ 16.5-13.0 (bm, 2H); 7.76-7.46 (m, 4H); 7.00 (d, 2H, J=9 Hz); 6.94 (d, 2H, J=9 Hz); 5.13 (s, 2H); 2.07 (t, 2H, J=7 Hz); 1.50 (t of t, 2H, J=7,7 Hz); 1.28 (t of q, 2H, J=7,7 Hz); 0.82 (t, 3H, J=7 Hz). Mass calcd. for $C_{24}H_{22}ClN_9O_2$: 503.1585. Found: 503.1594.

EXAMPLE 346

Part A: Preparation of 2-n-Butyl-1-[(2'-carbomethoxybiphenyl-4-yl)methyl]-4-chloro-5-[1-(2-methoxyphenyl)piperazin-4-yl)methyl-]imidazole 2-n-butyl-1-[(2'-carbomethoxybiphenyl-4-yl)methyl]-4-chloro-5-(chloromethyl)imidazole hydrochloride (1.56 g, 3.3 mmol, 1 eq.), 1-(2-methoxyphenyl)piperazine (0.64 g, 3.3 mmol, 1 eq.) and acetonitrile (100 mL) were mixed and refluxed for 48 h. The solvent was removed in vacuo and the residue chromatographed over silica gel in ethanol to 4:1 chloroform/methanol, yielding 960 mg of a yellow oil. NMR showed the presence of both 1-(2-methoxyphenyl)piperazine and product. The above isolated product was suitable for further transformation; MS detects $(M+H)^+=601$.

Part B: Preparation of 2-n-Butyl-1-[(2'-carboxybiphenyl-4-yl)methyl]-4-chloro-5-[(1-(2-methoxyphenyl)piperazine-4-yl)methyl-]imidazole A mixture of the compound in Part A (960 mg), 1.000N NaOH (8.3 mL), methanol (15 mL) and water (5 mL) was refluxed under nitrogen overnight. The organic solvents were removed in vacuo and the pH adjusted to 6 with conc. HCl. The resultant precipitate was filtered, washed with water and dried under a high vacuum yielding 244 mg of a light yellow amorphous powder. Titration of 200 mg with 1.000N NaOH required 0.36 mL. Theoretical: 0.35 mL. NMR (DMSO-$d_6$): δ 7.53-7.17 (m, 7H); 6.80-6.60 (m, 5H); 4.98 (s, 2H); 3.78 (s, 2H); 3.68 (s, 3H); 3.02 (s, 8H); 2.32 (t, 2H, J=7 Hz); 1.38 (t of t, 2H, J=7,7 Hz); 1.20 (t of q, 2H, J=7,7 Hz); 0.75 (t, 3H, J=7 Hz). Mass calcd. for $C_{33}H_{37}ClN_4O_3$: 572.2554. Found: 572.2554.

EXAMPLE 347

Part A: Preparation of Methyl 2-n-butyl-4-chloroimidazole-5-carboxylate

The titled compound was prepared by the procedure described in Example 126 from 2-n-butyl-4-chloroimidazole-5-carboxaldehyde: m.p. 92.5-93.5 (methylcyclohexane). NMR (DMSO-$d_6$): δ 13.05 (bm, 1H); 3.80 (s, 3H); 2.60 (t, 2H, J=7 Hz); 1.59 (t of t, 2H, J=7,7 Hz); 1.26 (t of q, 2H, J=7,7 Hz); 0.87 (t, 3H, J=7 Hz). Anal. calcd. for $C_9H_{13}ClN_2O_2$: C, 49.89; H, 6.05; Cl, 16.36; N, 12.93. Found: C, 49.93; H, 6.02; Cl, 16.18; N, 12.96.

Part B: Preparation of Methyl 2-n-butyl-4-chloro-1-[(2'-(N-triphenylmethyl (1H-tetrazol-5-yl))biphenyl-4-yl)methyl]imidazole-5-carboxylate and its 4-carbomethoxy regioisomer Methyl 2-n-butyl-4-chloroimidazole-5-carboxylate (10.00 g, 46.2 mmol, 1 eq.), 2'-(N-triphenyl methyl-1H-tetrazol-5-yl)-4-bromomethylbiphenyl (25.7 g, 46.2 mmol, 1 eq.), tetraethylammonium bromide (970 mg, 4.62 mmol, 0.1 eq.), 10.0N NaOH (9.2 mL, 92.3 mmol, 2 eq.), water (40 mL) and methylene chloride (200 mL) were mixed and stirred overnight at 25°. Water was then added and the layers were separated. The organic layer was washed with additional water (2×), dried ($MgSO_4$) and the solvent removed in vacuo. Chromatography in 9:1 hexane/ethyl acetate to 1:1 hexane/ethyl acetate yielded the 5-carbomethoxy regioisomer which eluted first followed by the slower 4-carbomethoxy regioisomer. 5-Carbomethoxy Regioisomer: m.p. 177.5°-178.0 (dec.)°C. NMR ($CDCL_3$): δ 7.91 (m, 1H); 7.53-7.23 (m, 18H); 7.10 (d, 1H), J=9 Hz); 6.95 (d, 2H, J=9 Hz); 6.77 (d, 1H, J=9 Hz); 5.47 (s, 2H); 3.76 (s, 3H); 2.53 (t, 2H, J=7 Hz); 1.67 (t of t, 2H, J=7,7 Hz); 1.30 (t of q, 2H, J=7,7 Hz); 0.89 (t, 3H, J=7 Hz). Anal. calcd. for $C_{42}H_{37}ClN_6O_2$: C, 72.77; H, 5.38; Cl, 5.11; N, 12.12. Found: C, 72.48; H, 5.28; Cl, 5.37; N, 11.82.

4-Carbomethoxy Regioisomer: amorphous glass. NMR ($CDCl_3$): δ 7.95 (m, 1H); 7.53 (m, 2H); 7.40-7.16 (m, 9H); 7.12 (d, 2H, J=9 Hz); 6.97-6.83 (m, 7H); 6.77 (d, 2H, J=9 Hz); 5.02 (s, 2H); 3.94 (s, 3H); 2.52 (t, 2H, J=7 Hz); 1.60 (t of t, 2H, J=7,7 Hz); 1.26 (t of q, 2H, J=7,7 Hz); 0.83 (t, 3H, J=7 Hz).

Part C: Preparation of 2-n-Butyl-4-chloro-5-[4-(2-methoxyphenyl)piperazin-1-ylcarbonyl]-1-[(2'-(N-triphenylmethyl-1-H-tetrazol-5-yl)biphenyl-4-yl)methyl]imidazole n-Butyllithium (2.5M, 2.56 mL, 6.3 mmol, 1.1 eq.) was slowly added to a solution of 1-(2-methoxyphenyl)-piperazine (1.12 g, 5.8 mmol, 1 eq.) in THF (30 mL) at 0° C. The solution was allowed to stir for 15 min. at 0° C. Afterwards, a THF solution (30 mL) of the ester from Part B (4.00 g, 5.8 mmol, 1 eq.) was slowly added maintaining the temperature at 0° C. The solution was allowed to warm to 25° C. After 24 h, the solvent was removed in vacuo and the residue chromatographed in 1:1 hexane/ethyl acetate to 100% ethyl acetate yielding 2.24 g of a yellow glass which was suitable for further transformation. NMR (DMSO-$d_6$): δ 7.77 (d, 1H, J=9 Hz); 7.57-6.60 (m, 26H); 5.16 (s, 2H); 4.05-1.15 (m, 8H); 3.72 (s, 3H); 2.68 (m, 2H); 1.64 (t of t, 2H, J=7,7 Hz); 1.33 (t of q, 2H, J=7,7 Hz); 0.87 (t, 3H, J=7 Hz).

Part D: Preparation of 2-n-Butyl-4-chloro-5-[4-(2-methoxyphenyl)piperazin-1-yl carbonyl]-1-[(2'-(1H-tetrazol-5-yl)biphenyl-4yl)methyl-]imidazole The product from Part C (500 mg) was detritylated by the procedure described in Example 342, Part B, to yield 421 mg of a white solid. The product (417.3 mg) was converted to its sodium salt by titration with 1.000N NaOH. Theory: 0.68 mL; Found 0.70 mL. m.p. salt 103 (wet), 149 (dec.)° C. NMR (DMSO-$d_6$): δ 7.52 (d, 1H J=9 Hz); 7.47-6.55 (m, 11H); 5.25 (bm, 1H); 5.14 (bm, 1H); 4.15-2.37 (m, 6H); 3.72 (s, 3H); 2.77 (m, 2H); 2.48 (m, 2H); 1.65 (t of t, 2H, J=7,7 Hz); 1.35 (t of q, 2H, J=7,7 Hz); 0.87 (t, 3H, J=7 Hz). FABMS, M/E 611.54 (M+H)+, 633.50 (M+Na)+.

The compounds of Table 24 can be made using the methods described in Example 347:

TABLE 24

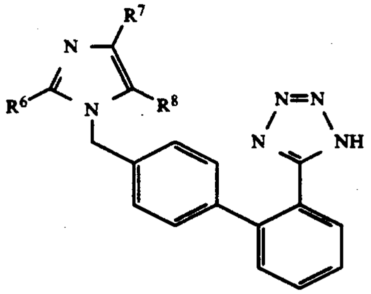

| Ex. No. | $R^6$ | $R^7$ | $R^8$ | m.p. °C. |
|---|---|---|---|---|
| 348 | n-butyl | 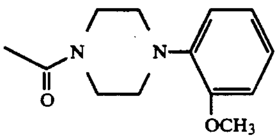 | Cl | (amorphous solid)[a] |
| 349 | n-propyl | Cl | 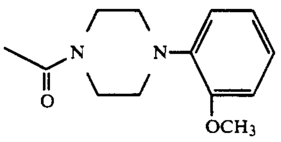 | |

TABLE 24-continued

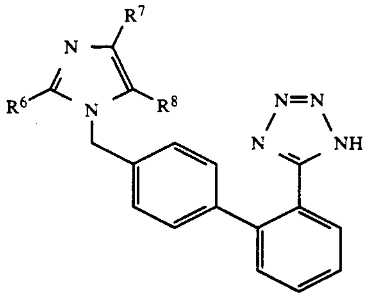

| Ex. No. | $R^6$ | $R^7$ | $R^8$ | m.p. °C. |
|---|---|---|---|---|
| 350 | n-propyl | 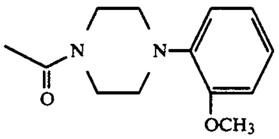 | Cl | |
| 351 | n-butyl | Cl | 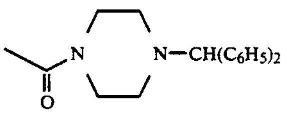 | |
| 352 | n-propyl | Cl | 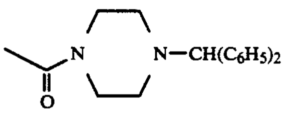 | |
| 353 | n-butyl | 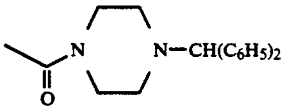 | Cl | |

*NMR($DMSO-d_6$): δ16.25(bm, 1H); 7.75-7.50(m, 4H); 7.17-6.84(m, 8H); 5.25(s, 2H); 3.95(m, 2H); 3.80(s, 3H); 3.75(m, 2H); 3.00(m, 4H); 2.65(t, 2H, J=7Hz); 1.55(t of t, 2H, J=7, 7Hz); 1.30(t of q, 2H, J=7, 7Hz); 0.83(t, 3H, J=7Hz).

EXAMPLE 354

Preparation of 2-n-Butyl-4-chloro-5-[(4-(2-methoxyphenyl)piperazin-1-yl)methyl]-1-[(2'-(1H-tetrazol-5-yl)biphenyl-4-yl)methyl]imidazole The amide in Example 347, Part B (1.01 g, 1.2 mmol, 1 eq.) was dissolved in toluene (25 mL) and to this solution, sodium bis(2-methoxyethoxy)aluminum hydride in toluene (3.4M, 2.44 mL, 8.3 mmol, 7 eq.) was added. The mixture was refluxed for 0.5 h. Water (10 mL) was slowly added (foaming) to quench, followed by the addition of THF (10 mL) and trifluoroacetic acid (5 mL). After 1 hour, the detritylation was complete. The pH was adjusted to 12 with 10N NaOH, and the organic solvents removed in vacuo. More water (30 mL) was added and the trityl alcohol was filtered off as a gum. TLC showed the gum to contain all of the product. The gum was dissolved in methanol, evaporated onto silica gel, and chromatographed in 1:1 hexane/ethyl acetate to 7:3 ethyl acetate/isopropanol, and finally crystallized from hexane/ethyl acetate to yield 189 mg of product as a white solid: m.p. 153.5°-157.5° C. NMR ($CDCl_3$): δ 7.94 (d of d, 1H, J=1,9 Hz); 7.56 (m, 2H); 7.40 (d of d, 1H, J=1,9 Hz); 7.10 (d, 2H, J=9 Hz); 7.00 (m, 2H); 6.90 (d, 2H, J=9 Hz); 6.80 (d, 2H, J=9 Hz); 5.20 (s, 2H); 3.83 (s, 3H); 3.33 (s, 2H); 2.97 (m, 4H); 2.50 (m, 4H); 2.44 (t, 2H, J=7 Hz); 1.61 (t of t, 2H, J=7,7 Hz); 1.30 (t of q, 2H, J=7,7 Hz); 0.87 (t, 3H, J=7 Hz).

UTILITY

The hormone angiotensin II (AII) produces numerous biological responses (e.g. vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by [Glossmann et al., *J. Biol. Chem.*, 249, 825 (1974)], but with some modifications. The reaction mixture contained rat adrenal cortical microsomes (source of AII receptor) in Tris buffer and 2 nM of $^3$H-AII with or without potential AII antagonist. This mixture was incubated for 1 hour at room temperature and the reaction was subsequently terminated by rapid filtration and rinsing through glass micro-fibre filter. Receptor-bound $^3$H-AII trapped in filter was quantitated by scintillation counting. The inhibitory concentration ($IC_{50}$) of potential AII antagonist which gives 50% displacement of the total specifically bound $^3$H-AII is presented as a measure of the affinity of such compound for the AII receptor (see Table 20).

The potential antihypertensive effects of the compounds of this invention may be demonstrated by administering the compounds to awake rats made hypertensive by ligation of the left renal artery [Cangiano et al., *J. Pharmacol. Exp. Ther.*, 208, 310 (1979)]. This procedure increases blood pressure by increasing renin production with consequent elevation of AII levels. Compounds are administered orally at 100 mg/kg and/or intravenously via a cannula in the jugular vein at 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds (See Table 25).

TABLE 25

| | Angiotensin II Receptor Binding | Antihypertensive Effects in Renal Hypertensive Rats | |
|---|---|---|---|
| Ex. No. | $IC_{50}$ (μmolar) | Intravenous Activity[1] | Oral Activity[2] |
| 1 | 1.80 | + | NA |
| 2 (sodium salt) | 0.140 | + | NA |
| 3 (sodium salt) | 0.420 | | NA |
| 4 (sodium salt) | 0.280 | + | NA |
| 5 (sodium salt) | 0.190 | | NA |
| 6 | 5.70 | NT | |
| 7 | 0.420 | + | NA |
| 8 (sodium salt) | 0.790 | | NA |
| 9 (sodium salt) | 5.80 | NT | |
| 10 (sodium salt) | 0.190 | NT | |
| 11 (sodium salt) | 0.380 | NA | NA |
| 12 (sodium salt) | 0.030 | + | NA |
| 13 (sodium salt) | 6.90 | + | NA |
| 14 | 3.20 | NT | |
| 15 (sodium salt) | 9.4 | + | NA |
| 16 | 0.018 | + | NA |
| 17 (sodium salt) | 0.042 | + | NA |
| 18 | 0.08 | + | NA |
| 19 (sodium salt) | 1.70 | NT | |
| 20 (sodium salt) | 5.30 | NT | |
| 21 (sodium salt) | 2.10 | + | NA |
| 25 | 3.90 | NT | |
| 26 (sodium salt) | 3.80 | | NA |
| 27 (sodium salt) | 1.20 | + | + |
| 28 | 8.00 | NT | |
| 29 | 3.10 | + | NA |
| 30 (sodium salt) | 0.39 | + | + |
| 31 | 0.64 | NT | |
| 32 (sodium salt) | 0.43 | NT | |
| 33 | 0.940 | NT | |
| 35 (sodium salt) | 3.40 | + | + |
| 36 (sodium salt) | 0.19 | + | NA |
| 51 | 2.30 | NA | NA |
| 52 | 1.10 | NT | |
| 53A | 0.81 | NA | NA |
| 53B | 0.36 | + | NT |
| 53C | 0.21 | + | NT |
| 54 | 7.20 | + | |
| 55 | 0.930 | + | NA |
| 56 | 4.40 | NT | |
| 57 | 4.90 | + | NA |
| 58 | 8.30 | + | NA |
| 59 | 3.00 | NA | NA |
| 60 | 1.20 | NT | |
| 61 | 5.00 | NT | |
| 62 (sodium salt) | 9.20 | NT | |
| 63 (sodium salt) | 3.70 | | NA |
| 64 | 0.620 | + | NA |
| 65 | 0.240 | + | NA |
| 66 | 0.350 | + | NA |
| 67 | 1.10 | + | NA |
| 70 | 2.50 | + | NA |
| 71 | 2.80 | NT | |
| 72 | 6.50 | + | NA |
| 74 (trans compound) | 3.90 | + | NA |
| (cis compound) | 4.50 | + | NA |
| 75 (sodium salt) | 7.60 | + | + |
| 76 (sodium salt) | 2.70 | + | NA |
| 77 (sodium salt) | 5.70 | NA | NA |
| 78 (sodium salt) | 8.00 | + | + |
| 79 (sodium salt) | 0.50 | + | NA |
| 80 (sodium salt) | 0.50 | + | + |
| 81 (sodium salt) | 0.57 | NA | NA |

TABLE 25-continued

| | Angiotensin II Receptor Binding | Antihypertensive Effects in Renal Hypertensive Rats | |
|---|---|---|---|
| Ex. No. | $IC_{50}$ (μmolar) | Intravenous Activity[1] | Oral Activity[2] |
| 82 | 6.10 | NT | |
| 83 | 6.40 | NT | |
| 85 | 0.49 | + | + |
| 86 | 2.90 | + | NA |
| 87 | 2.50 | NT | |
| 88 | 1.30 | | + |
| 89 | 0.039 | + | + |
| 90 (sodium salt) | 0.020 | + | + |
| 91 | 0.26 | + | NA |
| 92 | 0.062 | + | |
| 93 | 0.89 | + | NA |
| 94 | 0.280 | + | + |
| 95 | 1.20 | + | NA |
| 96 | 1.10 | NT | |
| 97 | 0.270 | + | NA |
| 98 (sodium salt) | 0.099 | + | + |
| 99 | 0.090 | + | + |
| 100 | 0.090 | + | + |
| 102 | 0.061 | + | + |
| 105 | 0.680 | + | + |
| 106 | 1.90 | + | + |
| 107 | 1.70 | NT | |
| 108 | 0.160 | + | + |
| 109 | 0.98 | + | + |
| 110 | 1.30 | + | + |
| 113 | 0.020 | NT | |
| 114 | 0.050 | + | + |
| 115 | 0.43 | + | + |
| 116 | 0.26 | + | + |
| 117 | 0.89 | + | + |
| 118 | 0.089 | + | + |
| 121 | 0.330 | + | + |
| 123 | 5.60 | + | NA |
| 124 | 1.80 | + | NA |
| 125 | 0.650 | + | + |
| 126 | 0.340 | + | + |
| 127 | 0.150 | + | + |
| 128 | 0.08 | + | + |
| 129 | 0.330 | + | + |
| 130 | 0.470 | + | + |
| 132 | 0.020 | + | + |
| 133 | 0.036 | + | + |
| 134 | 0.180 | + | + |
| 135 | 1.30 | + | + |
| 137 | 0.053 | + | + |
| 140I | 0.052 | + | + |
| 141 | 0.190 | + | + |
| 144 | 0.083 | + | + |
| 148 (sodium salt) | 0.200 | + | + |
| 149 (sodium salt) | 0.450 | + | + |
| 150 (sodium salt) | 0.200 | + | + |
| 151 (sodium salt) | 0.560 | + | + |
| 152 (sodium salt) | 0.250 | + | + |
| 153 (sodium salt) | 0.200 | + | + |
| 154 (sodium salt) | 0.60 | + | + |
| 156 | 0.060 | + | |
| 160 (sodium salt) | 0.120 | + | + |
| 162 (sodium salt) | 0.140 | + | + |
| 165 (sodium salt) | 3.00 | + | NA |
| 166 (sodium salt) | 0.240 | + | NA |
| 171 (sodium salt) | 0.600 | + | NA |
| 173 (sodium salt) | 0.700 | + | |
| 174 (sodium salt) | 0.300 | + | NA |
| 175 (DCHA salt) | 1.50 | + | NA |
| 176 | 0.200 | + | NA |
| 177 | 9.60 | + | NA |
| 178 | 4.20 | + | + |
| 179 | 4.40 | + | NA |
| 180 | 2.90 | + | NA |
| 181 | 4.90 | + | NA |
| 182 | 4.10 | + | NA |
| 183 | 6.30 | + | NA |
| 184 | 0.40 | + | NA |
| 185 | 0.400 | + | NA |
| 192 | 2.30 | | NA |
| 193 | 0.31 | + | NA |

TABLE 25-continued

| Ex. No. | Angiotensin II Receptor Binding IC50 (μmolar) | Antihypertensive Effects in Renal Hypertensive Rats Intravenous Activity[1] | Oral Activity[2] |
|---|---|---|---|
| 194 | 1.20 | NT | |
| 195 | 0.92 | + | + |
| 199 | 1.80 | | NA |
| 202 (sodium salt) | 0.160 | + | NA |
| 203 (sodium salt) | 0.340 | + | + |
| 204 (sodium salt) | 1.90 | + | NA |
| 205 (sodium salt) | 2.50 | NT | |
| 206 (sodium salt) | 1.40 | NT | |
| 207 (sodium salt) | 0.15 | + | + |
| 208 (sodium salt) | 0.330 | + | NA |
| 209 (sodium salt) | 0.27 | NT | |
| 215 (sodium salt) | 0.200 | + | NA |
| 217 (sodium salt) | 2.70 | NT | |
| 218 (sodium salt) | 2.0 | NT | |
| 219 | 0.68 | NT | |
| 223 | 5.40 | NT | |
| 224 | 5.90 | NT | |
| 227 | 0.110 | + | |
| 228 | 0.530 | NT | |
| 229 | 2.10 | + | + |
| 230 | 1.60 | + | |
| 231 | 0.076 | NT | |
| 232 | 0.510 | + | |
| 233 | 0.600 | + | + |
| 234 | 0.064 | + | NA |
| 235 | 0.160 | + | NA |
| 236 | 0.110 | + | |
| 237 | 0.120 | + | NA |
| 238 | 0.110 | + | NA |
| 239 | 0.120 | + | |
| 240 | 0.092 | + | |
| 241 | 0.170 | + | |
| 242 | 0.270 | + | |
| 243 | 0.200 | NT | |
| 244 | 0.088 | + | |
| 246 | 0.120 | + | |
| 247 | 0.110 | NT | |
| 248 | 0.250 | + | |
| 249 | 0.072 | + | NA |
| 250 | 0.120 | + | NA |
| 264 | 0.250 | + | + |
| 265 | 0.270 | + | + |
| 266 | 2.30 | + | |
| 292 | 0.700 | + | + |
| 314 | 0.630 | + | NA |
| 318 | 0.14 | + | NA |
| 325 | 0.73 | + | NT |
| 326 | 0.79 | + | NT |
| 341 | 0.27 | + | + |
| 346 | 0.74 | + | NT |
| 354 | 0.35 | NT | NT |

[1]Significant decrease in blood pressure at 10 mg/kg or less
[2]Significant decrease in blood pressure at 100 mg/kg or less
NA - Not active at 100 mg/kg dosage administered. Although many of the compounds tested were not active orally, they were active intravenously. A few compounds (Examples 10, 51, 53A, 59, 77 and 81) did not produce a significant decrease in blood pressure at 10 mg/kg intravenously, but did produce some decrease at that level, and it is expected that they would be active intravenously at a higher dosage, e.g., 30 mg/kg.
NT - Not tested.

Compounds listed in Table 26 were tested in the same manner as described for Table 25, except that in the test for antihypertensive effects in renal hypertensive rats, the compounds were administered orally at 30 mg/kg and intravenously at 3 mg/kg.

TABLE 26

| Ex. No. | Angiotensin II Receptor Binding IC50 (μmolar) | Antihypertensive Effects in Renal Hypertensive Rats Intravenous Activity[1] | Oral Activity[2] |
|---|---|---|---|
| 18A | 0.012 | + | + |
| 92A | 0.04 | + | + |
| 92B | 0.012 | + | NT[3] |
| 124A | 0.13 | + | + |
| 124B | 0.05 | + | + |
| 124C | 0.02 | + | + |
| 124D | 0.006 | + | + |
| 124E | 0.007 | + | + |
| 124F | 0.001 | NT | NT |
| 124G | 0.074 | + | + |
| 124H | 0.29 | + | + |
| 124I | 2.5 | + | NA |
| 124J | 0.68 | + | + |
| 124K | 0.013 | + | + |
| 124L | 0.020 | + | + |
| 139 | 0.011 | NT | NT |
| 140A | 0.39 | NT | + |
| 140B | 0.16 | NT | + |
| 140C | 0.02 | + | + |
| 140D | 0.40 | + | + |
| 140E | 0.033 | + | + |
| 140F | 0.20 | + | + |
| 140G | NT | NT | + |
| 140H | 0.076 | + | + |
| 140J | 0.027 | + | + |
| 140K | 0.038 | + | + |
| 140L | 5.7 | + | + |
| 240A | 0.15 | + | + |
| 251A | 0.045 | + | + |
| 252 | 0.011 | + | + |
| 265A | 1.1 | + | + |
| 265B | 1.4 | + | + |
| 265C | NT | + | NT |
| 265D | 1.10 | + | NT |
| 265E | 1.60 | + | NT |
| 327 | 0.66 | NA | NA |
| 327A | 0.29 | + | + |
| 327D | 5.2 | NA | NA |
| 328 | 6.7 | + | + |
| 329 | 0.076 | + | + |
| 333 | 0.051 | + | + |
| 334 | 0.015 | + | + |
| 335 | 0.26 | + | + |
| 336 | 0.28 | NA | NA |
| 337 | 0.76 | + | NA |
| 338 | 0.26 | NA | NA |
| 339 | 1.7 | + | + |
| 340 | 0.37 | + | + |
| 342 | 0.037 | | |
| 343 | 0.51 | + | NA |
| 344 | 0.16 | + | + |
| 345 | 1.1 | + | NT |
| 347 | 0.20 | + | + |
| 348 | 1.3 | + | NA |
| 354 | 0.35 | NT | NT |

[1]Significant decrease in blood pressure at 3.0 mg/kg or less
[2]Significant decrease in blood pressure at 30 mg/kg or less
NA - Not active at 3 mg/kg or 30 mg/kg dosage tested. Although some of the compounds tested were not active orally, they were active intravenously. A few compounds (Examples 327, 327D, 336 and 338) did not produce a significant decrease in blood pressure at 3 mg/kg intravenously, but did produce some decrease at that level, and it is expected that they would be active intravenously at a higher dosage, e.g., 30 mg/kg.
NT Not tested.
NT[3] Not tested at 30 mg/kg p.o.

Figure 2B:
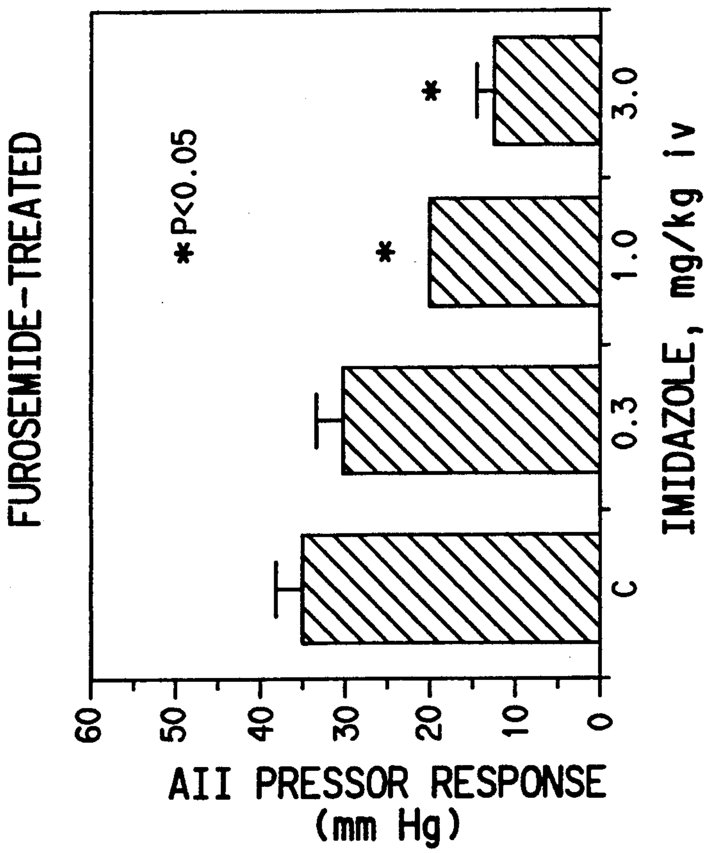
FIG. 2 shows inhibitory effect of imidazole on A-II pressor response in control and furosemide-treated dogs.
Figure 2A:
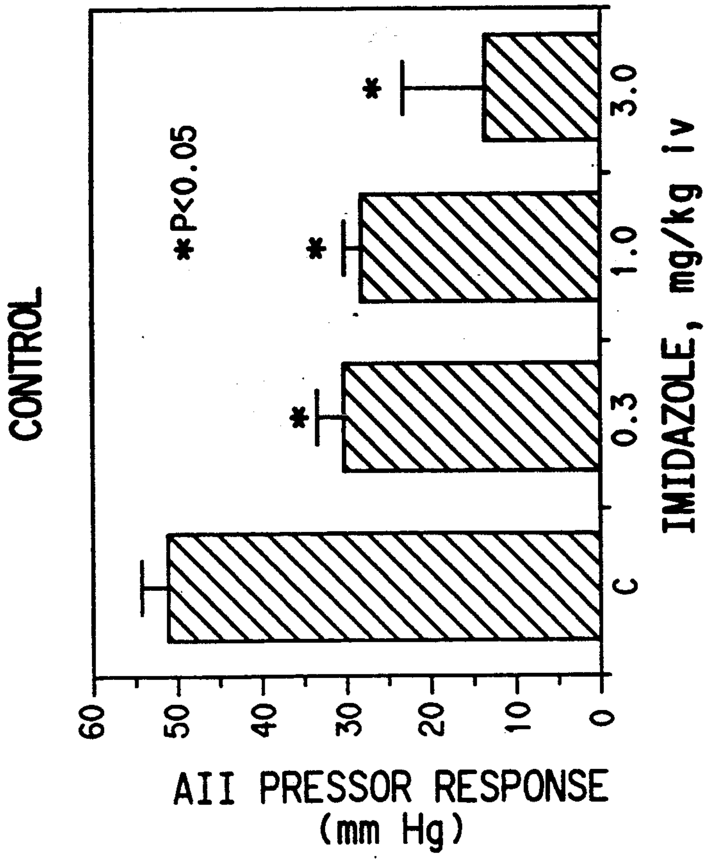

The hypotensive effects of 2-butyl-4-chloro-1-[2'-(1H-tetrazol-5-yl)biphenyl-4-yl)methyl]-5-hydroxymethylimidazole sodium salt were compared before and after furosemide administration to conscious dogs. Cumulative intravenous injections of imidazole at 0.3 to 3 mg/kg did not lower blood pressure in normotensive conscious dogs (n=4, FIG. 1) but they were effective in inhibiting the pressor response to AII (0.1 μg/kg iv) determined at 10 min post dose (FIG. 2). Plasma renin activity (PRA) in these animals was 1.5±0.5 ng AI/ml/hr. Four days later, furosemide was given to three of these dogs at 10 mg/kg im at 18 and 2 hours before the experiment and increased PRA to 19.9±7.2 ng AI/ml/hr. Imidazole was then given cumulatively iv at the same doses and caused a significant decrease in blood pressure in a dose-dependent manner (FIG. 1). It also inhibited the pressor response to AII at the two higher doses (FIG. 2). A similar hypotensive enhancement by furosemide was also observed with captopril at 0.3 mg/kg iv (FIG. 2). These results indicate that diuretics enhance the hypotensive efficacy of imidazole AII blockers. Thus a combined therapy of these two classes of drugs will be likely to increase the response rate to therapy among hypertensive patients.

DOSAGE FORMS

The compounds of this invention can be administered for the treatment of hypertension according to the invention by any means that effects contact of the active ingredient compound with the site of action in the body of a warm-blooded animal. For example, administration can be parenteral, i.e., subcutaneous, intravenous, intramuscular, or intra peritoneal. Alternatively, or concurrently, in some cases administration can be by the oral route.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

For the purpose of this disclosure, a warm-blooded animal is a member of the animal kingdom possessed of a homeostatic mechanism and includes mammals and birds.

The dosage administered will be dependent on the age, health and weight of the recipient, the extent of disease, kind of concurrent treatment, if any, frequency of treatment and the nature of the effect desired. Usually, a daily dosage of active ingredient compound will be from about 1-500 milligrams per day. Ordinarily, from 10 to 100 milligrams per day in one or more applications is effective to obtain desired results. These dosages are the effective amounts both for treatment of hypertension and for treatment of congestive heart failure, i.e., for lowering blood pressure and for correcting the hemodynamic burden on the heart to relieve the congestion.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propylparaben, and chlorobutanol.

Suitable pharmaceutical carriers are described in *Remington's Pharmaceutical Sciences*, A. Osol, a standard reference text in this field.

Useful pharmaceutical dosage-forms for administration of the compounds of this invention can be illustrated as follows:

CAPSULES

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

SOFT GELATIN CAPSULES

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol. The solution is made to volume with water for injection and sterilized.

SUSPENSION

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs. Suitable dosages, dosage forms and administration routes are illustrated in Tables 27 and 28.

TABLE 27

| Examples of NSAID's that can be combined with AII blockers of this invention: | | | |
|---|---|---|---|
| Drug | Dose (mg) | Formulation | Route |
| Indomethacin | 25 (2/3 times daily) | Tablet | Oral |
| Meclofenamate | 50–100 (2/3 times daily) | Tablet | Oral |
| Ibuprofen | 300–400 (3/4 times daily) | Tablet | Oral |
| Piroxicam | 10–20 (1/2 times daily) | Tablet | Oral |
| Sulindac | 150–200 (2 times daily) | Tablet | Oral |
| Azapropazone | 200–500 (3/4 times daily) | Tablet | Oral |

TABLE 28

| Examples of diuretics that can be combined with AII blockers of this invention: | | | |
|---|---|---|---|
| Drug | Dose (mg) | Formulation | Route |
| Benzothiadizides (e.g. hydrochlorothiazide) | 25–100 (daily) | Tablet | Oral |
| Loop diuretics (e.g. furosemide) | 50–80 (daily) | Tablet | Oral |

When used with an NSAID, the dosage of AII blockers will generally be the same as when the AII blocker is used alone, i.e., 1–500 milligrams per day, ordinarily from 10 to 100 milligrams per day in one or more applications. When used with diuretics, the initial dose of AII blocker can be less, e.g., 1–100 milligrams per day and for the more active compounds 1–10 milligrams per day.

It is expected that the compounds of this invention will also be useful in the treatment of chronic renal failure.

We claim:

1. A method of preventing renal failure in a warm-blooded animal resulting from administration of a non-steroidal anti-inflammatory drug (NSAID) which comprises administering, stepwise or in combination with the NSAID, an imidazole compound of the following formula, in an amount effective to prevent renal failure:

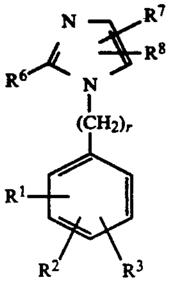

wherein:

$R^1$ is

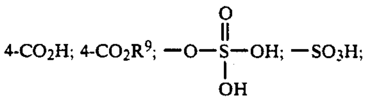

-continued

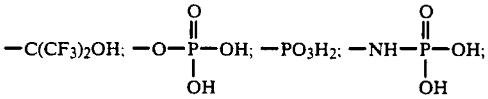

4-$NHSO_2CH_3$; 4-$NHSO_2CF_3$; $-CONHOR^{12}$;

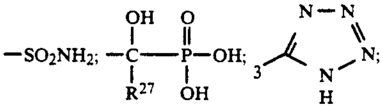

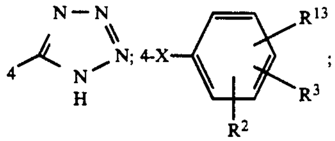

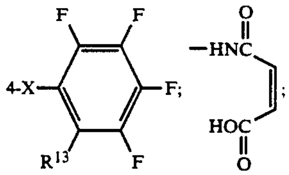

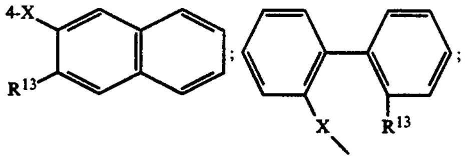

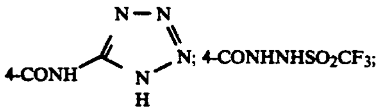

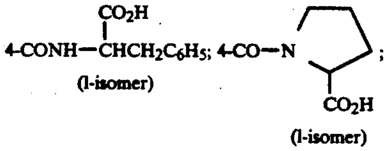

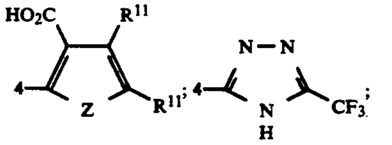

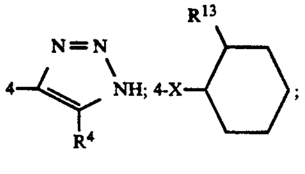

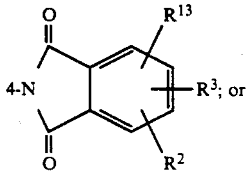

R³; or

-continued

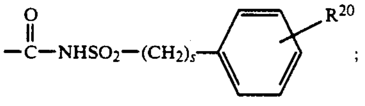

$R^2$ is H, Cl, Br, I, F, $NO_2$, CN, alkyl of 1 to 4 carbon atoms, acyloxy of 1 to 4 carbon atoms, alkoxy of 1 to 4 carbon atoms, $CO_2H$, $CO_2R^9$, $NHSO_2CH_3$, $NHSO_2CF_3$, $CONHOR^{12}$, $SO_2NH_2$, aryl, furyl or

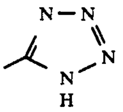

$R^3$ is H, Cl, Br, I, F, alkyl of 1 to 4 carbon atoms, or alkoxy of 1 to 4 carbon atoms;

$R^4$ is CN, $NO_2$, or $CO_2R^{11}$;

$R^5$ is H, alkyl of 1 to 6 carbon atoms, cycloalkyl of 3 to 6 carbon atoms, alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms; cycloalkylalkyl of 4 to 10 carbon atoms; cycloalkylalkenyl or cycloalkylalkynyl of 5 to 10 carbon atoms; $(CH_2)_sZ(CH_2)_mR^5$ optionally substituted with F or $CO_2R^{14}$; benzyl or benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1-6, $C_6F_5$, CN,

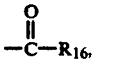

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the alkenyl portion is 2 to 6 carbon atoms; $—(CH_2)_m$-imidazol-1-yl; $—(CH_2)_m$-1,2,3-triazolyl optionally substituted with one or two groups selected from $CO_2CH_3$ or alkyl of 1 to 4 carbon atoms; $—(CH_2)_s—$ tetrazolyl;

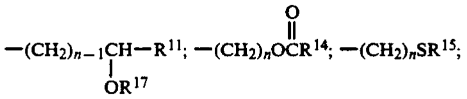

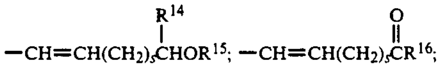

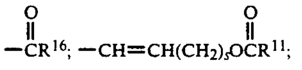

-continued

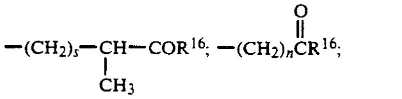

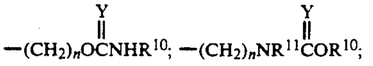

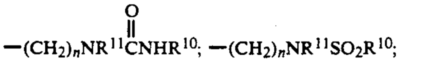

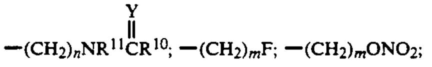

$—CH_2N_3$; $—(CH_2)_mNO_2$; $—CH=N—NR^{11}R^{17}$;

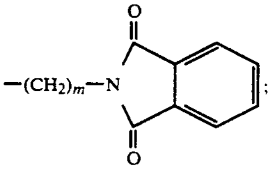 ; 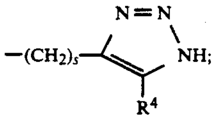

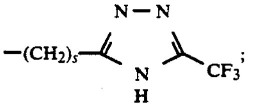

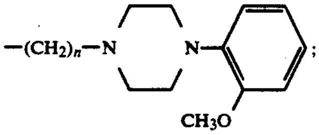

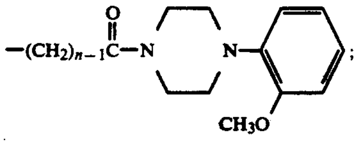

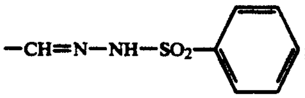 ; or

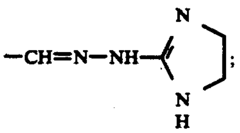

$R^9$ is

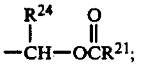

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl, or benzyl;

$R^{13}$ is $-CO_2H$; $CO_2R^9$; $-CH_2CO_2H$; $-CH_2CO_2R^9$;

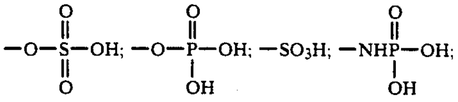

$-PO_3H_2$; $-C(CF_3)_2OH$; $-NHSO_2CH_3$; $-NHSO_2CF_3$;

$-NHCOCF_3$; $-CONHOR^{12}$; $-SO_2NH_2$;

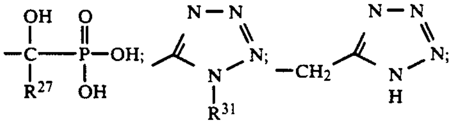

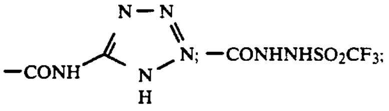

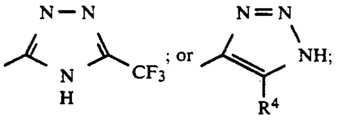

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, or phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently H, alkyl of 1 to 4 carbon atoms, phenyl, benzyl, α-methylbenzyl, or taken together with the nitrogen form a ring of the formula:

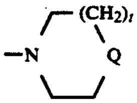

Q is $NR^{20}$, O or $CH_2$;

$R^{20}$ is H, alkyl of 1 to 4 carbon atoms or phenyl;

$R^{21}$ is alkyl or 1 to 6 carbon atoms, $-NR^{22}R^{23}$, or

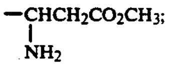

$R^{22}$ and $R^{23}$ independently are H, alkyl of 1 to 6 carbon atoms, benzyl, or are taken together as $(CH_2)_u$, where u is 3-6;

$R^{24}$ is H, $CH_3$ or $C_6H_5$;

$R^{25}$ is $NR^{27}R^{28}$, $OR^{28}$, $NHCONH_2$, $NHCSNH_2$,

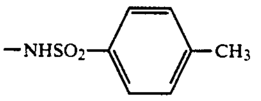

-continued or

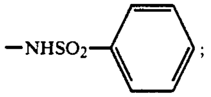

$R^{26}$ is H, alkyl with from 1 to 6 carbon atoms, benzyl or allyl;

$R^{27}$ and $R^{28}$ are independently H, alkyl with from 1 to 5 carbon atoms, or phenyl;

$R^{29}$ and $R^{30}$ are independently alkyl of 1 to 4 carbon atoms, or taken together are $-(CH_2)_q-$;

$R^{31}$ is H, alkyl of 1 to 4 carbon atoms, $-CH_2CH{=}CH_2$ or $-CH_2C_6H_4R^{32}$;

$R^{32}$ is H, $NO_2$, $NH_2$, OH or $OCH_3$;

X is a carbon—carbon single bond, $-CO-$, $-CH_2-$, $-O-$, $-S-$, $-NH-$,

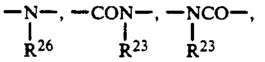

$-OCH_2-$, $-CH_2O$, $-SCH_2-$, $-CH_2S-$, $-NHC(R^{27})(R^{28})-$, $-NR^{23}SO_2-$, $-SO_2NR^{23}-$, $-C(R^{27})(R^{28})NH-$, $-CH{=}CH-$, $-CF{=}CF-$, $-CH{=}CF-$, $-CF{=}CH-$, $-CH_2CH_2-$, $-CF_2CF_2-$,

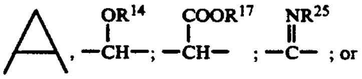

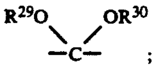

Y is O or S;

Z is O, $NR^{11}$, or S;

m is 1 to 5;

n is 1 to 10;

p is 0 to 3;

q is 2 to 3;

r is 0 to 2;

s is 0 to 5;

t is 0 or 1;

and pharmaceutically acceptable salts of these compounds; provided that:

(1) the $R^1$ group is not in the ortho position;

(2) when $R^1$ is

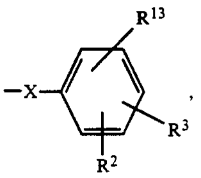

X is a single bond, and $R^{13}$ is $CO_2H$ or

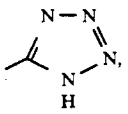

then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

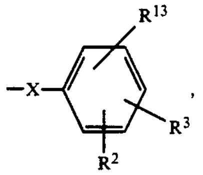

and X is other than a single bond, then $R^{13}$ must be ortho, except when $X=NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$ or $CH_2CO_2H$;

(6) when $R^1$ is

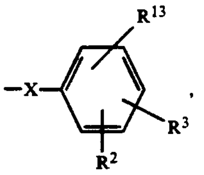

X is $-OCH_2-$, and $R^{13}$ is 2-$CO_2H$, and $R^7$ is H, then $R^6$ is not $C_2H_5S$;

(7) when $R^1$ is

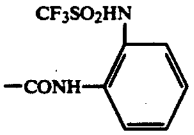

and $R^6$ is n-hexyl, then $R^7$ and $R^8$ are not both hydrogen;

(8) when $R^1$ is

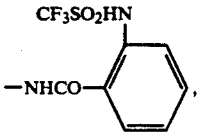

$R^6$ is not methoxybenzyl;

(9) the $R^6$ group is not

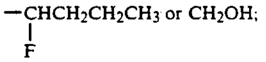

(10) when r=0, $R^1$ is

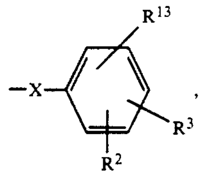

X is

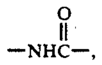

$R^{13}$ is 2-$NHSO_2CF_3$, and $R^6$ is n-propyl, then $R^7$ and $R^8$ are not $-CO_2CH_3$;

(11) when r=0, $R^1$ is

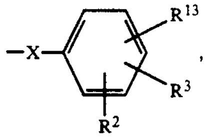

X is

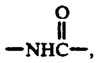

$R^{13}$ is 2-COOH, and $R^6$ is n-propyl, then $R^7$ and $R^8$ are not $-CO_2CH_3$.

(12) when r=1, $R^1$ is

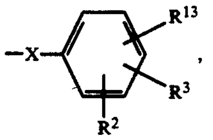

X is a single bond, $R^7$ is Cl and $R^8$ is —CHO, then $R^{13}$ is not 3-(tetrazol-5-yl);

(13) when r=1, $R^1$ is

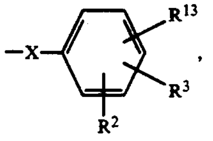

X is a single bond, $R^7$ is Cl and $R^8$ is —CHO, then $R^{13}$ is not 4-(tetrazol-5-yl);

(14) when r=0, then $R^1$ is not 4-$NHSO_2CH_3$ or 4-$NHSO_2CF_3$.

2. Method of claim 1 wherein the imidazole compound is a compound having the formula:

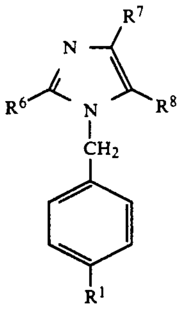

(II)

wherein $R^1$ is $-CO_2H$; $-NHSO_2CF_3$;

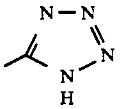

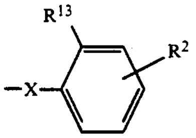

or

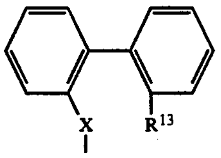

$R^6$ is alkyl of 3 to 10 carbon atoms, alkenyl of 3 to 10 carbon atoms, alkynyl of 3 to 10 carbon atoms; cycloalkyl of 3 to 8 carbon atoms; benzyl or benzyl substituted on the phenyl ring with 1 or 2 groups selected from alkoxy of 1 to 4 carbon atoms, halogen, alkyl of 1 to 4 carbon atoms, and nitro;

$R^8$ is phenylalkenyl wherein the aliphatic portion is 2 to 4 carbon atoms; $-(CH_2)_m$-imidazol-1-yl; $-(CH_2)_m$-1,2,3-triazolyl optionally substituted with one or two groups selected from $CO_2CH_3$ or alkyl of 1 to 4 carbon atoms; $-(CH_2)_m$-tetrazolyl;

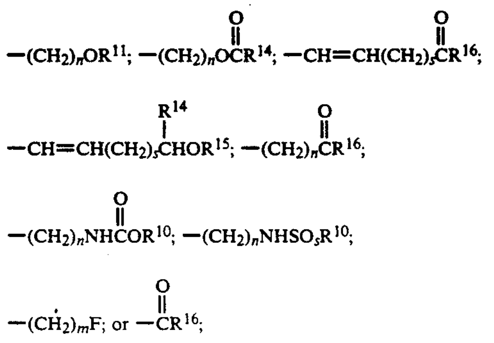

$R^{13}$ is $-CO_2H$, $-CO_2R^9$, $NHSO_2CF_3$, $SO_3H$ or

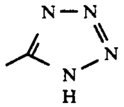

$R^{16}$ is H, alkyl of 1 to 5 carbon atoms, $OR^{17}$ or $NR^{18}R^{19}$;

X is a carbon—carbon single bond, —CO—, $-CONR^{23}-$, $-CH_2CH_2-$, $-NR^{23}CO-$, $-OCH_2-$, $-CH_2O$, —O—, $-SCH_2-$, $-CH_2S-$, $-NHCH_2-$, $-CH_2NH-$ or —CH═CH—;

or a pharmaceutically suitable salt thereof.

3. Method of claim 2 wherein the imidazole compound is a compound wherein:

$R^2$ is H, alkyl of 1 to 4 carbon atoms, halogen, or alkoxy of 1 to 4 carbon atoms;

$R^6$ is alkyl, alkeny or alkynyl of 3 to 7 carbon atoms;

$R^7$ is H, Cl, Br, I; $C_vF_{2v+1}$, where v=1-3; or $-COR^{16}$;

$R^8$ is

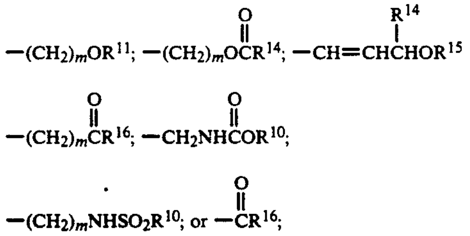

$R^{10}$ is $CF_3$, alkyl of 1 to 6 carbon atoms, or phenyl;

$R^{11}$ is H or alkyl of 1 to 4 carbon atoms;

$R^{13}$ is $CO_2H$, $CO_2CH_2OCOC(CH_3)_3$; $NHSO_2CF_3$; or

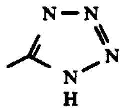

$R^{14}$ is H, alkyl of 1 to 4 carbon atoms;

$R^{15}$ is H, alkyl of 1 to 4 carbon atoms, or acyl of 1 to 4 carbon atoms;

$R^{16}$ is H, alkyl of 1 to 5 carbon atoms; $OR^{17}$; or

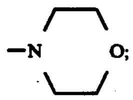

m is 1 to 5;

X is a single bond, —O—, —CO—, —NHCO— or —OCH2—;

or a pharmaceutically suitable salt thereof.

4. Method of claim 3 wherein the imidazole compound is a compound wherein $R^1$ is

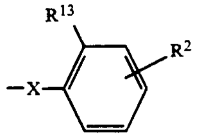

and X is a single bond; or a pharmaceutically suitable salt thereof.

5. Method of claim 4 wherein the imidazole compound is 2-Butyl-4-chloro-1-[(2'-(1H-tetrazol-5-yl)biphenyl-4-yl)methyl]-5-(hydroxymethyl)imidazole, or a pharmaceutically acceptable salt thereof.

6. Method of claim 4 wherein the imidazole compound is 2-Butyl-4-chloro-1-[(2'-carboxybiphenyl-4-yl)methyl]-5-(hydroxymethyl)-imidazole, or a pharmaceutically acceptable salt thereof.

7. Method of claim 4 wherein the imidazole compound is 2-Butyl-4-chloro-1-[(2'-carboxybiphenyl-4-yl)methyl]-5-[(methoxycarbonyl)-aminomethyl-]imidazole, or a pharmaceutically acceptable salt thereof.

8. Method of claim 4 wherein the imidazole compound is 2-Butyl-4-chloro-1-[(2'-carboxybiphenyl-4-yl)methyl]-5-[(propoxycarbonyl)-aminomethyl-]imidazole, or a pharmaceutically acceptable salt thereof.

9. Method of claim 4 wherein the imidazole compound is 2-Butyl-4-chloro-1-[(2'-carboxybiphenyl-4-yl)methyl]imidazole-5-carboxaldehyde, or a pharmaceutically acceptable salt thereof.

10. Method of claim 4 wherein the imidazole compound is 2-Butyl-1-[(2'-carboxybiphenyl-4-yl)methyl-]imidazole-5-carboxaldehyde, or a pharmaceutically acceptable salt thereof.

11. Method of claim 4 wherein the imidazole compound is 2-(1E-Butenyl)-4-chloro-1-[(2'-carboxybiphenyl-4-yl)methyl]-5-(hydroxymethyl)imidazole, or a pharmaceutically acceptable salt thereof.

12. Method of claim 4 wherein the imidazole compound is 2-(1E-Butenyl)-4-chloro-1-[(2'-carboxybiphenyl-4-yl)methyl]imidazole-5-carboxaldehyde, or a pharmaceutically acceptable salt thereof.

13. Method of claim 4 wherein the imidazole compound is 2-propyl-4-chloro-1-[(2'-(1H-tetrazol-5-yl)biphenyl-4-yl)methyl]-5-(hydroxymethyl)imidazole, or a pharmaceutically acceptable salt thereof.

14. Method of claim 4 wherein the imidazole compound is 2-propyl-4-chloro-1-[(2'-(1H-tetrazol-5-yl)biphenyl-4-yl)methyl]imidazole-5-carboxaldehyde, or a pharmaceutically acceptable salt thereof.

15. Method of claim 4 wherein the imidazole compound is 2-butyl-4-chloro-1-[(2'-(1H-tetrazol-5-yl)biphenyl-4-yl)methyl)imidazole-5-carboxaldehyde, or a pharmaceutically acceptable salt thereof.

16. Method of claim 4 wherein the imidazole compound is 2-(1E-butenyl)-4-chloro-1-[(2'-(1H-tetrazol-5-yl)biphenyl-4-yl)methyl]-5-hydroxymethyl)imidazole, or a pharmaceutically acceptable salt thereof.

17. Method of claim 4 wherein the imidazole compound is 2-(1E-butenyl)-4-chloro-1-[(2'(1H-tetrazol-5-yl)biphenyl-4-yl)methyl]-imidazole-5-carboxaldehyde, or a pharmaceutically acceptable salt thereof.

18. Method of claim 4 wherein the imidazole compound is 2-butyl-4-chloro-1-[(2'-(1H-tetrazol-5-yl)biphenyl-4-yl)methyl]-imidazole-5-carboxylic acid, or a pharmaceutically acceptable salt thereof.

19. Method of claim 4 wherein the imidazole compound is 2-propyl-4-chloro-1-[(2'-(1H-tetrazol-5-yl)biphenyl-4-yl)methyl]-imidazole-5-carboxylic acid, or a pharmaceutically acceptable salt thereof.

20. Method of claim 4 wherein the imidazole compound is 2-propyl-4-trifluoromethyl-1-[(2'-(1H-tetrazol-5-yl)biphenyl-4-yl)-methyl]imidazole-5-carboxylic acid, or a pharmaceutically acceptable salt thereof.

21. Method of claim 4 wherein the imidazole compound is 2-propyl-4-trifluoromethyl-1-[(2'-(1H-tetrazol-5-yl)biphenyl-4-yl)-methyl-5-(hydroxymethyl-)imidazole, or a pharmaceutically acceptable salt thereof.

22. Method of claim 4 wherein the imidazole compound is 2-butyl-4-trifluoromethyl-1-[(2'-1H-tetrazol-5-yl)biphenyl-4-yl)-methyl]imidazole-5-carboxylic acid, or a pharmaceutically acceptable salt thereof.

23. Method of claim 4 wherein the imidazole compound is 2-propyl-4-trifluoromethyl-1-[(2'-carboxybiphenyl-4-yl)methyl]-imidazole-5-carboxaldehyde, or a pharmaceutically acceptable salt thereof.

24. Method of claim 4 wherein the imidazole compound is 2-propyl-4-pentafluoroethyl-1-[(2'-(1H-tetrazol-5-yl)biphenyl-4-yl)methyl]-5-(hydroxymethyl-)imidazole, or a pharmaceutically acceptable salt thereof.

25. Method of claim 4 wherein the imidazole compound is 2-Propyl-1-[(2'-(1H-tetrazol-5-yl)biphenyl-4-yl)methyl]imidazole-4,5-dicarboxylic acid, or a pharmaceutically acceptable salt thereof.

26. Method of claim 4 wherein the imidazole compound is 2-Propyl-4-pentafluoroethyl-1-[(2'-(1H-tetrazol-5-yl)biphenyl-4-yl)methyl]imidazole-5-carboxylic acid, or a pharmaceutically acceptable salt thereof.

27. Method of claim 4 wherein the imidazole compound is 2-Propyl-4-pentafluoroethyl-[(2'-(1H-tetrazol-5-yl)biphenyl-4-yl)methyl]imidazole-5-carboxaldehyde, or a pharmaceutically acceptable salt thereof.

28. A pharmaceutical composition comprising a pharmaceutically suitable carrier, a non-steroidal anti-inflammatory drug (NSAID) and an imidazole compound of the formula:

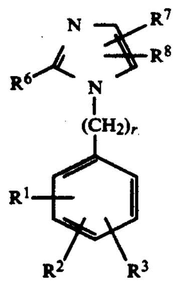

wherein:

$R^1$ is

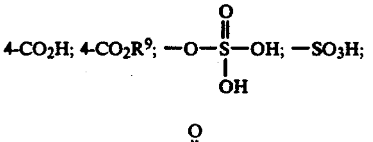

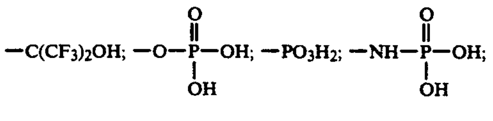

4-$NHSO_2CH_3$; 4-$NHSO_2CF_3$; —$CONHOR^{12}$;

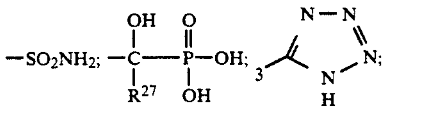

-continued

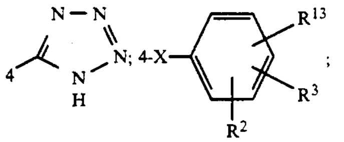

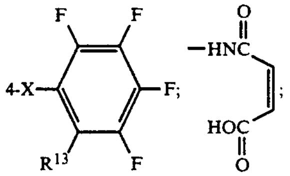

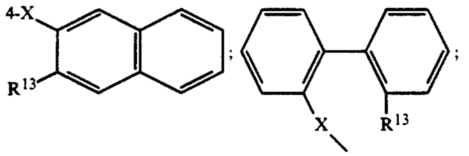

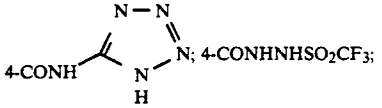

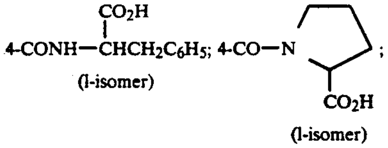

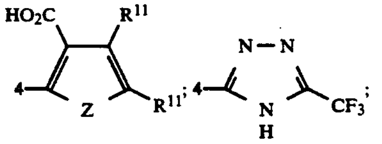

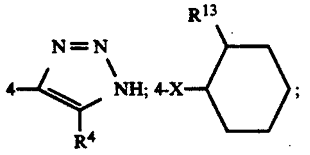

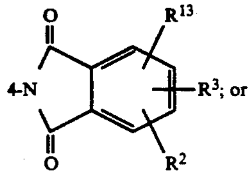

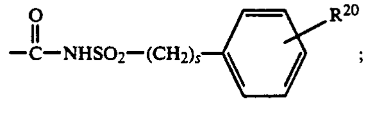

$R^2$ is H, Cl, Br, I, F, $NO_2$, CN, alkyl of 1 to 4 carbon atoms, acyloxy of 1 to 4 carbon atoms, alkoxy of 1 to 4 carbon atoms, $CO_2H$, $CO_2R^9$, $NHSO_2CH_3$, $NHSO_2CF_3$, $CONHOR^{12}$, $SO_2NH_2$, aryl, furyl or

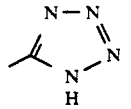

$R^3$ is H, Cl, Br, I, F, alkyl of 1 to 4 carbon atoms, or alkoxy of 1 to 4 carbon atoms;

$R^4$ is CN, $NO_2$, or $CO_2R^{11}$;

$R^5$ is H, alkyl of 1 to 6 carbon atoms, cycloalkyl of 3 to 6 carbon atoms, alkenyl or alkynyl of 2 to 4 carbon atoms;

$R^6$ is alkyl of 2 to 10 carbon atoms, alkenyl or alkynyl of 3 to 10 carbon atoms or the same groups substituted with F or $CO_2R^{14}$; cycloalkyl of 3 to 8 carbon atoms; cycloalkylalkyl of 4 to 10 carbon atoms; cycloalkylalkenyl or cycloalkylalkynyl of 5 to 10 carbon atoms; $(CH_2)_sZ(CH_2)_mR^5$ optionally substituted with F or $CO_2R^{14}$; benzyl or benzyl substituted on the phenyl ring with 1 or 2 halogens, alkoxy of 1 to 4 carbon atoms, alkyl of 1 to 4 carbon atoms or nitro;

$R^7$ is H, F, Cl, Br, I, $NO_2$, $C_vF_{2v+1}$, where v=1-6, $C_6F_5$, CN,

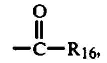

straight or branched alkyl of 1 to 6 carbon atoms; phenyl or phenylalkyl, where alkyl is 1 to 3 carbon atoms; or substituted phenyl or substituted phenylalkyl, where alkyl is 1 to 3 carbon atoms, substituted with one or two substituents selected from alkyl of 1 to 4 carbon atoms, F, Cl, Br, OH, $OCH_3$, $CF_3$, and COOR, where R is H, alkyl of 1 to 4 carbon atoms, or phenyl;

$R^8$ is H, CN, alkyl of 1 to 10 carbon atoms, alkenyl of 3 to 10 carbon atoms, or the same groups substituted with F; phenylalkenyl wherein the alkenyl portion is 2 to 6 carbon atoms; $-(CH_2)_m$-imidazol-1-yl; $-(CH_2)_m$-1,2,3-triazolyl optionally substituted with one or two groups selected from $CO_2CH_3$ or alkyl of 1 to 4 carbon atoms; $-(CH_2)_s$-tetrazolyl;

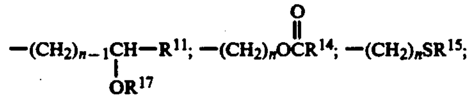

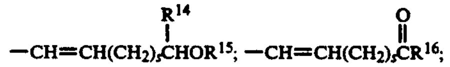

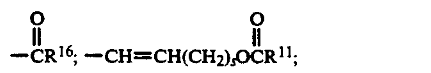

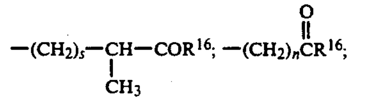

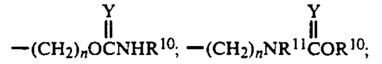

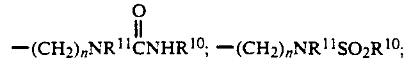

-continued

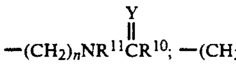; $-(CH_2)_mF$; $-(CH_2)_mONO_2$;

$-CH_2N_3$; $-(CH_2)_mNO_2$; $-CH{=}N-NR^{11}R^{17}$;

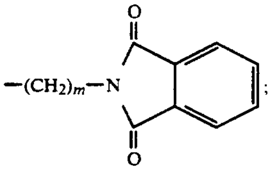; 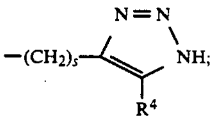;

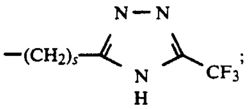;

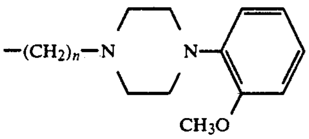;

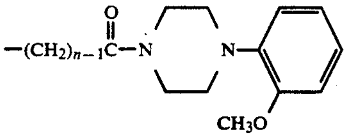;

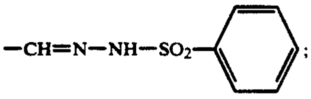; or

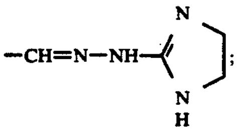;

$R^9$ is

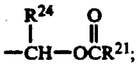;

$R^{10}$ is alkyl of 1 to 6 carbon atoms or perfluoroalkyl of 1 to 6 carbon atoms, 1-adamantyl, 1-naphthyl, 1-(1-naphthyl)ethyl, or $(CH_2)_pC_6H_5$;

$R^{11}$ is H, alkyl of 1 to 6 carbon atoms, cycloalkyl of 3 to 6 carbon atoms, phenyl or benzyl;

$R^{12}$ is H, methyl, or benzyl;

$R^{13}$ is $-CO_2H$; $CO_2R^9$; $-CH_2CO_2H$; $-CH_2CO_2R^9$;

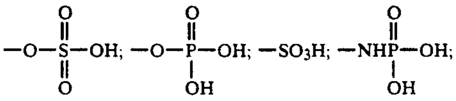

$-PO_3H_2$; $-C(CF_3)_2OH$; $-NHSO_2CH_3$; $-NHSO_2CF_3$;

-continued $-NHCOCF_3$; $-CONHOR^{12}$; $-SO_2NH_2$; 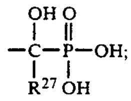;

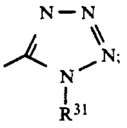; 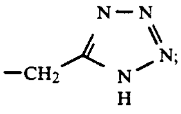;

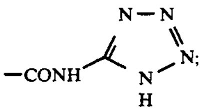; or $CONHNHSO_2CF_3$;

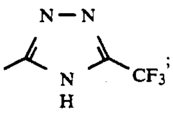; or 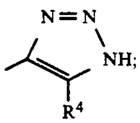;

$R^{14}$ is H, alkyl or perfluoroalkyl of 1 to 8 carbon atoms, cycloalkyl of 3 to 6 carbon atoms, phenyl or benzyl;

$R^{15}$ is H, alkyl of 1 to 6 carbon atoms, cycloalkyl of 3 to 6 carbon atoms, phenyl, benzyl, acyl of 1 to 4 carbon atoms, or phenacyl;

$R^{16}$ is H, alkyl of 1 to 6 carbon atoms, cycloalkyl of 3 to 6 carbon atoms, $(CH_2)_pC_6H_5$, $OR^{17}$, or $NR^{18}R^{19}$;

$R^{17}$ is H, alkyl of 1 to 6 carbon atoms, cycloalkyl of 3 to 6 carbon atoms, phenyl or benzyl;

$R^{18}$ and $R^{19}$ independently H, alkyl of 1 to 4 carbon atoms, phenyl, benzyl, α-methylbenzyl, or taken together with the nitrogen form a ring of the formula:

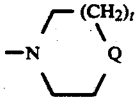

Q is $NR^{20}$, O or $CH_2$;

$R^{20}$ is H, alkyl of 1 to 4 carbon atoms or phenyl;

$R^{21}$ is alkyl or 1 to 6 carbon atoms, $-NR^{22}R^{23}$, or

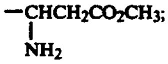;

$R^{22}$ and $R^{23}$ independently are H, alkyl of 1 to 6 carbon atoms, benzyl, or are taken together as $(CH_2)_u$, where u is 3–6;

$R^{24}$ is H, $CH_3$ or $C_6H_5$;

$R^{25}$ is $NR^{27}R^{28}$, $OR^{28}$, $NHCONH_2$, $NHCSNH_2$,

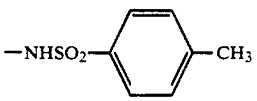

or

-continued

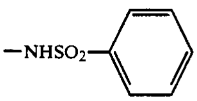;

$R^{26}$ is H, alkyl with from 1 to 6 carbon atoms, benzyl or allyl;
$R^{27}$ and $R^{28}$ are independently H, alkyl with from 1 to 5 carbon atoms, or phenyl;
$R^{29}$ and $R^{30}$ are independently alkyl of 1 to 4 carbon atoms, or taken together are $-(CH_2)_q-$;
$R^{31}$ is H, alkyl of 1 to 4 carbon atoms, $-CH_2CH{=}CH_2$ or $-CH_2C_6H_4R^{32}$;
$R^{32}$ is H, $NO_2$, $NH_2$, OH or $OCH_3$;
X is a carbon—carbon single bond, $-CO-$, $-CH_2-$, $-O-$, $-S-$, $-NH-$,

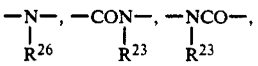

$-OCH_2-$, $-CH_2O$, $-SCH_2-$, $-CH_2S-$, $-NHC(R^{27})(R^{28})-$, $-NR^{23}SO_2-$, $-SO_2NR^{23}-$, $-C(R^{27})(R^{28})NH-$, $-CH{=}CH-$, $-CF{=}CF-$, $-CH{=}CF-$, $-CF{=}CH-$, $-CH_2CH_2-$, $-CF_2CF_2-$,

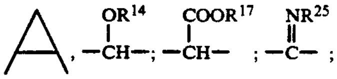 ; or

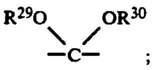 ;

Y is O or S;
Z is O, $NR^{11}$, or S;
m is 1 to 5;
n is 1 to 10;
p is 0 to 3;
q is 2 to 3;
r is 0 to 2;
s is 0 to 5;
t is 0 or 1;

and pharmaceutically acceptable salts of these compounds; provided that:

(1) the $R^1$ group is not in the ortho position;

(2) when $R^1$ is

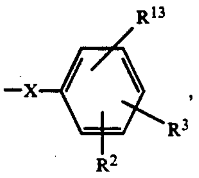,

X is a single bond, and $R^{13}$ is $CO_2H$ or

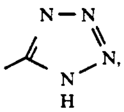, then $R^{13}$ must be in the ortho or meta position; or when $R^1$ and X are as above and $R^{13}$ is $NHSO_2CF_3$ or $NHSO_2CH_3$, $R^{13}$ must be ortho;

(3) when $R^1$ is

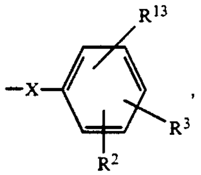, and X is other than a single bond, then $R^{13}$ must be ortho, except when $X{=}NR^{23}CO$ and $R^{13}$ is $NHSO_2CF_3$ or $NHSO_2CH_3$, then $R^{13}$ must be ortho or meta;

(4) when $R^1$ is 4-$CO_2H$ or a salt thereof, $R^6$ cannot be S-alkyl;

(5) when $R^1$ is 4-$CO_2H$ or a salt thereof, the substituent on the 4-position of the imidazole cannot be $CH_2OH$, $CH_2OCOCH_3$ or $CH_2CO_2H$;

(6) when $R^1$ is

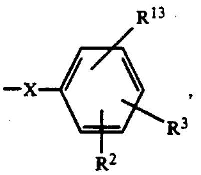,

X is $-OCH_2-$, and $R^{13}$ is 2-$CO_2H$, and $R^7$ is H, then $R^6$ is not $C_2H_5S$;

(7) when $R^1$ is

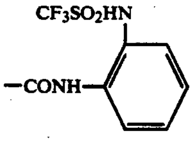

and $R^6$ is n-hexyl, then $R^7$ and $R^8$ are not both hydrogen;

(8) when $R^1$ is

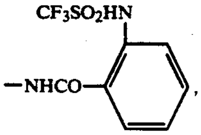, $R^6$ is not methoxybenzyl;

(9) the $R^6$ group is not

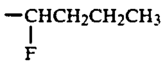 or $CH_2OH$;

(10) when r=0, $R^1$ is

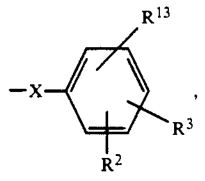

X is

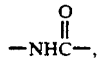

$R^{13}$ is 2-$NHSO_2CF_3$, and $R^6$ is n-propyl, then $R^7$ and $R^8$ are not $—CO_2CH_3$;

(11) when r=0, $R^1$ is

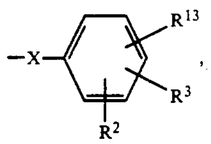

X is

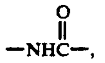

$R^{13}$ is 2-COOH, and $R^6$ is n-propyl, then $R^7$ and $R^8$ are not $—CO_2CH_3$

(12) when r=1, $R^1$ is

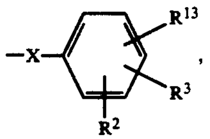

X is a single bond, $R^7$ is Cl and $R^8$ is —CHO, then $R^{13}$ is not 3-(tetrazol-5-yl);

(13) when r=1, $R^1$ is

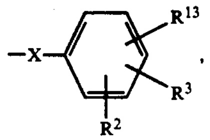

X is a single bond, $R^7$ is Cl and $R^8$ is —CHO, then $R^{13}$ is not 4-(tetrazol-5-yl);

(14) when r=0, then $R^1$ is not 4-$NHSO_2CH_3$ or 4-$NHSO_2CF_3$.

29. Pharmaceutical composition of claim 28 wherein the imidazole compound is a compound having the formula:

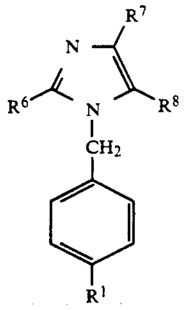

(II)

wherein $R^1$ is $—CO_2H$; $—NHSO_2CF_3$;

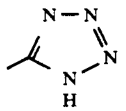

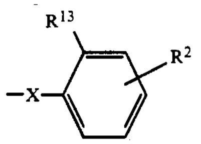

or

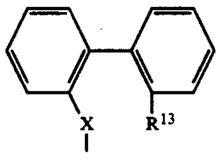

$R^6$ is alkyl of 3 to 10 carbon atoms, alkenyl of 3 to 10 carbon atoms, alkynyl of 3 to 10 carbon atoms; cycloalkyl of 3 to 8 carbon atoms; benzyl or benzyl substituted on the phenyl ring with 1 or 2 groups selected from alkoxy of 1 to 4 carbon atoms, halogen, alkyl of 1 to 4 carbon atoms, and nitro;

$R^8$ is phenylalkenyl wherein the aliphatic portion is 2 to 4 carbon atoms; $—(CH_2)_m$-imidazol-1-yl; $—(CH_2)_m$-1,2,3-triazolyl optionally substituted with one or two groups selected from $CO_2CH_3$ or alkyl of 1 to 4 carbon atoms; $—(CH_2)_m$-tetrazolyl;

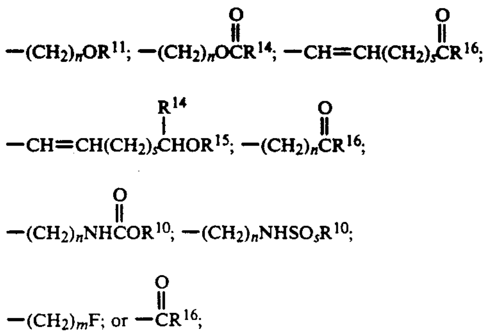

$R^{13}$ is $—CO_2H$, $—CO_2R^9$, $NHSO_2CF_3$, $SO_3H$ or

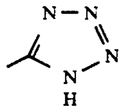

$R^{16}$ is H, alkyl of 1 to 5 carbon atoms, $OR^{17}$ or $NR^{18}R^{19}$;

X is a carbon—carbon single bond, —CO—, $—CONR^{23}—$, $—CH_2CH_2—$, $—NR^{23}CO—$, $—OCH_2—$, $—CH_2O$, —O—, $—SCH_2—$, $—CH_2S—$, $—NHCH_2—$, $—CH_2NH—$ or —CH═CH—;

or a pharmaceutically suitable salt thereof.

30. Pharmaceutical composition of claim 29 wherein the imidazole compound is a compound wherein:

$R^2$ is H, alkyl of 1 to 4 carbon atoms, halogen, or alkoxy of 1 to 4 carbon atoms;

$R^6$ is alkyl, alkeny or alkynyl of 3 to 7 carbon atoms;

$R^7$ is H, Cl, Br, I; $C_vF_{2v+1}$, where v=1-3; or $—COR^{16}$;

$R^8$ is

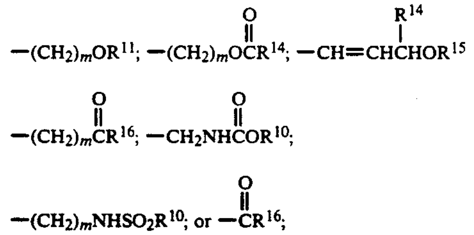

$R^{10}$ is $CF_3$, alkyl of 1 to 6 carbon atoms, or phenyl;

$R^{11}$ is H or alkyl oF 1 to 4 carbon atoms;

$R^{13}$ is $CO_2H$, $CO_2CH_2OCOC(CH_3)_3$;$NHSO_2CF_3$; or

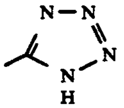

$R^{14}$ is H, alkyl of 1 to 4 carbon atoms;

$R^{15}$ is H, alkyl of 1 to 4 carbon atoms, or acyl of 1 to 4 carbon atoms;

$R^{16}$ is H, alkyl of 1 to 5 carbon atoms; $OR^{17}$; or

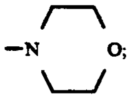

m is 1 to 5;

X is a single bond, —O—, —CO—, —NHCO— or —OCH2—;

or a pharmaceutically suitable salt thereof.

31. Pharmaceutical composition of claim 30 wherein the imidazole compound is a compound wherein $R^1$ is

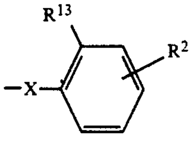

and X is a single bond; or a pharmaceutically suitable salt thereof.

32. Pharmaceutical composition of claim 31 wherein the imidazole compound is 2-Butyl-4-chloro-1-[(2'-(1H-tetrazol-5-yl)biphenyl-4-yl)methyl]-5-(hydroxymethyl-)imidazole, or a pharmaceutically acceptable salt thereof.

33. Pharmaceutical composition of claim 31 wherein the imidazole compound is 2-Butyl-4-chloro-1-[(2'-carboxybiphenyl-4-yl)methyl]-5-(hydroxymethyl)-imidazole, or a pharmaceutically acceptable salt thereof.

34. Pharmaceutical composition of claim 31 wherein the imidazole compound is 2-Butyl-4-chloro-1-[(2'-carboxybiphenyl-4-yl)methyl]-5-[(methoxycarbonyl-)aminomethyl]imidazole, or a pharmaceutically acceptable salt thereof.

35. Pharmaceutical composition of claim 31 wherein the imidazole compound is 2-Butyl-4-chloro-1-[(2'-carboxybiphenyl-4-yl)methyl]-5-[(propoxycarbonyl-)aminomethyl]imidazole, or a pharmaceutically acceptable salt thereof.

36. Pharmaceutical composition of claim 31 wherein the imidazole compound is 2-Butyl-4-chloro-1-[(2'-carboxybiphenyl-4-yl)methyl]imidazole-5-carboxaldehyde, or a pharmaceutically acceptable salt thereof.

37. Pharmaceutical composition of claim 31 wherein the imidazole compound is 2-Butyl-1-[(2'-carboxybiphenyl-4-yl)methyl]imidazole-5-carboxaldehyde, or a pharmaceutically acceptable salt thereof.

38. Pharmaceutical composition of claim 31 wherein the imidazole compound is 2-(1E-Butenyl)-4-chloro-1-[(2'-carboxybiphenyl-4-yl)methyl]-5-(hydroxymethyl-)imidazole, or a pharmaceutically acceptable salt thereof.

39. Pharmaceutical composition of claim 31 wherein the imidazole compound is 2-(1E-Butenyl)-4-chloro-1-[(2'-carboxybiphenyl-4-yl)methyl]imidazole-5-carboxaldehyde, or a pharmaceutically acceptable salt thereof.

40. Pharmaceutical composition of claim 31 wherein the imidazole compound is 2-propyl-4-chloro-1-[(2'-(1H-tetrazol-5-yl)biphenyl-4-yl)methyl]-5-(hydroxymethyl)imidazole, or a pharmaceutically acceptable salt thereof.

41. Pharmaceutical composition of claim 31 wherein the imidazole compound is 2-propyl-4-chloro-1-[(2'-(1H-tetrazol-5-yl)biphenyl-4-yl)methyl]imidazole-5-carboxaldehyde, or a pharmaceutically acceptable salt thereof.

42. Pharmaceutical composition of claim 31 wherein the imidazole compound is 2-butyl-4-chloro-1-[(2'-(1H-tetrazol-5-yl)biphenyl-4-yl)methyl)imidazole-5-carboxaldehyde, or a pharmaceutically acceptable salt thereof.

43. Pharmaceutical composition of claim 31 wherein the imidazole compound is 2-(1E-butenyl)-4-chloro-1-[(2'-(1H-tetrazol-5-yl)biphenyl-4-yl)methyl]-5-hydroxymethyl)imidazole, or a pharmaceutically acceptable salt thereof.

44. Pharmaceutical composition of claim 31 wherein the imidazole compound is 2-(1E-butenyl)-4-chloro-1-[(2'-(1H-tetrazol-5-yl)biphenyl-4-yl)methyl]-imidazole-5-carboxaldehyde, or a pharmaceutically acceptable salt thereof.

45. Pharmaceutical composition of claim 31 wherein the imidazole compound is 2-butyl-4-chloro-1-[(2'-(1H-tetrazol-5-yl)biphenyl-4-yl)methyl]-imidazole-5-carboxylic acid, or a pharmaceutically acceptable salt thereof.

46. Pharmaceutical composition of claim 31 wherein the imidazole compound is 2-propyl-4-chloro-1-[(2'-(1H-tetrazol-5-yl)biphenyl-4-yl)methyl]-imidazole-5-carboxylic acid, or a pharmaceutically acceptable salt thereof.

47. Pharmaceutical composition of claim 31 wherein the imidazole compound is 2-propyl-4-tri-fluoromethyl-1-[(2'-(1H-tetrazol-5-yl)biphenyl-4-yl)-methyl-]imidazole-5-carboxylic acid, or a pharmaceutically acceptable salt thereof.

48. Pharmaceutical composition of claim 31 wherein the imidazole compound is 2-propyl-4-tri-fluoromethyl-1-[(2'-(1H-tetrazol-5-yl)biphenyl-4-yl)-methyl-5-(hydroxymethyl)imidazole, or a pharmaceutically acceptable salt thereof.

49. Pharmaceutical composition of claim 31 wherein the imidazole compound is 2-butyl-4-tri-fluoromethyl-1-[(2'-1H-tetrazol-5-yl)biphenyl-4-yl)-methyl-]imidazole-5-carboxylic acid, or a pharmaceutically acceptable salt thereof.

50. Pharmaceutical composition of claim 31 wherein the imidazole compound is 2-propyl-4-tri-fluoromethyl-1-[(2'-carboxybiphenyl-4-yl)methyl]-imidazole-5-carboxaldehyde, or a pharmaceutically acceptable salt thereof.

51. Pharmaceutical composition of claim 31 wherein the imidazole compound is 2-propyl-4-pentafluoroethyl-1-[(2'-(1H-tetrazol-5-yl)biphenyl-4-yl)methyl]-5-(hydroxymethyl)imidazole, or a pharmaceutically acceptable salt thereof.

52. Pharmaceutical composition of claim 31 wherein the imidazole compound is 2-Propyl-1-[(2'-(1H-tetrazol-5-yl)biphenyl-4-yl)methyl]imidazole-4,5-dicarboxylic acid, or a pharmaceutically acceptable salt thereof.

53. Pharmaceutical composition of claim 31 wherein the imidazole compound is 2-Propyl-4-pentafluoroethyl-1-[(2'-(1H-tetrazol-5-yl)biphenyl-4-yl)methyl-]imidazole-5-carboxylic acid, or a pharmaceutically acceptable salt thereof.

54. Pharmaceutical composition of claim 31 wherein the imidazole compound is 2-Propyl-4-pentafluoroethyl-[(2'-(1H-tetrazol-5-yl)biphenyl-4-yl)methyl-]imidazole-5-carboxaldehyde, or a pharmaceutically acceptable salt thereof.

* * * * *